United States Patent
Josephson et al.

(10) Patent No.: US 10,954,287 B2
(45) Date of Patent: Mar. 23, 2021

(54) RAS BINDING PEPTIDES AND METHODS OF USE

(71) Applicant: Ra Pharmaceuticals, Inc., Cambridge, MA (US)

(72) Inventors: Kristopher Josephson, San Carlos, CA (US); Zhong Ma, Lexington, MA (US); Yili Sun, Cambridge, MA (US); Nathan Ezekiel Nims, Winchester, MA (US); Kathleen Seyb, Wakefield, MA (US); Sylvia Tobe, Cambridge, MA (US); Ping Ye, Lexington, MA (US); Douangsone D. Vadysirisack, Boston, MA (US); Guo-Qing Tang, Acton, MA (US); Douglas A. Treco, Arlington, MA (US)

(73) Assignee: RA PHARMACEUTICALS, INC., Cambridge, MA (US)

( * ) Notice: Subject to any disclaimer, the term of this patent is extended or adjusted under 35 U.S.C. 154(b) by 2 days.

(21) Appl. No.: 16/093,762

(22) PCT Filed: Apr. 14, 2017

(86) PCT No.: PCT/US2017/027697
§ 371 (c)(1),
(2) Date: Oct. 15, 2018

(87) PCT Pub. No.: WO2017/181061
PCT Pub. Date: Oct. 19, 2017

(65) Prior Publication Data
US 2019/0119358 A1    Apr. 25, 2019

Related U.S. Application Data

(60) Provisional application No. 62/323,115, filed on Apr. 15, 2016.

(51) Int. Cl.
| | | |
|---|---|---|
| *A61K 38/00* | (2006.01) |
| *C07K 14/82* | (2006.01) |
| *C07K 7/08* | (2006.01) |
| *G01N 33/574* | (2006.01) |
| *A61K 47/65* | (2017.01) |
| *A61K 47/64* | (2017.01) |
| *A61P 35/00* | (2006.01) |
| *A61K 47/14* | (2017.01) |
| *C07K 7/54* | (2006.01) |

(52) U.S. Cl.
CPC .............. *C07K 14/82* (2013.01); *A61K 38/00* (2013.01); *A61K 47/14* (2013.01); *A61K 47/64* (2017.08); *A61K 47/65* (2017.08); *A61P 35/00* (2018.01); *C07K 7/08* (2013.01); *C07K 7/54* (2013.01); *G01N 33/574* (2013.01)

(58) Field of Classification Search
CPC . C07K 14/82; C07K 7/08; C07K 7/54; A61K 47/65; A61K 47/64; A61K 38/00; A61K 47/14; A61P 35/00; G01N 33/574
See application file for complete search history.

(56) References Cited

U.S. PATENT DOCUMENTS

| | | | |
|---|---|---|---|
| 5,910,478 A | 6/1999 | Hlavka | |
| 6,348,584 B1 | 2/2002 | Hodgson | |
| 6,673,901 B2 | 1/2004 | Koide | |
| 7,074,761 B1* | 7/2006 | Hinuma | C07K 14/575 514/11.1 |
| 7,744,910 B2 | 6/2010 | Gschneidner | |
| 2008/0146490 A1 | 6/2008 | Joabsson | |
| 2015/0166606 A1* | 6/2015 | Wang | A61K 47/60 514/20.3 |
| 2015/0239935 A1 | 8/2015 | Arora | |
| 2016/0264627 A1 | 9/2016 | Henning et al. | |

FOREIGN PATENT DOCUMENTS

| | | |
|---|---|---|
| EP | 0404097 | 12/1990 |
| WO | 1993011161 | 6/1993 |
| WO | 2009067191 | 5/2009 |
| WO | 2012078559 | 6/2012 |
| WO | 2012162628 A2 | 11/2012 |
| WO | 2012162628 A3 | 11/2012 |

OTHER PUBLICATIONS

Upadhyaya et al., Agnew. Chem. Int. Ed. 2015 54 7602-7606 (Year: 2015).*
Trinh et al., ACS Comb Sci., 2016 18 75-85 (Year: 2016).*
Extended European Search Report for corresponding European Application No. 17783273.0 dated Oct. 23, 2019.
Watkins et al. "Structure-based inhibition of protein-protein interactions" European Journal of Medicinal Chemistry, Elsevier, Amsterdam, NL, vol. 94 (2014).
Upadhyaya et al. "Inhibition of Ras Signaling by Blocking Ras-Effector Interactions with Cyclic Peptides" Angewandte Communications, vol. 54, No. 26 (2015).
Trinh et al. "Discovery of a Direct Ras Inhibitor by Screening a Combinatorial Library of Cell-Permeable Bicyclic Peptides" American Chemical Society, vol. 18, No. 1 (2016).
Burmer et al. (1989) Mutations in the KRAS2 oncogene during progressive stages of human colon carcinoma, Proc. Natl. Acad. Sci. U.S.A. 86 (7): 2403-7.
Castellano et al. (2011) RAS interaction with PI3K: More than just another effector pathway, Genes Cancer 2(3):261-274.

(Continued)

*Primary Examiner* — Larry D Riggs, II
*Assistant Examiner* — Joseph Fischer
(74) *Attorney, Agent, or Firm* — DT Ward, PC; Donna T. Ward; Christopher P. Sullivan

(57) ABSTRACT

The present invention provides Ras modulators including inhibitors and/or antagonists of Ras, Ras binding, and Ras-dependent cell signaling activity. Also provided are methods of utilizing the Ras modulators as therapeutics.

22 Claims, 14 Drawing Sheets
Specification includes a Sequence Listing.

(56) References Cited

OTHER PUBLICATIONS

Chamorro-Jorganes et al. (2010) Targeted Genomic Disruption of H-Ras Induces Hypotension Through a NO—cGMP—PKG Pathway-Dependent Mechanism, Hypertension, 56(3):484-9.

Chang et al. (1982) Human genome contains four genes homologous to transforming genes of Harvey and Kirsten murine sarcoma viruses, Proc. Natl. Acad. Sci. U.S.A. 79(16): 4848-52.

Crews et al. (2008) Targeted intracellular protein degradation induced by a small molecule: En route to chemical proteomics, Bioorg. Med. Chem. Lett., 18, 5904-5908).

Crews et al. (2012) Identification of hydrophobic tags for the degradation of stabilized proteins, ChemBioChem, 13, 538-541.

Davis et al. (1993) The mitogen-activated protein kinase signal transduction pathway, J. Biol. Chem. 268(20):14553-6.

Davis et al. (2000) Signal Transductin by the JNK Group of MAP Kinases; Cell, vol. 103, 239-252, Oct. 13, 2000.

Davis et al. (2011) Catalytic, enantioselective synthesis of stilbenecis-diamines: A concise preparation of (–)-Nutlin-3, a potent p53/MDM2 inhibitor, Chem. Sci., 2, 1076-1079.

Dennis et al. (2002) Albumin binding as a general strategy for improving the pharmacokinetics of proteins, J Biol Chem. 277(38):35035-43.

Eisfeld et al. (2014) NRAS isoforms differentially affect downstream pathways, cell growth, and cell transformation, Proc. Natl. Acad. Sci., 111(11):4179-4184.

International Search Report and Written Opinion dated Sep. 11, 2017 in application No. PCTUS2017027697, entitled "Ras Binding Peptides and Methods of Use".

Upadhyaya et al., "Inhibition of Ras Signaling by Blocking Ras-Effector Interactions with Cyclic Peptides" Angew Chem Int Ed Engl, Jun. 22, 2015; 54(26):7602-7606.

Trinh et al. "Discovery of a Direct Ras Inhibitor by Screening a Combinational Library of Cell-Permeable Bicyclic Peptides" ACS Combinational Science, 2016, 18, 75-85.

Almoguera et al. (1988) Most human carcinomas of the exocrine pancreas contain mutant c—K—ras genes, Cell, 53 (4): 549-54.

Altschul et al. (1997) Gapped Blast and PSI-Blast: a new generation of protein database search programs, Nucleic Acids Res., 25:3389-3402.

Berge et al. (1977) Pharmaceutical salts, J. Pharmaceutical Sciences, 66, 1-19.

Bezieau et al. (2001) High incidence of N and K—Ras activating mutations in multiple myeloma and primary plasma cell leukemia at diagnosis, Hum. Mutat, 18(3):212-224.

Boguski et al. (1993) Proteins regulating Ras and its relatives, Nature, 366:643-654.

Buckley et al. (2014) Small-Molecule Control of Intracellular Protein Levels through Modulation of the Ubiquitin Proteosome System, Angewandte Chemie International Edition, 53(9), 2312-2330.

Erhhardt et al. (2002) Ras and relatives—job sharing and networking keep an old family together, Experimental Hematology 30:1089-1106.

Fernandez-Sarabia et al. (1993) Bcl-2 associates with the ras-related protein R-rasp23, Nature 366:274-275.

Guldenhaupt et al. (2012) N—Ras Forms Dimers at POPC Membranes, Biophysical Journal, 103(7), 1585-1593.

Hall et al. (1983) Identification of transforming gene in two human sarcoma cell lines as a new member of the ras gene family located on chromosome 1, Nature 303 (5916): 396-400.

Herrmann et al. (2003) Ras-effector interactions: after one decade, Curr. Opin. Struct. Biol. 13(1):122-129.

Inouye et al. (2000) Formation of the Ras Dimer Is Essential for Raf-1 Activation, Journal of Biological Chemistry, 275 (6), 3737-3740.

Leevers et al. (1994) Requirement for Ras in Raf activation is overcome by targeting Raf to the plasma membrane, Nature 369:411-4.

Lin et al. (2014) H-Ras forms dimers on membrane surfaces via a protein-protein interface, PNAS, www.pnas.org/cgi/doi/10.1073/pnas.1321155111.

Malumbres M, Barbacid M (2003) RAS oncogenes: The first 30 years. Nat. Rev. Cancer 3(6):459-465.

Marshall et al. (1982) A transforming gene present in human sarcoma cell lines, Nature 299: 171-173.

Marshall et al. (1995) Ras target proteins in eukaryotic cells, FASEB J. 9:1311-1318.

Mascaux et al. (2005) The role of RAS oncogene in survival of patients with lung cancer: a systematic review of the literature with meta-analysis; British Journal of Cancer (2005) 92, 131-139.

Mascaux et al. (2006) Has Cox-2 a prognostic role in non-small-cell lung cancer? A systematic review of the literature with meta-analysis of the survival results, Br. J. Cancer. 95(2):139-145.

Matallanas et al. (2011) Raf family kinases: old dogs have learned new tricks, Genes Cancer., 2(3): 232-260.

McGrath et al. (1984) Inhibitors of the Ras Superfamily G-proteins, Part 1, Nature 310(5979): 644-649).

Millettiet al. (2012) Cell-penetrating peptides: classes, origin, and current landscape. Drug Discov Today; 17 (15-16):850-60.

Moodie et al. (1993) Complexes of Ras.GTP with Raf-1 and mitogen-activated protein kinase kinase, Science 260 (5114):1658-1661.

Nan et al. (2015) Ras-GTP dimers activate the Mitogen-Activated Protein Kinase (MAPK) pathway, PNAS. 112(26): 7996-8001.

Neklesa et al. (2011) Small-molecule hydrophobic tagging-induced degradation of HaloTag fusion proteins, Nat. Chem. Biol. 7, 538-543.

Nguyen et al. (2006) The pharmacokinetics of an albumin-binding Fab (AB.Fab) can be modulated as a function of affinity for albumin. Protein Eng Des Sel;19(7):291-7.

Niihori T et al. (2006) Germline KRAS and BRAF mutations in cardio-facio-cutaneous syndrome, Nat. Genet. 38 (3): 294-6.

Panowski et al. 2014) Site-specific antibody drug conjugates for cancer therapy, mAbs 6:1, 34-45.

Parada et al. (1982) Human EJ bladder carcinoma oncogene is homologue of Harvey sarcoma virus ras gene, Nature 297 (5866): 474-8.

Plowman et al. (2005) H-ras, K-ras, and inner plasma membrane raft proteins operate in nanoclusters with differential dependence on the actin cytoskleton, PNAS. 102(43): 15500-5.

Rajalingam et al. (2007) Ras oncogenes and their downstream targets, Biochimica et Biophysica Acta—Molecular Cell Research 1773(8):1177-95.

Ramos et al. (2009) H-RAS Controls Phenotypic Profiles of Vascular Smooth Muscle Cells and the Pathogenesis of Vascular Proliferative Disorders, Circulation Research 104(10):1139-41.

Reuter et al. (2000) Targeting the Ras signaling pathway: a rational, mechanism-based treatment for hematologic malignancies?, Blood. 96(5):1655-69.

Roberts et al. (1997) RNA-peptide fusions for the in vitro selection of peptides and proteins, Proc. Natl. Acad. Sci. USA 94, 12297-12302.

Santos et al. (1982) T24 human bladder carcinoma oncogene is an activated form of the normal human homologue of BALB- and Harvey-MSV transforming genes, Nature 298 (5872): 343-7.

Santos et al. (2014) Dimerization Opens New Avenues into Ras Signaling Research, Science Signaling. 7(324).

Schubbert et al. (2006) Germline KRAS mutations cause Noonan syndrome, Nat. Genet. 38 (3): 331-6.

Shimizu et al. (1983) Isolation and preliminary characterization of the transforming gene of a human neuroblastoma cell line, PNAS 80 (2): 383-7.

Sjölander et al. (1991) Association of p21ras with phosphatidylinositol 3-kinase. Proc Natl Acad Sci USA 88(18):7908-7912.

Smith et al. (1993) Biocomputing: Informatics and Genome Projects, Academic Press, New York.

Spencer-Smith et al. (2016) Inhibition of RAS function through targeting an allosteric regulatory site; Nature Chemical Biology, vol. 13, pp. 62-68 (2017).

Stokoe et al. (1994) Activation of Raf as a result of recruitment to the plasma membrane, Science 264:1463-7.

(56) References Cited

OTHER PUBLICATIONS

Stokoe et al. (1997) Activation of c-Raf-1 and Src through different mechanisms: activation in vivo and in vitro;The EMBO Journal vol. 16 No. 9 pp. 2384-2396, 1997.

Tam et al. (2006) Distinct epidermal growth factor receptor and KRAS mutation patterns in non-small cell lung cancer patients with different tobacco exposure and clinicopathologic features, Clin. Cancer Res. 12 (5): 1647-53.

Tanaka et al. (2007) Tumour prevention by a single antibody domain targeting the interaction of signal transduction proteins with RAS, The EMBO Journal, 26, 3250-9.

Taparowsky et al. (1982) Activation of the T24 bladder carcinoma transforming gene is linked to a single amino acid change, Nature 300 (5894): 762-5.

Vojtek et al. (1993) Mammalian Ras interacts directly with the serine/threonine kinase Raf. Cell 74(1):205-214.

Von Heinje et al. (1987) Sequence Analysis in Molecular Biology, Academic Press e-book.

Wong-Staal et al. (1981) Three distinct genes in human DNA related to the transforming genes of mammalian sarcoma retroviruses, Science 213 (4504): 226-8.

Yang et al. (2012) Regulation of RAS oncogenicity by acetylation, Proc. Natl. Acad. Sci. U.S.A. vol. 109, No. 27, 10843-10848, Jul. 3, 2012.

\* cited by examiner

H-Ras-Cys

Biotinylated H-Ras-Cys

H-Ras

Biotinylated H-Ras

Co-injection of GDP and GMPPNP standards

GMPPNP released from H-Ras-Cys

Kd=35.7nM, R2=0.97

Kd=1.34uM, R2=0.94

US 10,954,287 B2

RAS BINDING PEPTIDES AND METHODS OF USE

CROSS REFERENCE TO RELATED APPLICATIONS

This application is a 35 U.S.C. § 371 U.S. National Stage Entry of International Application No. PCT/US2017/027697 filed Apr. 14, 2017, which claims the benefit of priority of U.S. Provisional Patent Application No. 62/323,115, filed Apr. 15, 2016, entitled RAS BINDING PEPTIDES AND METHODS OF USE, the contents of each of which are herein incorporated by reference in their entirety.

SEQUENCE LISTING

The instant application contains a Sequence Listing which has been submitted electronically in ASCII format and is hereby incorporated by reference in its entirety. Said ASCII copy, created on Aug. 27, 2020, is named 2011_1015US371_SL.txt and is 68,175 bytes in size.

FIELD OF THE INVENTION

The present invention relates to compounds, including polypeptides, which are useful as binders, inhibitors and/or antagonists of Ras or Ras-mediated pathways. Also provided are methods of utilizing the compounds as therapeutics.

BACKGROUND OF THE INVENTION

Many well-validated oncology targets regulate signaling pathways through interactions with other proteins. Addressing these targets, which often lack suitable small molecule binding sites, requires larger and more complex molecules that are capable of binding relatively large or flat surfaces.

The Ras oncogene family is one such group of targets. The name "Ras" is an abbreviation of 'Rat sarcoma', reflecting the way the first members of the protein family were discovered. The name Ras is also used to refer to the entire family of genes encoding those proteins related to the transforming genes of mammalian sarcoma retroviruses. These viruses were discovered originally in rats during the 1960s (Harvey J J (1964), Nature 204 (4963): 1104-5; Kirsten W H, et al., (1970), Bibl Haematol (36): 246-9; Cooper G M (1982), Science 217 (4562): 801-6; Santos E, et al., (1982), Nature 298 (5872): 343-7; Parada L, et al., (1982), Nature 297 (5866): 474-8; Taparowsky E, et al., (1982), Nature 300 (5894): 762-5).

The Ras protein family members belong to a class of protein called small GTPases, which can bind GTP and GDP and are involved in transmitting signals within cells (cellular signal transduction).

There are three canonical members of the Ras gene family (Wong-Staal F, et al., (1981) Science 213 (4504): 226-8), designated H-Ras, N-Ras and K-Ras, and each encode extremely similar proteins made up of chains of 188 to 189 amino acids. Alternative splicing of K-Ras pre-mRNA results in the production of K-Ras isoforms K-Ras4A and K-Ras4B At least five different mutations in H-Ras (also known as transforming protein p21) have been shown to cause Costello syndrome, a disease characterized by increased growth at the prenatal stage, growth deficiency at the postnatal stage, predisposition to tumor formation, mental retardation, skin and musculoskeletal abnormalities, distinctive facial appearance and cardiovascular abnormalities. Defects in this gene are also implicated in a variety of cancers, including bladder cancer, follicular thyroid cancer, and oral squamous cell carcinoma. Multiple transcript variants, which encode different isoforms, have been identified for this gene.

K-Ras, a Kirsten rat sarcoma viral oncogene homolog from the mammalian ras gene family, encodes a protein that is a member of the small GTPase superfamily and is usually tethered to cell membranes due to the presence of an isoprenyl group on its C-terminus. Importantly, a single amino acid substitution is responsible for an activating mutation. The transforming protein that results is implicated in various malignancies, including lung adenocarcinoma, mucinous adenoma, ductal carcinoma of the pancreas and colorectal carcinoma.

Several germline K-Ras mutations have been found to be associated with Noonan syndrome and cardio-facio-cutaneous syndrome, whereas somatic K-Ras mutations are found at high rates in leukemias, colon cancer, pancreatic cancer and lung cancer (Schubbert S, et al. (2006) Nat. Genet. 38 (3): 331-6; Niihori T, et al. (2006), Nat. Genet. 38 (3): 294-6; Burmer G C, Loeb L A (1989), Proc. Natl. Acad. Sci. U.S.A. 86 (7): 2403-7; Almoguera C, et al., (1988), Cell 53 (4): 549-54; Tam I Y, et al. (2006), Clin. Cancer Res. 12 (5): 1647-53).

A third Ras gene was discovered in 1982 and named N-Ras, for its initial identification in human neuroblastoma cells (Marshall C J, et al., (1982), Nature 299 (5879): 171-3; Hall A, et al., (1983), Nature 303 (5916): 396-400; and Shimizu K, et al., (1983), PNAS 80 (2): 383-7).

Despite the enormous amount of research focused on the Ras family over the more than 30 years since its discovery, these targets are still considered essentially undruggable.

Therefore, there is a need for the development of compounds capable of selectively binding to and/or blocking Ras or Ras-mediated signaling pathways toward the treatment of diseases such as cancer and those mediated by mutant forms of Ras and/or aberrant Ras signaling.

SUMMARY OF THE INVENTION

In some embodiments, the present disclosure provides a polypeptide comprising the sequence of SEQ ID NO: 7 or the formula $R_1$-Xaa0-Xaa1-Xaa2-Xaa3-Xaa4-Xaa5-Xaa6-Xaa7-Xaa8-Xaa9-Xaa10-Xaa11-Xaa12-Xaa13-$R_2$, wherein: $R_1$ is selected from the group consisting of H, an acyl group containing an optionally substituted C1-20 aliphatic group, a heptanoyl group, an amide, a carbamate, urea, PEG, hydroxyalkyl starch, a peptide, and a protein; Xaa0 is absent, or an amino acid selected from the group consisting of an unnatural amino acid, Met and norvaline; Xaa1 is Cys or Ser; Xaa2 is selected from the group consisting of a natural amino acid; Xaa3 is selected from the group consisting of an unnatural amino acid; Xaa4 is selected from the group consisting of a natural amino acid; Xaa5 is selected from the group consisting of a natural amino acid or unnatural amino acid; Xaa6 is selected from the group consisting of an N-methylated amino acid or Pro; Xaa7 is selected from the group consisting of an unnatural amino acid; Xaa8 is selected from the group consisting of an unnatural amino acid; Xaa9 is selected from the group consisting of a natural amino acid; Xaa10 is selected from the group consisting of an N-methylated amino acid or unnatural amino acid; Xaa 11 is selected from the group consisting of N-methylated amino acid or Pro; Xaa12 is Cys or Ser; Xaa13 is selected from the group consisting of an unnatural amino acid; and $R_2$ is absent or selected from the group consisting of —$NH_2$ and —$N(CH_3)_2$. A cyclic loop may be formed by a bridging moiety between two amino acids. The bridging moiety may include a structure selected from the group consisting of structures I-XIX

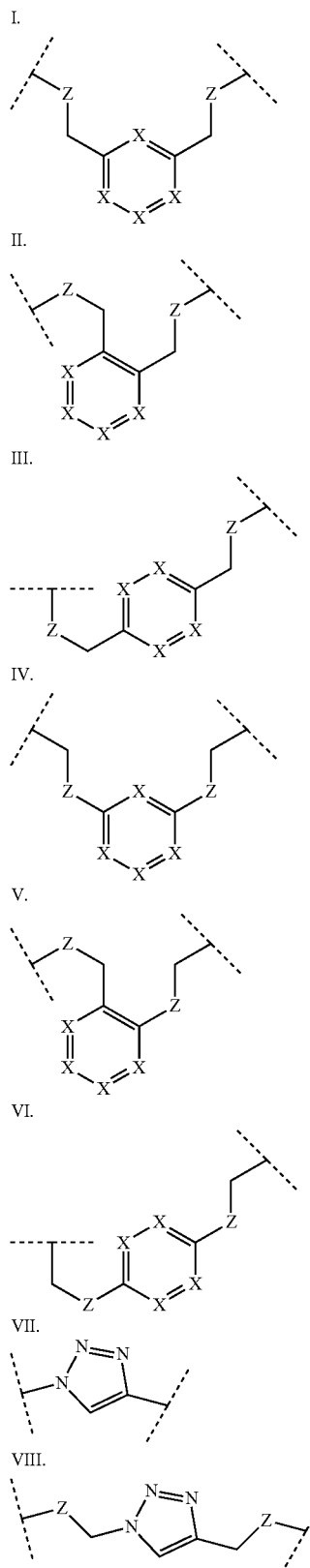

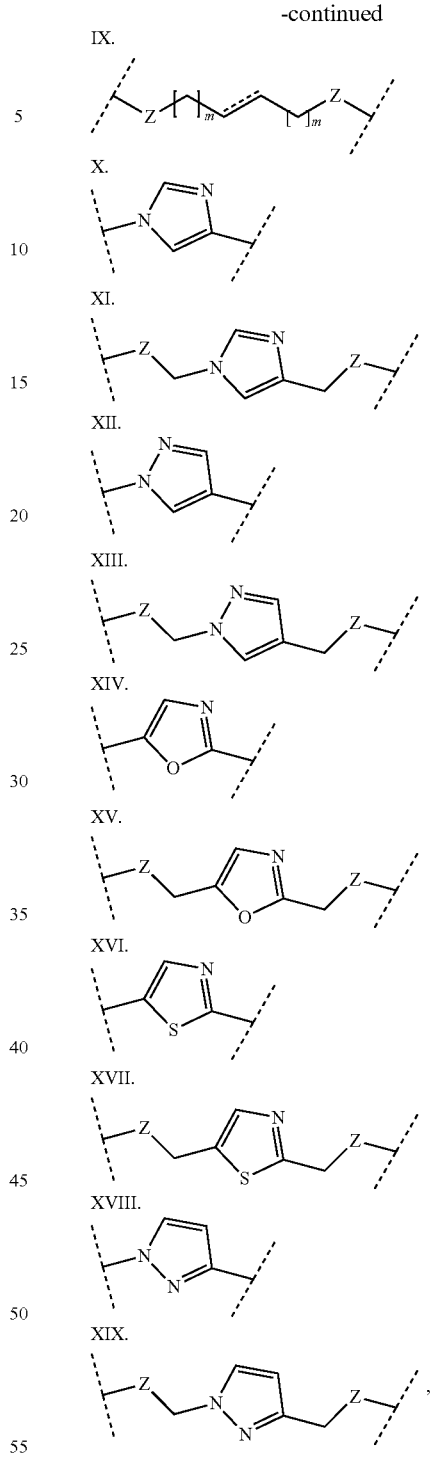

wherein each X is independently N or CH, provided that no more than two Xs in any ring are N; each Z is independently a bond, —NR—, —O—, —S—, —CH2-, —C(O)NR—, —NRC(O)—, —S(O)vNR—, —NRS(O)v-; each m is independently selected from 0, 1, 2, and 3; each v is independently selected from 1 and 2; each R is independently selected from H and optionally substituted C1-C6 aliphatic; and each bridging moiety is optionally connected to the peptide by independently selected optionally substituted C1-C6 aliphatic groups. The bridging moiety may include a feature selected from the group consisting of a lactam bridge, a disulfide bond, a thioether bond and an aromatic ring. The cyclic loop may be of a length selected from the group consisting of 1 amino acid, 2 amino acids, 3 amino acids, 4 amino acids, 5 amino acids, 6 amino acids, 7 amino acids, 8 amino acids, 9, amino acids, 10 amino acids, 11 amino acids, 12 amino acids, 13 amino acids, 14 amino acids, 15 amino acids and 16 amino acids. The bridging moiety may form a cyclic loop between residue Xaa1 and a residue selected from the group consisting of Xaa4, Xaa5, Xaa6, Xaa7, Xaa8, Xaa9, Xaa10, Xaa11, Xaa12, and Xaa13. The bridging moiety may include an aromatic ring produced by reaction with a reagent comprising poly(bromomethyl) benzene. The poly(bromomethyl)benzene may be selected from the group consisting of 1,2-bis(bromomethyl)benzene, 1,3-bis(bromomethyl)benzene and 1,4-bis(bromomethyl) benzene. The bridging moiety may include a disulfide bond between two cysteine residues. The bridging moiety may include an aromatic ring produced by reaction with a compound selected from the group consisting of 2,6-bis(bromomethyl)pyridine, (E)-1,4-dibromobut-2-ene, and 1,2-bis(bromomethyl)-4-alkylbenzene.

Compositions of the present disclosure may include one or more of the polypeptides described herein with an acceptable carrier or excipient. The one or more polypeptides may be conjugated to a water-soluble polymer. The water-soluble polymer may be a hydrophilic polymer. The hydrophilic polymer may be selected from the group consisting of polyalkylene oxide homopolymers, polypropylene glycols, polyoxyethylenated polyols, and copolymers thereof. The water-soluble polymer may include polyethylene glycol (PEG).

In some embodiments, the present disclosure provides a method of treating or preventing a Ras-related or Ras-mediated disease or disorder in a subject in need thereof by administering to the subject in need thereof a therapeutically effective amount of a polypeptide or composition described herein. Administration may include one or more of buccal administration, intranasal administration, oral administration, intravenous administration, intramuscular administration, intraperitoneal administration, subcutaneous administration, transdermal administration, and intravitreal administration. The one or more polypeptides may be conjugated to a water-soluble polymer. The water-soluble polymer may be a hydrophilic polymer. The hydrophilic polymer may be selected from the group consisting of polyalkylene oxide homopolymers, polypropylene glycols, polyoxyethylenated polyols, and copolymers thereof. The water-soluble polymer may include polyethylene glycol (PEG). The disease, disorder, and/or condition may include cancer. The cancer may include one or more of bladder cancer, follicular thyroid cancer, oral squamous cell carcinoma, lung adenocarcinoma, mucinous adenoma, ductal carcinoma of the pancreas, colorectal carcinoma, and leukemia.

In some embodiments, the present disclosure provides a kit for the diagnosis, prognosis, prophylaxis, or treatment of a disease, disorder, and/or condition in a mammal. The kit may include one or more polypeptides or compositions described herein, optionally with reagents and/or instructions for use. The one or more polypeptides may include a detectable label or be able to bind to a detectable label to form a detectable complex. The one or more polypeptides may include a BODIPY-TMR label.

Methods of the present disclosure may include modulating cell growth; modulating the concentration of one or more Ras proteins in a cell; inhibiting dimerization of a Ras protein; and/or altering the cellular localization of a Ras protein in a cell by contacting a cell, tissue, or organism with a polypeptide or composition described herein.

The polypeptides of the present disclosure may include a lipid moiety. The lipid moiety may include an optionally substituted aliphatic group of 6, 8, 10, 12, 14, 16, or 18 carbon atoms. The lipid moiety may be attached to a propargyl group to create a triazole linkage.

In some embodiments, the present disclosure provides a polypeptide-Ras complex that includes a polypeptide described herein, wherein the polypeptide is cross-linked to a Ras protein. The Ras protein may be selected from H-Ras, K-Ras, and N-Ras. The cross-link of the polypeptide and the Ras protein may include a covalent bond with Cys118 of the Ras protein. The cross-link may be formed through an electrophilic moiety.

In some embodiments, the present disclosure provides a method of targeting a Ras protein for degradation in a cell comprising contacting the cell with a polypeptide or composition described herein. The polypeptide may be conjugated to a targeting moiety. The targeting moiety may be attached to a propargyl group, and may be configured to form a triazole linkage. The Ras protein may be one or more of H-Ras, K-Ras, and N-Ras.

DESCRIPTION OF THE FIGURES

The file of this patent contains at least one drawing/photograph executed in color. Copies of this patent with color drawing(s)/photograph(s) will be provided by the Office upon request and payment of the necessary fee The foregoing and other objects, features and advantages will be apparent from the following description of particular embodiments of the invention, as illustrated in the accompanying drawings in which like reference characters refer to the same parts throughout the different views. The drawings are not necessarily to scale, emphasis instead being placed upon illustrating the principles of various embodiments of the invention.

FIG. 1A: H-Ras-Cys before biotinylation. FIG. 1B: H-Ras-Cys after biotinylation. FIG. 1C: H-Ras before biotinylation. FIG. 1D: H-Ras after biotinylation.

FIG. 2A: Co-injection of GDP and GMPPNP standards. FIG. 2B: GMPPNP released from H-Ras-Cys. FIG. 2C: GDP released from H-Ras-Cys.

DETAILED DESCRIPTION

Figure 1A:
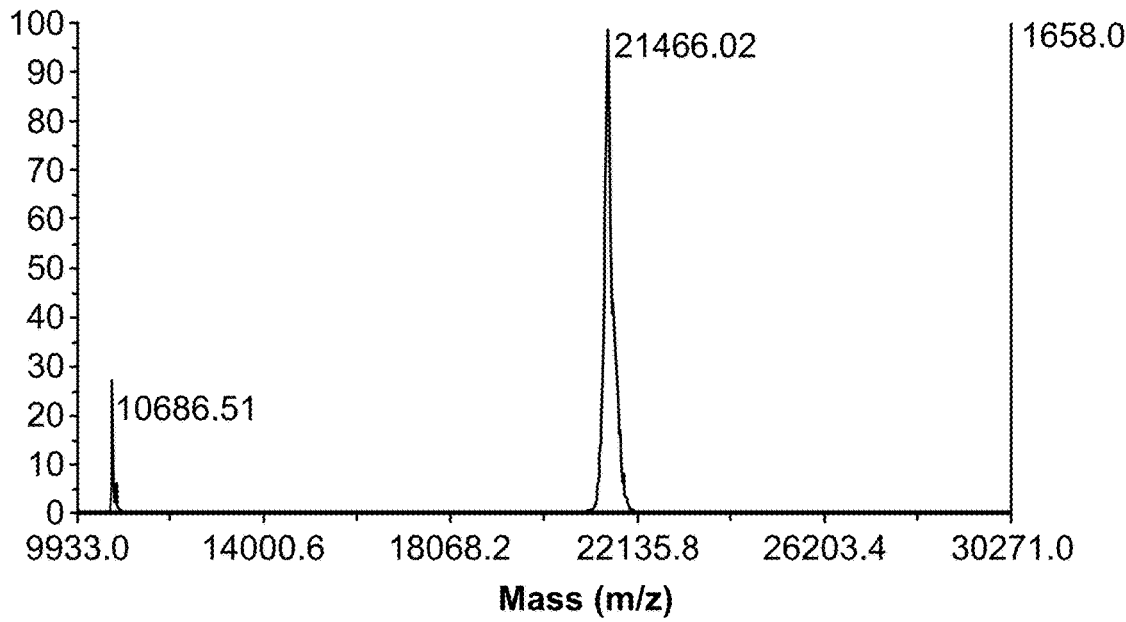
FIG. 1A-1D is a series of graphs showing results from MALDI TOF MS analyses of biotinylated H-Ras and H-Ras-Cys proteins.

The present invention relates to the discovery of novel compounds capable of modulating Ras, referred to herein as "Ras modulators." Such compounds include compounds capable of binding Ras, modulating Ras dimerization, modulating Ras activity, modulating Ras post-translational modifications, modulating interactions between Ras and other factors and/or modulating Ras-related cell signaling. In some cases, Ras modulators are polypeptides (including, but not limited to cyclic polypeptides and polypeptide mimetics). Some Ras modulators are useful in the diagnosis and/or treatment of diseases in which the alteration of the binding properties, signaling or function of one or more Ras proteins is desirable. In some embodiments, Ras modulators specifically bind one or more Ras proteins. In further embodiments, Ras modulators of the invention modulate Ras function, either inhibiting or activating Ras signaling. In some embodiments, the Ras modulators specifically alter the cellular or subcellular concentration of one or more Ras proteins by either altering the expression and/or destruction and/or sequestration (e.g., localization) of the Ras protein.

Oncogenes such as RAS are derived from normal genes (the proto-oncogene) coding for a protein which plays a role in a physiological cellular process such as regulation of gene expression or growth signal transduction.

The Ras small GTPases are generally known for their regulatory role in oncogenic, mitogenic and developmental signaling pathways. The human Ras oncogenes were discovered in studies of the transforming genes from two mammalian cancer-causing retroviruses (Harvey rat sarcoma virus and Kirsten rat sarcoma virus): thus, the v-Ha-ras Harvey rat sarcoma viral oncogene homolog (H-Ras or HRAS) and v-Ki-ras2 Kirsten rat sarcoma viral oncogene homolog (K-Ras or KRAS) human homologues of Ras genes were identified (Chang E H, Gonda M A, Ellis R W, Scolnick E M, Lowy D R (1982). *Proc. Natl. Acad. Sci. U.S.A.* 79(16): 4848-52). Later, the neuroblastoma RAS viral (v-ras) oncogene homolog (N-Ras or NRAS) was discovered in human neuroblastoma cells (Marshall, C J, Hall, A, Weiss, R A (1982) *Nature* 299: 171-173), and related RAS viral (r-ras) oncogene homolog (R-Ras or RRAS) (Fernandez-Sarabia and Bischoff, 1993: *Nature* 366: 274-275) was also identified (Fernandez-Sarabia and Bischoff, 1993: *Nature* 366:274-275).

Ras is a guanosine-nucleotide-binding protein ("G protein"). In general, small G-proteins are in the range of 20 to 29 kDa, share sequence homologies and common motifs and are nearly identical at their tertiary structure, which is composed of six β-sheets surrounded by α-helices. More than 150 RAS-like genes have been identified in mammalian genomes. The whole RAS superfamily has been divided into five subfamilies: RAS, RHO, RAB, ARF and Gα subunits of heterotrimeric G-proteins. In some classifications, Gα subunits are assigned to a distinct RAN subfamily. In either case, RAP, RAL, RHEB and other GTPases are included into the subfamily of RAS proteins, which trigger effector pathways not primarily used by RAS. Other classifications rely on the simplistic view that there are only three true RAS proteins (H—, N—, and KRAS), and subsume other family members as RAS-like proteins. However, MRAS, RRAS and ERAS definitely belong to the RAS subfamily, as they signal through at least one of the RAS effector pathways, sometimes in a cell type- and/or adaptor-dependent manner (Rajalingam, et al., (2007), *Biochimica et Biophysica Acta—Molecular Cell Research* 1773(8): 1177-1195).

Ras Proteins as Molecular Switches

Ras is a G protein; specifically, it is a single-subunit small GTPase, which is related in structure to the Gα subunit of heterotrimeric G proteins (large GTPases). G proteins function as binary signaling switches with "on" and "off" states. In the "off" state it is bound to the nucleotide guanosine diphosphate (GDP), while in the "on" state, Ras is bound to guanosine triphosphate (GTP). The additional phosphate of GTP holds two switch regions in a "loaded-spring" configuration (specifically the Thr-35 and Gly-60). When released, the switch regions relax which causes a conformational change into the inactive state. Hence, activation and deactivation of Ras and other small G proteins are controlled by cycling between the active GTP-bound and inactive GDP-bound forms (Vetter I R, Wittinghofer A (2001) *Science* 294(5545): 1299-1304).

The intrinsic GTPase activity of Ras can hydrolyze a bound GTP molecule into GDP, but this process is generally too slow for efficient function; thus, the process of exchanging the Ras-bound nucleotide is facilitated by guanine nucleotide exchange factors (GEFs) and GTPase activating proteins (GAPs). The balance between GEF and GAP activity determines the guanine nucleotide status of Ras, thereby regulating Ras activity.

RasGAP can bind to and stabilize the catalytic machinery of Ras, supplying additional catalytic residues (e.g., an "arginine finger") such that a water molecule is optimally positioned for nucleophilic attack on the gamma-phosphate of GTP. An inorganic phosphate is released, leaving Ras bound to GDP. This GDP-bound form is "off" or "inactive" for signaling; thus, GAPs accelerate Ras inactivation by activating its GTPase activity.

In contrast, GEFs catalyze a "push and pull" reaction which releases GDP from Ras. They insert close to a P-loop and magnesium cation binding site and inhibit the interaction of these with the gamma phosphate anion. Acidic (negative) residues in switch II "pull" a lysine in the P-loop away from the GDP which "pushes" switch I away from the guanine. The contacts holding GDP in place are broken and it is released into the cytoplasm. Because intracellular GTP is abundant relative to GDP (approximately 10 fold more) GTP predominantly re-enters the nucleotide binding pocket of Ras and reloads the spring. Thus GEFs facilitate Ras activation. Exemplary GEFs which have a RasGEF domain include Son of Sevenless (Sos) and cdc25.

Other proteins exist which may augment the activity of Ras family proteins; these function by slowing the exchange of GDP for GTP, thereby prolonging the inactive state of Ras family members. One example is GDI (GDP Disassociation Inhibitor); as the name suggests, RasGD1 proteins inhibit GDP dissociation from Ras, thereby regulating the level of active Ras in the cell. Other proteins that further augment this cycle may exist.

Membrane Attachment

Differential localization of Ras proteins in different parts of the cell membrane may govern their responses to activation of cell surface receptors. Ras is attached to the cell membrane owing to its prenylation and palmitoylation (H-Ras and N-Ras) or the combination of prenylation and a polybasic sequence adjacent to the prenylation site (K-Ras). The C-terminal CaaX box of Ras first gets farnesylated at its Cys residue in the cytosol, allowing Ras to loosely insert into the membrane of the endoplasmic reticulum and other cellular membranes. The Tripeptide (aaX) is then cleaved from the C-terminus by a specific prenyl-protein specific endoprotease and the new C-terminus is methylated by a methyltransferase. K-Ras procession is completed at this stage. Dynamic electrostatic interactions between its positively charged basic sequence with negative charges at the inner leaflet of the plasma membrane account for its predominant localization at the cell surface at steady-state. N-Ras and H-Ras are further processed on the surface of the Golgi apparatus by palmitoylation of one or two Cys residues, respectively, adjacent to the CaaX box. The proteins thereby become stably membrane-anchored and are transported to the plasma membrane on vesicles of the secretory pathway. Depalmitoylation eventually releases the proteins from the membrane, allowing them to enter another cycle of palmitoylation and depalmitoylation. This cycle is believed to prevent the leakage of N-Ras and H-Ras to other membranes over time and to maintain their steady-state localization along the Golgi apparatus, secretory pathway, plasma membrane and inter-linked endocytosis pathway.

Ras Signaling Pathways

As binary molecular switches, GTPases of the Ras superfamily are activated upon growth factor stimuli, and control a wide range of essential biochemical pathways and intracellular signaling networks in eukaryotic cells. When Ras is 'switched on' by incoming signals, it subsequently switches on other proteins, which ultimately turn on genes involved in cell growth, differentiation and survival. The Ras p21 protooncogene protein products H-ras, K-ras, and N-ras transmit signals from growth factor receptors to a cascade of protein kinases that begins with the Raf protooncogene product, and leads to alterations in transcription factors and cell cycle proteins in the nucleus. This cascade is controlled at several points: Ras p21 proteins are regulated by GAPs and by GEFs, whose activities are altered by growth factor receptor activation (Boguski, M S and McCormick, F (1993) Nature 366:643-654). Transmission of signals from Ras to Raf is regulated by the Ras-related protein Rap1 (a protein capable of reverting cell transformation) and by cAMP. In the GTP-bound conformation, Ras has high affinity for numerous effectors which allow it to carry out its functions; one such effector is phosphatidylinositol-4,5-bisphosphate 3-kinase, catalytic subunit alpha (PI3K).

Ras-regulated signal pathways control such processes as actin cytoskeletal integrity, proliferation, cell adhesion, apoptosis, and cell migration. Many members of the Ras superfamily of GTPases have been implicated in the differentiation and function of hematopoietic cells, cytokine production, chemotaxis, vesicle-trafficking, phagocytosis, cell adhesion, and cell growth, survival and differentiation (Erhhardt, et al., (2002) *Experimental Hematology* 30:1089-1106).

Because Ras signaling can result in cell growth and division, overactive Ras signaling can ultimately lead to cancer. For example, mutations in Ras genes can lead to the production of permanently activated Ras proteins; this can cause unintended and overactive signaling inside the cell, even in the absence of incoming signals.

The well-known p21 Ras proteins H-Ras, N-Ras, K-Ras 4A, and K-Ras 4B are also frequently mutated in human cancer and leukemia. Besides the four p21 Ras proteins, the Ras branch/subfamily of the Ras superfamily includes small GTPases most closely related to Ras such as R-Ras, TC21 (R-Ras2), M-Ras (R-Ras3), Rap1A, Rap1B, Rap2A, Rap2B, RalA, RalB, Rheb, Rin and Rit proteins. These proteins exhibit remarkable overall amino acid identities, especially in the regions interacting with the GEFs that catalyze their activation. In addition, there is considerable sharing of various downstream effectors through which they transmit signals and of GAPs that downregulate their activity, resulting in overlap in their regulation and effector function. Although much is now known about Ras signaling and biology, several observations suggest that Ras function is more complex than previously believed. Notably, the three originally identified Ras proteins may not be functionally identical. Furthermore, Ras function involves functional cross-talk with their close relatives.

One of the most important functions of Ras proteins is activation of mitogen-activated protein kinase (MAPK) cascade, which transmits signals that result in the transcription of genes involved in cell growth and division (Davis R J. (1993) *J. Biol. Chem.* 268(20):14553-6; Davis R J. (2000) *Cell*, Vol. 103, 239-252; Marshall, (1995) *FASEB* 1 9:1311-1318). MAPK pathways are important intracellular cascades that couple signals from the cell surface to the nucleus. One of the most explored functions of MAPK signaling modules is regulation of gene expression in response to extracellular stimuli. MAPK activity is regulated through three-tiered cascades composed of MAPK, MAPK kinase (MAPKK, MKK or MEK) and MAPKK kinase or MEK kinase (MAPKKK or MEKK). Members of Ras and Rho subfamilies could activate MAPK cascades by stimulating MEKK kinases.

The main effector of Ras subfamily members is the v-raf-1 murine leukemia viral oncogene homolog 1 (c-Raf-1). Activated Raf proteins phosphorylate Mitogen-activated protein kinase kinases 1 and 2 (MEK1(MAP2K1) and MEK2(MAP2K2)), which subsequently phosphorylate Mitogen-activated protein kinases 1 and 3 (ERK1/2). ERK1/2 stimulation under Ras signaling leads to activation of a range of transcription factors, such as Jun oncogene (c-Jun), v-fos FBJ murine osteosarcoma viral oncogene homolog (c-Fos), ELK1, member of ETS oncogene family (Elk-1), and CCAAT/enhancer binding protein (C/EBP), beta (C/EBP beta).

Members of Rho subfamily Ras-related C3 botulinum toxin substrate 1 (Rac1) and Cell division cycle 42 (CDC42) promote activation of p21 protein (Cdc42/Rac)-activated kinase 1 (PAK1), Mitogen-activated protein kinase kinase kinase 1 (MEKK1(MAP3K1)) and Mitogen-activated protein kinase kinase kinase 4 (MEKK4(MAP3K4)), which phosphorylate Mitogen-activated protein kinase kinase 3 and 4 (MEK3(MAP2K3) and MEK4(MAP2K4)) and this leads to Mitogen-activated protein kinase 8-10 (JNK (MAPK8-10)) and Mitogen-activated protein kinase 14 (p38 MAPK) activation. Activated by Rac1 and CDC42, p38 MAPK and JNK(MAPK8-10) could activate their nuclear targets Activating transcription factor 2 (ATF-2) and c-Jun.

In most eukaryotes, Ras functions as a positive regulator of an ERK/MAPK signal transduction cascade through the activation of a MEKK. In mammalian cells the primary Ras-responsive MEKK is the protein kinase Raf. The role of Ras in activation of Raf kinase appears to be limited to the recruitment of Raf to the plasma membrane, at which time Raf becomes stably modified to render it active (Leevers et al., 1994: Nature 369:411-414; Stokoe et al., 1994: Science 264:1463-1467). The nature of these modifications is unclear. Raf in the plasma membrane becomes associated with insoluble structural cell components that may be part of the activation. Furthermore, Raf is associated with proteins of the 14-3-3 family that appear necessary for kinase activation. The 14-3-3 proteins interact with all three conserved regions of Raf, including the kinase domain.

In addition to Raf, Ras proteins interact with two known classes of proteins in a manner consistent with effector functions: these are the GAPs and regulators of the Ras-related protein Ral referred to as RalGDS. These biochemical data suggest that other functional pathways are regulated by Ras, including, perhaps, pathways involved in regulating cell shape and motility.

Other small GTPases may bind adaptors such as arfaptin or second messenger systems such as adenylyl cyclase. The Ras binding domain is found in many effectors and invariably binds to one of the switch regions, because these change conformation between the active and inactive forms. However, they may also bind to the rest of the protein surface.

In some embodiments, compounds of the invention may modulate Ras association with GAPs. In some embodiments, compounds of the invention may modulate Ras-association with GEFs. In some embodiments, compounds of the invention may modulate Ras-dependent signaling through the mitogenic cascade involving MAP kinases and/or the MEK/ERK cascade. In some embodiments, compounds of the invention may modulate Ras-association with an effector protein selected from the group consisting of RAF kinase, Ral guanine nucleotide dissociation stimulator (RalGDS), p120$^{GAP}$, Rin1, Tiam, Af6, Nore1, PLCε and PKCζ and phosphatidylinositol 3-kinase (PI3K).

Ras Dimerization

Recent reports have indicated the ability of Ras proteins to form dimers [Santos, E. 2014. Science Signaling. 7(324): pe12 and Lin, W-C et al., 2013. PNAS. 111(8):2996-3001, the contents of each of which are herein incorporated by reference in their entirety]. Spectroscopic as well as anisotropic data indicate dimer formation for each of N-Ras, H-Ras and K-Ras under various conditions, including lipidated, membrane-associated formats. Residues in a4 and 5 helices as well as loop residues between beta strands 2 and 3 in N-Ras may participate in dimer formation and these residues appear to be conserved among other Ras family members. Additionally, a Y64A point mutation has been shown to disrupt H-Ras dimer formation on membrane surfaces [Lin, W-C et al., 2013. PNAS. 111(8):2996-3001]. Further, Ras dimers may be homodimers while in some cases, Ras heterodimers may exist (e.g. N-Ras-H-Ras heterodimers, N-Ras-K-Ras heterodimers or H-Ras-K-Ras heterodimers).

In some embodiments, compounds of the invention may interact with one or more Ras proteins to modulate dimerization. In some cases, modulation of Ras dimerization leads to modulation of downstream Ras signal transduction. Some compounds of the invention may increase Ras dimerization. In other cases, compounds of the invention may disrupt Ras dimerization.

Compounds of the invention may alter Ras dimerization in a way that shifts the balance between one form of homo- or heterodimerization to another form, a function referred to herein as "dimer-shifting." Such dimer-shifting may modulate Ras signaling by increasing or decreasing overall downstream signaling. In some cases, dimer-shifting may favor signaling through one Ras signaling pathway over an alternative Ras signaling pathway.

In some embodiments, compounds of the invention may selectively modulate Ras dimerization based on Ras localization. For example, in some cases, compounds of the invention may only modulate membrane associated Ras dimerization. In other cases, compounds of the invention may only modulate non-membrane associated Ras proteins.

Ras dimerization contributes to Ras activity by promoting nanoclustering in lipid rafts, which may be observed using imaging and computational modeling (Plowman, S. J., et al. 2005. PNAS. 102(43): 15500-5, the contents of which are herein incorporated by reference in their entirety). These nanoclusters are stabilized by dimer formation and may include around 6 to 7 Ras subunits. Ras nanoclusters recruit Raf protein, leading to downstream signaling and eventual transcription of cell cycle regulatory genes. In some embodiments, the present disclosure provides inhibitors of Ras nanoclustering. Such inhibitors may block stabilizing interactions between neighboring Ras proteins within nanoclusters, e.g., Ras dimers. In some embodiments, Ras binding polypeptides provided herein may reduce or inhibit Ras nanoclustering. Such Ras binding polypeptides may reduce or inhibit Raf recruitment to Ras nanoclusters. prevent Raf activation and subsequent cell signal transduction.

Ras proteins found in nanoclusters serve as scaffolds for recruiting and activating downstream effectors, such as Raf, on the cell membrane. In the GTP-bound state, Ras can form a Ras-GTP dimer or can directly bind to Raf initiating the plasma membrane recruitment of Raf. Two Ras-Raf complexes can further dimerize or the Ras-GTP dimer can recruit two Raf molecules. The result, in either case, is a Raf-Raf dimer. Dimerization of Raf is necessary for the activation of Raf kinase and subsequently the MAPK kinase signaling pathway (Nan X., et al. 2015. PNAS. 112(26): 7996-8001, the contents of which are herein incorporated by reference in their entirety). In some embodiments, Ras binding polypeptides provided herein may prevent the activation of Raf kinase and the activation of the MAPK kinase signaling pathway.

There are three Raf isoforms in mammals, Raf-1, B-Raf, and A-Raf. These isoforms have common modular structure, but each are regulated in a different way. Although there are differences in the regulation of each Raf isoform, all of them require the step of recruitment at the plasma membrane by Ras protein (Matallanas D., et al. 2011. Genes Cancer., 2(3): 232-260, the contents of which are herein incorporated by reference in their entirety). In some embodiments, Ras binding polypeptides disclosed herein may prevent the activation of Raf-1, B-Raf, and/or A-Raf.

Inhibition of Ras dimer formation may, according to one method, be monitored through the observation of cross-linking of lipidated Ras constructs immobilized on phosphatidylcholine liposomes. Suspensions of liposomes with lipidated Ras may be prepared and incubated with homobifunctional amine-reactive cross-linker [e.g. ethylene glycol bis(succinimidylsuccinate) or "EGS"] in the presence or absence of compounds of the invention. Samples may then be subjected to Western blot analysis to look for Ras dimers.

In other cases, the effect of compounds of the present invention on Ras dimer formation may be analyzed using fluorescence resonance energy transfer (FRET). Such analysis may be carried out as described by Guldenhaupt et al., (Biophysical Journal 2012 103(7), 1585-1593, the contents of which are incorporated herein by reference in their entirety). This allows the disruption of Ras dimers to be monitored as a decrease in FRET efficiency between the two fluorophores.

Further assays for assessing dimerization effects include protein-fragmentation complementation assays. Such assays can be used to monitor the inhibition of Ras dimer formation in intact cells. Using these assays, two deletion mutants of β-gal, Δα and αω, are fused to the N-terminus of Ras and transiently expressed in HEK293 cells. Cells are then fixed and incubated with X-gal to monitor β-galactosidase activity resulting from Ras dimerization: the formation of Ras dimers brings Δα and Δω in close proximity, so that the co-expression of both mutants restores β-gal activity. Inhibition of dimer formation in the presence of inhibitory compounds leads to disruption of β-gal activity and a decrease in blue-stained (i.e. β-gal-positive) cells observed. (Inouye et al, 2000).

Polypeptide Features

Polypeptides of the invention may be polypeptide mimetics. As used herein, a "mimetic" refers to a molecule which exhibits some of the properties or features of another molecule. A polypeptide mimetic (also referred to as a "polypeptidomimetic" or "peptidomimetic") is a mimetic in which the molecule contains structural elements that are not found in natural polypeptides (i.e. polypeptides comprised of only the 20 proteinogenic amino acids). In a preferred embodiment, peptide mimetics are capable of recapitulating or mimicking the biological action(s) of a natural peptide. A peptidomimetic may differ in many ways from natural peptides, such as: amino acid side chains that are not found among the known 20 proteinogenic amino acids, non-peptide-based bridging moieties used to effect cyclization between the ends or internal portions of the molecule, substitutions of the amide bond hydrogen moiety by methyl groups (N-methylation) or other alkyl groups, replacement of a peptide bond with a chemical group or bond that is resistant to chemical or enzymatic treatments, N- and C-terminal modifications, and conjugation with a non-peptidic extension (such as polyethylene glycol, lipids, carbohydrates, nucleosides, nucleotides, nucleoside bases, various small molecules, or phosphate or sulfate groups). As used herein, the term "cyclic peptide mimetic" or "cyclic polypeptide mimetic" is a peptide mimetic that has as part of its structure one or more cyclic features such as a loop, bridging moiety, and/or an internal linkage.

As used herein, the term "bridging moiety" refers to one or more components of a bridge formed between two adjacent or non-adjacent amino acids in a polypeptide. The bridging moiety may be of any size or composition. In some embodiments, a bridging moiety comprises one or more chemical bonds between two adjacent or non-adjacent amino acids, unnatural amino acids, or non-amino acids in a polypeptide. Bridging moieties may be of any size or composition. In some embodiments, bridging moieties may comprise one or more chemical bonds between two adjacent or non-adjacent amino acids, unnatural amino acids, non-amino acid residues or combinations thereof. Such chemical bonds may be between one or more functional groups on adjacent or non-adjacent amino acids, unnatural amino acids, non-amino acid residues or combinations thereof. In some embodiments, a bridging moiety comprises one or more features including, but not limited to amide bonds (lactam), disulfide bonds, thioether bonds and cyclic rings.

In some embodiments, the bridging moiety comprises a lactam bridge. As used herein, the term "lactam bridge" refers to an amide bond that forms a bridge between chemical groups in a molecule. In some cases, lactam bridges are formed between amino acids, unnatural amino acids, non-amino acid residues or combinations thereof in a polypeptide. In some embodiments, the bridging moiety comprises a disulfide bond formed between two cysteine residues. In some embodiments, the bridging moiety comprises one or more thioether bonds. In some embodiments, bridging moieties comprise non-protein or non-peptide based moieties, including, but not limited to cyclic rings [including, but not limited to aromatic ring structures (e.g. xylyls)]. Such bridging moieties may be introduced by reaction with reagents containing multiple reactive halides, including, but not limited to poly(bromomethyl)benzenes, poly(bromomethyl)pyridines, poly(bromomethyl)alkylbenzenes and/or (E)-1,4-dibromobut-2-ene. In some embodiments, bridging moieties of the present invention include, but are not limited to the following structures:

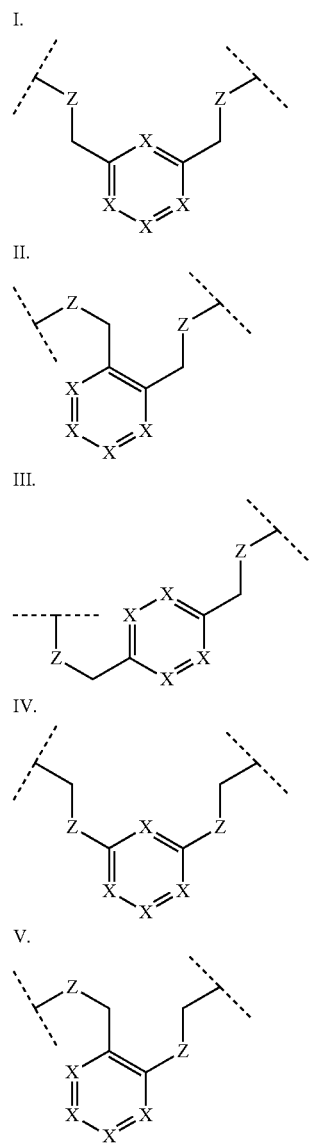

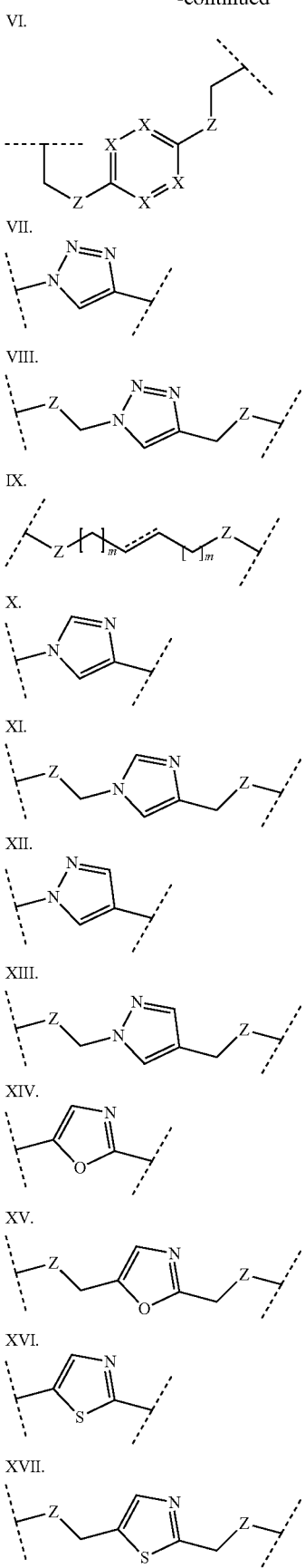

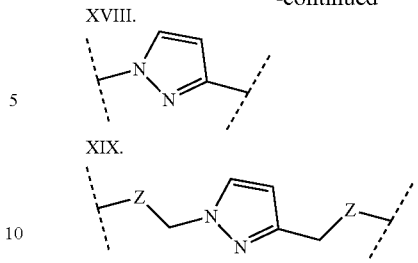

wherein each X is independently N or CH, provided that no more than two Xs in any ring are N; each Z is independently a bond, —NR—, —O—, —S—, —CH$_2$—, —C(O)NR—, —NRC(O)—, —S(O)$_v$NR—, —NRS(O)$_v$—; each m is independently selected from 0, 1, 2, and 3; each v is independently selected from 1 and 2; each R is independently selected from H and optionally substituted C$_1$-C$_6$ aliphatic group; and each bridging moiety is optionally connected to the peptide by independently selected optionally substituted C$_1$-C$_6$ aliphatic groups.

In some embodiments, polypeptides may be conjugated with a targeting moiety. As used herein, a "targeting moiety" refers to an attached molecule or functional group that directs an agent it is conjugated with to a particular location (e.g., a protein, cell, cellular compartment, or cellular membrane). Targeting moieties may be lipid moieties or fatty acid groups. Such groupds may act to alter the distribution of polypeptides in lipid bilayers or membranes such that access and/or binding to one or more Ras proteins is altered. This may alter the concentration, binding properties, and/or signaling properties of Ras. Targeting moieties may be attached to a propargyl group of a polypeptide. In some cases, the attachment forms or results in a triazole linkage.

Polypeptides of the present disclosure may be modified with one or more electrophiles suitable for cross-linking, whether to free thiols or to other groups. Such modifications may act to alter the binding properties of the peptides to Ras proteins such that access and/or binding to one or more Ras proteins is made permanent, thereby altering the concentration, binding properties, and/or signaling of Ras. The conversion of molecules that reversibly bind drug target proteins to irreversible covalent modifers by the rational introduction Cysteine reactive electrophiles may be employed to improve target residence time and prolong exposure by reducing clearance or "wash out". This strategy can also increase target selectivity. (Sing, et. al, 2011, Nature Reviews Drug Discovery, 10, 307-317).

Some polypeptides of the present disclosure may include or be modified with one or more chemical moieties for inducing proteasome-mediated degradation of intracellular Ras. Such modifications may act to alter the concentration of Ras thereby altering Ras signaling pathways. Buckley and Crews, 2014, Small-Molecule Control of Intracellular Protein Levels through Modulation of the Ubiquitin Proteosome System, Angewandte Chemie International Edition, 53(9), 2312-2330.

Some polypeptides of the present disclosure may be modified with a CAAX lipidation motif from the C-terminal hypervarialble region of Ras. This motif may be processed in the same manner as the CAAX motif of Ras: farnesylated or gerenylgerenylated on the cysteine (C), cleaved by Ras converting enzyme 1 (Rce1), and carboxymethyated by isoprenylcysteine carboxylmethyltransferase 1 (ICMT1). The CAAX motif from K-Ras 4B is CVIM (SEQ ID NO:

74) where V, I, and M are the one letter codes for Valine, Isoleucine, and Methionine, respectively, and may be attached to polypeptides of the present disclosure (e.g., through the C-terminus). A flexible linker, such as three consecutive glycine residues, may be used to displace the CAAX motif from polypeptides.

Unless otherwise defined, all technical and scientific terms used herein have the same meaning as commonly understood by one of ordinary skill in the art to which this invention belongs. Although methods and materials similar or equivalent to those described herein can be used in the practice or testing of the cyclic peptides and methods featured in the invention, suitable methods and materials are described below.

Peptides as Drugs

By virtue of their size and complexity, peptides are able to form numerous, highly specific contacts with their biological targets and can show a high level of selectivity for the correct or desired target as compared to a closely related target within the same family. Off-target effects (known also as side effects) can be caused by non-specific binding to unintended targets and often cause highly effective drugs to fail regulatory approval due to safety concerns.

Numerous peptides and peptidomimetics have been developed into effective drugs. These include, but are not limited to, insulin, glucagon-like peptide 1 (GLP-1), somatostatin, vasopressin, cyclosporine A, and the like. In a case such as insulin, the therapeutic peptide can be identical to the naturally occurring molecule (i.e. that which circulates in humans and is considered "wild-type" in the human population) or may contain amino acid sequence modifications which are introduced to improve certain properties. In many other cases, the peptide is not suitable or optimal for therapeutic use due to a short circulating half-life that is often due to metabolic instability in the body. In these cases a modified or a variant form of the peptide (peptidomimetic) is used which results in improved pharmacokinetic and pharmacodynamic behavior. In other cases a peptide derived from a natural source has an equivalent mechanism of action and a preferred pharmaceutical profile and can be used as a therapy. For example, exenatide, a synthetic version of exedin-4 isolated from the saliva of the gila monster (Heloderma suspectum), has biological properties similar to human glucagon-like peptide-1 (GLP-1) but improved pharmacokinetics, and has been approved by the FDA for the treatment of diabetes mellitus type 2. As another example, salmon calcitonin, calcitonin extracted from the ultimobranchial glands of salmon, resembles human calcitonin but is more active than human calcitonin and may be used to treat postmenopausal osteoporosis, hypercalcaemia, Paget's disease, bone metastases and phantom limb pain.

Peptides are typically limited to non-oral routes of administration. In nearly all cases, peptides and peptidomimetics must be delivered by injection, since even very short peptides (e.g., peptides with 4-10 amino acid residues) are incapable or poorly capable of passing through the cell membranes lining the intestinal tract. For efficient oral availability, drugs typically need to pass through both the luminal and basolateral membranes of gut epithelial cells in order to enter the systemic circulation. The poor membrane permeability and lack of oral bioavailability of peptides significantly limits their therapeutic use. It is possible, however, and contemplated herein that peptides may be formulated for oral delivery. Some peptides, such as cyclosporine A however, are intrinsically membrane permeable due to their chemical structures.

The effectiveness of a peptide as a drug may be influenced by its proteolytic stability. Within the body, peptides can be modified or degraded by enzymes, which can limit their effectiveness for interacting with an intended target.

Metabolic stability of peptides is important as it is related to their global flexibility, intramolecular fluctuations, various internal dynamic processes as well as many biologic functions. The metabolic stability of peptides may be critical in the development of pharmaceuticals, affecting parameters such as, but not limited to, clearance, half-life and bioavailability of the drugs.

Maintaining a given level of a therapeutic peptide within the body or the bloodstream may be difficult due to efflux. The rate of efflux of a peptide from the body may vary and should be monitored when considering the administration of therapeutic peptides.

In general, the properties of natural peptides are generally not well suited for use as human therapeutics. Inhibitors of Ras-mediated or Ras-related disorders comprised exclusively of natural amino acids are unlikely to display the proteolytic and metabolic stability needed for use as human therapeutics. There remains a significant medical need for inhibitors of Ras activity and inhibitor formulations that are highly potent and highly specific.

Ras Modulators

In one embodiment, it is a goal of the present invention to provide Ras modulators (including, but not limited to cyclic peptide mimetics). In some cases, these may be designed to be metabolically stable, cell permeable, and/or orally available.

According to the present invention, once a single peptide or a pool of candidate peptide molecules is identified, they may undergo one or more rounds of structure-activity relationship (SAR) optimization using standard chemical and peptide synthesis techniques. Such optimization may include considerations such as avoiding charged polar side chains (Asp, Glu, Arg, Lys) that may inhibit cell penetration, avoidance of side chains that pose metabolic liabilities (Tyr, Met, Trp, Cys), improving solubility, avoidance of unnecessary molecular weight, avoidance of rotatable bonds, and altering lipophilicity.

Ras constructs utilized in identifying Ras modulators may include any of the amino acid sequences listed in Table 1. These constructs may be used to identify polypeptides that bind to such constructs. Ras binding polypeptides (also referred to herein as "Ras binders") may be used to modulate Ras activity, dimerization, nanoclustering, localization, and/ or degradation (e.g., used as Ras modulators).

TABLE 1

Ras constructs

| Construct | Sequence | SEQ ID NO. |
|---|---|---|
| H-Ras (gi: AAA72806.1) | MTEYKLVVVGAVGVGKSALTIQLIQNHFVDEYDP TIEDSYRKQVVIDGETCLLDILDTAGQEEYSAMR DQYMRTGEGFLCVFAINNTKSFEDIHQYREQIKR VKDSDDVPMVLVGNKCDLAARTVESRQAQDLARS YGIPYIETSAKTRQGVEDAFYTLVREIRQHKLRK LNPPDESGPGCMSCKCVLS | 1 |
| Amino acids 2-166 of SEQ ID NO: 1 | TEYKLVVVGAVGVGKSALTIQLIQNHFVDEYDPT IEDSYRKQVVIDGETCLLDILDTAGQEEYSAMRD QYMRTGEGFLCVFAINNTKSFEDIHQYREQIKRV KDSDDVPMVLVGNKCDLAARTVESRQAQDLARSY GIPYIETSAKTRQGVEDAFYTLVREIRQHK | 2 |

TABLE 1-continued

Ras constructs

| Construct | Sequence | SEQ ID NO. |
|---|---|---|
| C-terminal tag | GSGSGSGSGSCGSG | 3 |
| SEQ ID NO: 2 with C-terminal tag | TEYKLVVVGAVGVGKSALTIQLIQNHFVDEYDPT IEDSYRKQVVIDGETCLLDILDTAGQEEYSAMRD QYMRTGEGFLCVFAINNTKSFEDIHQYREQIKRV KDSDDVPMVLVGNKCDLAARTVESRQAQDLARSY GIPYIETSAKTRQGVEDAFYTLVREIRQHKGSGS GSGSGSCGSG | 4 |
| K-Ras4B isoform | MTEYKLVVVGAGGVGKSALTIQLIQNHFVDEYDP TIEDSYRKQVVIDGETCLLDILDTAGQEEYSAMR DQYMRTGEGFLCVFAINNTKSFEDIFIHYREQIK RVKDSEDVPMVLVGNKCDLPSRTVDTKQAQDLAR SYGIPFIETSAKTRQGVDDAFYTLVREIRKHKEK MSKDGKKKKKKSKTKCVIM | 5 |
| K-Ras4B isoform with G12D mutation | MTEYKLVVVGADGVGKSALTIQLIQNHFVDEYDP TIEDSYRKQVVIDGETCLLDILDTAGQEEYSAMR DQYMRTGEGFLCVFAINNTKSFEDIFIHYREQIK RVKDSEDVPMVLVGNKCDLPSRTVDTKQAQDLAR SYGIPFIETSAKTRQGVDDAFYTLVREIRKHKEK MSKDGKKKKKKSKTKCVIM | 6 |

Ras binders and/or modulators of the present disclosure may include, but are not limited to the compounds presented in Table 2 or variants thereof. Variants of the Ras modulators listed may include fragments of such Ras modulators. Some variants include one or more additional residues when compared to those listed (e.g., 1, 2, 3, 4, 5, 6, 7, 8, 9, 10, or more additional residues. Variants may include one or more natural and/or non-natural amino acid substitutions and/or deletions in comparison to the Ras modulators listed. Variants of the Ras modulators listed may have a sequence with from about 50% to 100% sequence identity to the Ras modulators listed (e.g., about 50%, about 55%, about 60%, about 65%, about 70%, about 75%, about 80%, about 85%, about 90%, or about 95% sequence identity). Some variants may include one or more cyclic bonds. Some variants may be linear. Some variants may include a cyclic bond formed with an alternative bridging moiety.

TABLE 2

Ras Binders/Modulators

| Compound Number | Sequence | SEQ ID NO. |
|---|---|---|
| R4000 | ACE-NVA-CYS*-TYR-TBG-LYS-HIS-NMA-PHG-7AW-TYR-MFF-SAR-CYS*-NH2 | 7 |
| R4001 | ACE-NVA-CYS*-TYR-TBG-LYS-HIS-NMA-PHG-7AW-TYR-MFF-SAR-CYS*-PRG | 8 |
| R4002 | NVA-CYS*-TYR-TBG-LYS-HIS-NMA-PHG-7AW-TYR-MFF-SAR-CYS*-NH2 | 9 |
| R4005 | ACE-NVA-SER-TYR-TBG-ALA-DAPTZAC1-NMA-RPHG-7AW-TYR-MFF-SAR-SER-NH2 | 10 |
| R4100 | ACE-NVA-CYS*-TBG-TYR-HIS-THR-7AW-7AW-GLU-7AW-NVA-HIS-CYS*-NH2 | 11 |
| R4101 | ACE-NVA-CYS*-TYR-TBG-LYS-HIS-NMA-PHG-7AW-TYR-MFF-NMA-CYS*-NH2 | 12 |
| R4102 | ACE-NVA-CYS*-TYR-TBG-LYS-HIS-NMA-PHG-7AW-TYR-MFF-SAR-CYS*-DSER-DALA-GLY-CYS-VAL-ILE-MET | 13 |
| R4103 | GLA-NVA-CYS*-TYR-TBG-LYS-HIS-NMA-PHG-7AW-TYR-MFF-SAR-CYS*-NH2 | 14 |
| R4104 | ACE-SER-CYS*-TYR-TBG-LYS-HIS-NMA-PHG-7AW-TYR-MFF-SAR-CYS*-NH2 | 15 |
| R4105 | ACE-NVA-CYS*-TYR-TBG-LYS-HIS-NMA-PHG-7AW-TYR-MFF-SAR-CYS*-DSER-LYS-GLY-CYS-VAL-ILE-MET | 16 |
| R4106 | UBX-AHPA-NVA-CYS*-TYR-TBG-LYS-HIS-NMA-PHG-7AW-TYR-MFF-SAR-CYS*-NH2 | 17 |
| R4107 | ACE-NVA-CYS*-TYR-TBG-LYS-HIS-NMA-PHG-7AW-TYR-MFF-SAR-CYS*-PEG4PA-PRG-NH2 | 18 |
| R4108 | ACE-NVA-CYS*-TYR-TBG-LYS-HIS-NMA-PHG-7AW-TYR-MFF-SAR-CYS* | 19 |
| R4109 | ACE-NVA-CYS*-TYR-TBG-LYS-HIS-NMA-PHG-7AW-TYR-MFF-SAR-CYS*-DSER-LYS-GLY-TDSPA-VAL-ILE-MET | 20 |
| R4110 | ACE-NVA-CYS*-TYR-TBG-LYS-HIS-NMA-PHG-7AW-TYR-MFF-SAR-CYS*-DSER-LYS-GLY-TDSPA-VAL-VAL-LEU | 21 |
| R4111 | ACE-NVA-CYS*-TYR-TBG-LYS-HIS-NMA-PHG-7AW-TYR-MFF-SAR-CYS*-DSER-DALA-LYS-TDSPA-VAL-ILE-MET | 22 |
| R4112 | ACE-CYS*-TYR-TBG-LYS-HIS-NMA-PHG-7AW-TYR-MFF-SAR-CYS*-NH2 | 23 |
| R4113 | NVA-CYS*-TYR-TBG-LYS-HIS-NMA-PHG-7AW-TYR-MFF-SAR-CYS*-DSER-LYS-GLY-TDSPA-VAL-ILE-MET | 24 |
| R4114 | NVA-CYS*-TYR-TBG-LYS-HIS-NMA-PHG-7AW-TYR-MFF-SAR-CYS*-DSER-LYS-GLY-CYS-VAL-ILE-MET | 25 |
| R4115 | ACE-NVA-CYS*-TYR-TBG-LYS-HIS-NMA-PHG-TRP-TYR-MFF-SAR-CYS*-NH2 | 26 |
| R4116 | ACE-NVA-CYS*-TYR-TBG-LYS-HIS-NMA-PHG-7AW-TYR-MFF-SAR-CYS*-GLY-CYS-MET-SER-CYS-LYS-CYS-VAL-LEU-SER-NH2 | 27 |
| R4117 | ACE-NVA-CYS*-NMY-TBG-LYS-HIS-NMA-PHG-7AW-TYR-MFF-SAR-CYS*-NH2 | 28 |
| R4118 | ACE-NVA-CYS*-TYR-TBG-LYS-HIS-NMA-PHG-7AW-TYR-MFF-NMS-CYS*-NH2 | 29 |
| R4119 | ACE-NVA-CYS*-TYR-TBG-LYS-HIS-NMA-PHG-7AW-TYR-MFF-SAR-CYS*-GLY-CYS-GLY-VAL-GLY-ILE-MET | 30 |
| R4120 | ACE-NVA-CYS*-TYR-TBG-LYS-HIS-NMA-PHG-S7AW-TYR-MFF-AR-CYS*-GLY-GLY-GLY-CYS-ALA-ILE-LEU-NH2 | 31 |
| R4121 | ACE-NVA-CYS*-TYR-TBG-LYS-HIS-NMA-DPHG-7AW-TYR-MFF-NMA-CYS*-NH2 | 32 |
| R4122 | ACE-NVA-CYS*-TYR-TBG-ALA-ORAC-NMA-PHG-7AW-TYR-MFF-SAR-CYS*-NH2 | 33 |

TABLE 2-continued

Ras Binders/Modulators

| Compound Number | Sequence | SEQ ID NO. |
|---|---|---|
| R4123 | ACE-NVA-CYS*-TYR-TBG-ALA-KAC-NMA-PHG-7AW-TYR-MFF-SAR-CYS*-NH2 | 34 |
| R4124 | PEG2PA*-TYR-TBG-LYS-HIS-NMA-PHG-7AW-TYR-MFF-SAR* | 35 |
| R4125 | ACE-NVA-CYS*-TYR-TBG-ALA-HIS-NMK-PHG-7AW-TYR-MFF-SAR-CYS*-NH2 | 36 |
| R4126 | ACE-NVA-CYS*-TYR-TBG-LYS-ALA-NMA-PHG-7AW-TYR-MFF-SAR-CYS*-NH2 | 37 |
| R4127 | ACE-NVA-CYS*-TYR-TBG-LYS-HIS-NMA-PHG-7AW-TYR-MFF-SAR-CYS*-GLY-GLY-GLY-CYS-VAL-ILE-MET-NH2 | 38 |
| R4128 | APA*-TYR-TBG-LYS-HIS-NMA-PHG-7AW-TYR-MFF-SAR-PRG* | 39 |
| R4129 | ACE-NVA-CYS*-NMY-TBG-LYS-HIS-NMA-PHG-7AW-TYR-MFF-SAR-CYS*-DSER-DALA-LYS-TDSPA-VAL-ILE-MET | 40 |
| R4130 | PEG1*-TYR-TBG-LYS-HIS-NMA-PHG-7AW-TYR-MFF-SAR-PRG* | 41 |
| R4131 | ACE-NVA-CYS*-TYR-TBG-LYS-HIS-NMA-PHG-7AW-TYR-MFF-SAR-CYS*-GLY-GLY-GLY-CYS-VAL-ILE-MET | 42 |
| R4132 | ACE-NVA-CYS*-TYR-TBG-LYS-HIS-NMS-PHG-SA7AW-TYR-MFF-R-CYS*-NH2 | 43 |
| R4133 | ACE-NVA-CYS*-TYR-TBG-ALA-HIS-MKAC-PHG-7AW-TYR-MFF-SAR-CYS*-NH2 | 44 |
| R4134 | ACE-NVA-CYS*-TYR-TBG-DMABZK1-HIS-NMA-PHG-7AW-TYR-MFF-SAR-CYS*-NH2 | 45 |
| R4135 | ACE-NVA-CYS*-TYR-TBG-LYS-(DDE)-HIS-NMA-PHG-7AW-TYR-MFF-SAR-CYS* | 46 |
| R4136 | ACE-NVA-CYS*-TYR-TBG-ALA-DABAC2-NMA-PHG-7AW-TYR-MFF-SAR-CYS*-NH2 | 47 |
| R4137 | AHX*-TYR-TBG-LYS-HIS-NMA-PHG-7AW-TYR-MFF-SAR-PRG* | 48 |
| R4138 | GLA-NVA-CYS*-TYR-TBG-LYS-(DDE)-HIS-NMA-PHG-7AW-TYR-MFF-SAR-CYS*-NH2 | 49 |
| R4139 | AEP*-TYR-TBG-LYS-HIS-NMA-PHG-7AW-TYR-MFF-SAR-PRG* | 50 |
| R4140 | ACE-NVA-CYS*-TYR-TBG-ALA-DBA-NMA-PHG-7AW-TYR-MFF-SAR-CYS*-NH2 | 51 |
| R4141 | ACE-NVA-CYS*-TYR-TBG-ALA-DAP-NMA-PHG-7AW-TYR-MFF-SAR-CYS*-NH2 | 52 |
| R4142 | ACE-NVA-CYS*-TYR-TBG-ALA-HIS-MORAC-PHG-7AW-TYR-MFF-SAR-CYS*-NH2 | 53 |
| R4143 | ACE-NVA-CYS*-TYR-TBG-LYS-HIS-NMA-ALA-7AW-TYR-NMA-SAR-CYS*-GLY-GLY-GLY-CYS-VAL-ILE-MET | 54 |
| R4144 | ACE-NVA-CYS*-TYR-TBG-LYS-DPRO-NMA-PHG-7AW-TYR-MFF-SAR-CYS*-NH2 | 55 |
| R4145 | TYR*-TBG-LYS-HIS-NMA-PHG-7AW-TYR-MFF-SAR-PRG* | 56 |
| R4146 | ACE-NVA-CYS*-TYR-TBG-ALA-DABAC1-NMA-PHG-7AW-TYR-MFF-SAR-CYS*-NH2 | 57 |
| R4147 | ACE-NVA-CYS*-TYR-TBG-LYS-HIS-NMA-PHG-7AW-TYR-MFF-SAR-CYS*-PEG4PA-ADTZPA-NH2 | 58 |
| R4148 | ACE-NVA-SER-TYR-TBG-ALA-DAPTZAC3-NMA-RPHG-7AW-TYR-MFF-SAR-SER-NH2 | 59 |
| R4149 | ACE-NVA-CYS*-TYR-TBG-LYS-HIS-NMA-CHG-7AW-TYR-MFF-SAR-CYS*-NH2 | 60 |
| R4150 | ACE-NVA-CYS*-TYR-TBG-DMABZK2-HIS-NMA-PHG-7AW-TYR-MFF-SAR-CYS*-NH2 | 61 |
| R4151 | ACE-NVA-SER-TYR-TBG-ALA-DAPTZAC2-NMA-RPHG-7AW-TYR-MFF-SAR-SER-NH2 | 62 |
| R4152 | ACE-NVA-CYS*-ALA-TBG-LYS-HIS-NMA-PHG-7AW-TYR-MFF-SAR-CYS*-NH2 | 63 |
| R4153 | ACE-NVA-CYS*-TYR-TBG-LYS-ALA-NMA-DPHG-7AW-TYR-MFF-SAR-CYS*-NH2 | 64 |
| R4154 | ALF-NVA-CYS*-TYR-NVA-PHG-MFF-THR-PRO-7AW-CYS*-7AW-GLU-GLU-NH2 | 65 |

"*" indicate residues involved in cyclic bond formation. Compounds R4124, R4128, R4130, R4137, R4139, and R4145 are cyclized by lactam bridge formation. R4005, R4148, and R4151 are linear. The remaining compounds listed are cyclized by a m-xylylene thioether bridge.

In some embodiments, polypeptides presented herein may be characterized by their ability to displace one or more polypeptides that bind to Ras. Displacement indicates binding of the polypeptides being characterized to Ras at a site at or near that of the polypeptide being displaced. Polypeptides capable of displacing one or more other polypeptides that bind to Ras may thus be characterized by assigning a half-maximal inhibitory concentration ($IC_{50}$) representing the concentration necessary to displace half of the one or more other polypeptides that bind to Ras. In some embodiments, Ras binding polypeptides may be characterized by the $IC_{50}$ for displacement of R4000. Ras binding polypeptides of the present disclosure may have an $IC_{50}$ for displacement of R4000 of from about 0.01 nM to about 10 nM, from about 0.1 nM to about 20 nM, from about 1 nM to about 100 nM, from about 0.05 μM to about 5 μM, from about 0.1 μM to about 10 μM, from about 1 μM to about 50 μM, from about 20 μM to about 100 μM, from about 40 μM to about 200 μM, or from about 150 μM to about 500 μM.

Post-Translational Modification

Ras modulators may be modified with additional polypeptide sequences from proteins, or their synthetic mimetics, which constitute substrates or sites for different cellular post-translational modifying enzymes. These sites can be sequences of additional amino acids extended from the N or C-termini of the peptide. Alternatively, these sites can be linked through various non-peptidic linkers to the N or C termini, side-chains, or to groups used to cyclize the peptide. Examples of post-translational modification sites include but are not limited to prenylation (i.e., farnesyl, gerenyl-gerenyl, palmitoyl) sequences, which could co-localize the peptide in various membranes with Ras, altering the effect of the peptide on Ras function and signaling. Tanaka and Rabbitts (2007, The EMBO Journal, 26, 3250-3259) illustrated this principle with an anti-Ras intrabody that could only effect Ras signaling when it was extended with the C-terminal prenylation sequence from Ras.

This sequence in Ras and other prenylated proteins typically has a "CAAX" box or motif where "C" is Cysteine, "A" is an aliphatic residue such as Leucine or Methionine, and "X" is Methionine, Serine, Glutamine, Alanine, or Cysteine for farnesylation and Leucine or Glutamic acid for gerenyl-gerenylation. In either case the Cysteine residue is the site of attachment for the prenyl group. There can also be additional modifications to the CAAX motif in addition to prenylation and these may also effect the interaction of a Ras-binding peptide carrying this motif with Ras. In Ras the "CA" peptide bond is cleaved and the C-terminal carboxy group is methylated.

Amino Acid Variants

As used herein, the term "amino acid" includes the residues of the natural amino acids as well as unnatural and non-natural amino acids. The term also includes amino acids bearing a conventional amino protecting group (e.g. acetyl or benzyloxycarbonyl), as well as natural, non-natural, and unnatural amino acids protected at the carboxy terminus (e.g., as a (C1-C6) alkyl, phenyl or benzyl ester or amide; or as an alpha-methylbenzyl amide). Other suitable amino and carboxy protecting groups are known to those skilled in the art (See for example, Greene, T. W.; Wutz, P. G. M., Protecting Groups In Organic Synthesis; second edition, 1991, New York, John Wiley & sons, Inc., and documents cited therein). Polypeptides and/or polypeptide compositions of the present invention may also include modified amino acids.

Unnatural amino acids useful for the optimization of polypeptides and/or polypeptide compositions of the present invention include, but are not limited to 1,2,3,4-tetrahydroisoquinoline-1-carboxylic acid, 1-amino-2,3-hydro-1H-indene-1-carboxylic acid, homolysine, homoarginine, homoserine, 2-aminoadipic acid, 3-aminoadipic acid, beta-alanine, aminopropionic acid, 2-aminobutyric acid, 4-aminobutyric acid, 6-aminocaproic acid, 2-aminoheptanoic acid, 2-aminoisobutyric acid, 3-aminoisbutyric acid, 2-aminopimelic acid, desmosine, 2,3-diaminopropionic acid, N-ethylglycine, N-ethylasparagine, homoproline, hydroxylysine, allo-hydroxylysine, 3-hydroxyproline, 4-hydroxyproline, isodesmosine, allo-isoleucine, N-methylpentylglycine, naphthylalanine, ornithine, pentylglycine, thioproline, norvaline, tert-butylglycine, phenylglycine, azatryptophan, 5-azatryptophan, 7-azatryptophan, 4-fluorophenylalanine, penicillamine, sarcosine, homocysteine, 1-aminocyclopropanecarboxylic acid, 1-aminocyclobutanecarboxylic acid, 1-aminocyclopentanecarboxylic acid, 1-aminocyclohexanecarboxylic acid, 4-aminotetrahydro-2H-pyran-4-carboxylic acid, (S)-2-amino-3-(1H-tetrazol-5-yl)propanoic acid, cyclopentylglycine, cyclohexylglycine, cyclopropylglycine, η-ω-methyl-arginine, 4-chlorophenylalanine, 3-chlorotyrosine, 3-fluorotyrosine, 5-fluorotryptophan, 5-chlorotryptophan, citrulline, 4-chloro-homophenylalanine, homophenylalanine, 4-aminomethyl-phenylalanine, 3-aminomethyl-phenylalanine, octylglycine, norleucine, tranexamic acid, 2-amino pentanoic acid, 2-amino hexanoic acid, 2-amino heptanoic acid, 2-amino octanoic acid, 2-amino nonanoic acid, 2-amino decanoic acid, 2-amino undecanoic acid, 2-amino dodecanoic acid, aminovaleric acid, and 2-(2-aminoethoxy)acetic acid, pipecolic acid, 2-carboxy azetidine, hexafluoroleucine, 3-Fluorovaline, 2-amino-4,4-difluoro-3-methylbutanoic acid, 3-fluoro-isoleucine, 4-fluoroisoleucine, 5-fluoroisoleucine, 4-methyl-phenylglycine, 4-ethyl-phenylglycine, 4-isopropyl-phenylglycine, (S)-2-amino-5-(3-methylguanidino) pentanoic acid, (S)-2-amino-3-(4-(aminomethyl)phenyl)propanoic acid, (S)-2-amino-3-(3-(aminomethyl)phenyl)propanoic acid, (S)-2-amino-4-(2-aminobenzo[d]oxazol-5-yl)butanoic acid, (S)-leucinol, (S)-valinol, (S)-tert-leucinol, (R)-3-methylbutan-2-amine, (S)-2-methyl-1-phenylpropan-1-amine, and (S)—N,2-dimethyl-1-(pyridin-2-yl)propan-1-amine, (S)-2-amino-3-(oxazol-2-yl)propanoic acid, (S)-2-amino-3-(oxazol-5-yl)propanoic acid, (S)-2-amino-3-(1,3,4-oxadiazol-2-yl)propanoic acid, (S)-2-amino-3-(1,2,4-oxadiazol-3-yl)propanoic acid, (S)-2-amino-3-(5-fluoro-1H-indazol-3-yl)propanoic acid, and (S)-2-amino-3-(1H-indazol-3-yl)propanoic acid, (S)-2-amino-3-(oxazol-2-yl)butanoic acid, (S)-2-amino-3-(oxazol-5-yl) butanoic acid, (S)-2-amino-3-(1,3,4-oxadiazol-2-yl) butanoic acid, (S)-2-amino-3-(1,2,4-oxadiazol-3-yl) butanoic acid, (S)-2-amino-3-(5-fluoro-1H-indazol-3-yl) butanoic acid, and (S)-2-amino-3-(1H-indazol-3-yl) butanoic acid, 2-(2'MeOphenyl)-2-amino acetic acid, tetrahydro 3-isoquinolinecarboxylic acid and stereoisomers thereof (including, but not limited to D and L isomers).

Additional unnatural amino acids that are useful in the optimization of polypeptides or polypeptide compositions of the invention include but are not limited to fluorinated amino acids wherein one or more carbon bound hydrogen atoms are replaced by fluorine. The number of fluorine atoms included can range from 1 up to and including all of the hydrogen atoms. Examples of such amino acids include but are not limited to 3-fluoroproline, 3,3-difluoroproline, 4-fluoroproline, 4,4-difluoroproline, 3,4-difluroproline, 3,3, 4,4-tetrafluoroproline, 4-fluorotryptophan, 5-flurotryptophan, 6-fluorotryptophan, 7-fluorotryptophan, and stereoisomers thereof.

Further amino acids unnatural amino acids that are useful in the optimization of polypeptides or polypeptide compositions of the invention include but are not limited to those that are disubstituted at the α-carbon. These include amino acids in which the two substituents on the α-carbon are the same, for example α-amino isobutyric acid, and 2-amino-2-ethyl butanoic acid, as well as those where the substituents are different, for example α-methylphenylglycine and α-methylproline. Further the substituents on the α-carbon may be taken together to form a ring, for example 1-aminocyclopentanecarboxylic acid, 1-aminocyclobutanecarboxylic acid, 1-aminocyclohexanecarboxylic acid, 3-aminotetrahydrofuran-3-carboxylic acid, 3-aminotetrahydropyran-3-carboxylic acid, 4-aminotetrahydropyran-4-carboxylic acid, 3-aminopyrrolidine-3-carboxylic acid, 3-aminopiperidine-3-carboxylic acid, 4-aminopiperidinnne-4-carboxylix acid, and stereoisomers thereof.

Additional unnatural amino acids that are useful in the optimization of polypeptides or polypeptide compositions of the invention include but are not limited to analogs of tryptophan in which the indole ring system is replaced by another 9 or 10 membered bicyclic ring system comprising 0, 1, 2, 3 or 4 heteroatoms independently selected from N, O, or S. Each ring system may be saturated, partially unsaturated or fully unsaturated. The ring system may be substituted by 0, 1, 2, 3, or 4 substituents at any substitutable atom. Each substituent is independently selected from H, F, Cl, Br, CN, COOR, CONRR', oxo, OR, NRR'. Each R and R' is independently selected from H, C1-C20 alkyl, C1-C20 alkyl-O—C1-20 alkyl.

In some embodiments, analogs of tryptophan (also referred to herein as "tryptophan analogs") that are useful in the optimization of polypeptides or polypeptide compositions of the invention include, but are not limited to 5-fluorotryptophan [(5-F)W], 5-methyl-O-tryptophan [(5-MeO) W], 1-methyltryptophan [(1-Me-W) or (1-Me)W], D-tryptophan (D-Trp), azatryptophan, 7-azatryptophan, 5-azatryptophan, 5-chlorotryptophan, 4-fluorotryptophan, 6-fluorotryptophan, 7-fluorotryptophan, and stereoisomers thereof.

Modified amino acid residues useful for the optimization of polypeptides and/or polypeptide compositions of the present invention include, but are not limited to those which are chemically blocked, reversibly or irreversibly, or chemically modified on their N-terminal amino group or their side chain groups, or chemically modified in the amide backbone, as for example, N-methylated, D (unnatural amino acids) and L (natural amino acids) stereoisomers or residues wherein the side chain functional groups are chemically modified to another functional group. For example, modified amino acids include without limitation, methionine sulfoxide; methionine sulfone; aspartic acid-(beta-methyl ester), a modified amino acid of aspartic acid; N-ethylglycine, a modified amino acid of glycine; or alanine carboxamide, and a modified amino acid of alanine. Unnatural amino acids may be purchased from Sigma-Aldrich (St. Louis, Mo.), Bachem (Torrance, Calif.) or other suppliers. Unnatural amino acids may further include any of those listed in Table 2 of US patent publication US 2011/0172126, the contents of which are incorporated herein by reference in their entirety.

In some embodiments, the amino acid sequences of polypeptides and/or polypeptide compositions of the present invention may comprise only naturally occurring amino acids and as such may be considered to be peptides, polypeptides, and/or fragments thereof. While it is known in the art that these terms imply relative size, these terms as used herein should not be considered limiting with respect to the size of the various polypeptide based molecules referred to herein and which are encompassed within this invention, unless otherwise noted. In some embodiments of the present invention, peptides, polypeptides and/or fragments thereof may comprise both naturally and non-naturally occurring and/or modified amino acids or be exclusively comprised of non-naturally occurring amino acids. Such molecules may be referred to herein as "peptide mimetics" or "peptidomimetics."

Polypeptide Variants

According to the present invention, any amino acid based molecule (natural or unnatural) may be termed a "polypeptide" and this term embraces "peptides", and "proteins", as well as certain "polypeptide mimetics", "peptide mimetics", and "peptidomimetics" that contain at least one amide bond. Peptides are also a category of protein and are traditionally considered to range in size from about 4 to about 50 amino acids. Dipeptides, those having two amino acid residues, are a category of peptide as are tripeptides (peptides comprising 3 amino acids). Polypeptides larger than about 50 amino acids are generally termed "proteins." Peptide, polypeptide and/or protein sequences may be linear or cyclic. For example, a cyclic peptide can be prepared or may result from the formation of disulfide bonds between two cysteine residues in a sequence. A peptide can be cyclized through the carboxy terminus, the amino terminus, or through any other convenient point of attachment, such as, for example, through the sulfur of a cysteine or any side-chain of an amino acid residue or other linkage including, but not limited to, a maleimide linkage, an amide linkage, an ester linkage, an ether linkage, a thiol ether linkage, a hydrazone linkage, or an acetamide linkage. In some embodiments, cyclic peptides are formed when a molecule acts as a bridging moiety to link two regions of the peptide.

The term "amino acid sequence variant" refers to polypeptides with some differences in their amino acid sequences as compared to a native or parent sequence. The amino acid sequence variants may possess substitutions, deletions, and/or insertions at certain positions within the amino acid sequence. Ordinarily, variants will possess at least about 50%, at least about 60%, at least about 70%, at least about 80% or at least about 90% homology to a native or starting sequence.

"Homology" as it applies to amino acid sequences is defined as the percentage of residues in the candidate amino acid sequence that are identical with the residues in the amino acid sequence of a second sequence after aligning the sequences and introducing gaps, if necessary, to achieve the maximum percent homology. Methods and computer programs for the alignment are well known in the art. It is understood that homology depends on a calculation of percent identity but may differ in value due to gaps and penalties introduced in the calculation.

By "homologs" as it applies to amino acid sequences is meant the corresponding sequence of other species having substantial identity to a second sequence of a second species.

"Analogs" is meant to include amino acid sequence variants which differ by one or more amino acid alterations, e.g., substitutions, additions or deletions of amino acid residues that still maintain one or more of the properties of the parent or starting polypeptide.

The present invention contemplates several types of compositions that include polypeptides including variants and derivatives. These include substitutional, insertional, deletion and covalent variants and derivatives. The term "derivative" is used synonymously with the term "variant" and refers to a molecule that has been modified or changed in any way relative to a reference molecule or starting molecule.

As such, included within the scope of this invention are polypeptides containing substitutions, insertions and/or additions, deletions and covalent modifications. For example, sequence tags or amino acids, such as one or more lysines, can be added to the peptide sequences of the invention (e.g., at the N-terminal or C-terminal ends). Sequence tags can be used for peptide purification or localization. Lysines can be used to increase peptide solubility or to allow for site specific modifications, such as, but not limited to, conjugation of a lipid moiety (also referred to herein as "lipidation"), farnesylation, geranylation, isoprenylation, biotinylation or conjugation of a polyethylene glycol (PEG) moiety (also referred to herein as "PEGylation"). Alternatively, amino acid residues located at the carboxy and amino terminal regions of the amino acid sequence of a peptide or protein may optionally be deleted providing for truncated sequences. Certain amino acids (e.g., C-terminal or N-terminal residues) may alternatively be deleted depending on the use of the sequence, as for example, expression of the sequence as part of a larger sequence, which is soluble, or linked to a solid support.

"Substitutional variants" when referring to polypeptides are those that have at least one amino acid residue in a native or starting sequence removed and a different amino acid inserted in its place at the same position. The substitutions may be single, where only one amino acid in the molecule has been substituted, or they may be multiple, where two or more amino acids have been substituted in the same molecule.

As used herein the term "conservative amino acid substitution" refers to the substitution of an amino acid that is normally present in the sequence with a different amino acid of similar size, charge, or polarity. Examples of conservative substitutions include the substitution of a non-polar (hydrophobic) residue such as isoleucine, valine and leucine for another non-polar residue. Likewise, examples of conservative substitutions include the substitution of one polar (hydrophilic) residue for another such as between arginine and lysine, between glutamine and asparagine, and between glycine and serine. Additionally, the substitution of a basic residue such as lysine, arginine or histidine for another, or the substitution of one acidic residue such as aspartic acid or glutamic acid for another acidic residue are additional examples of conservative substitutions. Examples of non-conservative substitutions include the substitution of a non-polar (hydrophobic) amino acid residue such as isoleucine, valine, leucine, alanine, methionine for a polar (hydrophilic) residue such as cysteine, glutamine, glutamic acid or lysine and/or a polar residue for a non-polar residue.

"Isosteres" are one of two or more molecules that exhibit some similarity of biological properties as a result of having the same number of total or valence electrons in the same arrangement and that consist of different atoms, not necessarily the same number of atoms. There are two classes of isosteres, classical and non-classical. Classical isosteres have the same number of atoms and/or the same number of valence electrons whereas non-classical isosteres are molecules that produce a similar biological effect in vivo but do not have the same number of atoms and/or valence electrons.

According to the present invention, "peptide bond isosteres" are defined as isosteres having properties resembling peptide bonds. Peptide bond isosteres may be of a linear type comprising at least one peptide bond replacement or may be cyclic and comprise an amine and a carboxylic acid function. Such replacement may be with any moiety which improves the physicochemical, structural or functional properties of the molecule. Replacement of the peptide bond may increase the metabolic stability of the peptides and reduce or increase the flexibility. Peptide bond isosteres described herein may be mono-, di-, tri-, tetra-, penta-, sexta-, septa-, octa-, nona-, or deca-peptide bond isosteres, meaning that at least 1, 2, 3, 4, 5, 6, 7, 8, 9 or 10 peptidic bonds may be replaced. Non-limiting examples of linear dipeptide bond isosteres for amide (peptidic) bonds include thioamide, sulfonamide, sulfonate, phosphonamide, phosphonate phosphothioate, phosphinate, alkane, 1 or 2 hydroxyethylene, dihydroxyethylene, C—C single bond (alkane), C—C double bond (alkene), C—C triple bond (alkyne), C—O bond (methyleneoxy), O—N or N—O bond, (methylenemino), triazole, hydrazide, urea, ketone, urethane bond, (di)haloalkene, methylenemercapto, methyleneamino, trifluoroethylamino, hydrazide, amideoxy, and others known to those of skill in the art.

Peptide bond isosteres may also be cyclic molecules that are decorated with an amine and a carboxylic acid function. Non-limiting examples of cyclic peptide bond isosteres with varying ring sizes include carbacycles, azacycles and oxacycles. Azacycles may be based on an alkaloid core which forms a bicyclic structure isostere. An example of an aza-cyclic isostere includes an isostere based on a triazole ring formed by a copper catalyzed azide-alkyne cycloaddtion. Cyclic peptide bond isosteres described herein may be bi-, tri-, tetra-, penta- sexta-, septa-, octa- nona- deca-peptide cyclic isosteres "Insertional variants" when referring to polypeptides are those with one or more amino acids inserted immediately adjacent to an amino acid at a particular position in a native or starting sequence. "Immediately adjacent" to an amino acid means connected to either the alpha-carboxy or alpha-amino functional group of the amino acid.

"Deletional variants" when referring to polypeptides are those with one or more amino acids in the native or starting amino acid sequence removed. Ordinarily, deletional variants will have one or more amino acids deleted in a particular region of the molecule.

"Truncated variants" when referring to polypeptides are those with one or more amino acids in the native or starting amino acid sequence removed from either terminus of the peptide.

According to the present invention, polypeptides and/or polypeptide compositions may be modified by the addition of one or more conjugate groups. In some embodiments, peptides may be administered in combination with one or more additional molecules.

As used herein, a "conjugate" refers to any molecule or moiety appended to another molecule. In the present invention, conjugates may be protein (amino acid) based or not. Conjugates may comprise lipid moieties, small molecules, RNA, DNA, proteins, polymers, or combinations thereof. Functionally, conjugates may serve as targeting molecules or may serve as payload to be delivered to a cell, organ or tissue. Conjugates are typically covalent modifications introduced by reacting targeted amino acid residues or the termini of the polypeptide with an organic derivatizing agent that is capable of reacting with selected side-chains or terminal residues. Such modifications are within the ordinary skill in the art and are performed without undue experimentation.

The conjugation process may involve PEGylation, lipidation, albumination, the addition of other protein tails, or grafting onto antibody Fc domains, CDR regions of intact antibodies, or antibody domains produced by any number of means. The conjugate may include anchors including cholesterol oleate moiety, cholesteryl laurate moiety, an α-tocopherol moiety, a phytol moiety, an oleate moiety, or an unsaturated cholesterol-ester moiety or a lipophilic compound selected from acetanilides, anilides, aminoquinolines, benzhydryl compounds, benzodiazepines, benzofurans, cannabinoids, cyclic peptides, dibenzazepines, digitalis gylcosides, ergot alkaloids, flavonoids, imidazoles, quinolines, macrolides, naphthalenes, opiates (such as, but not limited to, morphinans or other psychoactive drugs), oxazines, oxazoles, phenylalkylamines, piperidines, polycyclic aromatic hydrocarbons, pyrrolidines, pyrrolidinones, stilbenes, sulfonylureas, sulfones, triazoles, tropanes, and vinca alkaloids. The conjugate may include an isoprenyl group, such as a farnesyl or geranyl group.

Polypeptides and/or polypeptide compositions of the present invention may be conjugated to a peptide that increases or decreases plasma protein binding including but not limited to those described in Dennis, M. S. et al., Albumin binding as a general strategy for improving the pharmacokinetics of proteins. J Biol Chem. 2002 Sep. 20; 277(38):35035-43; Nguyen, A. et al., The pharmacokinetics of an albumin-binding Fab (AB.Fab) can be modulated as a function of affinity for albumin. Protein Eng Des Sel. 2006 July; 19(7):291-7 and Langerheim, J. F. et al., Improving the pharmacokinetics/pharmacodynamics of prolactin, GH, and their antagonists by fusion to a synthetic albumin-binding peptide. J Endocrinol. 2009 December; 203(3):375-87, the contents of each of which are incorporated herein by reference in their entirety. In some embodiments, such peptides bind serum albumin (referred to herein as "albumin-binding peptides"). In some embodiments, albumin-binding peptides are cyclized by disulfide bond formation between cysteine residues present in their polypeptide sequences. In some embodiments, albumin-binding peptides are conjugated by either their N or C-terminal ends. In some embodiments, conjugation to an albumin-binding peptide modulates the amount of time that a polypeptide of the present invention remains intact in a subject. In a preferred embodiment, conjugation to an albumin-binding peptide increases the amount of time that a polypeptide of the present invention remains in the blood of a subject.

Polypeptides and/or polypeptide compositions of the present invention may be conjugated to peptides that have cell penetrating properties (referred to herein as "cell penetrating peptides") including but not limited those disclosed in Milletti, F., Cell-penetrating peptides: classes, origin, and current landscape. Drug Discov Today. 2012 August; 17(15-16):850-60. Additional cell penetrating peptides are known to those skilled in the art. Polypeptides and/or polypeptide compositions of the present invention may be conjugated to any of the peptide conjugates taught, for example, in US patent publications US20110172126 or US20030040472 the contents of which are incorporated herein by reference in their entirety.

As used herein, the term "covalent derivative" when referring to a polypeptide includes modification of a native or starting protein with an organic proteinaceous or non-proteinaceous derivatizing agent, and/or post-translational modification. Covalent modifications are traditionally introduced by reacting targeted amino acid residues of the protein with an organic derivatizing agent that is capable of reacting with selected side-chains or terminal residues, or by harnessing mechanisms of post-translational modifications that function in selected recombinant host cells. The resultant covalent derivatives are useful in programs directed at identifying residues important for biological activity, for immunoassays, or for the preparation of anti-protein antibodies for immunoaffinity purification of the recombinant protein. Such modifications are within the ordinary skill in the art and are performed without undue experimentation.

Certain post-translational modifications are the result of the action of recombinant host cells on an expressed polypeptide. Glutaminyl and asparaginyl residues are frequently post-translationally deamidated to the corresponding glutamyl and aspartyl residues. Alternatively, these residues are deamidated under mildly acidic conditions. Either form of these residues may be present in the polypeptides produced in accordance with the present invention.

Other post-translational modifications include hydroxylation of proline and lysine, phosphorylation of hydroxyl groups of tyrosinyl, seryl or threonyl residues, methylation of the alpha-amino groups of lysine, arginine, and histidine side chains (Creighton, T. E., Proteins: Structure and Molecular Properties, W. H. Freeman & Co., San Francisco, 1983, pp. 79-86).

Covalent modifications specifically include the bonding of non-proteinaceous polymers to proteins, peptides or polypeptides of the invention. Non-proteinaceous polymers may include a hydrophilic synthetic polymer, i.e. a polymer not otherwise found in nature. However, polymers that exist in nature and are produced by recombinant or in vitro methods are useful, as are polymers which are isolated from nature. Hydrophilic polyvinyl polymers fall within the scope of this invention, e.g. polyvinylalcohol and polyvinylpyrrolidone. The proteins, peptides or polypeptides may be linked to various non-proteinaceous polymers, such as polyethylene glycol, polypropylene glycol or polyoxyalkylenes, in the manner set forth in U.S. Pat. Nos. 4,640,835; 4,496,689; 4,301,144; 4,670,417; 4,791,192 or 4,179,337, the contents of which are incorporated herein by reference in their entirety.

"Features" when referring to polypeptides are defined as distinct amino acid sequence-based components of a molecule. Features of the polypeptide of the present invention include surface manifestations, local conformational shape, folds, loops, half-loops, domains, half-domains, sites, termini or any combination thereof.

As used herein when referring to polypeptides the term "fold" refers to the resultant conformation of an amino acid sequence upon energy minimization. A fold may occur at the secondary or tertiary level of the folding process. Examples of secondary level folds include beta sheets and alpha helices. Examples of tertiary folds include domains and regions formed due to aggregation or separation of physicochemicaly distinct regions. Regions formed in this way include hydrophobic and hydrophilic pockets, and the like.

As used herein the term "turn" as it relates to protein conformation means a bend which alters the direction of the backbone of a peptide or polypeptide and may involve one, two, three or more amino acid residues.

As used herein when referring to polypeptides the term "loop" refers to a structural feature of a polypeptide which may serve to reverse the direction of the backbone of a peptide or polypeptide. Where the loop is found in a polypeptide and only alters the direction of the backbone, it may comprise four or more amino acid residues. Oliva et al. have identified at least 5 classes of protein loops (Oliva, B. et al., An automated classification of the structure of protein loops. J Mol Biol. 1997 Mar 7; 266(4):814-30). Loops may be open or closed. Closed loops or "cyclic" loops may be formed when two amino acids are connected by a bridging moiety. The cyclic loop comprises the amino acids along the polypeptide present between the bridged amino acids. Cyclic loops may comprise 2, 3, 4, 5, 6, 7, 8, 9, 10 or more amino acids.

As used herein when referring to polypeptides the term "half-loop" refers to a portion of an identified loop having at least half the number of amino acid resides as the loop from which it is derived. It is understood that loops may not always contain an even number of amino acid residues. Therefore, in those cases where a loop contains or is identified to comprise an odd number of amino acids, a half-loop of the odd-numbered loop will comprise the whole number portion or next whole number portion of the loop (number of amino acids of the loop/2+/−0.5 amino acids). For example, a loop identified as a 7 amino acid loop could produce half-loops of 3 amino acids or 4 amino acids (7/2=3.5+/−0.5 being 3 or 4).

As used herein when referring to proteins, the term "region" refers to a zone or general area. In some embodiments, when referring to a protein, a region may comprise a linear sequence of amino acids along the protein or may comprise a specific secondary or tertiary structure and/or one or more features or protein domains.

As used herein, the term "domain," when referring to proteins, refers to a motif of a polypeptide having one or more identifiable structural (such as secondary or tertiary structures) or functional characteristics or properties (e.g., binding capacity, serving as a site for protein-protein interactions).

As used herein, the term "half-domain," when referring to proteins, refers to a portion of an identified domain having at least half the number of amino acid resides as the domain from which it is derived. It is understood that domains may not always contain an even number of amino acid residues.

Therefore, in those cases where a domain contains or is identified to comprise an odd number of amino acids, a half-domain of the odd-numbered domain will comprise the whole number portion or next whole number portion of the domain (number of amino acids of the domain/2+/−0.5 amino acids). For example, a domain identified as a 7 amino acid domain could produce half-domains of 3 amino acids or 4 amino acids (7/2=3.5+/−0.5 being 3 or 4). It is also understood that sub-domains may be identified within domains or half-domains, these subdomains possessing less than all of the structural or functional properties identified in the domains or half domains from which they were derived. It is also understood that the amino acids that comprise any of the domain types herein need not be contiguous along the backbone of the polypeptide (i.e., nonadjacent amino acids may fold structurally to produce a domain, half-domain or subdomain).

As used herein when referring to polypeptides the term "site" as it pertains to amino acid based embodiments is used synonymously with "amino acid residue" and "amino acid side chain." A site represents a position within a peptide or polypeptide that may be modified, manipulated, altered, derivatized or varied within the polypeptide based molecules of the present invention.

As used herein the terms "termini or terminus" when referring to polypeptides refers to an extremity of a peptide or polypeptide. Such extremity is not limited only to the first or final site of the peptide or polypeptide but may include additional amino acids in the terminal regions. The polypeptide based molecules of the present invention may be characterized as having both an N-terminus and a C-terminus. Peptides and/or peptide compositions of the present invention are in some cases made up of multiple polypeptide chains brought together by disulfide bonds or by non-covalent forces (multimers, oligomers). These sorts of proteins will have multiple N- and C-termini. Alternatively, the termini of the polypeptides may be modified such that they begin or end, as the case may be, with a non-polypeptide based moiety such as an organic conjugate.

In one embodiment, peptides of the present invention may include a terminal region. As used herein, "terminal region" is a terminal region of amino acids that may include a cysteine. The terminal region may be an N- and/or a C-terminal region. In some embodiments, terminal regions may be connected to the parent polypeptides using a bridging moiety. As used herein, "parent polypeptide" refers to the part of the polypeptide that does not include the terminal region. The terminal region may be separated from the parent polypeptide by 1, 2, 3, 4, 5, 6, 7, 8, 9, 10 or more residues. The residues added may be selected from, but are not limited to, any natural or unnatural amino acid, the N-methylated form of any natural or unnatural amino acid, the D-steroisomer of any natural or unnatural amino acid, norvaline, tert-butylglycine, phenylglycine, azatryptophan, 7-azatryptophan, 4-fluorophenylalanine, penicillamine, sarcosine, homocysteine, 1-aminocyclopropanecarboxylic acid, 1-aminocyclobutanecarboxylic acid, 1-aminocyclopentanecarboxylic acid, 1-aminocyclohexanecarboxylic acid, 4-aminotetrahydro-2H-pyran-4-carboxylic acid, aminoisobutyric acid, (S)-2-amino-3-(1H-tetrazol-5-yl)propanoic acid, cyclopentylglycine, cyclohexylglycine, cyclopropylglycine, η-ω-methyl-arginine, 4-chlorophenylalanine, 3-chlorotyrosine, 3-fluorotyrosine, 5-fluorotryptophan, 5-chlorotryptophan, citrulline, 4-chloro-homophenylalanine, homophenylalanine, 4-aminomethyl-phenylalanine, 3-aminomethyl-phenylalanine, octylglycine, norleucine, tranexamic acid, 2-amino pentanoic acid, 2-amino hexanoic acid, 2-amino heptanoic acid, 2-amino octanoic acid, 2-amino nonanoic acid, 2-amino decanoic acid, 2-amino undecanoic acid, 2-amino dodecanoic acid, aminovaleric acid, and 2-(2-aminoethoxy)acetic acid, pipecolic acid, 2-carboxy azetidine, hexafluoroleucine, 3-Fluorovaline, 2-amino-4,4-difluoro-3-methylbutanoic acid, 3-fluoro-isoleucine, 4-fluoroisoleucine, 5-fluoroisoleucine, 4-methyl-phenylglycine, 4-ethyl-phenylglycine, 4-isopropyl-phenylglycine, (S)-2-amino-5-(3-methylguanidino) pentanoic acid, (S)-2-amino-3-(4-(aminomethyl)phenyl) propanoic acid, (S)-2-amino-3-(3-(aminomethyl)phenyl) propanoic acid, (S)-2-amino-4-(2-aminobenzo[d]oxazol-5-yl)butanoic acid, (S)-leucinol, (S)-valinol, (S)-tert-leucinol, (R)-3-methylbutan-2-amine, (S)-2-methyl-1-phenylpropan-1-amine, and (S)—N,2-dimethyl-1-(pyridin-2-yl)propan-1-amine, (S)-2-amino-3-(oxazol-2-yl)propanoic acid, (S)-2-amino-3-(oxazol-5-yl)propanoic acid, (S)-2-amino-3-(1,3,4-oxadiazol-2-yl)propanoic acid, (S)-2-amino-3-(1,2,4-oxadiazol-3-yl)propanoic acid, (S)-2-amino-3-(5-fluoro-1H-indazol-3-yl)propanoic acid, and (S)-2-amino-3-(1H-indazol-3-yl)propanoic acid.

Additional unnatural amino acids that are useful in the optimization of polypeptides or polypeptide compositions of the invention include but are not limited to fluorinated aminoacids wherein one or more carbon bound hydrogen atoms are replaced by fluorine. The number of fluorine atoms included can range from 1 up to and including all of the hydrogen atoms. Examples of such amino acids include but are not limited to 3-fluoroproline, 3,3-difluoroproline, 4-fluoroproline, 4,4-difluoroproline, 3,4-difluroproline, 3,3,4,4-tetrafluoroproline, 4-fluorotryptophan, 6-fluorotryptophan, 7-fluorotryptophan, and stereoisomers thereof.

In one embodiment, polypeptides of the present invention may include a terminal modification at the N- or C-termini with the addition of 1, 2, 3, 4, 5, 6, 7, 8, 9, 10 or more residues and/or a cysteine in the terminal region. The residues added may be selected from, but are not limited to, any natural or unnatural amino acid, the N-methylated form of any natural or unnatural amino acid, the D-steroisomer of any amino acid, norvaline, tert-butylglycine, phenylglycine, azatryptophan, 7-azatryptophan, 4-fluorophenylalanine, penicillamine, sarcosine, homocysteine, 1-aminocyclopropanecarboxylic acid, 1-aminocyclobutanecarboxylic acid, 1-aminocyclopentanecarboxylic acid, 1-aminocyclohexanecarboxylic acid, 4-aminotetrahydro-2H-pyran-4-carboxylic acid, aminoisobuteric acid, (S)-2-amino-3-(1H-tetrazol-5-yl)propanoic acid, cyclopentylglycine, cyclohexylglycine, cyclopropylglycine, η-ω-methyl-arginine, 4-chlorophenylalanine, 3-chlorotyrosine, 3-fluorotyrosine, 5-fluorotryptophan, 5-chlorotryptophan, citrulline, 4-chloro-homophenylalanine, homophenylalanine, 4-aminomethyl-phenylalanine, 3-aminomethyl-phenylalanine, octylglycine, norleucine, tranexamic acid, 2-amino pentanoic acid, 2-amino hexanoic acid, 2-amino heptanoic acid, 2-amino octanoic acid, 2-amino nonanoic acid, 2-amino decanoic acid, 2-amino undecanoic acid, 2-amino dodecanoic acid, aminovaleric acid, and 2-(2-aminoethoxy)acetic acid, pipecolic acid, 2-carboxy azetidine, hexafluoroleucine, 3-Fluorovaline, 2-amino-4,4-difluoro-3-methylbutanoic acid, 3-fluoro-isoleucine, 4-fluoroisoleucine, 5-fluoroisoleucine, 4-methyl-phenylglycine, 4-ethyl-phenylglycine, 4-isopropyl-phenylglycine, (S)-2-amino-5-(3-methylguanidino) pentanoic acid, (S)-2-amino-3-(4-(aminomethyl)phenyl)propanoic acid, (S)-2-amino-3-(3-(aminomethyl)phenyl)propanoic acid, (S)-2-amino-4-(2-aminobenzo[d]oxazol-5-yl)butanoic acid, (S)-leucinol, (S)-valinol, (S)-tert-leucinol, (R)-3-methylbutan-2-amine, (S)-2-methyl-1-phenylpropan-1-amine, and (S)—N,2-dimethyl-1-(pyridin-2-yl)propan-1-amine, (S)-2-amino-3-(oxazol-2-yl)propanoic acid, (S)-2-amino-3-(oxazol-5-yl)propanoic acid, (S)-2-amino-3-(1,3,4-oxadiazol-2-yl)propanoic acid, (S)-2-amino-3-(1,2,4-oxadiazol-3-yl)propanoic acid, (S)-2-amino-3-(5-fluoro-1H-indazol-3-yl)propanoic acid, and (S)-2-amino-3-(1H-indazol-3-yl)propanoic acid.

Once any of the features have been identified or defined as a desired component of a polypeptide, any of several manipulations and/or modifications of these features may be performed by moving, swapping, inverting, deleting, randomizing or duplicating. Furthermore, it is understood that manipulation of features may result in the same outcome as a modification to the molecules of the invention. For example, a manipulation which involved deleting a domain would result in the alteration of the length of a molecule just as modification of a nucleic acid to encode less than a full length molecule would.

Modifications and manipulations can be accomplished by methods known in the art such as, but not limited to, site directed mutagenesis. The resulting modified molecules may then be tested for activity using in vitro or in vivo assays such as those described herein or any other suitable screening assay known in the art.

According to the present invention, the polypeptides may comprise a consensus sequence which is discovered through rounds of experimentation. As used herein a "consensus" sequence is a single sequence which represents a collective population of sequences allowing for variability at one or more sites.

The term "identity" as known in the art, refers to a relationship between the sequences of two or more peptides, as determined by comparing the sequences. In the art, identity also means the degree of sequence relatedness between peptides, as determined by the number of matches between strings of two or more amino acid residues. Identity measures the percent of identical matches between the smaller of two or more sequences with gap alignments (if any) addressed by a particular mathematical model or computer program (i.e., "algorithms"). Identity of related peptides can be readily calculated by known methods. Such methods include, but are not limited to, those described previously by others (Lesk, A. M., ed., Computational Molecular Biology, Oxford University Press, New York, 1988; Smith, D. W., ed., Biocomputing: Informatics and Genome Projects, Academic Press, New York, 1993; Griffin, A. M. et al., ed., Computer Analysis of Sequence Data, Part 1, Humana Press, New Jersey, 1994; von Heinje, G., Sequence Analysis in Molecular Biology, Academic Press, 1987; Gribskov, M. et al., ed., Sequence Analysis Primer, M. Stockton Press, New York, 1991; and Carillo et al., Applied Math, SIAM J, 1988, 48, 1073).

In some embodiments, a polypeptide variant may have the same or a similar activity as the reference polypeptide. Alternatively, a variant may have an altered activity (e.g., increased or decreased) relative to a reference polypeptide. Generally, variants of a particular polypeptide of the invention will have at least about 40%, 45%, 50%, 55%, 60%, 65%, 70%, 75%, 80%, 85%, 90%, 91%, 92%, 93%, 94%, 95%, 96%, 97%, 98%, 99% but less than 100% sequence identity to that of a particular reference polypeptide as determined by sequence alignment programs and parameters described herein and known to those skilled in the art. Such tools for alignment include those of the BLAST suite (Altschul, S. F. et al., Gapped BLAST and PSI-BLAST: a new generation of protein database search programs, Nucleic Acids Res. 1997, 25:3389-3402) Other tools are described herein, specifically in the definition of "identity." Some variants may have 100% sequence identity, but include one or more alternative variation (e.g., presence or absence of a cyclic bond, alternative bridging moiety, hydrophobic moiety, hydrophilic moiety, and/or detectable label.

Default parameters in the BLAST algorithm include, for example, an expected threshold of 10, Word size of 28, Match/Mismatch Scores 1, -2, Gap costs Linear. Any filter can be applied as well as a selection for species specific repeats, e.g., Homo sapiens.

Abbreviations Used in Peptides

Peptide-based compounds, presented herein, may be described using the abbreviations listed in Table 3.

TABLE 3

List of abbreviations

| Compound/Feature | Abbreviation |
| --- | --- |
| 7AW | L-7-azatryptophan |
| ACE | acetyl |
| ADTZPA | (S)-2-amino-3-(1-dodecyl-1H-1,2,3-triazol-4-yl)propanoic acid |
| AEP | 3-(2-aminoethoxy)propanoic acid |
| AHPA | 7-aminoheptanoic acid |
| AHX | ε-Aminocaproic acid |
| ALA | L-Alanine |
| ALF | Alexa fluor 594 |
| APA | 5-Aminovaleric acid |
| CHG | Cyclohexyl-L-glycine |
| CYS | L-Cysteine |
| DABAC1 | (S)-4-acrylamido-2-aminobutanoic acid |
| DABAC2 | (S)-3-acrylamido-2-aminopropanoic acid |
| DAP | L-2,3-Diaminopropionic acid or DAP or 3-Amino-L-alanine |
| DAPTZAC1 | (S)-3-(4-(acrylamidomethyl)-1H-1,2,3-triazol-1-yl)-2-aminopropanoic acid |
| DAPTZAC2 | (S)-3-(4-(2-acrylamidoethyl)-1H-1,2,3-triazol-1-yl)-2-aminopropanoic acid |
| DAPTZAC3 | (S)-3-(4-(3-acrylamidopropyl)-1H-1,2,3-triazol-1-yl)-2-aminopropanoic acid |
| DBA | Dab or L-2,4-diaminobutyric acid |
| DMABZK1 | $N^6$-(4-(dimethylamino)benzoyl)-L-lysine |
| DMABZK2 | $N^6$-(4-(dimethylamino)benzoyl-2,3,5,6-$d_4$)-L-lysine |
| DPHG | D-Phenylglycine |
| DPRO | D-Proline |
| DSER | D-Serine |
| GLA | Glutaric acid |
| GLU | L-Glutamic acid |
| GLY | L-Glycine |
| HIS | L-Histidine |
| ILE | L-Isoleucine |
| KAC | w-acrylamido-L-Lysine |
| LEU | L-Leucine |
| LYS | L-Lysine |
| LYS-(DDE) | L-Lysine(ivDde) |
| MET | L-Methionine |
| MFF | N-Methyl-4-fluoro-L-phenylalanine |
| MKAC | w-acrylamido-N-methyl-L-Lysine |
| MORAC | (S)-5-acrylamido-2-(methylamino)pentanoic acid |
| NH2 | C-terminal amide |
| NMA | (S)-2-(methylamino)propanoic acid |
| NMK | N-Methyl Lysine |
| NMS | N-Methyl-L-serine |
| NMY | N-Methyl-L-tyrosine |
| NVA | L-Norvaline |
| ORAC | (S)-5-acrylamido-2-aminopentanoic acid |
| PEG1 | 8-amino-3,6-dioxaoctanoic acid (AEEA) |
| PEG2PA | 3-(2-(2-aminoethoxy)ethoxy)propanoic acid |
| PEG4PA | 1-amino-3,6,9,12-tetraoxapentadecan-15-oic acid |
| PHG | L-Phenylglycine |
| PRG | L-Propargylglycine |
| RPHG | DL-α-Phenylglycine |
| SAR | Sarcosine |

TABLE 3-continued

List of abbreviations

| Compound/Feature | Abbreviation |
|---|---|
| SER | L-Serine |
| TBG | L-α-tert-butyl-glycine |
| TDSPA | (R)-2-amino-3-(tert-butyldisulfanyl)propanoic acid |
| THR | L-Threonine |
| TRP | L-Tryptophan |
| TYR | L-Tyrosine |
| UBX | ((2S,3R)-3-amino-2-hydroxy-4-phenylbutanoyl)-L-leucine |
| VAL | L-Valine |

Antibodies

In some embodiments, compounds and/or compositions of the present invention may comprise antibodies or fragments thereof. As used herein, the term "antibody" is refered to in the broadest sense and specifically covers various embodiments including, but not limited to monoclonal antibodies, polyclonal antibodies, multispecific antibodies (e.g. bispecific antibodies formed from at least two intact antibodies), and antibody fragments such as diabodies so long as they exhibit a desired biological activity. Antibodies of the present invention may also comprise human antibodies or humanized antibodies. Antibodies are primarily amino-acid based molecules but may also comprise one or more modifications (including, but not limited to the addition of sugar moieties, fluorescent moieties, chemical tags, etc.)

As used herein the term, "antibody fragment" refers to any portion of an intact antibody. In some embodiments, antibody fragments comprise antigen binding regions from intact antibodies. Examples of antibody fragments may include, but are not limited to Fab, Fab', F(ab')$_2$, and Fv fragments; diabodies; linear antibodies; single-chain antibody molecules; and multispecific antibodies formed from antibody fragments. Papain digestion of antibodies produces two identical antigen-binding fragments, called "Fab" fragments, each with a single antigen-binding site. Also produced is a residual "Fc" fragment, whose name reflects its ability to crystallize readily. Pepsin treatment yields an F(ab')$_2$ fragment that has two antigen-binding sites and is still capable of cross-linking antigen. Compounds and/or compositions of the present invention may comprise one or more of these fragments. For the purposes herein, an "antibody" may comprise a heavy and light variable domain as well as an Fc region.

As used herein, the term "native antibody" refers to a usually heterotetrameric glycoprotein of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain.

As used herein, the term "variable domain" refers to specific antibody domains that differ extensively in sequence among antibodies and are used in the binding and specificity of each particular antibody for its particular antigen.

As used herein, the term "Fv" refers to antibody fragments comprising complete antigen-recognition and antigen-binding sites. These regions consist of a dimer of one heavy chain and one light chain variable domain in tight, non-covalent association.

As used herein, the term "light chain" refers to a component of an antibody from any vertebrate species assigned to one of two clearly distinct types, called kappa and lambda based on amino acid sequences of constant domains. Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2.

As used herein, the term "Single-chain Fv" or "scFv" refers to a fusion protein of $V_H$ and $V_L$ antibody domains, wherein these domains are linked together into a single polypeptide chain. In some embodiments, the Fv polypeptide linker enables the scFv to form the desired structure for antigen binding.

As used herein, the term "diabody" refers to a small antibody fragment with two antigen-binding sites. Diabodies comprise a heavy chain variable domain $V_H$ connected to a light chain variable domain $V_L$ in the same polypeptide chain. By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al. (Hollinger, P. et al., "Diabodies": Small bivalent and bispecific antibody fragments. PNAS. 1993. 90:6444-8) the contents of each of which are incorporated herein by reference in their entirety.

As used herein, the term "monoclonal antibody" refers to an antibody obtained from a population of substantially homogeneous cells (or clones), i.e., the individual antibodies comprising the population are identical and/or bind the same epitope, except for possible variants that may arise during production of the monoclonal antibodies, such variants generally being present in minor amounts. In contrast to polyclonal antibody preparations that typically include different antibodies directed against different determinants (epitopes), each monoclonal antibody is directed against a single determinant on the antigen The modifier "monoclonal" indicates the character of the antibody as being obtained from a substantially homogeneous population of antibodies, and is not to be construed as requiring production of the antibody by any particular method. The monoclonal antibodies herein include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies.

As used herein, the term "humanized antibody" refers to a chimeric antibody comprising a minimal portion from one or more non-human (e.g., murine) antibody source with the remainder derived from one or more human immunoglobulin sources. For the most part, humanized antibodies are human immunoglobulins (recipient antibody) in which residues from the hypervariable region from an antibody of the recipient are replaced by residues from the hypervariable region from an antibody of a non-human species (donor antibody) such as mouse, rat, rabbit or nonhuman primate having the desired specificity, affinity, and/or capacity.

As used herein, the term "hypervariable region" refers to regions within the antigen binding domain of an antibody comprising amino acid residues responsible for antigen binding. The amino acids present within the hypervariable regions determine the structure of the complementarity determining region (CDR). As used herein, the term "CDR" refers to regions of antibodies comprising a structure that is complimentary to its target antigen or epitope.

In some embodiments, compounds and/or compositions of the present invention may be antibody mimetics. As used herein, the term "antibody mimetic" refers to any molecule which mimics the function or effect of an antibody and which binds specifically and with high affinity to their molecular targets. In some embodiments, antibody mimetics may be monobodies, designed to incorporate the fibronectin type III domain (Fn3) as a protein scaffold (U.S. Pat. Nos. 6,673,901 and 6,348,584, the contents of each of which are herein incorporated by reference in their entirety). In some embodiments, antibody mimetics may include those known in the art including, but not limited to affibody molecules, affilins, affitins, anticalins, avimers, Centyrins, DARPINS™, Fynomers and Kunitz and domain peptides. In other embodiments, antibody mimetics may include one or more non-peptide region.

As used herein, the term "antibody variant" refers to a biomolecule resembling an antibody in structure and/or function comprising some differences in their amino acid sequence, composition or structure as compared to a native antibody.

The preparation of antibodies, whether monoclonal or polyclonal, is known in the art. Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999, the contents of which are incorporated herein by reference in its entirety.

In some embodiments, peptides and/or peptide sequences provided herein may be utilized in the production of one or more antibodies. In some cases, such peptides and/or peptide sequences may be incorporated into antibody variable domains or conjugated to antibodies. Such variable domains may be incorporated into antibodies, antibody mimetics or antibody variants.

In some embodiments, polypeptides of the invention may be delivered as part of an antibody-drug conjugate (ADC). ADCs are antibodies in which one or more cargo (e.g. therapeutic compounds or cytotoxic agents) are attached [directly or with the use of a linker (e.g. a cleavable linker or a non-cleavable linker)]. ADCs are useful for delivery of such cargo to one or more target cells or tissues (Panowski, S. et al., 2014. mAbs 6:1, 34-45). In some cases, ADCs may be designed to bind to a surface antigen on a targeted cell. Upon binding, the entire antibody-antigen complex may be internalized and directed to a cellular lysosome. ADCs may then be degraded, releasing the bound cargo. Bounds polypeptides of the invention delivered in such a manner may then be free to interact with intracellular targets.

Small Molecules

In some embodiments, compounds of the present invention may be small molecules. Such compounds may comprise a size from about 100 to about 2000 Daltons (e.g. from about 100 to about 200, to about 300, to about 400, to about 500, to about 600, to about 700, to about 800, to about 900, to about 1000, to about 1100, to about 1200, to about 1300, to about 1400, to about 1500, to about 1600, to about 1700, to about 1800, to about 1900 or to about 2000 Daltons.)

As described herein, compounds of the invention may optionally be substituted with one or more substituents, such as illustrated generally below, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position. When the term "optionally substituted" precedes a list, said term refers to all of the subsequent substitutable groups in that list. If a substituent radical or structure is not identified or defined as "optionally substituted", the substituent radical or structure is unsubstituted. For example, if X is optionally substituted C1-C6alkyl or phenyl; X may be either optionally substituted C1-C3 alkyl or optionally substituted phenyl. Likewise, if the term "optionally substituted" follows a list, said term also refers to all of the substitutable groups in the prior list unless otherwise indicated. For example: if X is C1-C3alkyl or phenyl wherein X is optionally and independently substituted by Jx, then both C1-C3alkyl and phenyl may be optionally substituted by Jx.

The phrase "up to", as used herein, refers to zero or any integer number that is equal or less than the number following the phrase. For example, "up to 3" means any one of 0, 1, 2, and 3. As described herein, a specified number range of atoms includes any integer therein. For example, a group having from 1-4 atoms could have 1, 2, 3, or 4 atoms.

Selection of substituents and combinations of substituents envisioned by this invention are those that result in the formation of stable or chemically feasible compounds. The term "stable", as used herein, refers to compounds that are not substantially altered when subjected to conditions to allow for their production, detection, and, specifically, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week. Only those choices and combinations of substituents that result in a stable structure are contemplated. Such choices and combinations will be apparent to those of ordinary skill in the art and may be determined without undue experimentation.

The term "aliphatic" or "aliphatic group", as used herein, means a straight chain (i.e., unbranched), or branched, hydrocarbon chain that is completely saturated or that contains one or more units of unsaturation but is non-aromatic. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments, aliphatic groups contain 1-4 aliphatic carbon atoms. Aliphatic groups may be linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl and acetylene.

The term "alkyl" as used herein means a saturated straight or branched chain hydrocarbon. The term "alkenyl" as used herein means a straight or branched chain hydrocarbon comprising one or more double bonds. The term "alkynyl" as used herein means a straight or branched chain hydrocarbon comprising one or more triple bonds. Each of the "alkyl", "alkenyl" or "alkynyl" as used herein can be optionally substituted as set forth below. In some embodiments, the "alkyl" is C1-C6 alkyl or C1-C4 alkyl. In some embodiments, the "alkenyl" is C2-C6 alkenyl or C2-C4 alkenyl. In some embodiments, the "alkynyl" is C2-C6 alkynyl or C2-C4 alkynyl.

The term "cycloaliphatic" (or "carbocycle" or "carbocyclyl" or "carbocyclic") refers to a non-aromatic carbon only containing ring system which can be saturated or contains one or more units of unsaturation, having three to fourteen ring carbon atoms. In some embodiments, the number of carbon atoms is 3 to 10. In other embodiments, the number of carbon atoms is 4 to 7. In yet other embodiments, the number of carbon atoms is 5 or 6. The term includes monocyclic, bicyclic or polycyclic, fused, spiro or bridged carbocyclic ring systems. The term also includes polycyclic ring systems in which the carbocyclic ring can be "fused" to one or more non-aromatic carbocyclic or heterocyclic rings or one or more aromatic rings or combination thereof, wherein the radical or point of attachment is on the carbocyclic ring. "Fused" bicyclic ring systems comprise two rings which share two adjoining ring atoms. Bridged bicyclic group comprise two rings which share three or four adjacent ring atoms. Spiro bicyclic ring systems share one ring atom. Examples of cycloaliphatic groups include, but are not limited to, cycloalkyl and cycloalkenyl groups. Specific examples include, but are not limited to, cyclohexyl, cyclopropenyl, and cyclobutyl.

The term "heterocycle" (or "heterocyclyl", or "heterocyclic" or "non-aromatic heterocycle") as used herein refers to a non-aromatic ring system which can be saturated or contain one or more units of unsaturation, having three to fourteen ring atoms in which one or more ring carbons is replaced by a heteroatom such as, N, S, or O and each ring in the system contains 3 to 7 members. In some embodiments, non-aromatic heterocyclic rings comprise up to three heteroatoms selected from N, S and O within the ring. In other embodiments, non-aromatic heterocyclic rings comprise up to two heteroatoms selected from N, S and O within the ring system. In yet other embodiments, non-aromatic heterocyclic rings comprise up to two heteroatoms selected from N and O within the ring system. The term includes monocyclic, bicyclic or polycyclic fused, spiro or bridged heterocyclic ring systems. The term also includes polycyclic ring systems in which the heterocyclic ring can be fused to one or more non-aromatic carbocyclic or heterocyclic rings or one or more aromatic rings or combination thereof, wherein the radical or point of attachment is on the heterocyclic ring. Examples of heterocycles include, but are not limited to, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydrofuranyl, tetrahydrothiophenyl, tetrahydrothiophenyl, morpholino, including, for example, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolanyl, benzodithianyl, 3-(1-alkyl)-benzimidazol-2-onyl, and 1,3-dihydro-imidazol-2-onyl.

The term "aryl" (or "aryl ring" or "aryl group") used alone or as part of a larger moiety as in "aralkyl", "aralkoxy", or "aryloxyalkyl" refers to carbocyclic aromatic ring systems. The term "aryl" may be used interchangeably with the terms "aryl ring" or "aryl group".

"Carbocyclic aromatic ring" groups have only carbon ring atoms (typically six to fourteen) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring" or "carbocyclic aromatic", as it is used herein, is a group in which an aromatic ring is "fused" to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The terms "heteroaryl", "heteroaromatic", "heteroaryl ring", "heteroaryl group", "aromatic heterocycle" or "heteroaromatic group", used alone or as part of a larger moiety as in "heteroaralkyl" or "heteroarylalkoxy", refer to heteroaromatic ring groups having five to fourteen members, including monocyclic heteroaromatic rings and polycyclic aromatic rings in which a monocyclic aromatic ring is fused to one or more other aromatic ring. Heteroaryl groups have one or more ring heteroatoms. Also included within the scope of the term "heteroaryl", as it is used herein, is a group in which an aromatic ring is "fused" to one or more non-aromatic rings (carbocyclic or heterocyclic), where the radical or point of attachment is on the aromatic ring. Bicyclic 6,5 heteroaromatic ring, as used herein, for example, is a six membered heteroaromatic ring fused to a second five membered ring, wherein the radical or point of attachment is on the six membered ring. Examples of heteroaryl groups include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As used herein, "cyclo", "cyclic", "cyclic group" or "cyclic moiety", include mono-, bi-, polycyclic, fused, spiro, or bridged ring systems including cycloaliphatic, heterocycloaliphatic, carbocyclic aryl, or heteroaryl, each of which has been previously defined.

As used herein, a "bicyclic ring system" includes 8-12 (e.g., 9, 10, or 11) membered structures that form two rings, wherein the two rings have at least one atom in common (e.g., 2 atoms in common). Bicyclic ring systems include bicycloaliphatics (e.g., bicycloalkyl or bicycloalkenyl), bicycloheteroaliphatics, bicyclic carbocyclic aryls, and bicyclic heteroaryls.

As used herein, a "bridged bicyclic ring system" refers to a bicyclic heterocycloalipahtic ring system or bicyclic cycloaliphatic ring system in which the rings are bridged. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxa-tricyclo[3.3.1.03,7]nonyl. A bridged bicyclic ring system can be optionally substituted with one or more substituents such as alkyl (including carboxyalkyl, hydroxyalkyl, and haloalkyl such as trifluoromethyl), alkenyl, alkynyl, cycloalkyl, (cycloalkyl)alkyl, heterocycloalkyl, (heterocycloalkyl)alkyl, carbocyclic aryl, heteroaryl, alkoxy, cycloalkyloxy, heterocycloalkyloxy, (carbocyclic aryl)oxy, heteroaryloxy, aralkyloxy, heteroaralkyloxy, aroyl, heteroaroyl, nitro, carboxy, alkoxycarbonyl, alkylcarbonyloxy, aminocarbonyl, alkylcarbonylamino, cycloalkylcarbonylamino, (cycloalkylalkyl)carbonylamino, (carbocyclic aryl)carbonylamino, aralkylcarbonylamino, (heterocycloalkyl)carbonylamino, (heterocycloalkylalkyl)carbonylamino, heteroarylcarbonylamino, heteroaralkylcarbonylamino, cyano, halo, hydroxy, acyl, mercapto, alkylsulfanyl, sulfoxy, urea, thiourea, sulfamoyl, sulfamide, oxo, or carbamoyl.

As used herein, the term "spiro" refers to ring systems having one atom (usually a quaternary carbon) as the only common atom between two rings.

The term "ring atom" is an atom such as C, N, O or S that is in the ring of an aromatic group, cycloalkyl group or non-aromatic heterocyclic ring.

A "substitutable ring atom" in an aromatic group is a ring carbon or nitrogen atom bonded to a hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to a moiety other than hydrogen.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR+ (as in N-substituted pyrrolidinyl)).

As used herein an optionally substituted aralkyl can be substituted on both the alkyl and the aryl portion. Unless otherwise indicated as used herein optionally substituted aralkyl is optionally substituted on the aryl portion.

In some embodiments, an aliphatic or heteroaliphatic group, or a non-aromatic heterocyclic ring may contain one or more substituents. Suitable substituents on the saturated carbon of an aliphatic or heteroaliphatic group, or of a heterocyclic ring are selected from those listed above. Other suitable substituents include those listed as suitable for the unsaturated carbon atom of a carbocyclic aryl or heteroaryl group and additionally include the following: =O, =S, alkyl), alkyl), or =NR*, wherein each R* is independently selected from hydrogen or an optionally substituted Ci_6 aliphatic. Optional substituents on the aliphatic group of R are selected from $NH_2$, $NH(C1-4$ aliphatic), $N(C1-4$ aliphatic$)_2$, halogen, C1-4 aliphatic, OH, O(C1-4 aliphatic), $O_2$, CN, $CO_2H$, $CO_2$(C1-4 aliphatic), O(halo C1-4 aliphatic), or halo(C1-4 aliphatic), wherein each of the foregoing C1-4 aliphatic groups of R is unsubstituted.

In some embodiments, optional substituents on the nitrogen of a heterocyclic ring include those used above. Other suitable substituents include —$R^+$, —$N(R^+)_2$, —$C(O)R^+$, —$CO_2R^+$, —$C(O)C(O)R^+$, —$C(O)CH_2C(O)R^+$, —$SO_2R^+$, —$SO_2N(R^+)_2$, —$C(=S)N(R^+)_2$, —$C(=NH)$—$N(R^+)_2$, or —$R^+SO_2R^+$; wherein $R^+$ is hydrogen, an optionally substituted C1-6 aliphatic, optionally substituted phenyl, optionally substituted —O(Ph), optionally substituted —$CH_2$(Ph), optionally substituted —$(CH_2)_{1-2}$(Ph); optionally substituted —CH=CH(Ph); or an unsubstituted 5-6 membered heteroaryl or heterocyclic ring having one to four heteroatoms independently selected from oxygen, nitrogen, or sulfur, or, two independent occurrences of $R^+$, on the same substituent or different substituents, taken together with the atom(s) to which each $R^+$ group is bound, form a 5-8-membered heterocyclyl, carbocyclic aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group or the phenyl ring of R+ are selected from —$NH_2$, —NH(C1-4 aliphatic), —N(C1-4 aliphatic$)_2$, halogen, C1-4 aliphatic, —OH, —O(C1-4 aliphatic), —$NO_2$, —CN, —$CO_2H$, —$CO_2$(C1-4 aliphatic), —O(halo C1-4 aliphatic), or halo(C1-4 aliphatic), wherein each of the foregoing C1-4aliphatic groups of $R^+$ is unsubstituted.

In some embodiments, an aryl (including aralkyl, aralkoxy, aryloxyalkyl and the like) or heteroaryl (including heteroaralkyl and heteroarylalkoxy and the like) group may contain one or more substituents. Suitable substituents on the unsaturated carbon atom of a carbocyclic aryl or heteroaryl group are selected from those listed above. Other suitable substituents include: halogen; —$R^°$; —$OR^°$; —$SR^°$; 1,2-methylenedioxy; 1,2-ethylenedioxy; phenyl (Ph) optionally substituted with $R^°$; —O(Ph) optionally substituted with $R^°$; —$(CH_2)$1-2(Ph), optionally substituted with $R^°$; —CH=CH(Ph), optionally substituted with $R^°$; —$NO_2$; —CN; —$N(R^°)_2$; —$NR^°C(O)R^°$; —$NR^°C(S)R^°$; —$NR^°C(O)N(R^°)_2$; —$NR^°C(S)N(R^°)_2$; —$NR^°CO_2R^°$; —$NR^°NR^°C(O)R^°$; —$NR^°NROC(O)N(R^°)_2$; —$NR^°NROCO_2R^°$; —$C(O)C(O)R^°$; —$C(O)CH_2C(O)R^°$; —$CO_2R^°$; —$C(O)R^°$; —$C(S)R^°$; —$C(O)N(R^°)_2$; —$C(S)N(R^°)_2$; —$OC(O)N(R^°)_2$; —$OC(O)R^°$; —$C(O)N(OR^°)R^°$; —$C(NOR^°)$ $R^°$; —$S(O)_2R^°$; —$S(O)_3R^°$; —$SO_2N(R^°)_2$; —$S(O)R^°$; —$NR^°SO_2N(R^°)_2$; —$NR^°SO_2R^°$; —$N(OR^°)$ $R^°$; —$C(=NH)N(R^°)_2$; or —$(CH_2)O_2NHC(O)R^°$; wherein each independent occurrence of $R^°$ is selected from hydrogen, optionally substituted C1-6 aliphatic, an unsubstituted 5-6 membered heteroaryl or heterocyclic ring, phenyl, —O(Ph), or —$CH_2$(Ph), or, two independent occurrences of $R^°$, on the same substituent or different substituents, taken together with the atom(s) to which each $R^°$ group is bound, form a 5-8-membered heterocyclyl, carbocyclic aryl, or heteroaryl ring or a 3-8-membered cycloalkyl ring, wherein said heteroaryl or heterocyclyl ring has 1-3 heteroatoms independently selected from nitrogen, oxygen, or sulfur. Optional substituents on the aliphatic group of $R^°$ are selected from —$NH_2$, —NH(C1-4aliphatic), —N(C1-4 aliphatic)₂, halogen, C1-4aliphatic, —OH, —O(C1-4aliphatic), —NO₂, —CN, —CO₂H, —CO2(C1-4aliphatic), —O(haloC1-4 aliphatic), or haloC1-4aliphatic, —CHO, —N(CO)(C1-4 aliphatic), —C(O)N(C1-4 aliphatic), wherein each of the foregoing C1-4aliphatic groups of R° is unsubstituted.

Non-aromatic nitrogen containing heterocyclic rings that are substituted on a ring nitrogen and attached to the remainder of the molecule at a ring carbon atom are said to be N substituted. For example, an N alkyl piperidinyl group is attached to the remainder of the molecule at the two, three or four position of the piperidinyl ring and substituted at the ring nitrogen with an alkyl group. Non-aromatic nitrogen containing heterocyclic rings such as pyrazinyl that are substituted on a ring nitrogen and attached to the remainder of the molecule at a second ring nitrogen atom are said to be N' substituted-N-heterocycles. For example, an N' acyl N-pyrazinyl group is attached to the remainder of the molecule at one ring nitrogen atom and substituted at the second ring nitrogen atom with an acyl group.

The term "unsaturated", as used herein, means that a moiety has one or more units of unsaturation.

The term "hydroxyl' or "hydroxy" or "alcohol moiety" refers to —OH.

As used herein, an "alkoxycarbonyl," which is encompassed by the term carboxy, used alone or in connection with another group refers to a group such as (alkyl-O)—C(O)—.

As used herein, a "carbonyl" refers to —C(O)—.

As used herein, an "oxo" refers to =O.

As used herein the term "acyl" refers to —C(O)R°.

As used herein the term "carbamate" refers to —OC(O)N(R°)₂ or —NR°CO₂R°.

As used herein the term "urea" refers to —NR°C(O)N(R°)₂.

As used herein the term "heptanoyl" refers to —C(O)C₆R°₁₃.

As used herein the term "amide" refers to —C(O)N(R°)₂ or —NR°C(O)R°.

As used herein, the term "alkoxy", or "alkylthio", as used herein, refers to an alkyl group, as previously defined, attached to the molecule through an oxygen ("alkoxy" e.g., —O—alkyl) or sulfur ("alkylthio" e.g., —S-alkyl) atom.

As used herein, the terms "halogen", "halo", and "hal" mean F, CI, Br, or I.

As used herein, the term "cyano" or "nitrile" refer to —CN or —C≡N.

The terms "alkoxyalkyl", "alkoxyalkenyl", "alkoxyaliphatic", and "alkoxyalkoxy" mean alkyl, alkenyl, aliphatic or alkoxy, as the case may be, substituted with one or more alkoxy groups.

The terms "haloalkyl", "haloalkenyl", "haloaliphatic", and "haloalkoxy" mean alkyl, alkenyl, aliphatic or alkoxy, as the case may be, substituted with one or more halogen atoms. This term includes perfluorinated alkyl groups, such as —CF3 and —CF2CF3.

The terms "cyanoalkyl", "cyanoalkenyl", "cyanoaliphatic", and "cyanoalkoxy" mean alkyl, alkenyl, aliphatic or alkoxy, as the case may be, substituted with one or more cyano groups. In some embodiments, the cyanoalkyl is (C)-alkyl-.

The terms "aminoalkyl", "aminoalkenyl", "aminoaliphatic", and "aminoalkoxy" mean alkyl, alkenyl, aliphatic or alkoxy, as the case may be, substituted with one or more amino groups, wherein the amino group is as defined above. In some embodiments, the aminoaliphatic is a C1-C6 aliphatic group substituted with one or more —H2 groups. In some embodiments, the aminoalkyl refers to the structure (RxRY)N-alkyl-, wherein each of Rx and RY independently is as defined above. In some specific embodiments, the aminoalkyl is C1-C6 alkyl substituted with one or more —NH2 groups. In some specific embodiments, the aminoalkenyl is C1-C6 alkenyl substituted with one or more —H2 groups. In some embodiments, the aminoalkoxy is -0(C1-C6 alkyl) wherein the alkyl group is substituted with one or more —NH2 groups.

The terms "hydroxyalkyl", "hydroxyaliphatic", and "hydroxyalkoxy" mean alkyl, aliphatic or alkoxy, as the case may be, substituted with one or more —OH groups.

The terms "alkoxyalkyl", "alkoxyaliphatic", and "alkoxyalkoxy" mean alkyl, aliphatic or alkoxy, as the case may be, substituted with one or more alkoxy groups. For example, an "alkoxyalkyl" refers to an alkyl group such as (alkyl-O)-alkyl-, wherein alkyl is as defined above.

The term "carboxyalkyl" means alkyl substituted with one or more carboxy groups, wherein alkyl and carboxy are as defined above.

The term "disulfide bond" means "—S—S—".

The term "thioether bond" means "—S—".

The term "protecting group" and "protective group" as used herein, are interchangeable and refer to an agent used to temporarily block one or more desired functional groups in a compound with multiple reactive sites. In certain embodiments, a protecting group has one or more, or specifically all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. Gin "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

Unless otherwise indicated, structures depicted herein are also meant to include all isomeric (e.g., enantiomeric, diastereomeric, cis-trans, conformational, and rotational) forms of the structure. For example, the R and S configurations for each asymmetric center, (Z) and (E) double bond isomers, and (Z) and (E) conformational isomers are included in this invention, unless only one of the isomers is drawn specifically. As would be understood to one skilled in the art, a substituent can freely rotate around any rotatable bonds. For example, a substituent drawn as

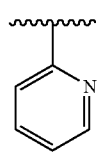

also represents

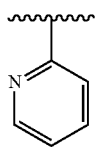

Therefore, single stereochemical isomers as well as enantiomeric, diastereomeric, cis/trans, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a 13C- or 14C-enriched carbon are within the scope of this invention. Such compounds are useful, for example, as analytical tools or probes in biological assays. Such compounds, especially deuterium analogs, can also be therapeutically useful.

The terms "a bond" and "absent" are used interchangeably to indicate that a group is absent.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Pharmaceutically Acceptable Salts, Solvates, Chlatrates, Prodrugs and Other Derivatives The compounds described herein can exist in free form, or, where appropriate, as salts. Those salts that are pharmaceutically acceptable are of particular interest since they are useful in administering the compounds described below for medical purposes. Salts that are not pharmaceutically acceptable are useful in manufacturing processes, for isolation and purification purposes, and in some instances, for use in separating stereoisomeric forms of the compounds of the invention or intermediates thereof.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al, describe pharmaceutically acceptable salts in detail in J. Pharmaceutical Sciences, 1977, 66, 1-19, incorporated herein by reference. Pharmaceutically acceptable salts of the compounds described herein include those derived from suitable inorganic and organic acids and bases. These salts can be prepared in situ during the final isolation and purification of the compounds.

Where the compound described herein contains a basic group, or a sufficiently basic bioisostere, acid addition salts can be prepared by 1) reacting the purified compound in its free-base form with a suitable organic or inorganic acid and 2) isolating the salt thus formed. In practice, acid addition salts might be a more convenient form for use and use of the salt amounts to use of the free basic form.

Examples of pharmaceutically acceptable, non-toxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenylpropionate, phosphate, picrate, pivalate, propionate, salicylate, stearate, succinate, sulfate, tartrate, thiocyanate, p-toluenesulfonate, undecanoate, valerate salts, and the like.

Where the compound described herein contains a carboxy group or a sufficiently acidic bioisostere, base addition salts can be prepared by 1) reacting the purified compound in its acid form with a suitable organic or inorganic base and 2) isolating the salt thus formed. In practice, use of the base addition salt might be more convenient and use of the salt form inherently amounts to use of the free acid form. Salts derived from appropriate bases include alkali metal (e.g., sodium, lithium, and potassium), alkaline earth metal (e.g., magnesium and calcium), ammonium and $N^+(C1\text{-}4alkyl)_4$ salts. This invention also envisions the quaternization of any basic nitrogen-containing groups of the compounds disclosed herein. Water or oil-soluble or dispersible products may be obtained by such quaternization.

Basic addition salts include pharmaceutically acceptable metal and amine salts. Suitable metal salts include the sodium, potassium, calcium, barium, zinc, magnesium, and aluminium. The sodium and potassium salts are usually preferred. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Suitable inorganic base addition salts are prepared from metal bases which include sodium hydride, sodium hydroxide, potassium hydroxide, calcium hydroxide, aluminium hydroxide, lithium hydroxide, magnesium hydroxide, zinc hydroxide and the like. Suitable amine base addition salts are prepared from amines which are frequently used in medicinal chemistry because of their low toxicity and acceptability for medical use. Ammonia, ethylenediamine, N-methyl-glucamine, lysine, arginine, ornithine, choline, N, N'-dibenzylethylenediamine, chloroprocaine, dietanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, dicyclohexylamine and the like.

Other acids and bases, while not in themselves pharmaceutically acceptable, may be employed in the preparation of salts useful as intermediates in obtaining the compounds described herein and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

The compounds described herein can also exist as pharmaceutically acceptable solvates (e.g., hydrates) and clathrates. As used herein, the term "pharmaceutically acceptable solvate," is a solvate formed from the association of one or more pharmaceutically acceptable solvent molecules to one of the compounds described herein. The term solvate includes hydrates (e.g., hemihydrate, monohydrate, dihydrate, trihydrate, tetrahydrate, and the like).

As used herein, the term "hydrate" means a compound described herein or a salt thereof that further includes a stoichiometric or non-stoichiometric amount of water bound by non-covalent intermolecular forces.

As used herein, the term "clathrate" means a compound described herein or a salt thereof in the form of a crystal lattice that contains spaces (e.g., channels) that have a guest molecule (e.g., a solvent or water) trapped within.

In addition to the compounds described herein, pharmaceutically acceptable derivatives or prodrugs of these compounds may also be employed in compositions to treat or prevent the herein identified disorders.

A "pharmaceutically acceptable derivative or prodrug" includes any pharmaceutically acceptable ester, salt of an ester or other derivative or salt thereof of a compound described herein which, upon administration to a recipient, is capable of providing, either directly or indirectly, a compound described herein or an inhibitorily active metabolite or residue thereof. Particularly favoured derivatives or prodrugs are those that increase the bioavailability of the compounds when such compounds are administered to a patient (e.g., by allowing an orally administered compound to be more readily absorbed into the blood) or which enhance delivery of the parent compound to a biological compartment (e.g., the brain or lymphatic system) relative to the parent species.

As used herein and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds described herein that comprise —NO, —N02, —ONO, or —ONO2 moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters. Pharmaceutically acceptable prodrugs of the compounds described herein include, without limitation, esters, amino acid esters, phosphate esters, metal salts and sulfonate esters.

As used herein the term "starch" is a polysaccharide comprising glucose monomers joined in a 1,4 linkages.

Isotopic Variations

Polypeptides and/or polypeptide compositions of the present invention may comprise one or more atoms that are isotopes. As used herein, the term "isotope" refers to a chemical element that has one or more additional neutrons. In one embodiment, Polypeptides and/or polypeptide compositions of the present invention may be deuterated. As used herein, the term "deuterated" refers to a substance that has had one or more hydrogen atoms replaced by deuterium isotopes. Deuterium isotopes are isotopes of hydrogen. The nucleus of hydrogen contains one proton while deuterium nuclei contain both a proton and a neutron. Compounds and pharmaceutical compositions of the present invention may be deuterated in order to change a physical property, such as stability, or to allow them to be used in diagnostic and experimental applications.

Formulation and Delivery

The term "pharmaceutical composition" refers to a composition comprising at least one active ingredient (e.g., such as a peptide) in a form and amount that permits the active ingredient to be therapeutically effective.

Polypeptide formulations of the present invention include controlled duodenal release formulations, time release formulations, osmotic-controlled release delivery systems, microemulsions, microspheres, liposomes, nanoparticles, patches, pumps, drug depots, and the like. Specifically included in the present invention are solid oral dosage forms, such as powders, softgels, gelcaps, capsules, pills, and tablets.

The polypeptides of the present disclosure or pharmaceutical compositions thereof may be administered by any route that results in a therapeutically effective outcome. These include, but are not limited to enteral, gastroenteral, epidural, oral, peridural, intracerebral (into the cerebrum), intratracheal (into the airways for delivery to the lung), intracerebroventricular (into the cerebral ventricles), epicutaneous (application onto the skin), intradermal, (into the skin itself), subcutaneous (under the skin), nasal administration (through the nose), intravenous (into a vein), intraarterial (into an artery), intramuscular (into a muscle), intracardiac (into the heart), intraosseous infusion (into the bone marrow), intrathecal (into the spinal canal), intraperitoneal, (infusion or injection into the peritoneum), intravesical infusion, intravitreal, (into the posterior chamber of the eye), intracavernous injection (into the base of the penis), intravaginal administration, intrauterine, extra-amniotic administration, transdermal (diffusion through the intact skin for systemic distribution), transmucosal (diffusion through a mucous membrane), insufflation (snorting), buccal, sublingual, sublabial, enema, eye drops (onto the conjunctiva), or in ear drops.

In some embodiments, polypeptides of the present invention are formulated in a sterile aqueous solution. In some embodiments, polypeptides of the present invention are formulated in a non-lipid formulation. In another embodiment, polypeptides of the present invention are formulated in a cationic or non-cationic lipid formulation. In either embodiment, the sterile aqueous solution may contain additional active or inactive components. Inactive components, also referred to herein as "excipients," can include, but are not limited to, physiologically compatible salts, sugars, bulking agents, surfactants, or buffers.

Polypeptides and/or polypeptide compositions of the present invention may comprise or be formulated or delivered in conjunction with one or more carrier agents. As used herein, the term "carrier" refers to a substance that aids in the delivery or improves the effectiveness of the polypeptides and/or polypeptide compositions of the present invention.

The carrier agent can be a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, or hyaluronic acid); or lipid. The carrier molecule can also be a recombinant or synthetic molecule, such as a synthetic polymer, e.g., a synthetic polyamino acid. Examples of polyamino acids include poly-L-lysine (PLL), poly-L-aspartic acid and, poly-L-glutamic acid, as well as polymers comprising the D-stereoisomers of these amino acids. Other carriers include poly(L-lactide-co-glycolide) copolymer, polyethylene glycol (PEG), polyvinyl alcohol (PVA), poly(2-ethylacryllic acid), and N-isopropylacrylamide polymers. Other useful carrier molecules can be identified by routine methods.

In some embodiments, pharmaceutical compositions comprise one or more active polypeptide ingredients together with ethanol, corn oil-mono-di-triglycerides, hydrogenated castor oil, DL-tocopherol, propylene glycol, gelatin, glycerol, colorants, flavors and sweeteners.

In other embodiments, pharmaceutical compositions comprise one or more active polypeptide ingredients together with a delivery agent such as 4-(2-hydroxy-4-methoxybenzamido)butanoic acid (or any of the delivery agents described in U.S. Pat. No. 7,744,910B2, the contents of which are incorporated herein by reference in their entirety), a pharmaceutically acceptable buffer, a disintegrant, a detergent, hydroxypropylmethylcellulose, colorants, flavors and sweeteners.

In other embodiments, pharmaceutical compositions comprise one or more active polypeptide ingredients together with ethanol, soy phosphatidyl choline, glycerol diolate which is injected into an excess of saline solution as described in US patent application 2008/0146490A1, the contents of which are incorporated herein by reference in their entirety.

The delivery of one or more polypeptides or cyclic polypeptides to a subject in need thereof can be achieved in a number of different ways. In vivo delivery can be performed directly by administering a composition comprising one or more polypeptides or cyclic polypeptides, to a subject. Alternatively, delivery can be performed indirectly by administering one or more vectors that encode and direct the expression of the polypeptides or cyclic polypeptides.

Local delivery avoids gut permeability and systemic exposure. For example, polypeptides and/or polypeptide compositions of the present invention may be used in the eye as a drop or in the posterior section of the eye by direct injection. They may be applied in the gut to target enzymes. They may be used topically in dermatologic applications (e.g., creams, ointments, transdermal patches).

Polypeptides and/or polypeptide compositions of the present invention may comprise or be formulated with one or more fusogenic agents. As used herein, the term "fusogenic agent" refers to an agent that is responsive to changes, such as pH changes in the environment for example. Upon encountering the pH of an endosome, a fusogenic agent can cause a physical change, e.g., a change in osmotic properties that disrupts or increases the permeability of the endosome membrane. Preferably, the fusogenic agent changes charge, e.g., becomes protonated, at pH lower than physiological range. For example, the fusogenic agent can become protonated at pH 4.5-6.5. A fusogenic agent may serve to release a polypeptide into the cytoplasm of a cell after a composition is taken up, e.g., via endocytosis, by the cell, thereby increasing the cellular concentration of the peptide in the cell.

In some embodiments, fusogenic agents may have a moiety, e.g., an amino group, which, when exposed to a specified pH range, will undergo a change, e.g., in charge, e.g., protonation. Changes in charge of fusogenic agents can trigger changes, e.g., osmotic changes, in vesicles, e.g., endocytic vesicles, e.g., endosomes. For example, the fusogenic agent, upon being exposed to the pH environment of an endosome, will cause a solubility or osmotic change substantial enough to increase the porosity of (preferably, to rupture) the endosomal membrane.

Fusogenic agents may be polymers, preferably polyamino chains, e.g., polyethyleneimine (PEI). PEI may be linear, branched, synthetic or natural. PEI may be, e.g., alkyl substituted PEI, or lipid substituted PEI.

In other embodiments, fusogenic agents may be polyhistidine, polyimidazole, polypyridine, polypropyleneimine, mellitin, or polyacetal substances, e.g., cationic polyacetals. In some embodiments, fusogenic agents may have an alpha helical structure. Fusogenic agents may be membrane disruptive agents, e.g., mellittin. Other suitable fusogenic agents can be tested and identified by a skilled artisan.

Polypeptides and/or polypeptide compositions of the present invention may comprise or be formulated with one or more condensing agents. Condensing agents of compositions described herein may interact with (e.g., attract, hold, or bind to) polypeptides and act to (a) condense, e.g., reduce the size or charge of polypeptides and/or (b) protect peptides, e.g., protect peptides against degradation. Condensing agents may include a moiety, e.g., a charged moiety, which can interact with polypeptides by ionic interactions. Condensing agents would preferably be charged polymers, e.g., polycationic chains. Condensing agents can be polylysine (PLL), spermine, spermidine, polyamine, pseudopeptide-polyamine, peptidomimetic polyamine, dendrimer polyamine, arginine, amidine, protamine, cationic lipid, cationic porphyrin, quarternary salt of a polyamine, or an alpha helical peptide.

In some embodiments, polypeptides of the present invention may be bicyclic peptides. As used herein, the term "bicyclic peptide" refers to a peptide with two loops. As a non-limiting example, bicyclic peptide inhibitors of RAS may be produced in combinatorial libraries. The bicyclic peptides may have 2, 3, 4, 5, 6 or more amino acids per loop.

In some embodiments, polypeptides and/or polypeptide compositions of the present invention may be provided as prodrugs. As used herein, the term "prodrug" refers to a drug that is provided in an inactive form that becomes active at some point after administration. In some embodiments wherein polypeptides are administered in the form of a prodrug, amino acids critical to polypeptide inhibitory activity are unavailable to interact with the target due to a reversible chemical bond, e.g., an ester bond. Upon administration, such prodrugs may be subject to cleavage of the reversible chemical bond, e.g., through enzymatic or acid hydrolysis in the stomach, blood and/or cells of a given target tissue. In other embodiments, polypeptides of the invention may be expressed as prodrugs. As used herein, the term "prodrug" refers to an inactive polypeptide that is activated by the cells' protein post-translational machinery. Post-translational protein modifications are recognized to those skilled in the art, and include but are not limited to phosphorylation, acetylation, alkylation, lipidation, glycosylation, and protease cleavage.

Ras Inhibitors

Polypeptides and/or polypeptide compositions of the present invention are useful in the binding of Ras proteins, alteration of Ras protein signaling and/or Ras protein concentration in cells. Such polypeptides and/or polypeptide compositions may find utility in treating various Ras-mediated diseases such as cancer and any accompanying disorders or conditions.

In some embodiments, polypeptides of the present invention may function as inhibitors of Ras function by binding one or more epitopes on the Ras protein. The binding polypeptides may function as allosteric inhbitors.

A small molecule or peptide inhibitor of Ras can also be created by rational design or a combination of high throughput screening followed by rational design. In this embodiment, X-ray crystallography is used to identify the precise manner by which a small molecule or peptide binds to protein. Computational analysis and medicinal chemistry principles are used to predict modications, substitutions, extensions, or conjugations that would produce an improved molecule. In some embodiments, the binding mode of a peptide is used to transform the peptide into a largely or completely non-peptidic molecule. In such cases, peptide bonds are replaced with peptide bond isosteres, and additional chemical modifications may be introduced to improve the binding properties, activity, solubility, stability, or pharmacokinetics of the compound. In other embodiments the binding mode of a peptide is used to design a small molecule that recapitulates the binding and activity of the peptide. In this embodiment, the contact points of the peptide with Ras are identified and a three-dimensional structure or scaffold is designed that mimics the presentation of the contact points to Ras in three-dimensional space. The principles of rationale design of non-peptidic or partially peptidic compounds based on polypeptides binding to target proteins are well-known to those skilled in the art.

In some embodiments, the present disclosure provides polypeptide-Ras complexes, including complexes between any of the Ras modulators provided herein and a Ras protein (e.g., H-Ras, K-Ras, and N-Ras). Polypeptides of the present disclosure may bind Ras through cross-linking. Such cross-links may include covalent bonds between polypeptides and Ras proteins. In some cases, cross-links are formed between polypeptides of the present disclosure and Cys118 (where numbering is in relation to the translated protein). Cross-linking may include bond formation with an electrophilic moiety present on the polypeptide.

Methods for Treating Disease

In some embodiments, polypeptides and/or polypeptide compositions of the present invention may be useful in the treatment of diseases, disorders and/or conditions including, but are not limited to cancer, hyperproliferation disorders, Costello syndrome, bladder cancer, follicular thyroid cancer, and oral squamous cell carcinoma, lung adenocarcinoma, mucinous adenoma, ductal carcinoma of the pancreas and colorectal carcinoma, and leukemias.

The invention relates in particular to the use of peptide or peptide mimetics, often cyclic, and compositions containing at least one peptide, for the treatment of a Ras-related, Ras-mediated or Ras-associated disorder, condition or disease.

As used herein the terms "treat," "treatment," and the like, refer to relief from or alleviation of pathological processes. In the context of the present invention insofar as it relates to any of the other conditions recited herein below, the terms "treat," "treatment," and the like mean to relieve or alleviate at least one symptom associated with such condition, or to slow or reverse the progression or anticipated progression of such condition, such as slowing the progression of a malignancy or cancer, or increasing the clearance of an infectious organism to alleviate/reduce the symptoms caused by the infection, e.g., hepatitis caused by infection with a hepatitis virus or reducing the destruction of red blood cells resulting from paroxysmal nocturnal hemoglobinuria.

By "lower" or "reduce" in the context of a disease marker or symptom is meant a statistically significant decrease in such level. The decrease can be, for example, at least 10%, at least 20%, at least 30%, at least 40% or more, and is preferably down to a level accepted as within the range of normal for an individual without such disorder.

By "increase" or "raise" in the context of a disease marker or symptom is meant a statistically significant rise in such level. The increase can be, for example, at least 10%, at least 20%, at least 30%, at least 40% or more, and is preferably up to a level accepted as within the range of normal for an individual without such disorder.

As used herein, the phrases "therapeutically effective amount" and "prophylactically effective amount" refer to an amount that provides a therapeutic benefit in the treatment, prevention, or management of pathological processes or an overt symptom of one or more pathological processes. The specific amount that is therapeutically effective can be readily determined by an ordinary medical practitioner, and may vary depending on factors known in the art, such as, for example, the type of pathological processes, the patient's history and age, the stage of pathological processes, and the administration of other agents that inhibit pathological processes.

As used herein, a "pharmaceutical composition" comprises a pharmacologically effective amount of a peptide and a pharmaceutically acceptable carrier. As used herein, "pharmacologically effective amount," "therapeutically effective amount" or simply "effective amount" refers to that amount of a peptide effective to produce the intended pharmacological, therapeutic or preventive result. For example, if a given clinical treatment is considered effective when there is at least a 10% alteration (increase or decrease) in a measurable parameter associated with a disease or disorder, a therapeutically effective amount of a drug for the treatment of that disease or disorder is the amount necessary to effect at least a 10% alteration in that parameter. For example, a therapeutically effective amount of a peptide may be one that alters binding of a target to its natural binding partner by at least 10%.

The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Agents included in drug formulations are described further herein below.

Efficacy of treatment or amelioration of disease can be assessed, for example by measuring disease progression, disease remission, tumor size, tumor growth rates, tumor metastases, disease severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. In connection with the administration of a peptide or pharmaceutical composition thereof, "effective against" a disease or disorder indicates that administration in a clinically appropriate manner results in a beneficial effect for at least a fraction of patients, such as an improvement of symptoms, a cure, a reduction in disease load, reduction in tumor mass or cell numbers, extension of life, improvement in quality of life, a reduction in the need for or reduced requirement for cancer chemotherapy or other effect generally recognized as positive by medical doctors familiar with treating the particular type of disease or disorder.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given peptide drug or formulation of that drug can also be judged using an experimental animal model for the given disease as known in the art. When using an experimental animal model, efficacy of treatment is evidenced when a statistically significant modulation in a marker or symptom is observed.

Compounds of the invention and an additional therapeutic agent can be administered in combination in the same composition, e.g., parenterally, or the additional therapeutic agent can be administered as part of a separate composition or by another method described herein.

In some embodiments, methods of the present disclosure include inhibiting Ras dimerization in a cell membrane and/or altering the cellular localization of Ras protein in a cell by contacting the cell membrane with a polypeptide of the present disclosure.

Indications Associated with Ras Genes

In some embodiments, compounds and compositions of the present invention may be used to treat one or more indication related to a Ras gene and/or gene product.

HRAS

The H-Ras protein undergoes a continuous cycle of de- and re-palmitoylation, which regulates its rapid exchange between the plasma membrane and the Golgi apparatus. H-Ras signaling can activate MEKK1(MAP3K1), which can promote ERK1/2 activation via c-Raf-1/MEK1(MAP2K1) or JNK(MAPK8-10) activation via MEK4(MAP2K4).

Diseases associated with HRAS include congenital myopathy with excess of muscle spindles, and Costello syndrome (see below). H-Ras is also reported to be involved in the pathogenesis of vascular proliferative disorders (Ramos, (2009) *Circulation Research* 104(10):1139-41). Targeted disruption of h-Ras in mice was found to induce hypotension, believed to be due to upregulation of the nitric oxide-cyclic guanosine monophosphate pathway (Chamorro-Jorganes, et al., (2010) *Hypertension,* 56(3):484-9).

Defects in the HRAS gene are also implicated in a variety of cancers, including bladder cancer, follicular thyroid cancer, and oral squamous cell carcinoma. Multiple transcript variants, which encode different isoforms, have been identified for the HRAS gene.

At least five inherited mutations in the HRAS gene have been identified in people with Costello syndrome. Each of these mutations changes an amino acid in a critical region of the HRAS protein. The most common mutation replaces the amino acid glycine with the amino acid serine at position 12 (written as Gly12Ser or G12S). The mutations responsible for Costello syndrome lead to the production of an HRAS protein that is permanently active. Instead of triggering cell growth in response to particular signals from outside the cell, the overactive protein directs cells to grow and divide constantly. This uncontrolled cell division can result in the formation of noncancerous and cancerous tumors. Researchers are uncertain how mutations in the HRAS gene cause the other features of Costello syndrome (such as mental retardation, distinctive facial features, and heart problems), but many of the signs and symptoms probably result from cell overgrowth and abnormal cell division.

Somatic mutations in the HRAS gene in bladder cells have been associated with bladder cancer. One specific mutation has been identified in a significant percentage of bladder tumors; this mutation substitutes one protein building block (amino acid) for another amino acid in the HRAS protein. Specifically, the mutation replaces the amino acid glycine with the amino acid valine at position 12 (written as Gly12Val or G12V). The altered HRAS protein is permanently activated within the cell. This overactive protein directs the cell to grow and divide in the absence of outside signals, leading to uncontrolled cell division and the formation of a tumor. Mutations in the HRAS gene also have been associated with the progression of bladder cancer and an increased risk of tumor recurrence after treatment.

Somatic mutations in the HRAS gene are also believed to be involved in the development of several other types of cancer. These mutations lead to an HRAS protein that is always active and can direct cells to grow and divide without control. Recent studies suggest that HRAS mutations may be common in thyroid and kidney cancers. The HRAS protein also may be produced at higher levels (overexpressed) in other types of cancer cells.

KRAS

KRAS mutations are involved in development of several cancers, such as: acute myelogenous leukemia (AML) and juvenile myelomonocytic leukemia (JMML), as well as malignant gastric cancer (GASC) and pylocytic astrocytoma (PA), involving neoplasms of the brain and spinal cord derived from glial cells. Defects in KRAS are also associated with developmental disorders such as Noonan syndrome 3 (NS3) and Cardiofaciocutaneous syndrome 2 (CFC2).

NRAS

The neuroblastoma rat sarcoma viral oncogene homolog (NRAS) gene encodes a membrane-bound protein with GTPase activity that functions as an important regulatory element in the signal transduction of numerous hormones, cytokines, and growth factors. It cycles between an active GTP-bound and an inactive GDP-bound state (Rajalingam K, Schreck R, Rapp U R, Albert S (2007) *Biochim Biophys Acta* 1773(8):1177-1195; Vetter I R, Wittinghofer A (2001) *Science* 294(5545):1299-1304). In the GTP-bound state, two regions, switch I and switch II, undergo a conformation change that enables binding of NRAS to effector molecules, including v-raf-1 murine leukemia viral oncogene homolog 1 (RAF-1) (Vojtek A B, Hollenberg S M, Cooper J A (1993) Mammalian Ras interacts directly with the serine/threonine kinase Raf. *Cell* 74(1):205-214) and PI3K (Castellano E, Downward J (2011) RAS interaction with PI3K: More than just another effector pathway. *Genes Cancer* 2(3):261-274). This leads to signaling cascades [e.g., RAF/MEK/ERK (MAP)-kinases and PI3/AKT-kinases] affecting cellular proliferation, differentiation, migration, and apoptosis (Rajalingam K, Schreck R, Rapp U R, Albert S (2007) *Biochim Biophys Acta* 1773(8):1177-1195; Malumbres M, Barbacid M (2003) RAS oncogenes: The first 30 years. *Nat. Rev. Cancer* 3(6):459-465). Aberrant activation of the RAS pathway is a crucial event in many cancers and is frequently caused by point mutations of hotspot codons located within exon 2 [codons 12 and 13 (Bezieau S, et al. (2001) *Hum. Mutat.* 18(3):212-224)] and exon 3 [codon 61 (Bezieau S, et al. (2001) *Hum. Mutat.* 18(3):212-224)]. The mutations disrupt intrinsic and RasGAP—mediated GTP hydrolysis, leading to constitutive activation (Herrmann C (2003) *Curr. Opin. Struct. Biol.* 13(1):122-129; McGrath J P, Capon D J, Goeddel D V, Levinson A D (1984) *Nature* 310(5979): 644-649) and increased affinity of NRAS to the direct effectors, RAF-1 (Moodie S A, Willumsen B M, Weber M J, Wolfman A (1993) Complexes of Ras.GTP with Raf-1 and mitogen-activated protein kinase kinase. *Science* 260(5114): 1658-1661) and PI3K (Sjölander A, Yamamoto K, Huber B, Lapetina E G (1991) Association of p21ras with phosphatidylinositol 3-kinase. *Proc Natl Acad Sci USA* 88(18):7908-7912).

Defects in NRAS are associated with juvenile myelomonocytic leukemia (JMML), noonan syndrome 1 (NS1), Noonan syndrome 6 (NS6), N-Ras-related noonan syndrome, autoimmune lymphoproliferative syndrome 4 (ALPS4), autoimmune lymphoproliferative syndrome, type ib, Ras-associated autoimmune leukoproliferative disease, exanthema, Lynch syndrome, pancreatitis, follicular thyroid carcinoma, familial adenomatous polyposis, adenoma, melanoma, neurocutaneous melanosis, epidermal nevus, congenital somatic melanocytic nevus syndrome, acral lentiginous melanoma, follicular thyroid carcinoma, myelodysplastic syndromescholangiocarcinoma, and cancers such as gallbladder, colorectal, endometrial, ovarian, lung, thyroid, pancreatic and bone marrow cancers.

RRAS

R-Ras is believed to play a role in apoptosis. The R-Ras p21 protein is about 50% identical to the Ras p21 protooncogene product. This protein is incapable of transforming cells, even though it interacts with Raf and other putative Ras effectors (Fernandez-Sarabia and Bischoff, 1993: *Nature* 366:274-275). On the other hand, it has also been shown that R-Ras binds to the protooncogene product Bcl-2, a protein that transforms B cells by blocking apoptosis. R-Ras is regulated by the same GAP molecules as H-Ras and the other Ras protooncogene products, and may therefore be activated in a manner co-ordinate with these growth-promoting proteins.

Ras Pathways in Cancer

Ras is an important regulator of cell growth in eukaryotic cells. Ras and Ras-related proteins are often deregulated in cancers, leading to increased invasion and metastasis, and decreased apoptosis. Activated Ras can stimulate signal transduction cascades, leading to cell proliferation, differentiation or apoptosis. It is also one of the most commonly mutated genes in both solid tumors and hematologic neoplasias. In leukaemia and tumors, aberrant Ras signaling can be induced directly by Ras mutation or indirectly by altering genes that associate with Ras or its signaling pathways. A requisite for Ras function is localization to the plasma membrane, which may be induced by the post-translational modification farnesylation. Ras is emerging as a dual regulator of cell functions, playing either positive or negative roles in the control of proliferation or apoptosis. The diversity of Ras-mediated effects may be related in part to the differential involvement of Ras homologues in distinct cellular processes or to the expanding array of Ras effectors.

Inappropriate activation of the Ras genes have been shown to play a role in unregulated signal transduction, proliferation and malignant transformation. Mutations that permanently activate Ras proto-oncogenes (H-Ras, N-Ras and K-Ras) are very common, being found in 20% to 30% of all human tumors and up to 90% in certain types of cancer (e.g., pancreatic cancer). Ras point mutations are the single most common abnormality of human proto-oncogenes.

Constitutively active Ras sometimes contains mutations that prevent GTP hydrolysis, locking Ras in a permanently 'On' state. Commonly, such mutations are found at residue G12 in the P-loop and the catalytic residue Q61. Residue 61 is responsible for stabilizing the transition state for GTP hydrolysis. Because enzyme catalysis in general is achieved by lowering the energy barrier between substrate and product, mutation of Q61 to K necessarily reduces the rate of intrinsic Ras GTP hydrolysis to physiologically meaningless levels.

A glycine to valine mutation at residue 12 (G12V) renders the GTPase domain of Ras insensitive to inactivation by GAP, leaving Ras stuck in the 'On' state.

"Dominant negative" mutants of Ras also exist, such as S17N and D119N.

Furthermore, mutations in a number of different genes as well as RAS itself can have this effect. Oncogenes such as p210BCR-ABL or the growth receptor erbB are upstream of Ras, and thus, if these oncogenes are constitutively activated their signals will transduce through Ras.

The tumor suppressor gene NF1 encodes a Ras-GAP; its mutation in neurofibromatosis means that Ras is less likely to be inactivated. Ras can also be amplified, although this only occurs occasionally in tumors.

Finally, Ras oncogenes can be activated by point mutations so that the GTPase reaction can no longer be stimulated by GAP, increasing the half-life of active Ras-GTP mutants (Reuter, et al., (2000) *Blood*.96(5):1655-69.

Alterations in post-translational modifications can also modulate Ras activity and/or subcellular localization. The Ras protein was found to be posttranslationally acetylated on lysine 104 (K104), and this modification was believed to affect the conformational stability of the Switch II domain, critical for the ability of Ras to interact with GEFs. An acetylation mimetic mutation in K-RAS4B suppressed GEF-induced nucleotide exchange and inhibited in vitro transforming activity, suggesting that lysine acetylation is a negative regulatory modification on Ras. Modulation of RAS acetylation may constitute a therapeutic approach (Yang, et al., (2012) *Proc. Natl. Acad. Sci. U.S.A.* 79(16): 4848-52).

The RAS oncogenes are involved in lung cancer development (Mascaux, et al., (2006) *Br. J. Cancer.* 95(2):139-145). These genes code for four highly homologous 21 kDa proteins called p21, with a common effector domain within the N-terminal region. To be biologically active, Ras proteins must be localized to the inner face of the plasma membrane, where they can effectively interact with their upstream activators and downstream targets. In physiologic conditions, GTP-bound active Ras initiates cell proliferation through the RAS-dependent kinase cascade. Inactive Ras is involved in control of cell growth. In tumors, a point mutation resulting in loss of the intrinsic GTPase activity appears to be associated with transforming activity of the protein, leading to uncontrolled cell proliferation. KRAS2 mutations are particularly common in pancreatic cancers, colorectal malignancies and lung cancer (Mascaux, et al., (2006) *Br. J. Cancer.* 95(2):139-145).

RAS mutations are detected in 15-20% of non-small-cell lung cancer (NSCLC) and, particularly, 30-50% of adenocarcinomas (ADC). In lung cancer, 90% of the mutations are located in the RAS2 gene and both NRAS mutations and HRAS mutations have occasionally been documented. In total, 80% of KRAS2 mutations occur in codon 12. Other mutations are located in codons 13 and 61. The predominant mutation is a G-T transversion (70% of tumours) (Mascaux, et al., (2006) *Br. J. Cancer.* 95(2): 139-145).

In addition to the canonical isoform (isoform 1) of neuroblastoma rat sarcoma viral oncogene homolog (NRAS), four additional naturally occurring NRAS isoforms (isoforms 2-5) have been identified. Expression analyses using a panel of human malignancies and matching normal tissue revealed distinct isoform expression patterns. Two of the novel isoforms were found in the nucleus and cytoplasm, whereas the others were exclusively cytoplasmic. The isoforms varied in their binding affinities to known downstream targets and differentially regulated the RAS signaling pathway. Strikingly, forced expression of isoform 5, which encodes only a 20-aa peptide, led to increased cell proliferation and to transformation by activation of known NRAS targets. Furthermore, three of the four novel NRAS isoforms are missing exon 3, which contains the mutational hotspot codon 61; NRAS isoforms 3,4, and 5 do not contain codon 61, which may modulate the activating effects (Eisfeld, et al., (2014) *Proc. Natl. Acad. Sci.,* 111(11):4179-4184).

Ras-Targeted Cancer Treatments

Due to its central role in intracellular signal transduction and malignant transformation, a plethora of drugs targeting Ras proteins or Ras effector pathways have been developed with the aim to either correct or eliminate aberrant Ras signaling. Early observations documenting that posttranslational modifications such as farnesylation, C-terminal peptide cleavage, and carboxymethylation are essential for oncogenic Ras mutants prompted development of farnesylation inhibitors targeting Ras. The first farnesyl transferase inhibitors (FTIs) mimicked the structure of the CAAX peptidic motif of Ras and/or the structure of the farnesyl substrate. Some FTIs initially showed promising pharmacological properties such as low ID50, pronounced tumor regression in animal models, high membrane permeability and low toxicity. For example, the FTI tipifarnib received FDA approval for the treatment of older patients with myelodysplastic syndrome, and Phase III trials suggested that tipifarnib might also be a drug of choice for treatment of older patients with acute myeloid leukemia. Oncogenic Ras was not inhibited by FTIs and was geranylgeranylated by the related geranylgeranyl transferase I upon FTI exposure; thus, although initially developed as Ras inhibitors with promising results in animal tumor models, FTIs seem to act via off-target inhibition of hitherto unidentified substrate(s) (Rajalingam, et al., (2007), *Biochimica et Biophysica Acta—Molecular Cell Research* 1773(8): 1177-1195).

The repair of defective GTPase activity of mutant Ras by GTP derivatives bearing residues required for GTP hydrolysis has also been reported. However, this avenue of Ras inhibition had problems such as specificity or transport of compounds modified by triphosphates through biological membranes (Rajalingam, et al., (2007), *Biochimica et Biophysica Acta—Molecular Cell Research* 1773(8): 1177-1195).

Drugs inhibiting the interaction of Ras with its effectors, immunological approaches and mutant-specific siRNAs are also in development, as are approaches to target aberrant Ras signaling by the inhibition of its downstream effector pathways. For example, inhibition of MEK by CI-1040 stopped the growth of some cell lines expressing Q61R NRAS. Also the inhibition of MEK was surprisingly efficient for cell lines harboring the V600E B-RAF mutation. However, another study demonstrated that certain tumor cell lines may develop resistance to CI-1040 by increasing endogenous KRAS expression. In combination with a precise molecular classification of tumors and additional classical treatment modalities, Ras-based therapies may eventually meet the ultimate goal of all tumor therapies: complete and irreversible remission (Rajalingam, et al., (2007), *Biochimica et Biophysica Acta—Molecular Cell Research* 1773(8):1177-1195).

The observation that Ras is directly regulated by microRNAs (miRNAs) added a new facet to the regulation of Ras. MicroRNAs (small, non-coding RNAs that can modulate expression of target mRNAs at a post-transcriptional level) are involved in the regulation of a wide variety of cellular processes. It was estimated that the number of human miRNAs is as high as 1000 and that miRNAs may regulate approximately 30% of all genes. One of the earliest reports linking miRNAs to cancer described that two miRNAs, miR-15 and miR-16, are frequently deleted in chronic lymphocytic lymphoma patients. In the meantime, more publications have appeared and proven that either the deregulated expression or mutations of miRNAs are linked to cancer and that miRNAs may function either as tumor suppressors or oncogenes (Rajalingam, et al., (2007), *Biochimica et Biophysica Acta—Molecular Cell Research* 1773(8): 1177-1195).

In 2005, it was discovered by in silico analysis that let-60, the C. elegans ortholog of the Ras oncogenes, harbors let-7 target sites in its 3'-untranslated region (UTR). let-7 is a heterochronic switch gene, whose loss causes reiterations of larval cell fates in the adult, whereas overexpression of let-7 evokes premature expression of adult fates during larval stages. It encodes a 22-nucleotide RNA negatively regulating the expression of protein-coding genes that contain regions of complementarity in their 3'-UTRs by target mRNA degradation. The amount of let-60/RAS was demonstrated to be regulated by let-7 family members in the context of vulva development and in human cell lines. Furthermore, various let-7 family members have been mapped to chromosomal regions frequently deleted in lung tumors, and let-7 expression was reported to be reduced in lung tumors in association with shortened postoperative survival; relative let-7 expression was reduced in 12 of 12 lung cancers, 4 of 6 colon cancers and 2 of 3 breast cancers and increased Ras protein levels were correlated with reduced let-7 expression. let-7 is also part of a unique miRNA expression profile that may be applicable as diagnostic and prognostic marker for human lung cancer. Thus, let-7 is believed to be a tumor suppressor—at least in lung tumors—and its effect appears to be mediated at least partially at the post-transcriptional level via down-regulation of Ras expression (Rajalingam, et al., (2007), *Biochimica et Biophysica Acta—Molecular Cell Research* 1773 (8):1177-1195).

Other molecules that interfere with Ras modification have been used as antitumor agents. A pharmacological approach that curtails Ras activity may represent a possible method to inhibit certain cancer types. Thus, Ras inhibitors are being studied as a treatment for cancer, and other diseases with Ras overexpression. Ras inhibitor trans-farnesylthiosalicylic acid (FTS, Salirasib) exhibits profound anti-oncogenic effects in many cancer cell lines.

Reovirus was noted to be a potential cancer therapeutic when early studies on reovirus suggested it reproduces well in certain cancer cell lines. It has since been shown to replicate specifically in cells that have an activated Ras pathway (a cellular signaling pathway that is involved in cell growth and differentiation). Reovirus replicates in and eventually kills Ras-activated tumor cells and as cell death occurs, progeny virus particles are free to infect surrounding cancer cells. This cycle of infection, replication and cell death is believed to be repeated until all tumor cells carrying an activated Ras pathway are destroyed. Another tumor lysing virus that specifically targets tumor cells with an activated Ras pathway is a type II herpes simplex virus (HSV-2) based agent, designated FusOn-H2. Both reolysin, a formulation of reovirus, and FusOn-H2 have been investigated for the treatment of various cancers. In addition, a treatment based on siRNA anti mutated K-RAS (G12D) called siG12D LODER has been investigated for the treatment of locally advanced pancreatic cancer.

In some embodiments, the present disclosure provides methods of modulating cell growth that include contacting a cell, tissue, or organism with a polypeptide of the present disclosure. In some embodiments, methods of the present disclosure include modulating the concentration of one or more Ras proteins in a cell by contacting the cell with a polypeptide of the present disclosure.

Dosage and Administration

For use as treatment of human subjects, polypeptides can be formulated as pharmaceutical compositions. Depending on the subject to be treated, the mode of administration, and the type of treatment desired (e.g., prevention, prophylaxis, or therapy) the peptides are formulated in ways consonant with these parameters. A summary of such techniques is found in Remington: The Science and Practice of Pharmacy, 21st Edition, Lippincott Williams & Wilkins, (2005); and Encyclopedia of Pharmaceutical Technology, eds. J. Swarbrick and J. C. Boylan, 1988-1999, Marcel Dekker, New York, each of which is incorporated herein by reference.

Compositions of the present invention are preferably provided in a therapeutically effective amount, which may be, for example, a daily amount of from about 0.1 mg to about 100 mg, from about 0.5 mg to about 200 mg, from about 1 mg to about 300 mg, from about 5 mg to about 500 mg, from about 10 mg to about 750 mg, from about 50 mg to about 1000 mg or at least 1000 mg. In one embodiment, a pharmaceutical composition comprises a capsule, for example in unit dosage form.

Unit Dosage Forms

Compositions comprising polypeptides of the invention may comprise from about 0.1-99.9% polypeptides by weight of the total weight of the composition. In some cases, composition may be provided in a dosage form that is suitable for oral administration. Thus, the pharmaceutical composition may be in the form of, e.g., hard capsules (e.g., hard gelatin capsules or hard hydroxypropyl methylcellulose capsules), soft gelatin capsules, tablets, caplets, enteric coated tablets, chewable tablets, enteric coated hard gelatin capsules, enteric coated soft gelatin capsules, minicapsules, lozenges, films, strips, gelcaps, dragees, solutions, emulsions, suspensions, syrups, or sprays.

Patients can be administered a therapeutic amount of a polypeptide, such as 0.01 mg/kg, 1.0 mg/kg, or 15 mg/kg. For administration to human subjects, the dosage of polypeptides of the present invention is typically 0.01 to 15 mg/kg, more preferably 3 to 5 mg/kg. However, dosage levels can be highly dependent on the nature of the condition, drug efficacy, the condition of the patient, the judgment of the practitioner, and the frequency and mode of administration.

In other embodiments, the polypeptides are administered at a frequency of e.g., every 4 hr, every 6 hr, every 12 hr, every 18 hr, every 24 hr, every 36 hr, every 72 hr, every 84 hr, every 96 hr, every 5 days, every 7 days, every 10 days, every 14 days, every 3 weeks, or more. The compositions can be administered once daily or the polypeptide can be administered as two, three, or more sub-doses at appropriate intervals throughout the day or delivery through a controlled release formulation. In that case, the polypeptide contained in each sub-dose must be correspondingly smaller in order to achieve the total daily dosage. The dosage unit can also be compounded for delivery over several days, e.g., using a conventional sustained release formulation, which provides sustained release of the polypeptide over a several-day-period.

Sustained release formulations are well known in the art and are particularly useful for delivery of agents to a particular site, such as could be used with the polypeptide compositions of the present invention. The effect of a single dose can be long-lasting, such that subsequent doses are administered at not more than 3-, 4-, or 5-day intervals, or at not more than 1, 2-, 3-, or 4-week intervals.

The polypeptide can be administered by intravenous infusion over a period of time, such as over a 5 minute, 10 minute, 15 minute, 20 minute, or 25 minute period. The administration may be repeated, for example, on a regular basis, such as biweekly (i.e., every two weeks) for one month, two months, three months, four months or longer. After an initial treatment regimen, the treatments can be administered on a less frequent basis. For example, after administration biweekly for three months, administration can be repeated once per month, for six months or a year or longer. Administration of the polypeptide or composition can reduce, lower, increase or alter binding or any physiologically deleterious process, e.g., in a cell, tissue, blood, urine or other compartment of a patient by at least 10%, at least 15%, at least 20%, at least 25%, at least 30%, at least 40%, at least 50%, at least 60%, at least 70%, at least 80% or at least 90% or more.

Before administration of a full dose of the polypeptide or composition, patients can be administered a smaller dose, such as a 5% infusion reaction, and monitored for adverse effects, such as an allergic reaction, or for elevated lipid levels or blood pressure. In another example, the patient can be monitored for unwanted immunostimulatory effects, such as increased cytokine (e.g., TNF-alpha or INF-alpha) levels.

Genetic predisposition plays a role in the development of some diseases or disorders. Therefore, a patient in need of a polypeptide or polypeptide composition may be identified by taking a family history, or, for example, screening for one or more genetic markers or variants. A healthcare provider, such as a doctor, nurse, or family member, can take a family history before prescribing or administering a therapeutic composition of the present invention.

Kits

Any of the compositions described herein may be comprised in a kit. In a non-limiting example, peptides may be included in a kit for treating a disease. The kit may include a vial of sterile, dry peptide powder, sterile solution for dissolving the dried powder, and a syringe for infusion set for administering the peptide.

When peptides are provided as a dried powder it is contemplated that between 10 micrograms and 1000 milligrams of polypeptide, or at least or at most those amounts are provided in kits of the invention The container means will generally include at least one vial, test tube, flask, bottle, syringe and/or other container means, into which the peptide formulations are placed, preferably, suitably allocated. The kits may also comprise a second container means for containing a sterile, pharmaceutically acceptable buffer and/or other diluent.

A kit can include instructions for employing the kit components as well the use of any other reagent not included in the kit. Instructions may include variations that can be implemented.

Equivalents and Scope

Those skilled in the art will recognize, or be able to ascertain using no more than routine experimentation, many equivalents to the specific embodiments in accordance with the invention described herein. The scope of the present invention is not intended to be limited to the above Description, but rather is as set forth in the appended claims.

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

It is also noted that the term "comprising" is intended to be open and permits but does not require the inclusion of additional elements or steps. When the term "comprising" is used herein, the term "consisting of" is thus also encompassed and disclosed.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention (e.g., any nucleic acid or protein encoded thereby; any method of production; any method of use; etc.) can be excluded from any one or more claims, for any reason, whether or not related to the existence of prior art.

All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

While various embodiments of the invention have been particularly shown and described, it will be understood by those skilled in the art that various changes in form and details may be made therein without departing from the spirit and scope of the invention as defined by the appended claims.

EXAMPLES

Example 1

Preparation of Biotinylated H-Ras-Cys and Loading with GMPPNP

1. Sequences

For H-Ras, the construct was derived from GenBank reference sequence AAA72806.1 gi number 208115, which contains the G12V point in H-Ras isoform 1. The sequence was as follows:

```
                                             (SEQ ID NO: 1)
MTEYKLVVVGAVGVGKSALTIQLIQNHFVDEYDPTIEDSYRKQVVIDGET

CLLDILDTAGQEEYSAMRDQYMRTGEGFLCVFAINNTKSFEDIHQYREQI

KRVKDSDDVPMVLVGNKCDLAARTVESRQAQDLARSYGIPYIETSAKTRQ

GVEDAFYTLVREIRQHKLRKLNPPDESGPGCMSCKCVLS.
```

Amino acids 2-166 of SEQ ID NO: 1 included the following sequence:

```
                                             (SEQ ID NO: 2)
TEYKLVVVGAVGVGKSALTIQLIQNHFVDEYDPTIEDSYRKQVVIDGET

CLLDILDTAGQEEYSAMRDQYMRTGEGFLCVFAINNTKSFEDIHQYREQI

KRVKDSDDVPMVLVGNKCDLAARTVESRQAQDLARSYGIPYIETSAKTRQ

GVEDAFYTLVREIRQHK.
```

A variant of SEQ ID NO: 2 having an alternative C-terminus, GSGSGSGSGSCGSG (SEQ ID NO: 3) has the following sequence:

```
                                             (SEQ ID NO: 4)
TEYKLVVVGAVGVGKSALTIQLIQNHFVDEYDPTIEDSYRKQVVIDGET

CLLDILDTAGQEEYSAMRDQYMRTGEGFLCVFAINNTKSFEDIHQYREQI

KRVKDSDDVPMVLVGNKCDLAARTVESRQAQDLARSYGIPYIETSAKTRQ

GVEDAFYTLVREIRQHKGSGSGSGSGSCGSG.
```

For K-Ras, the construct was full-length and derived from UniProt reference P01116-2 (K-Ras4B isoform) RASK_HUMAN Isoform 2B of GTPase KRas, Homo sapiens and comprised the following sequence:

```
                                             (SEQ ID NO: 5)
MTEYKLVVVGAGGVGKSALTIQLIQNHFVDEYDPTIEDSYRKQVVIDGET
```

-continued

CLLDILDTAGQEEYSAMRDQYMRTGEGFLCVFAINNTKSFEDIHHYREQI

KRVKDSEDVPMVLVGNKCDLPSRTVDTKQAQDLARSYGIPFIETSAKTRQ

GVDDAFYTLVREIRKHKEKMSKDGKKKKKKSKTKCVIM.

A variant of SEQ ID NO: 5 having a G12D mutation comprised the following sequence:

(SEQ ID NO: 6)
MTEYKLVVVGADGVGKSALTIQLIQNHFVDEYDPTIEDSYRKQVVIDGET

CLLDILDTAGQEEYSAMRDQYMRTGEGFLCVFAINNTKSFEDIHHYREQI

KRVKDSEDVPMVLVGNKCDLPSRTVDTKQAQDLARSYGIPFIETSAKTRQ

GVDDAFYTLVREIRKHKEKMSKDGKKKKKKSKTKCVIM.

2. Expression Plasmids

A nucleic acid sequence encoding amino acids 2-166 of human H-Ras with the mutation G12V (SEQ ID NO: 2) was synthesized (Genewiz, Cambridge, Mass.) and subcloned into a pET24a expression vector (Novagen, Darmstadt, Germany) for expression in *Escherichia coli*.

A nucleic acid molecule encoding the derivative of H-Ras G12V amino acid 2-166 with GSGSGSGSGSCGSG (SEQ ID NO: 3) at the C-terminus (SEQ ID NO: 4) was also synthesized and subcloned into pET24a. The later form of H-Ras (designated as H-Ras-Cys hereafter) was used for site-specific biotinylation at the cysteine residue with maleimide chemistry. The identity of expression constructs were confirmed by DNA sequencing.

3. Expression and Purification of H-Ras and H-Ras-Cys

Expression plasmids for H-Ras (containing the expression construct for SEQ ID NO: 2) or H-Ras-Cys were transformed into *E. Coli* BL21 (DE3). Cells were grown at 37° C. to an absorbance of 0.5 ($OD_{600}$) in LB media containing 25 µg/mL of kanamycin and the expression was induced with 0.1 mM IPTG. Cells were harvested and lysed with B-PER Bacteria Extraction Reagent (Pierce/Thermo Scientific, Rockford, Ill.) containing EDTA-free protease inhibitors. The clarified supernatanst of the B-PER lysates were subjected to Ni-nitrilotriacetate Agarose (Qiagen, Germantown, Md.) chromatography. The expression plasmid pET24a introduces a C-terminal His-tag to the Ras proteins (Novagen, Darmstadt, Germany), and the eluted His-tagged H-Ras and H-Ras-Cys (>90% pure as judged by SDS-polyacrylamide gel electrophoresis) were each dialyzed against TM buffer containing 64 mM Tris-HCl, pH 7.5, 5 mM $MgCl_2$, and 1 mM tris(2-carboxyethyl)phosphine (TCEP). The proteins were stored with 30 µM GDP in aliquots at −80° C.

4. Biotinylation of H-Ras-Cys

Figure 1B:
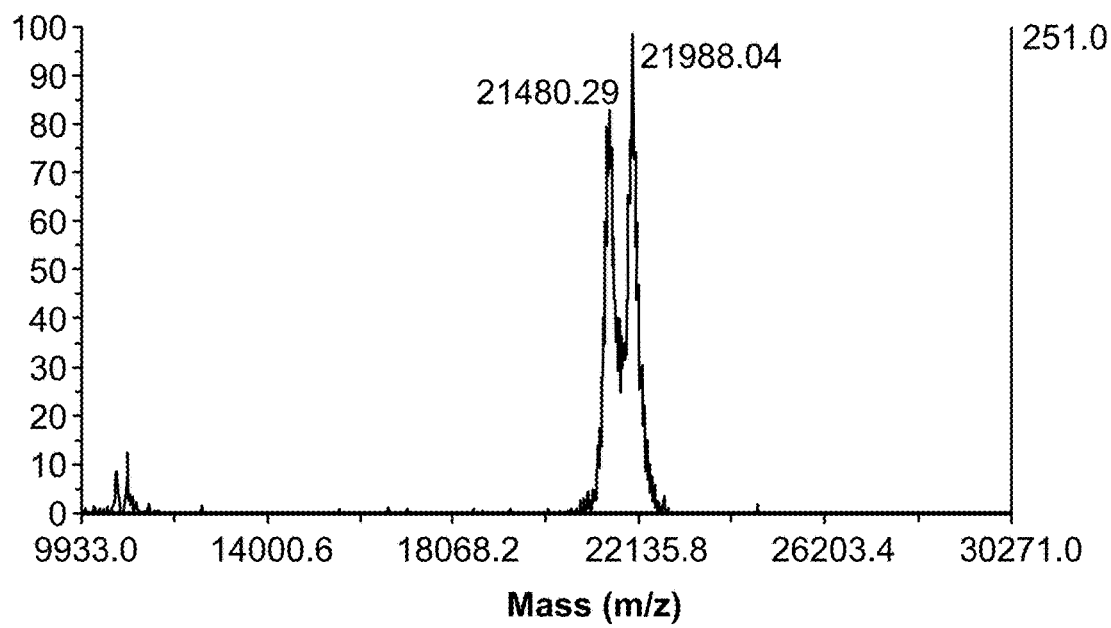
Figure 1C:
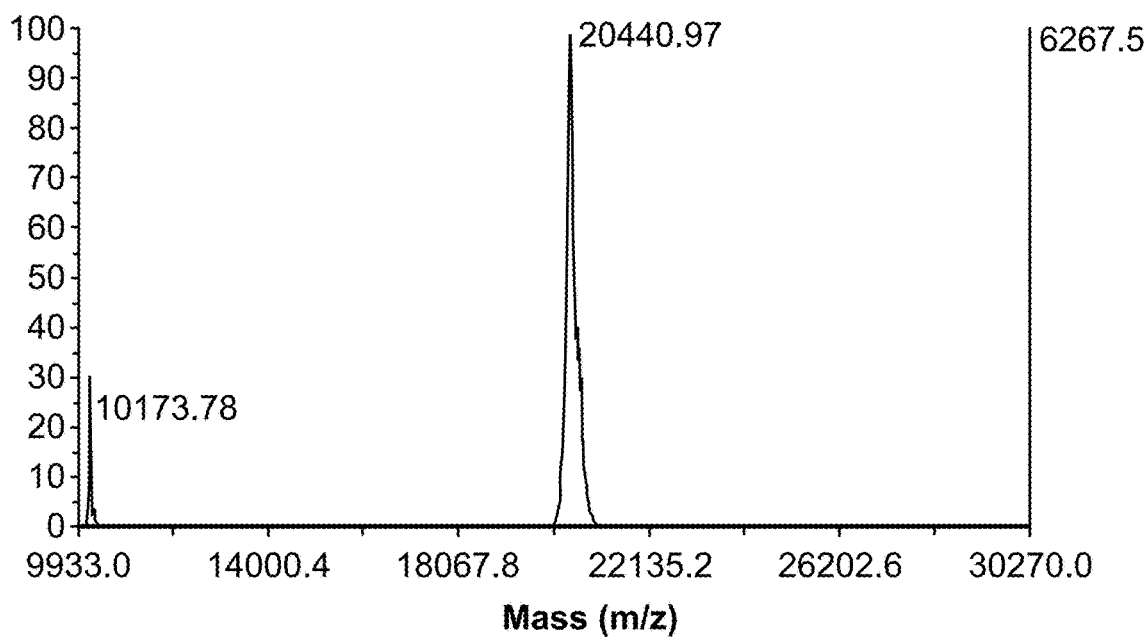
Figure 1D:
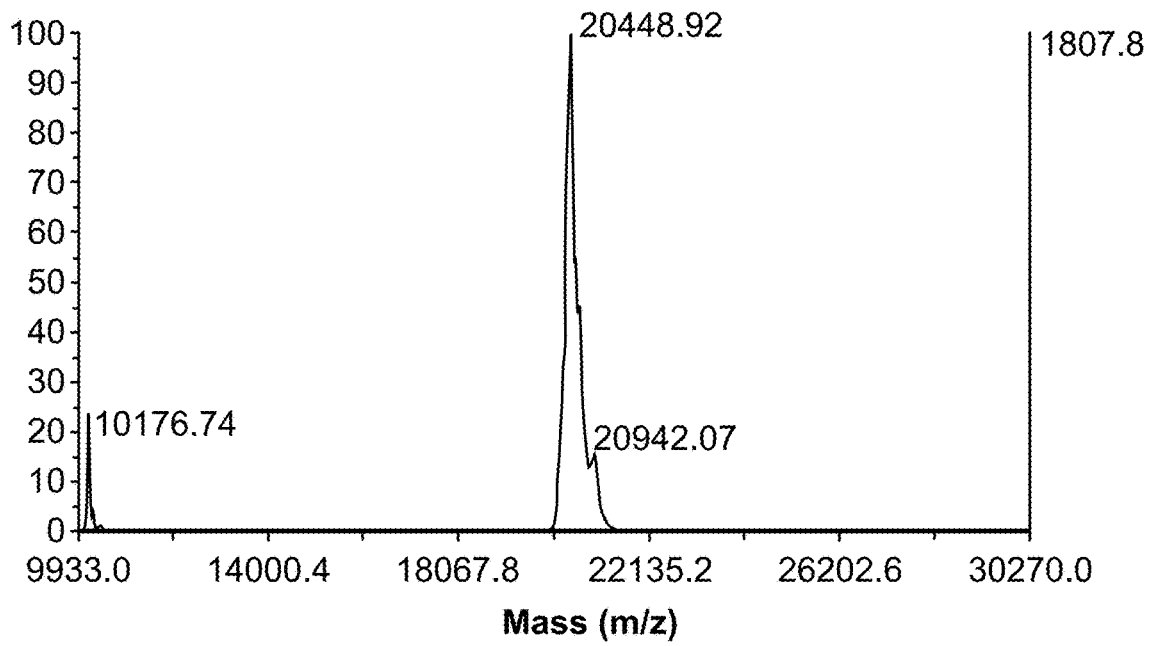

H-Ras-Cys was site-specifically biotinylated at the C-terminal cysteine residue using EZ-Link Maleimide-$PEG_2$-Biotin (Thermo Scientific, Rockford, Ill.). To achieve this, a range of molar ratios (Maleimide-PEG2-Biotin-to-protein) were screened in a pilot experiment. MALDI TOF mass spectrometry was used to confirm the biotinylation of H-Ras-Cys. Proteins were diluted 10-fold in MALDI matrix (10 mg/mL α-Cyano-4-hydroxycinnamic acid dissolved in 50% acetonitrile and 0.1% trifloroacetic acid) and analyzed on 4800 Plus MALDI TOF/TOF Analyzer (AB SciEX). See FIG. 1A-1D. A 10 molar ratio excess of biotin reagent to protein was found to only label H-Ras-Cys (FIG. 1B) but not H-Ras (FIG. 1D). Under this condition, about 50% of H-Ras-Cys is biotinylated at a biotin-to-protein ratio of 10 to 1, as detected by mass spectrometry, while the H-Ras shows less than 10% biotinylation under the same conditions, indicating the biotin is added to the C-terminal Cys on H-Ras-Cys. The reaction was incubated on ice for 2 hours and then quenched by adding DTT to a final concentration of 1 mM. Biotinylated H-Ras-Cys was dialyzed overnight against TM buffer with 1 mM DTT and stored with 30 µM GDP in aliquots at −80° C.

5. Nucleotide Loading of Biotinylated H-Ras-Cys

The procedure for H-Ras-Cys nucleotide loading was adapted from Seabra M. C., 1996, The Journal of Biological Chemistry, 271, 14398-14404, the contents of which are incorporated herein by reference in their entirety.

Biotinylated H-Ras-Cys (1-3 mg) was diluted with TM buffer, and concentrated by ultrafiltration using a 10 KD centrifugal concentrator (Millipore, Billerica, Mass. UFC501096) to remove the free GDP in the storage buffer. The protein was mixed with equal volume of 2× Exchange buffer 1 (40 mM Tris-HCl, pH 7.5, 10 mM EDTA, 500 mM $(NH4)_2SO_4$, 2 mM DTT, and 0.1% NP-40) and 88 units of Alkaline Phosphatase-Agarose (Sigma P0762). The mixture was incubated at room temperature for 15 minutes with rotation. Then, GMPPNP (5'-Guanylylimidodiphosphate) (Sigma G0635; Guanosine 5'[β,γ-imido]triphosphate trisodium salt hydrate) was added to a final concentration of 680 µM and another 44 units of Alkaline Phosphatase-Agarose were added to the reaction, and the tube was incubated for another 30 min at room temperature.

The Alkaline Phosphatase-Agarose was removed from the reaction using spin filter tubes (Corning 8169), and the cleared protein was concentrated by ultrafiltration. The protein was then incubated with 500 µM GMPPNP or GDP in 1 ml Exchange buffer 2 (20 mM Tris-HCl, pH 7.5, 1 mM EDTA, 250 mM $(NH4)_2SO_4$, 1 mM DTT, and 0.05% NP-40) for 60 minutes at 4° C. with rotation. The protein was concentrated again by ultrafiltration, adjusted to 500 µl with Ras loading buffer (20 mM Tris-HCl, pH 7.5, 5 mM $MgCl_2$, 1 mM EDTA, 50 mM NaCl, 1 mM DTT, and 0.05% Tween-80), and incubated with 800 µM of GMPPNP or GDP at 4° C. overnight. Loaded H-Ras-Cys was quantified by DC Assay (Bio-Rad 500-0112), and stored in aliquots at −80° C. The content of nucleotide loaded onto H-Ras-Cys was determined by reverse phase HPLC.

Example 2

Characterization of GMPPNP Loaded Biotinylated H-Ras-Cys

1. HPLC Analysis of Nucleotide Loading

Figure 2A:
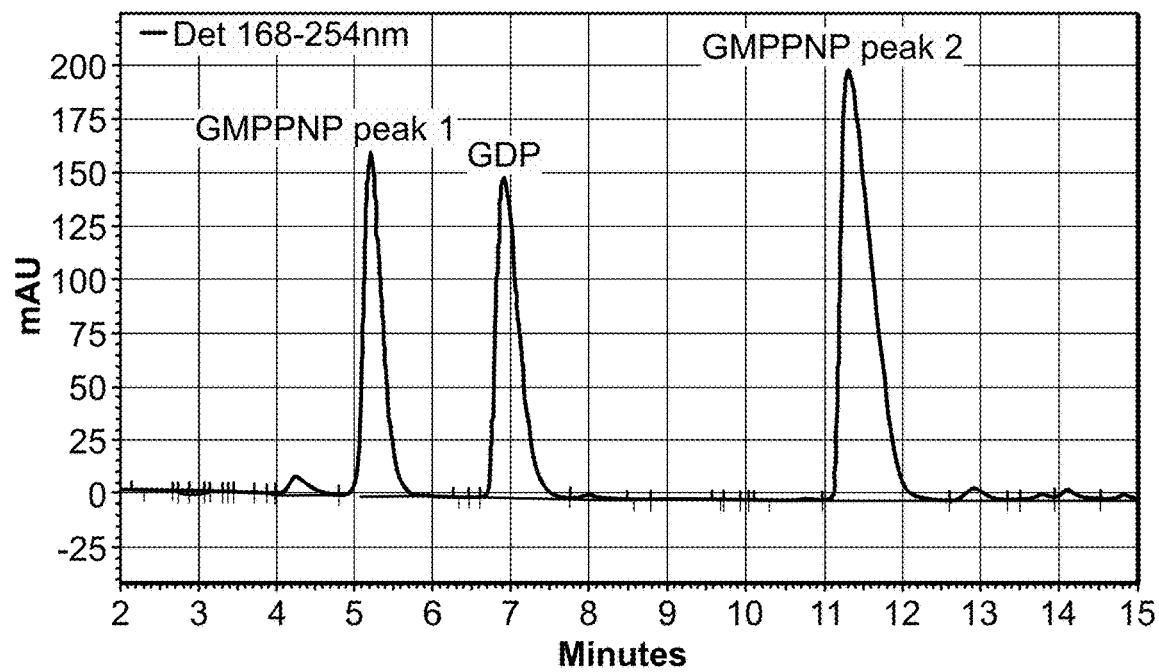
FIG. 2A-2C is a series of HPLC trace graphs showing the analysis of nucleotides extracted from H-Ras-Cys.
Figure 2B:
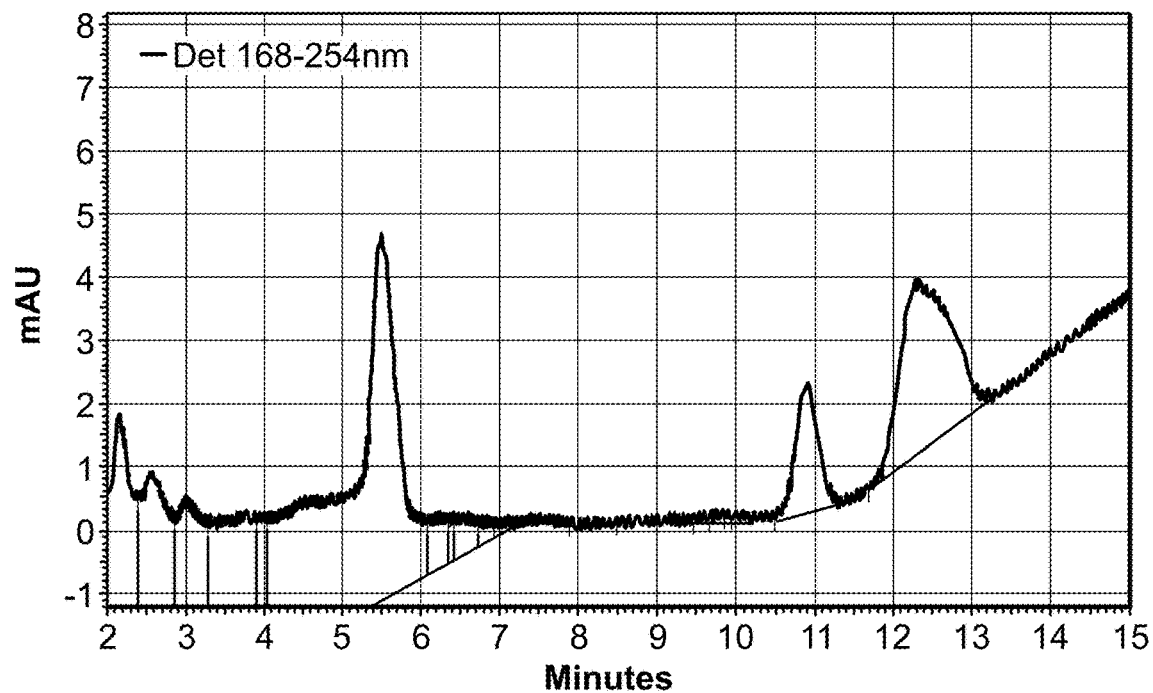
Figure 2C:
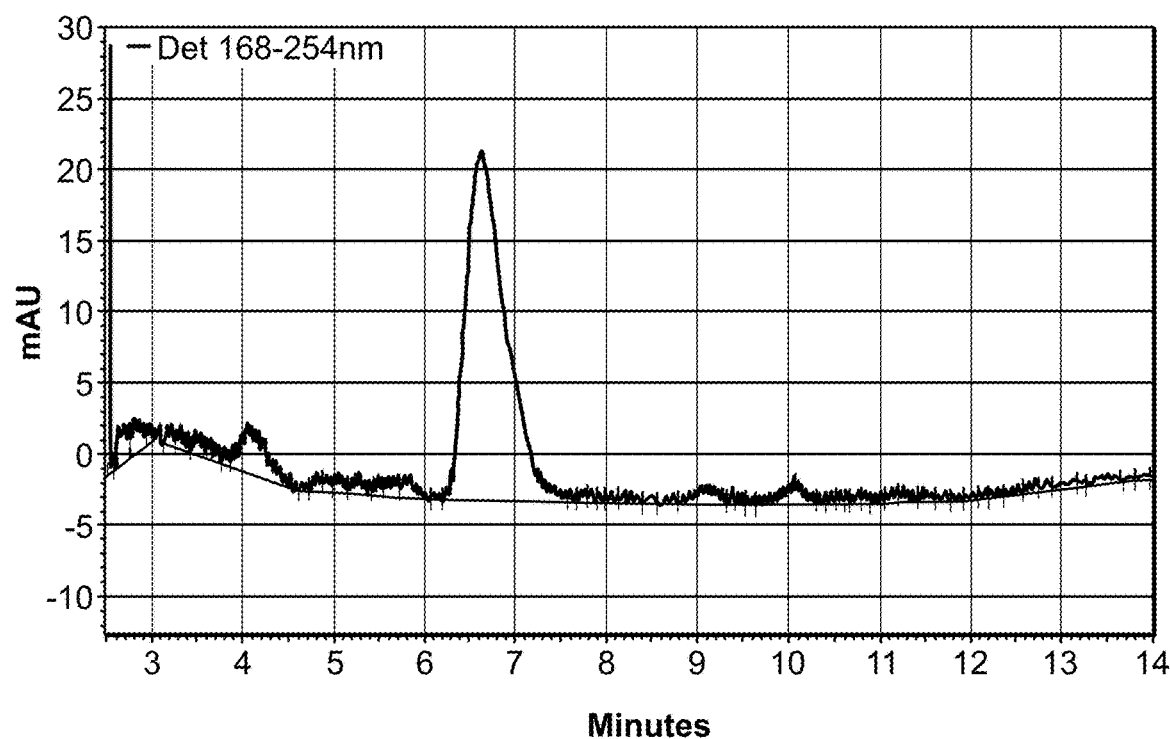

Nucleotide (GDP or GMPPNP) loaded H-Ras-Cys (100 µg) was diluted with TM buffer containing 1 mM DTT, and concentrated by ultrafiltration using a 10 KD centrifugal concentrator (Millipore, Billerica, Mass.) to remove free nucleotide and detergent. The protein was then boiled at 95° C. for 3 minutes to elute the nucleotides. For HPLC separation, eluted nucleotides (sample volume: 100 µL) were run on an Eclipse XDB-C18 reversed phase column (Agilent, Santa Clara, Calif.) equipped with a pre-column of the same material. The pre-column was used to adsorb denatured nucleotide-free Ras proteins. Nucleotides were resolved using an isocratic run of 7.5% acetonitrile in (10 mM tetrabutylammonium bromide, 100 mM $K_2HPO_4$/$KH_2PO_4$, pH 7.5) at 0.4 mL/min flow. Identity and retention times of the nucleotides were verified with GDP and GMPPNP standards (FIG. 2A-2B), and the identity and proportion of nucleotide (GMP or GMPPNP) bound to Ras could be readily ascertained by this assay.

2. Activity of GMPPNP Loaded H-Ras-Cys by GST-RAF-RBD Pull Down Assay

Figure 3:
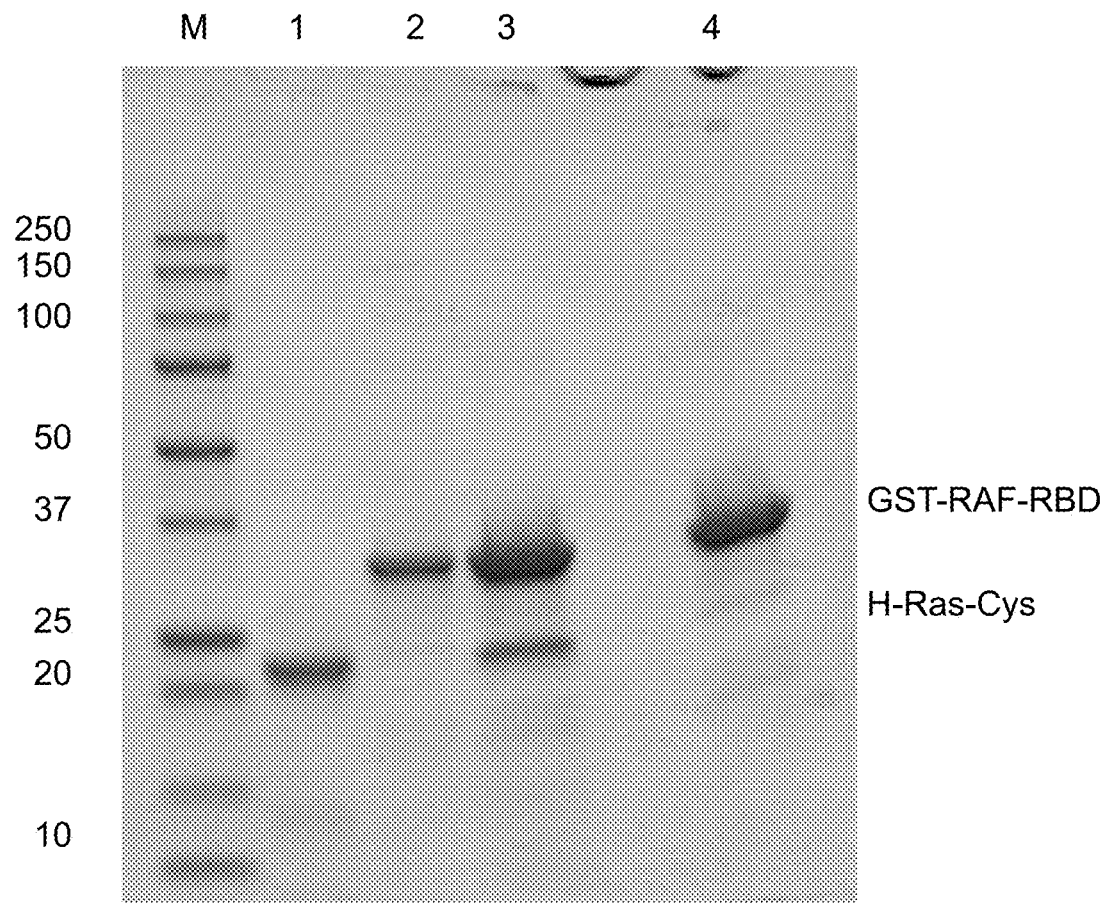
FIG. 3 is an image of a gel from a GST-RAF-RBD pull down assay showing the activity of GMPPNP loaded H-Ras-Cys.

50 μg GST fused RAF-RBD (Thermo Scientific 16117) was incubated with 14 μL of Glutathione Agarose beads (GE Healthcare) at 4° C. for 1 hour. The beads were washed four times with Ras loading buffer to remove the unbound GST-RAF-RBD. Then, 20 μg of GMPPNP or GDP loaded H-Ras-Cys was incubated with the immobilized GST-RAF-RBD in 500 μL Ras loading buffer at 4° C. for 1 hour. The beads were washed four times with 500 μl Ras loading buffer. Proteins were eluted by heating in 20 μl of SDS loading buffer at 95° C. for 5 minutes and analyzed by SDS-PAGE with Any-kD mini gel (Bio-Rad 456-9033). FIG. 3 shows that GMPPNP loaded H-Ras-Cys forms a complex with GST-RAF-RBD (lane 3), while GDP loaded H-Ras-Cys does not (lane 4). Other lanes shown include: M: Protein standards (Bio-Rad 161-0373); Lane 1: GMPPNP loaded H-Ras-Cys; and Lane 2: GST-RAF-RBD.

3. Activity of GMPPNP Loaded H-Ras-Cys by H-RAS Pull Down Assay

Figure 4:
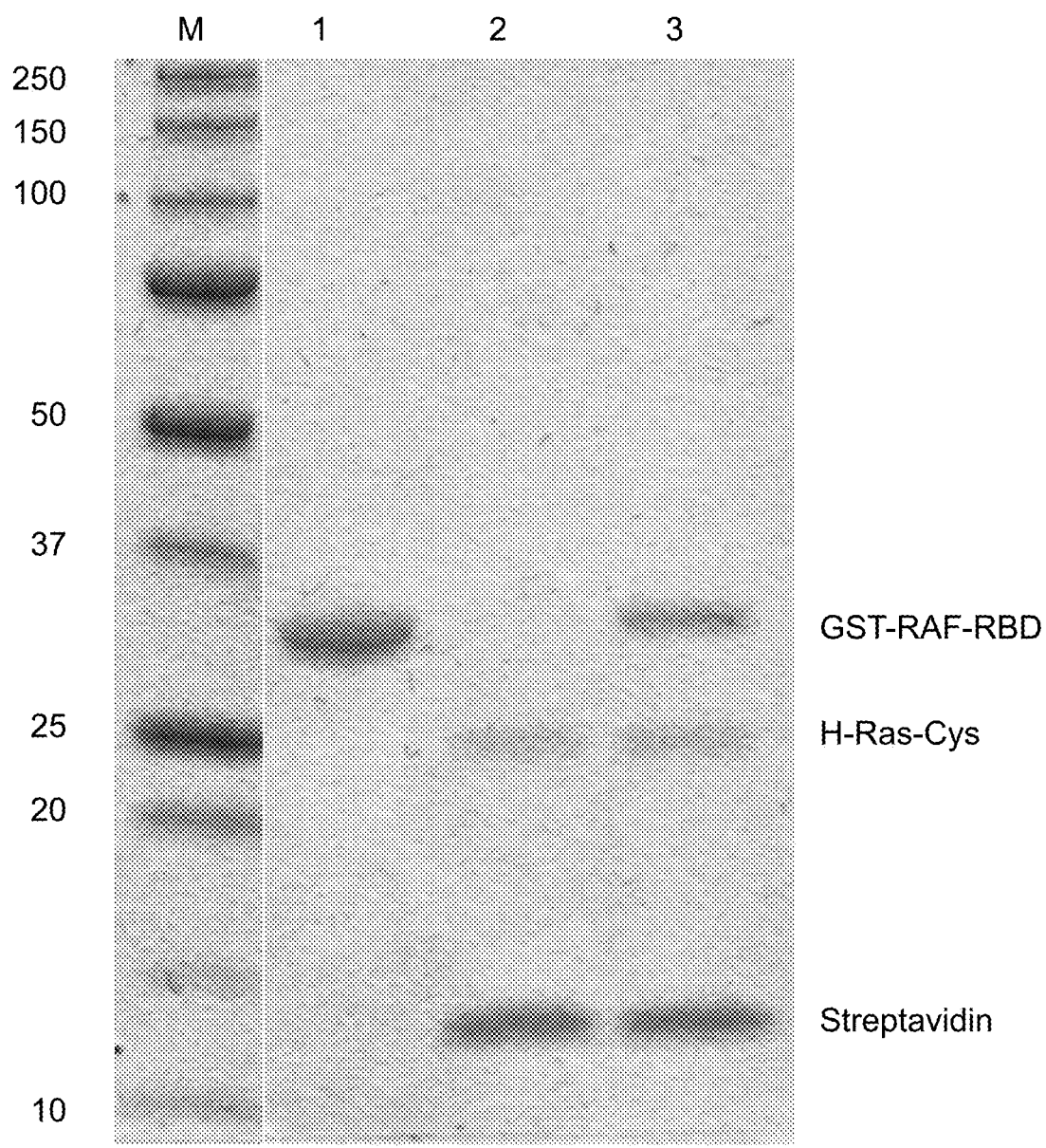
FIG. 4 is an image of a gel from an H-Ras-Cys pull down assay.

GMPPNP or GDP loaded biotinylated H-Ras-Cys (100 pmol) was immobilized onto 20 μL of Streptavidin Ultralink resin (Thermo Scientific 53114) at 4° C. for 1 hour. The free proteins were washed away in Ras loading buffer. Then, 300 pmol of GST-RAF-RBD was incubated with the immobilized H-Ras-Cys in 100 μl Ras loading buffer at 4° C. for 1 hour. The beads were washed four times with 500 μL Ras loading buffer. Proteins were eluted by heating in 20 μl of SDS loading buffer at 95° C. for 5 minutes and analyzed by SDS-PAGE with Any-KD gel (Bio-Rad 456-9033). An image of the analyzed gel is presented in FIG. 4. Lanes in the gel include: M: Protein standards (Bio-Rad 161-0373); Lane 1: GST-RAF-RBD; Lane 2: GST-RAF-RBD with GDP loaded H-Ras-Cys; and Lane 3: GST-RAF-RBD with GMPPNP loaded H-Ras-Cys. The results indicate that GMPPNP loaded H-Ras-Cys forms a complex with GST-RAF-RBD (lane 3), while GDP loaded H-Ras-Cys does not (lane 2).

4. Activity of GMPPNP Loaded H-Ras-Cys by Scintillation Proximity Assay

Scintillation Proximity Assay (SPA) technology permits the direct measurement of binding of one protein to another in a homogeneous assay format. GST-RAF-RBD was radioactively labeled with equivalent of N-succinimidyl (2, 3-$^3$H) propionate (Moravek Biochemicals cat. no. MT919) in 50 mM Hepes, pH 7.6, 150 mM NaCl, 1 mM DTT overnight at 4° C. The reaction was then quenched with 20 mM Tris-HCl, pH 7.5, and purified by gel filtration over a NAP-5 column (Pierce, Rockford, Ill.) equilibrated with Ras loading buffer containing 0.1% BSA.

Figure 5:
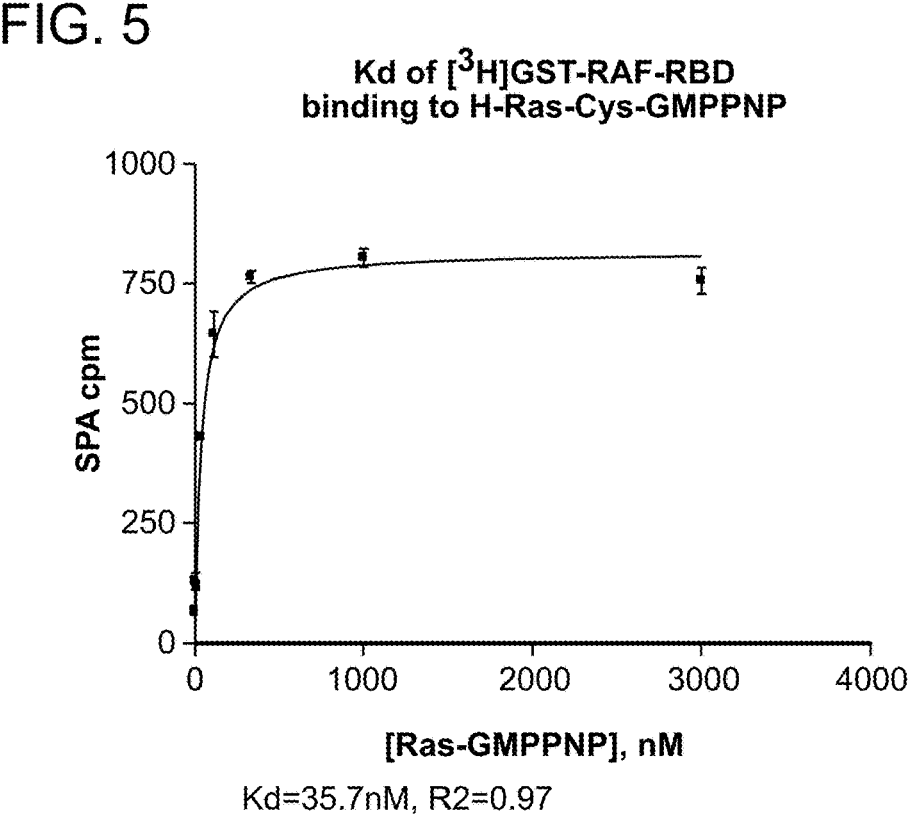
FIG. 5 is a series of plots from a Scintillation Proximity Assay (SPA) used to determine the equilibrium dissociation constants ($K_d$) for the complex of GST-RAF-RBD and H-Ras-Cys loaded with GMPPNP or GDP.
Figure 5:
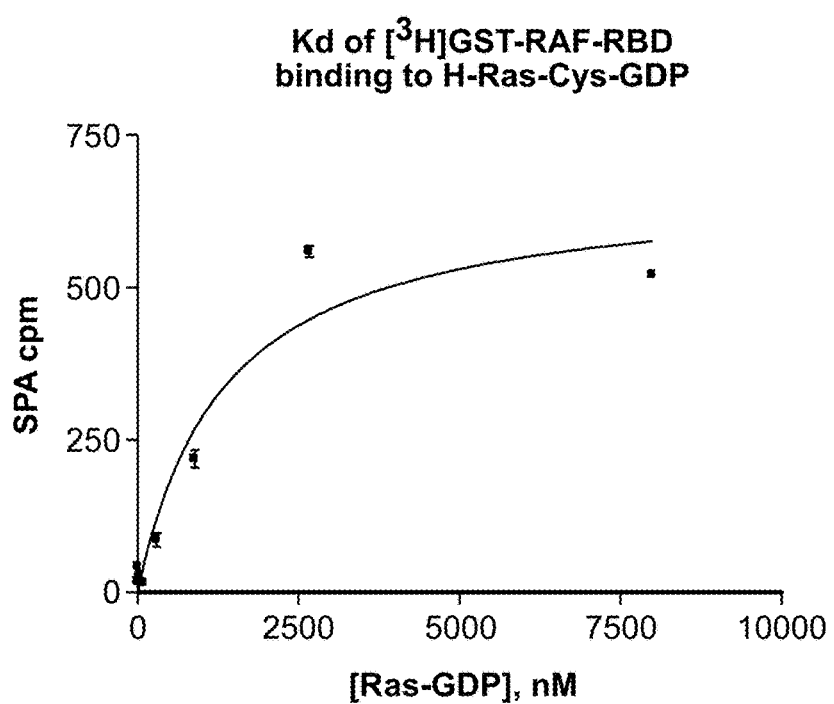

[$^3$H]GST-RAF-RBD and biotinylated H-Ras-Cys loaded with GMPPNP or GDP was added to 10 μg/μL Streptavidin polyvinyltoluene SPA beads (Perkin Elmer) in SPA assay buffer (50 mM Tris-HCl, pH 7.5, 4 mM MgCl$_2$, 2 mM DTT, 1 mg/ml bovine serum albumin, 0.0025% Tween-80). All experiments were run in Costar 96-well SPA plates using an assay volume of 100 μL. Typically, reactions included 25 nM [$^3$H]GST-RAF-RBD, and the indicated concentrations of biotinylated H-Ras-Cys loaded with GMPPNP or GDP. SPA plates were incubated for 1 h at room temperature under dark and counted in a TopCounter (Perkin Elmer). FIG. 5 shows that H-Ras-Cys loaded with GMPPNP binds GST-RAF-RBD with a Kd of 35.7 nM, while H-Ras-Cys loaded with GDP binds GST-RAF-RBD with a Kd of 1.34 μM.

Example 3

Figure 6:
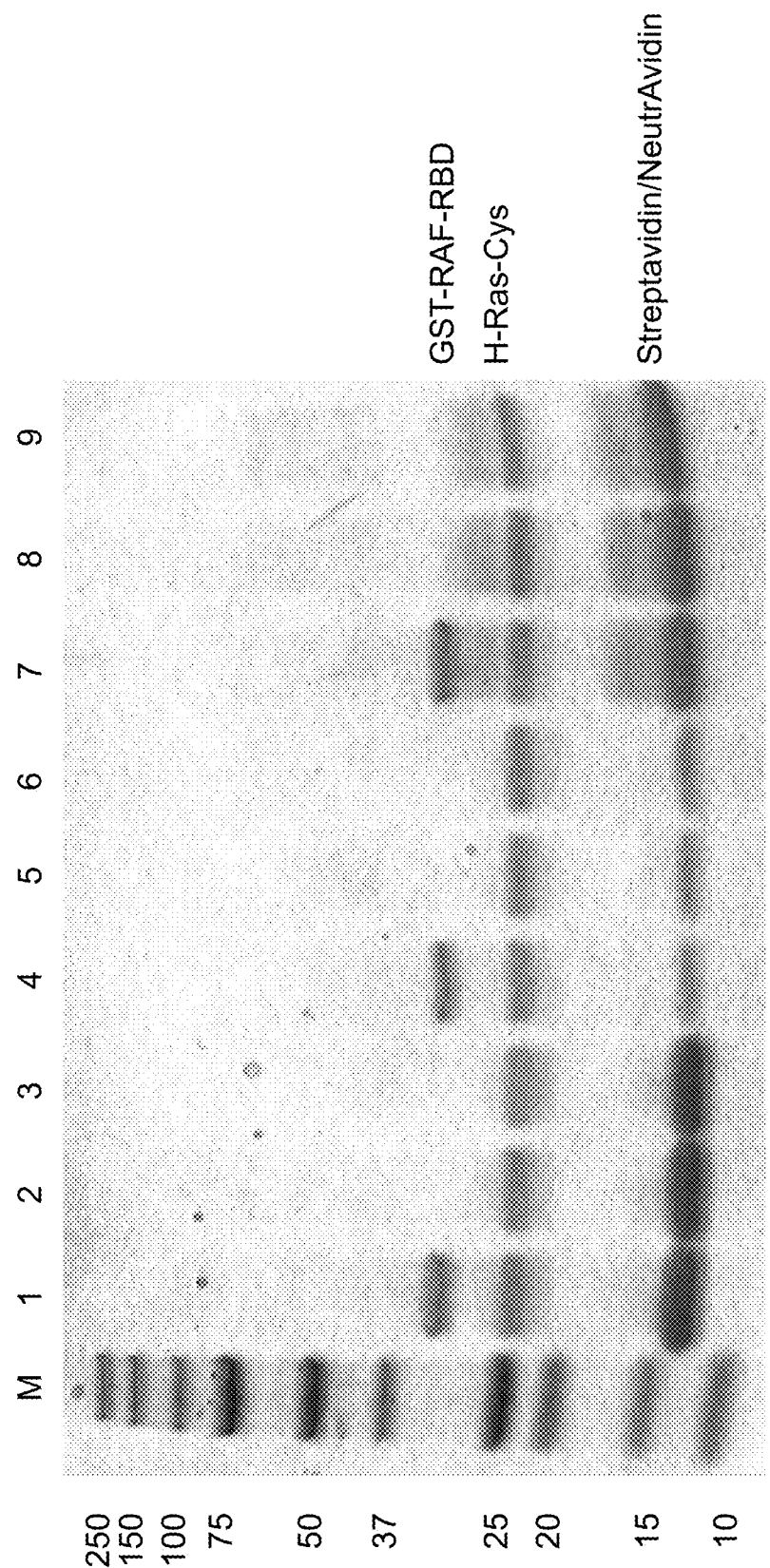
FIG. 6 is an image of a gel showing the capture of biotinylated H-Ras-Cys and the specific pull down of GST-RAF-RBD.

Capture of Biotinylated GMPPNP Loaded H-Ras-Cys by Beads and the Activity of Immobilized Protein The biotinylated H-Ras-Cys loaded with GMPPNP was tested for the immobilization on three types of resin and the ability to bind to GST-RAF-RBD. The resins were: Streptavidin Ultralink (Thermo Scientific 53114), Streptavidin Agarose (Thermo Scientific 20349), and NeutrAvidin Ultralink (Thermo Scientific 53150). Biotinylated H-Ras-Cys loaded with GMPPNP (388 pmol) was mixed with 20 μl slurry of each type of resin. The unbound protein was washed away after 1 hour incubation at 4° C. GST-RAF-RBD (290 pmol) was mixed with the immobilized H-Ras-Cys in 500 μL Ras loading buffer (containing 3 μM GMPPNP) and incubated for 1 hour at 4° C. Two controls were introduced to the binding assay, including a GST (290 pmol) control and a negative control. The beads were washed four times with 500 μL Ras loading buffer. Proteins were eluted by heating in 20 μL of SDS loading buffer at 95° C. for 5 minutes and analyzed by SDS-PAGE with Any-KD mini gel (Bio-Rad 456-9033). An image of the results is presented in FIG. 6. The lanes include: M: Protein standards (Bio-Rad 161-0373); Lane 1: H-Ras-Cys immobilized on Streptavidin Ultralink resin binds to GST-RAF-RBD; Lane 2: H-Ras-Cys immobilized on Streptavidin Ultralink resin does not bind to GST; Lane 3: H-Ras-Cys captured by Streptavidin Ultralink resin; Lane 4: H-Ras-Cys immobilized on Streptavidin Agarose resin binds to GST-RAF-RBD; Lane 5: H-Ras-Cys immobilized on Streptavidin Agarose resin does not bind to GST; Lane 6: H-Ras-Cys captured by Streptavidin Agarose resin; Lane 7: H-Ras-Cys immobilized on NeutrAvidin Ultralink resin binds to GST-RAF-RBD; Lane 8: H-Ras-Cys immobilized on NeutrAvidin Ultralink resin does not bind to GST; and Lane 9: Ras-Cys captured by Neutravidin Ultralink resin. The results indicate that all three resins were capable of capturing biotinylated H-Ras-Cys (lanes 3, 6, and 9), and immobilized H-Ras-Cys was capable of pulling down GST-RAF-RBD (lanes 1, 4, and 7). None of the resins with immobilized H-Ras-Cys were capable of binding GST (lanes 2, 5, and 8).

Example 4

Production of mRNA Display Library Containing Natural and Non-Natural Amino Acids and Selection of Polypeptides Ras inhibitors were identified through several rounds of mRNA display and selection. mRNA display was performed generally as described (Roberts, R. W., and Szostak, J. W. (1997). Proc. Natl. Acad. Sci. USA 94, 12297-12302; WO2009067191; herein incorporated by reference in its entirety). A library for the selection of natural peptides was prepared from eight individual libraries with a fixed cysteine codon in positions 5-13.

Recovery of the mRNA-displayed polypeptides was done using both Oligo dT and Ni-NTA affinity, to isolate fusion molecules containing both polyA mRNA and His tagged peptides. Oligo dT bead-bound peptides were then cyclized with dibromoxylene as described by others (J. Am. Chem.

Soc. 127:1 1727 (2005) the contents of which are incorporated herein by reference in its entirety).

Direct selection of the peptides by target affinity was then performed. mRNA-displayed polypeptides were allowed to bind for 1 hour at 4° C. to biotinylated protein in a 100 nM solution of biotinylated protein in PBST. The RNA corresponding to the affinity selected peptides was reverse transcribed and PCR amplified to create a double-stranded DNA pool. The DNA pool was in vitro transcribed to generate mRNA, and the mRNA produced was cross-linked as before at its 3' terminus with a puromycin-containing oligonucleotide. The mRNA-puromycin fusions were subjected to in vitro translation to generate the second round of the library, which is now enriched in peptides that bind Ras. The selection cycle was repeated for ten rounds. After the tenth round, the DNA pool representing the selected peptides was cloned and sequenced, and the amino acid sequences of candidate Ras inhibitors were determined based on the DNA sequences. The peptides identified are listed in Table 4.

TABLE 4

Peptide Sequences

| Compound Number | SEQ ID NO. |
| --- | --- |
| R4000 | 7 |
| R4001 | 8 |
| R4002 | 9 |
| R4005 | 10 |
| R4100 | 11 |
| R4101 | 12 |
| R4102 | 13 |
| R4103 | 14 |
| R4104 | 15 |
| R4105 | 16 |
| R4106 | 17 |
| R4107 | 18 |
| R4108 | 19 |
| R4109 | 20 |
| R4110 | 21 |
| R4111 | 22 |
| R4112 | 23 |
| R4113 | 24 |
| R4114 | 25 |
| R4115 | 26 |
| R4116 | 27 |
| R4117 | 28 |
| R4118 | 29 |
| R4119 | 30 |
| R4120 | 31 |
| R4121 | 32 |
| R4122 | 33 |
| R4123 | 34 |
| R4124 | 35 |
| R4125 | 36 |
| R4126 | 37 |
| R4127 | 38 |
| R4128 | 39 |
| R4129 | 40 |
| R4130 | 41 |
| R4131 | 42 |
| R4132 | 43 |
| R4133 | 44 |
| R4134 | 45 |
| R4135 | 46 |
| R4136 | 47 |
| R4137 | 48 |
| R4138 | 49 |
| R4139 | 50 |
| R4140 | 51 |
| R4141 | 52 |
| R4142 | 53 |
| R4143 | 54 |
| R4144 | 55 |
| R4145 | 56 |
| R4146 | 57 |

TABLE 4-continued

Peptide Sequences

| Compound Number | SEQ ID NO. |
| --- | --- |
| R4147 | 58 |
| R4148 | 59 |
| R4149 | 60 |
| R4150 | 61 |
| R4151 | 62 |
| R4152 | 63 |
| R4153 | 64 |
| R4154 | 65 |

Example 5

Characterization of Cyclic Peptidomimetics Binding Ras Protein

Surface Plasmon Resonance

Figure 7A:
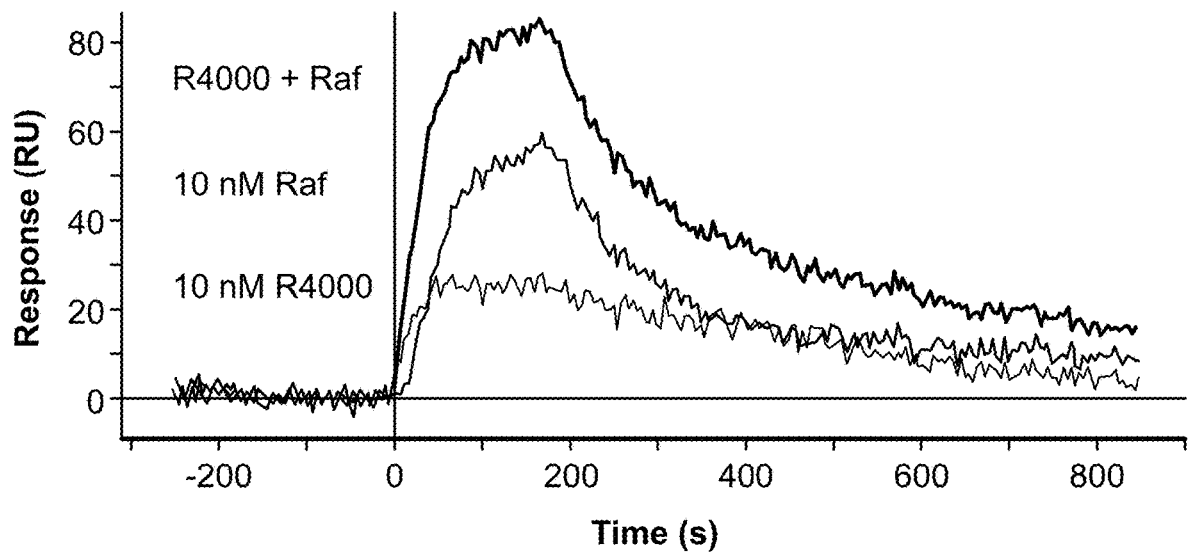
FIG. 7A is graph with results from surface plasmon resonance (SPR) analysis of peptide R4000, RAF, or R4000 and RAF binding to surface immobilized H-Ras-Cys.

Surface Plasmon Resonance (SPR) experiments were conducted at 25° C. using the ProteOn XPR36 system from BioRad Laboratories, Inc (Hercules, Calif.). His-tagged K-Ras (G12V) loaded with GDP or the non-hydrolyzable analog of GTP, GMPPNP, was immobilized by capture on a nickel (II)-nitrilotriacetate coated surface (immobilization/binding buffer: 20 mM Tris-HCl pH 7.5, 5 mM MgCl$_2$, 200 µM EDTA, 50 mM NaCl, 0.005% Tween-20, 1 mM DTT, 1 µM GDP or GMPPNP, 1% DMSO). Binding of the Ras binding domain of RAF (RAF-RBD) was used to evaluate the K-Ras surface. Kinetic characterization of cyclomimetic binding was performed to determine $k_{on}$, $k_{off}$, and $K_d$. R4000 was co-injected with RAF-RBD to evaluate competitive binding. Data analysis was performed using BioRad ProteOn Manager software. The kinetic parameters for peptide R4000 binding to K-Ras G12D loaded with GMPPNP were $5.7 \times 10^5$ Ms ($k_a$), $1.6 \times 10^{-3}$ s$^{-1}$ ($k_d$), and $2.8 \times 10^{-9}$ M ($K_d$). The corresponding values for K-Ras G12D loaded with GDP were $6.8 \times 10^5$ Ms ($k_a$), $3.0 \times 10^{-3}$ s$^{-1}$ ($k_d$), and $4.4 \times 10^{-9}$ M ($K_d$), indicating similar affinity for GDP and GMPPNP loaded K-Ras. FIG. 7A shows that RAF-RBD and R4000 binding to K-Ras yields additive signals, indicating that they bind to distinct sites on Ras.

Fluorescence Polarization Assay

Figure 7B:
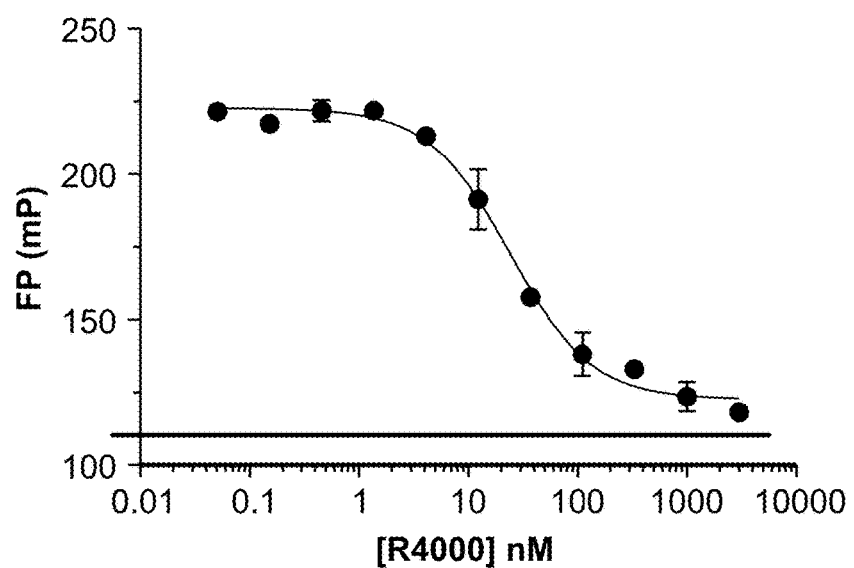
FIG. 7B is a graph showing results from fluorescence polarization analysis of R4000 binding to Ras.

R4000 was evaluated for competition with a TAMRA labeled probe (R4007) based on peptide R4000. The assay was performed in 384-well black, non-binding plates (Greiner Bio-One, Monroe, N.C.). GMPPNP-loaded H-Ras or GTP-loaded K-Ras, diluted in FP assay buffer (20 mM Tris-HCl, pH 7.5, 50 mM NaCl, 5 mM MgCl$_2$, 1 mM EDTA, 0.002% Triton-X-100) for a final concentration of 120 nM was incubated with 30 nM R4007 for 20 minutes at room temperature. R4000 was serially diluted, added to the assay and incubated for 60 minutes at room temperature. Fluorescence polarization was detected with a SpectraMax Paradigm plate reader (Molecular Devices, Sunnyvale, Calif.) using the Rhodamine FP detection cartridge (535 nm/595 nm). Data was analyzed using GraphPad Prism and Ki determined using One Site Ki Curve fitting model. Percent inhibition for each data point was calculated relative to the maximal binding control (absence of inhibitor, 0% inhibition) and the no binding control (absence of Ras, 100% inhibition of probe binding) and IC$_{50}$ determined by fitting data to a 4 parameter sigmoidal dose response curve fit. FIG. 7B presents a graph of results from the assay demonstrating that R4000 displaces R4007 with a half-maximal inhibitory concentration (IC$_{50}$) of 20 nM.

Differential Scanning Fluorimetry

Figure 8A:
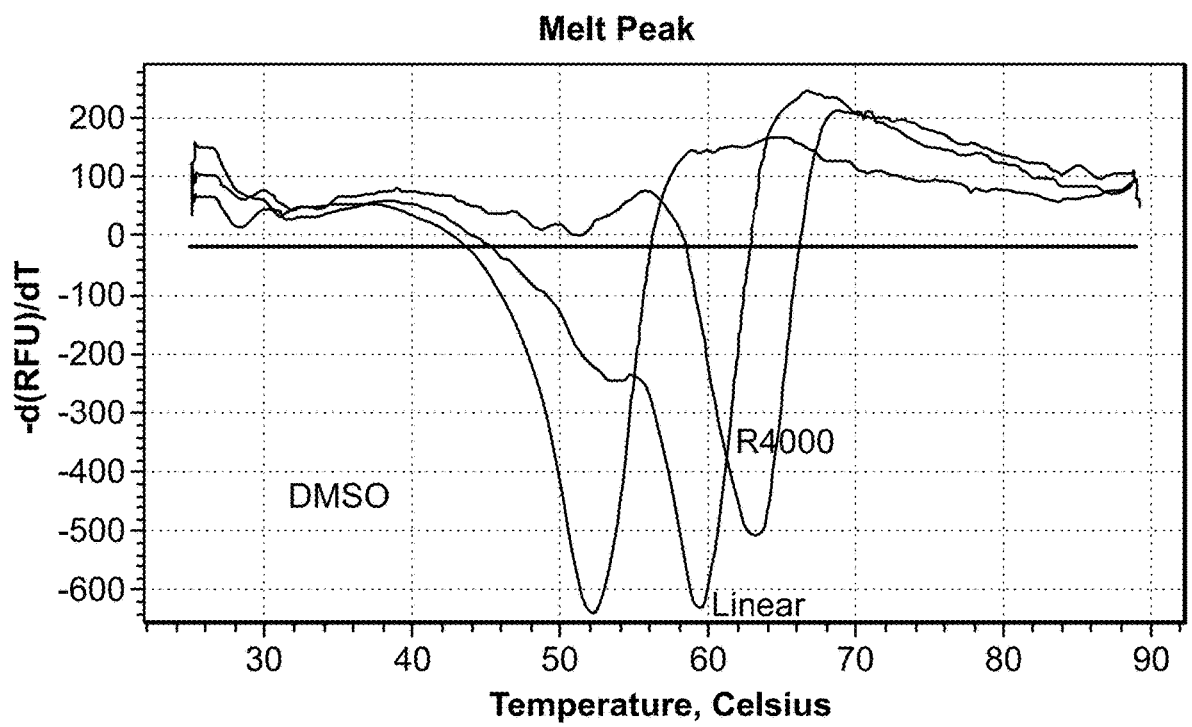
FIG. 8A is a Differential Scanning Fluorimetry (DSF) trace illustrating that peptide R4000 binds tightly to H-Ras and stabilizes Ras, with a Δ Tm=+11° C.

Differential scanning fluorimetry (DSF) is based on denaturation of the protein in the absence or presence of a ligand, exposing hydrophobic residues that can be detected with high sensitivity with a fluorescent dye. The melting temperature (Tm) of the protein is calculated from these data. DSF was performed on a CFX 96-well plate, real-time PCR instrument (Bio-Rad, Hercules, Calif.) according to Nettleship et al. [Nettleship, J. E., Brown, J., Groves, M. R., and Geerlof, A. (2008) Methods for protein characterization by mass spectrometry, thermal shift (ThermoFluor) assay, and multiangle or static light scattering. *Methods Mol. Biol.* 426: 299-318), the contents of which are incorporated herein by reference in their entirety]. SYPRO orange was purchased from Life Technologies (Carlsbad, Calif.). After incubation of Ras (5 µM) and peptide (20 µM) at room temperature for 15 minutes in 20 mM Tris-HCl (pH 8), 150 mM NaCl, 1 mM $MgCl_2$, 2 mM DTT, and 0.2% dimethyl sulfoxide, SYPRO orange was added to the final concentration of 10× (original stock at 5000×). The mixture was subsequently heated in Bio-Rad CFX 96 PCR instrument from 25 to 95° C. in increments of 0.3° C./10 s. Fluorescence intensity was measured using excitation and emission wavelengths of 483 and 610 nm, respectively. Changes in protein thermal stability (ΔTm) upon peptide binding were analyzed by using Bio-Rad CFX Manager Software provided by the manufacturer. FIG. 8A shows a Differential Scanning Fluorimetry (DSF) trace illustrating that peptide R4000 binds tightly to H-Ras and stabilizes Ras, with a Δ Tm=+11° C.

SOS-Mediated GTP Exchange

A sequence encoding the Ras exchanger motif and Cdc25 domains of human guanine nucleotide exchange factor SOS1 (amino acids 564-1049, designated as $SOS^{cat}$ hereafter) was synthesized at GeneArt (Life Technologies, Carlsbad, Calif.) and subcloned into the pET28a expression vector (Novagen, Darmstadt, Germany) for expression in *E. coli*. The identity of the expression construct was confirmed by DNA sequencing. The plasmid encoding $SOS^{cat}$ was transformed into BL21 (DE3). Cells were grown at 37° C. to an absorbance of 0.5 ($OD_{600}$) in LB media containing 25 µg/mL of kanamycin and then transferred to 20° C. prior to induction with 0.1 mM IPTG. Cells were harvested 15 hours after induction and the pellet was lysed with B-PER Bacteria Extraction Reagent (Pierce/Thermo Scientific, Rockford, Ill.) containing EDTA-free protease inhibitors. Cell lysates were incubated with Ni-nitrilotriacetate Agarose (Qiagen, Valencia, Calif.) for 1 hour at 4° C. and the Agarose was then packed into a Bio-Rad Econo column. After washing with 50 mM Tris-HCl, pH 8.0, 300 mM NaCl, 20 mM imidazole, bound $SOS^{cat}$ protein was eluted with 250 mM imidazole in the same buffer.

Figure 8B:
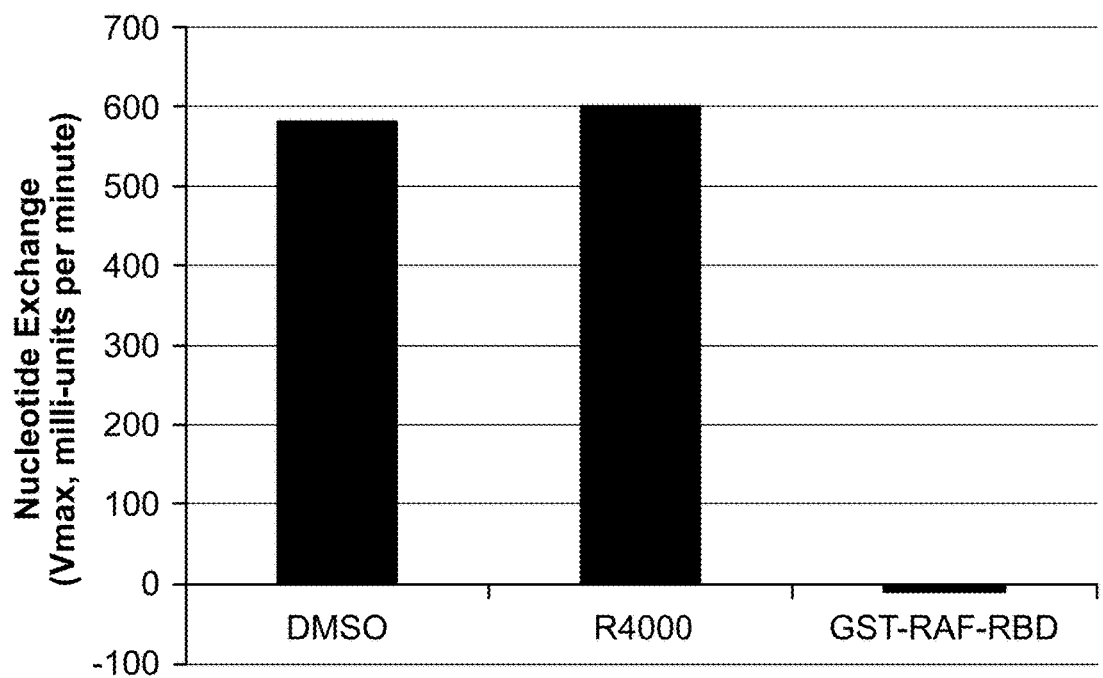
FIG. 8B is a graph showing the velocity of the SOS catalyzed nucleotide exchange in the presence of compound R4000 or control concentration of DMSO.

The $SOS^{cat}$ protein was then dialysed into a buffer containing 25 mM Tris-HCl, pH 7.5, 150 mM NaCl, 5 mM $MgCl_2$, and 1 mM DTT and stored at −80° C. The purity of the $SOS^{cat}$ protein was greater than 95% as assayed by SDS-PAGE with Coomassie brilliant blue staining. 1 µM H-Ras-GDP and 25 µM of R4000 or 2 µM of GST-RAF-RBD were pre-incubated for 30 minutes at room temperature in a buffer containing 40 mM Hepes-KOH, pH 7.4, 10 mM $MgCl_2$ 1 mM DTT, 1% DMSO, and 1 µM MANT-GMPPNP (Life Technologies, Carlsbad, Calif.). The $SOS^{cat}$ catalyzed nucleotide exchange was then initiated by addition of recombinant His-tagged $SOS^{cat}$ to a final concentration of 2 µM. Changes in fluorescence were measured by a fluorescence spectrometer (SpectraMax M3; Molecular Devices) in a black 96 half-area well plate (Corning 3686). Fluorescence was excited at λ=370 nm and emission was monitored at λ=450 nm every 20 s for over 30 minutes at 22° C. The nucleotide exchange rates were expressed as $V_{max}$ (milli-units per minute). FIG. 8B shows the velocity of the SOS catalyzed nucleotide exchange in the presence of compound R4000 or control concentration of DMSO. The compound does not effect the rate of exchange, while the RAD-RBD positive control nearly completely inhibits.

Time-Resolved Fluorescence Resonance Energy Transfer (TR-FRET)

Figure 8C:
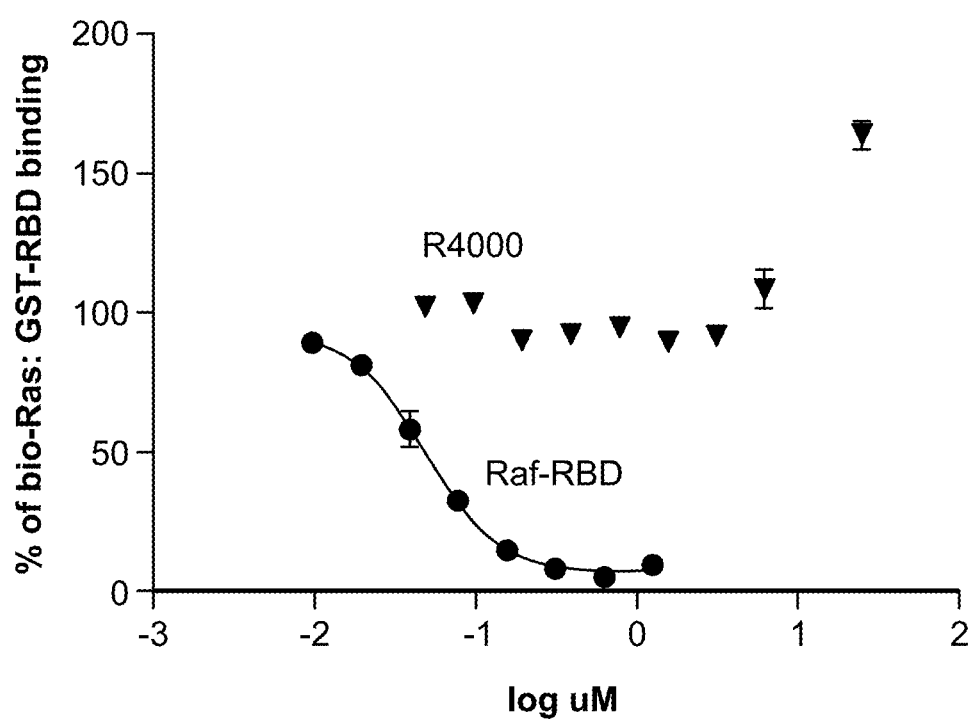
FIG. 8C is a graph showing percent binding between biotinylated H-Ras and GST-tagged RAF-RBD with increasing concentrations of R4000 or free RAF-RBD as determined using Time-Resolved Fluorescence Resonance Energy Transfer (TR-FRET) analysis.

The interaction between GST-tagged RAF-RBD and biotinylated H-Ras (Bio-H-Ras) loaded with GMPPNP was detected using TR-FRET. Assays were performed in 384 well plates (Proxiplate-384 plus, Perkin Elmer, Waltham, Mass.). Bio-H-Ras GMPPNP was diluted in assay buffer (50 mM Tris-HCl, pH 7.5, 5 mM $MgCl_2$, 0.0025% Tween-80, 1 mM DTT, and 50 nM GMPPNP) at a final concentration of 12.5 nM. R4000 was serially diluted in DMSO, then diluted in assay buffer and incubated with Bio-H-Ras GMPPNP for 30 minutes at room temperature (1% DMSO final). GST-RAF-RBD was added to the assay (10 nM final) and incubated 60 minutes at room temperature. Europium cryptate conjugated-anti-GST (donor; Perkin Elmer, Waltham, Mass.) and streptavidin conjugated to SureLight-Allophycocyanin (acceptor; Perkin Elmer, Waltham, Mass.) was added to the wells at final concentrations of 1 nM and 1.25 nM, respectively. Reaction mixtures were incubated at room temperature for 2 hours then detected using an EnVision Multilabel Plate Reader (Perkin Elmer, Waltham, Mass.) with excitation at 340 nm and emission at 615 nm (donor) and 665 nm (acceptor). FRET ratios (615 emission/665 emission) were calculated per well. Data was analyzed using GraphPad Prism, and $IC_{50}$ values were generated by fitting dose response data to a 4 parameter fit sigmoidal dose response curve. Percent binding between biotinylated H-Ras and GST-tagged RAF-RBD with increasing concentrations of R4000 or free RAF-RBD is shown in FIG. 8C. These results indicate that R4000 does not block binding to RAF, whereas free RAF-RBD does block binding with a half-maximal inhibitory concentration ($IC_{50}$) of 49 nM.

Example 6

Crystallography and Identification of the Binding Site of Compound R4000

A co-crystal structure of R4000 with mutant K-Ras-GDP revealed that this compound binds a novel site in the C-terminus of the Ras G-domain. This surface presents as a relatively flat featureless region of the protein. Binding of the pepetide at this site is not expected to interfere with RAF binding, GTPase, or nucleotide exchange.

Figure 9:
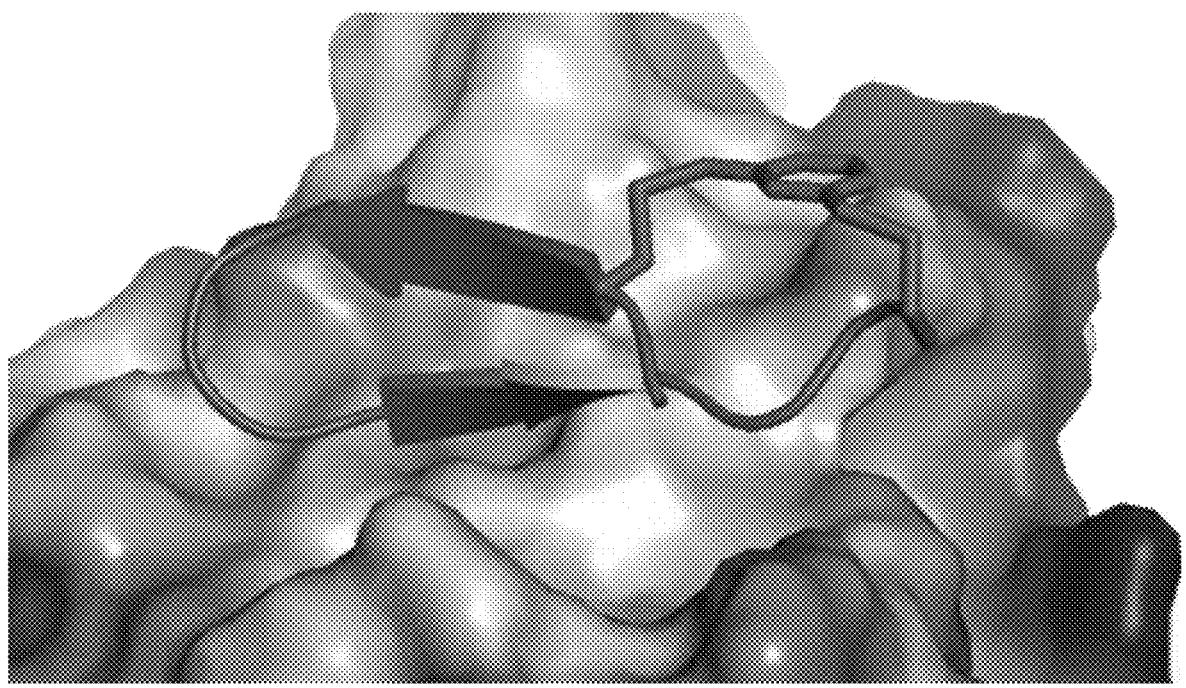
FIG. 9 is an illustration showing a portion of a co-crystal structure of R4000 with mutant K-Ras.

When bound to Ras the peptide forms a β-hairpin with an extensive network of intramolecular hydrogen bonds that are predicted to reduce interactions with water and may help to explain the intrinsic cell permeability of these molecules. The peptide binding surface on Ras is shown in FIG. 9. The bound peptide is shown in ribbon format, with the antiparallel strands of the β-hairpin represented as wide arrows and random coil regions as thinner ropes. The Cysteine side chains and the intervening xylene cyclization moiety are shown as sticks.

Example 7

Modifications of R4000

Figure 10:
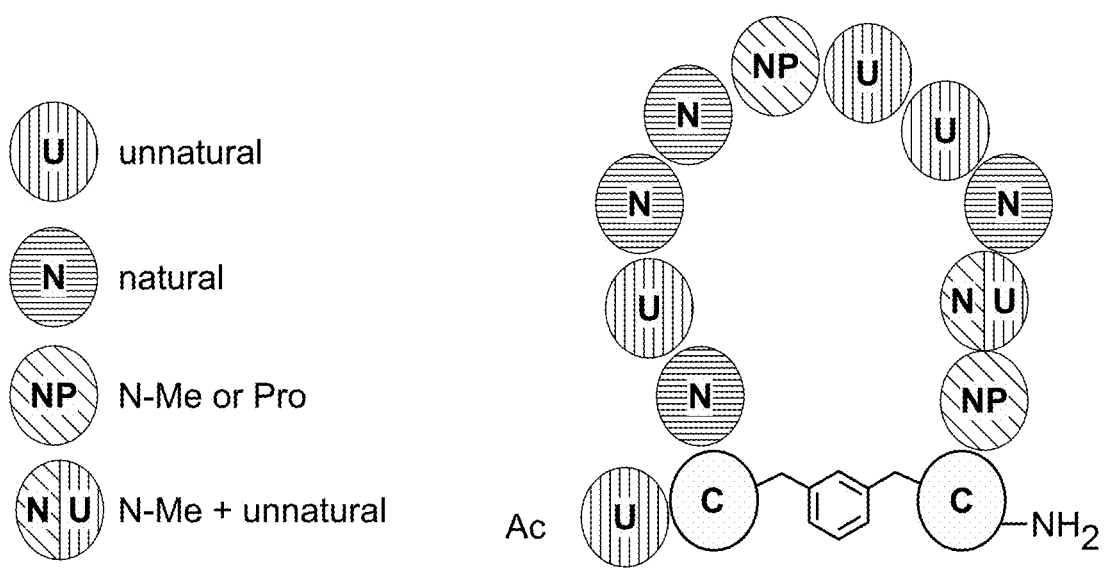
FIG. 10 is a schematic of general construct features of some embodiments of Ras binding polypeptides of the present disclosure.

FIG. 10 is a schematic of the general construct features of some Ras binding peptides or peptidomimetics of the present disclosure. The construct shown is 13 amino acids in length and cyclic. Other Ras binding peptides or peptidomimetics may be of differing lengths and may be linear or be conjugated to one or more biological moieties or molecules, such as lipids or other peptides.

Conjugation with a Fatty Acid Group

Peptides of the present invention are conjugated with one or more lipid moieties or fatty acid groups. Such modifications act to alter the distribution of the peptide in lipid bilayers or membranes such that access and/or binding to one or more Ras proteins is altered, thereby altering the concentration, binding properties and/or Ras signaling pathways.

Introduction of a Strong Electrophile Suitable for Covalent Cross-Linking

Peptides of the present invention are modified with one or more electrophiles suitable for cross-linking, whether to free thiols or to other groups. Such modifications act to alter the binding properties of the peptides to Ras proteins such that access and/or binding to one or more Ras proteins is made permanent, thereby altering the concentration, binding properties and/or Ras signaling pathways. The conversion of molecules that reversibly bind drug target proteins to irreversible covalent modifers by the rational introduction Cysteine reactive electrophiles is often employed to improve target residence time and prolong exposure by reducing clearance or "wash out". This strategy can also increase target selectivity. (Sing, et. al, 2011, Nature Reviews Drug Discovery, 10, 307-317).

Introduction of a Chemical Moiety for Inducing Proteosome-Mediated Degradation of Intracellular Ras Peptides of the present invention are modified with one or more chemical moieties for inducing proteasome-mediated degradation of intracellular Ras. Such modifications act to alter the concentration of Ras thereby altering Ras signaling pathways. Buckley and Crews, 2014, Small-Molecule Control of Intracellular Protein Levels through Modulation of the Ubiquitin Proteosome System, Angewandte Chemie International Edition, 53(9), 2312-2330.

Introduction of a Ras CAAX Motif for In Vivo Lipidation

Peptides of the present invention can be modified with the CAAX lipidation motif from the C-terminal hypervarialble region of Ras, which will be processed in the same manner as the CAAX motif of Ras: farnesylated or gerenylgerenylated on the cysteine (C), cleaved by Ras converting enzyme 1 (Rce1), and carboxymethyated by isoprenylcysteine carboxylmethyltransferase 1 (ICMT1). The CAAX motif from K-Ras 4B is CVIM (SEQ ID NO: 74) where V, I, and M are the one letter codes for Valine, Isoleucine, and Methionine, respectively, and is attached to the C-terminus of R4000. A flexible linker, such as three consectutive glycine residues, may be required between R4000 and CVIM (SEQ ID NO: 74) to displace the CAAX motif from R4000.

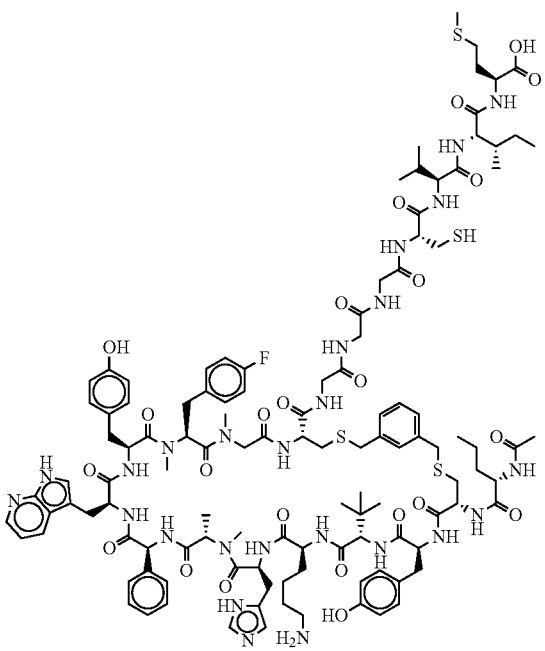

The ability of peptides of the present invention modified with a CAAX motif to enter cells and undergo Ras-like processing can be assessed by mass spectrometry. The peptide is diluted into cell culture medium, during which time it enters cells, is farnesylated or gerenylgerenylated, the CV peptide bond cleaved by Rce1, and the carboxyterminus methylated by ICMT1. Cells are harvested, cell lysates prepared, and lysates are analysed for ions with the mass of the fully processed derivative, intermediates, and parent compound.

Example 8

Cell-Based Characterization of Ras Binding Cyclic Peptidomimetics

Cell Permeability by Monitoring Intracellular Fluorescence

Figure 11:
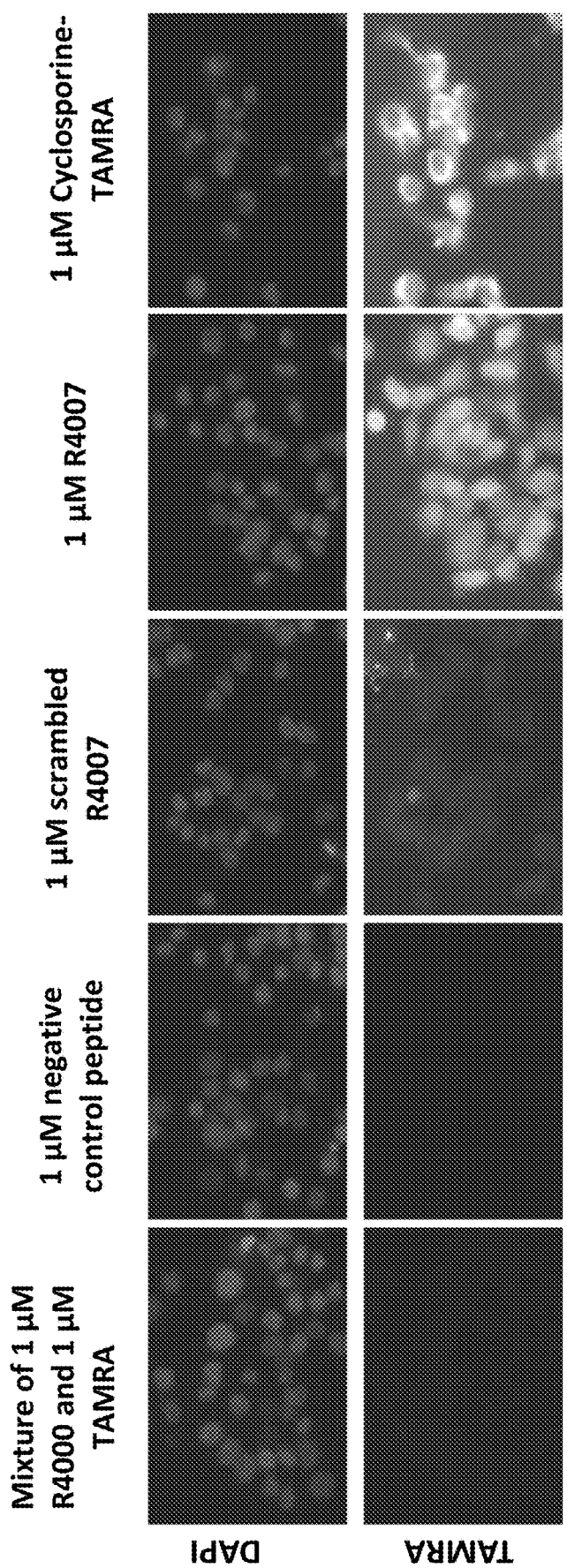
FIG. 11 is a series of photographic images showing the cell permeability of R4000 and R4007 (a TAMRA-labeled R4000 derivative) using TAMRA and DAPI stains.

Cell permeability of R4007 (a TAMRA-labeled R4000 derivative) was determined in the human lung cancer cell line H358 (ATCC, Manassas, Va.). Cells were maintained in RPMI-1640 with 10% FBS at 37° C., 95% relative humidity, 5% $CO_2$. For experiments, cells were seeded at 50,000 cells/well in growth media on 96-well glass bottom plates (Greiner, Monroe, N.C.) and incubated 24 hours prior to treatment. Media was removed from cells and replaced with indicated treatment solutions prepared in serum-free media (0.1% DMSO final). Cells were treated for 3.5 hours, then washed 3 times with PBS, fixed with 4% formaldehyde in PBS for 5 minutes at room temperature, and washed 3 times with PBS. Cell nuclei were stained with 1 µg/ml DAPI nuclear stain for 5 minutes at room temperature. Images were captured using a Zeiss Axio Observer inverted microscope with 63× oil objective with excitation 365 nm/emission 445 for DAPI and excitation 565 nm/emission 620 for TAMRA. Results are presented in FIG. 11. TAMRA signal was much stronger in cells treated with R4007 as compared to negative control and cells treated with scrambled R4007.

Ras Signaling

The effect of polypeptides on Ras signaling is determined by monitoring the activities, states, or levels of various proteins in Ras signaling pathways in cells treated with polypeptides. Common methods used to assess the effect of compounds on the levels of Ras signaling in cells include quantification of phosphorylated extracellular signaling-related kinase protein (phospho-ERK) levels using an anti-phospho-ERK monoclonal antibody in Western blot, ELISA (Abcam, Cambridge, Mass.), HTRF (Csbio, Bedford, Mass.) or Alpha Screen (Perkin Elmer, Waltham, Mass.) assays. Alternatively, a Ras-ERK pathway luciferase reporter cell assay could be used (BPS Biosciences, San Diego, Calif.) to monitor the effect of polypeptides on Epidermal Growth Factor (EFG) stimulation of the Ras pathway.

8C. Cell Proliferation

Effect of polypeptides on cell proliferation is determined by cell proliferation assay. Proliferation of H358 cells is determined following 72 hour exposure to peptides. Cells are seeded at 10,000 cells per well in 96 well tissue culture plates in growth media and allowed to adhere overnight. Peptides are serially diluted in DMSO then diluted in growth media for a constant final DMSO concentration of 1%. Media is removed from cells and replaced with treatment solutions and cells are incubated 72 hours prior to analysis. Brightfield images are captured then cell number assessed using the CyQuant NF assay kit (Life Technologies, Carlsbad, Calif.) to quantify cellular DNA content, as per manufacturer's protocol. Fluorescence is detected using a Molecular Devices Spectramax M4 at excitation 485 nm/emission 530 nm. Data are analyzed and $EC_{50}$ values determined by fitting dose response data to a 4 parameter sigmoidal dose response curve fit.

Colony Formation in Soft Agar

Soft agar assays are performed with H358 cells and HT1080 cells in an abbreviated (7 day) assay format or an extended (10-30 day) assay format. For the abbreviated assay, plates are prepared by adding 0.6% Bacto Select Agar (BD Biosciences, San Jose, Calif.) in media (DMEM for HT1080 or RPMI-1640 for H358 cells) at 55° C. to 96-well tissue culture treated plates (Corning, Corning, N.Y.). Plates are cooled to room temperature, and stored at 4° C. for up to 7 days. On day one of the assay, a cell suspension is prepared in media with test peptides and 0.4% Bacto Select Agar and seeded onto prepared agar plates. Plates are incubated at 37° C. with 95% relative humidity and 5% $CO_2$ for 7 days. Media containing 0.6% Bacto Select Agar and peptides are added to plates on day 3 after seeding. After 7 days incubation, colonies are visualized and counted and cell proliferation assessed by alamar blue staining (AbD Serotec, Oxford, UK) as described in the manufacturer's protocol. The plates are read using a Molecular Devices SpectraMax M4 (Sunnyvale, Calif.) with excitation at 530 nm and emission at 590 nm.

The extended assay is performed in 6 well tissue culture treated plates (USA Scientific, Orlando, Fla.). Plates are prepared by adding 0.5% Bacto Select Agar in media at 55° C. and cooling to room temperature. Cell suspensions are prepared in media with 0.35% Bacto Select Agar at 45° C. and added to the bottom layer of agar. The cell layer is cooled to room temperature to solidify. Treatment solutions prepared in media are added and plates are incubated at 37° C., 5% $CO_2$, and 95% relative humidity for 10 to 30 days. During this incubation, cells are fed twice per week with media containing the appropriate treatment condition. To detect colony formation, cells are stained with 0.005% crystal violet (Sigma-Aldrich, St. Louis, Mo.) for 1 hour and colonies are visualized and counted using Zeiss Axio Observer inverted microscope.

Example 9

Incorporation of Cell Penetrating Peptides

Some polypeptides are conjugated to peptides that have cell penetrating properties. These polypeptides [listed in Table 5 and described in Milletti, F., Cell-penetrating peptides: classes, origin, and current landscape. Drug Discov Today. 2012 August; 17(15-16):850-60, the contents of which are incorporated herein by reference in their entirety] are used to affect intracellular Ras signaling and/or trafficking.

TABLE 5

Cell penetrating peptides

| Cell penetrating peptide | SEQ ID NO |
|---|---|
| RKKRRRESRKKRRRES | 66 |
| RKKRRQRRR | 67 |
| RQIKIWFQNRRMKWKK | 68 |
| AAVLLPVLLAAP | 69 |
| VPTLK | 70 |
| PLILLRLLRGQF | 71 |

Example 10

Ras Dimer Crosslinking

Inhibition of Ras dimer formation is monitored through the cross-linking of lipidated Ras constructs immobilized on phosphatidylcholine liposomes. Liposomes are prepared as described in Inouye et al., Journal of Biological Chemistry 2000 275 (6), 3737-3740, the contents of which are incorporated herein by reference in their entirety. Briefly, phosphatidylcholine dissolved in chloroform is dried under nitrogen gas and resuspended in buffer by sonication. Large vesicles are removed by centrifugation, and smaller vesicles remaining in the supernatant are incubated with lipidated Ras for 2 hours at 4° C. for protein immobilization. The mixture is then ultracentrifuged and the pellet is resuspended in HEPES/NaOH (pH 7.4, 20 mM), $MgCl_2$ (5 mM), DTT (1 mM) and sucrose (250 mM). The resulting liposome suspension is incubated with a homobifunctional amine-reactive cross-linker (Ethylene glycol bis[succinimidylsuccinate], EGS, 2 mM) for one hour at 4° C. Samples are monitored by MALDI-MS or subjected to SDS-polyacrylamide gel electrophoresis followed by Western blotting using an anti-Ras antibody. In addition to monomeric Ras, the cross-linking of Ras by EGS results in the appearance of another band corresponding to the molecular weight of dimerized Ras. Incubation with peptides inhibiting dimer formation during the cross-linking step will result in a decrease in intensity of the dimeric Ras band.

Ras Dimer Formation by FRET Monitoring

Inhibition of Ras dimerization in liposomes can also be monitored by measuring the decrease in energy transfer between two fluorescent labels attached to individual Ras monomers. In this experiment, lipidated Ras monomers are loaded with Mant-GMPPNP (FRET donor, Jena) or TNP-GMPPNP (FRET acceptor, Jena) as described by Guldenhaupt et al., (Biophysical Journal 2012 103(7), 1585-1593, the contents of which are incorporated herein by reference in their entirety) and immobilized in phosphatidylcholine liposomes. The disruption of Ras dimers can then be monitored as a decrease in FRET efficiency between the two fluorophores.

Ras Protein Fragmentation Complementation Assay

A protein-fragmentation complementation assay is carried out to monitor the inhibition of Ras dimer formation in intact cells. Two deletion mutants of β-gal, Δα and Δω, are fused to the N-terminus of Ras and transiently expressed in HEK293 cells. Cells are then fixed and incubated with X-gal to monitor β-galactosidase activity resulting from Ras dimerization. The formation of Ras dimers brings Δα and Δω in close proximity, so that the co-expression of both mutants restores β-gal activity. Inhibition of dimer formation is observed (as indicated by a decrease in blue, β-gal-positive staining) in the presence of compounds of the invention that act as Ras inhibitors.

Example 11

Solid Phase Synthesis of Peptides

Automated solid phase peptide synthesis was performed on a CEM microwave peptide synthesizer. Rink Amide MBHA resin was purchased from Novabiochem. Reactions were typically performed at the 0.25 mmole scale.

Every synthesis cycle includes: Fmoc amino acid deprotection by 20% piperidine in DMF (75° C. microwave assisted heating, 3 min) and coupling with Fmoc protected amino acid/HATU/DIEA (5, 5, and 10 equiv respectively; 75° C. microwave assisted heating, 5 min). Cycles of FMOC deprotection and FMOC amino acid coupling were repeated with the desired monomers until the full linear peptide was formed. When required a final acylation step was performed using acetic anhydride (15% in DMF; 25° C. for 10 min). Cleavage from the resin was performed at room temperature using a cocktail (TFA/water/TIS/DTT, 92.5:2.5:2.5:2.5; 2 h). Peptides were precipitated from the cleavage solution using cold diethyl ether (80 mL), and collected by centrifugation. The crude peptide was washed with cold diethyl ether (2×), and blown dried by a stream of nitrogen gas.

Peptide Cyclization

After solid phase synthesis, crude peptides were dissolved in acetonitrile/water (1:2, v/v, 100 mL, degassed), $NH_4HCO_3$ (200 mM solution in $H_2O$, degassed) was added to adjust the pH to 8, followed by dropwise addition of α,α'-dibromo-m-xylene (0.1 M in acetonitrile, 1 equiv). The resulting mixture was stirred at r.t. for 1 hour and quenched by addition of trifluoroacetic acid.

Peptide Purification

Peptides were purified by RP-HPLC, luna 10μ-PREP C18(2), 100 Å, AXIA packed, column size 250×50 mm. Mobile phase A=0.1% TFA in water, mobile phase B=0.1% TFA in acetonitrile, gradient used was 15 to 45% B over 40 min, flow rate was 50 mL/min, UV wavelength λ=214 nm. UV absorbing fractions were collected and the fractions containing product were confirmed by LC/MS, combined and dried by lyophilization.

Example 12

Dibromoxylene Cyclization

A 100 mL flask is charged with acetonitrile (12 mL) and water (24 mL) and is degassed with argon for about 5 min. Linear peptide (0.01 mmole) and 200 mM ammonium bicarbonate (6 mL) are added followed by at least one compound (0.012 mmole) such as, but not limited to, 1,3-bis(bromomethyl) benzene, 1,2-bis(bromomethyl)benzene, 1,4-bis(bromomethyl)benzene, 2,6-bis(bromomethyl) pyridine, (E)-1,4-dibromobut-2-ene. The reaction mixture is stirred under argon at room temperature for approximately 2 hours and monitored by LC-MS. After the reaction is complete, the reaction solution is frozen and lyophilized. HPLC purification of the crude lyophilized product followed by lyophilization of fractions containing pure peptide results in the final cyclized product as a white power.

Example 13

Analysis of Compound Stability in Plasma

Compounds were assayed for stability in mouse and rat plasma under the following conditions. Plasma was adjusted to pH 7.4. DMSO stocks at 10 mM concentration were prepared for the test compounds. Aliquots of the DMSO solutions were dosed into 1 mL of plasma, which had been pre-warmed to 37° C., at a final test compound concentration of 10 μM. The vials were kept in a benchtop Thermomixer® (Eppendorf, Hauppauge, N.Y.) for the duration of the experiment. Aliquots (100 μL) were taken at each timepoint and added to a 96-well plate that had been pre-filled with 300 μL of an acetonitrile solution containing mixture of the internal standards (metoprolol, propranalol and warfarin each at 500 ng/mL). Samples were stored at 4° C. until the end of the experiment. After the final timepoint was sampled, the plate was mixed and then centrifuged at 3,000 rpm for 10 minutes. Aliquots of the supernatant were removed and analyzed by LC-HRAMS. Liquid chromatography settings are listed in Table 6 and mass spectrometry settings are listed in Table 7.

TABLE 6

| Liquid chromatography settings | |
|---|---|
| Column: | Luna C18 (Luna, Torrance, CA) 50 mm × 2.0 mm, 3 μm |
| M.P. Buffer: | Aqueous Reservoir (A): 0.1% Acetic acid in water Organic Reservoir (B): 0.1% Acetic acid in MeOH:MeCN = 1:1 |

| Gradient Program: | Time (Min) | Flow rate (mL/min) | % A | % B |
|---|---|---|---|---|
| | 0.0 | 0.3 | 100 | 0 |
| | 5 | 0.3 | 0 | 100 |
| | 7.5 | 0.3 | 0 | 100 |
| | 7.6 | 0.45 | 100 | 0 |
| | 10.5 | 0.3 | 100 | 0 |

| | |
|---|---|
| Total Run Time: | 10.5 minutes |
| Autosampler: | Agilent 1100 Bin (Agilent, Santa Clara, CA) |
| Injection loop volume: | 20 μL |
| Injection volume: | 10 μL |
| Autosampler Wash 1: | Methanol/water 1:1; with 0.2% formic acid |
| Autosampler Wash 2: | Methanol/2-propanol:1/1; with 0.2% formic acid |

TABLE 7

| Mass spectrometry settings | |
|---|---|
| Instrument: | LTQ Orbitrap XL (Thermo Scientific, St. Louis, MO) |
| Positive Mode: | Electrospray, positive mode (+5000 V) |
| Interface: | High Resolution Mass Spectroscopy |
| Mode: | Capillary Temperature: 275° C. |
| Ion Source Settings: | Capillary Voltage: 47 Sheath gas: 45 Auxiliary gas: 15 Sweep gas: 10 |
| Orbitrap Settings: | Scan Range 200-2000, Resolution = 30000 (Full width at half maximum) Setting for MS/MS Data Dependent Acquisition Isolation Width: 2 Normalized Collision Energy: 35 |

Plasma stability results indicated a $t_{1/2}$ of 5 hours for R4000 in mouse serum and a $t_{1/2}$ of 2.1 hours in rat serum.

Example 14

Synthesis of Specific Compounds

Compound 1 (R4000)

The linear 13 amino acid peptide, R4000 (SEQ ID NO: 7), was synthesized by solid phase peptide synthesis on a Rink Amide MBHA resin according to the general procedure. The peptide was cleaved from resin and protecting groups removed with 92.5% TFA, 2.5%/DL-dithiothreitol, 2.5% TIS and 2.5% water for 3 hours and isolated by precipitation with ether. The crude peptides are purified on a reverse phase preparative HPLC using a C18 column, with an acetonitrile/water 0.1% TFA gradient from 20%-50% over 30 min. Fractions containing the pure peptide are collected and lyophilized and all peptides are analyzed by LC-MS. After cleavage the peptide was cyclized and purified to yield compound R4000 (see structure below, Compound 1).

Compound 1

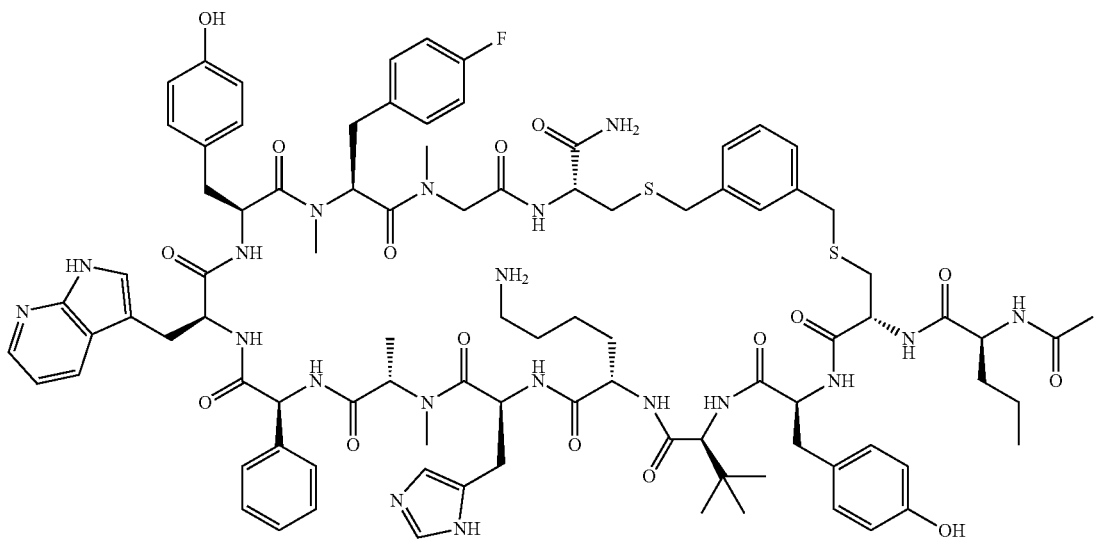

Compound 3—R4001 (R4000 Derivative for Click Chemistry)

The linear peptide R4001 (SEQ ID NO: 8) was synthesized by solid phase peptide synthesis on a Rink Amide MBHA resin according to the general procedure. After cleavage and deprotection the peptide was cyclized and purified to yield compound 2.

Compound 2

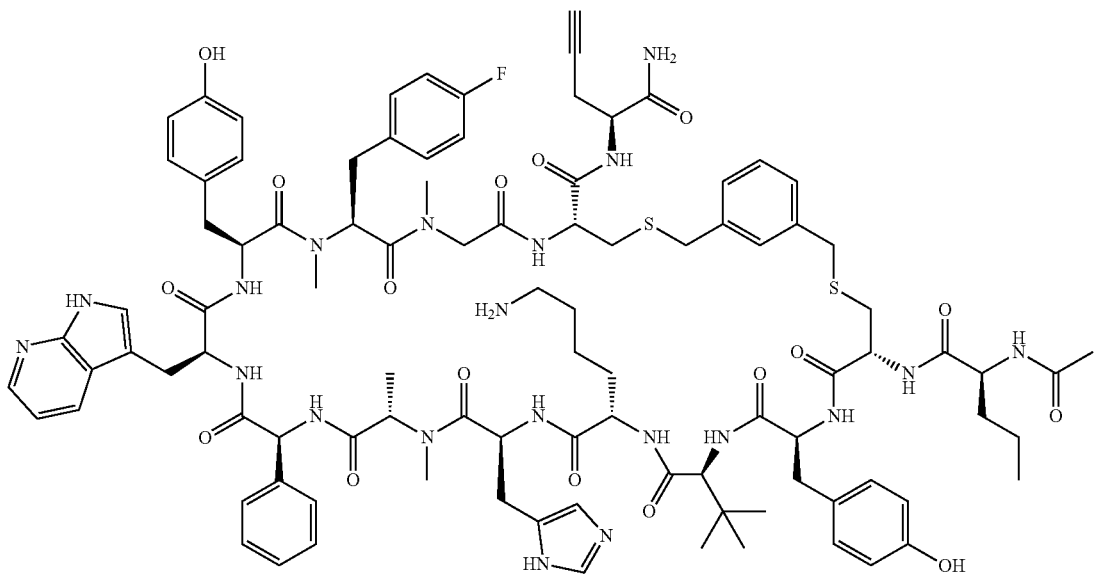

Compound 3 was synthesized by copper-catalyzed click chemistry. Compound 2 (5 mg, 2.2 µmol) was dissolved in 5 mL of H₂O/n-butanol (1:1), the pH was adjusted to 8 by addition of a 10% of Na₂CO₃ aqueous solution. An excess of CuBr and 4.4 equiv of 5-TAMRA azide (5 mg, 9.7 µmol) were then added to the peptide solution. The resulting mixture was stirred at r.t. for 3 hours. Conversion to the desired product, compound 3, was confirmed by LC/MS.

Compound 3 was purified by RP-HPLC, luna 5µ-PREP C18(2), 100 Å, column size 250×21.2 mm. Mobile phase A=0.1% TFA in water, mobile phase B=0.1% TFA in acetonitrile, gradient used was 20 to 40% B over 30 min, flow rate was 20 mL/min, UV wavelength λ=214 nm. The fractions containing product were collected and dried by lyophilization to give desired product as a dark red powder, 1 mg, yield 17%.

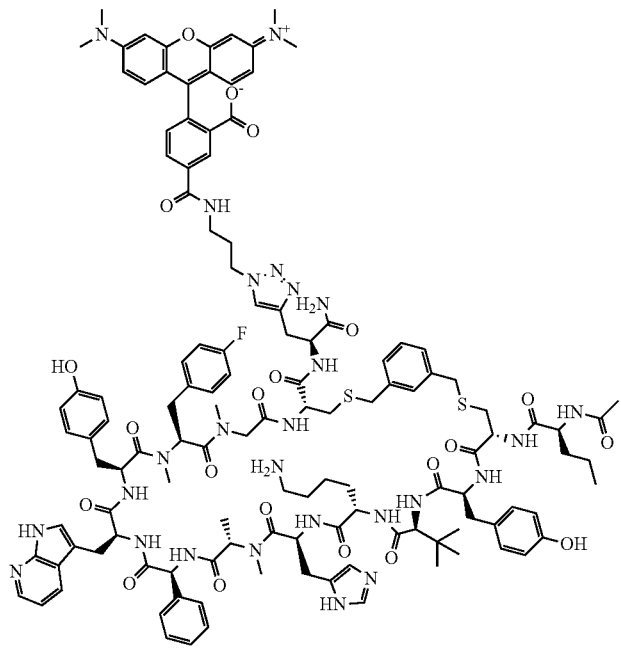

Compound 3

Compound 4 (Lipidated Derivative of R4000)

Compound 4 was synthesized by lipidation of compound 1 through the lysine side chain. Compound 1 (4.8 mg, 2.2 umol) was dissolved in 2 mL of diH2O. pH was adjusted to 8.0 by addition of a 1% Na₂CO₃ aqueous solution. Lauric acid NHS (2.6 mg, 8.8 umol) was dissolved in 0.5 mL of DMF and added dropwise to the peptide in two portions, the second portion was added one hour after the first. The resulting mixture was stirred at room temperature overnight. Formation into compound 4 was confirmed by LC/MS.

Compound 4 was purified by RP-HPLC, luna 5µ-PREP C18(2), 100 Å, column size 250×21.2 mm. Mobile phase A=0.1% TFA in water, mobile phase B=0.1% TFA in acetonitrile, gradient used was 35 to 55% B over 30 min, flow rate was 20 mL/min, UV wavelength λ=228 nm. The fractions were collected and desired product confirmed by LC/MS. The fractions were dried by lyophilization to give the desired product as a white powder, 1 mg, yield 20%.

Compound 4

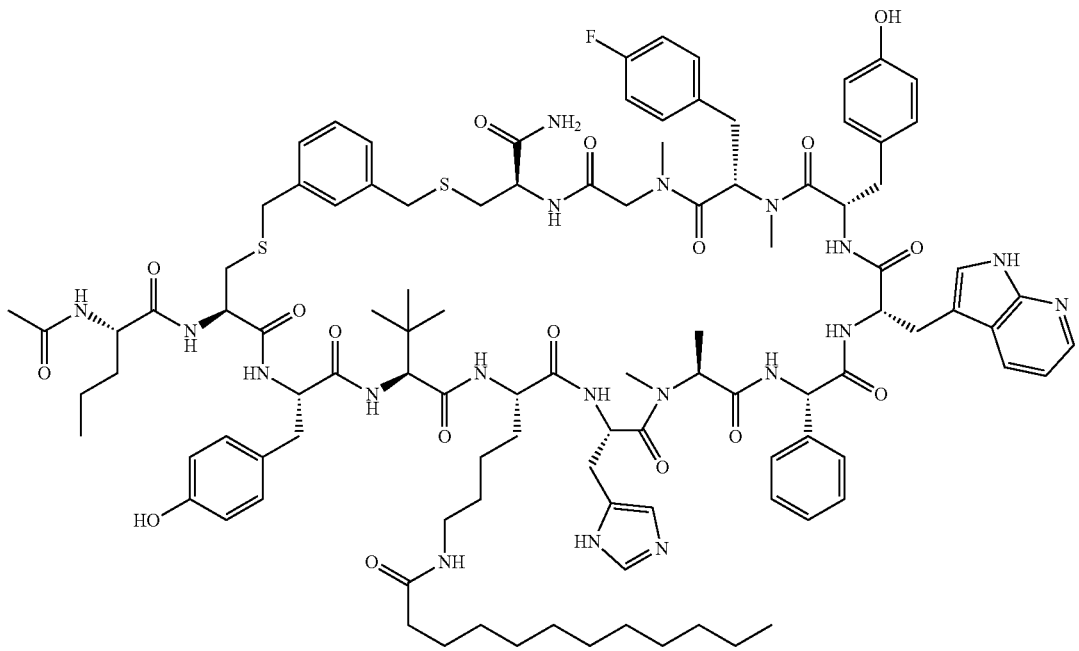

Compound 6 R4002 (Lipidated Derivative of R4000)

The linear peptide R4002 (SEQ ID NO: 9) was synthesized by solid phase peptide synthesis on a Rink Amide MBHA resin according to the general procedure. After cleavage and deprotection the peptide was cyclized and purified to yield compound 5

Compound 5 (4.8 mg, 2 umol) was dissolved in 2 mL of diH2O and the pH was adjusted to 8 by 1% Na$_2$CO$_3$ aqueous solution. Lauric acid NHS (2.6 mg, 8.8 umol) was dissolved in 0.5 mL of DMF. Lauric acid NHS was added dropwise to the peptide in two portions, the second portion was added one hour after the first. The resulting mixture was stirred at room temperature overnight. Formation of compound 6, was confirmed by LC/MS. Compound 6 was purified by RP-HPLC, luna 5μ-PREP C18(2), 100 Å, column size 250×21.2 mm. Mobile phase A=0.1% TFA in water, mobile phase B=0.1% TFA in acetonitrile, gradient used was 35 to 55% B over 30 min, flow rate was 20 mL/min, UV wavelength λ=228 nm. Fractions containing the desired product were combined and dried by lyophilization to give the desired product as a white powder, 1 mg, yield 20%.

Compound 5

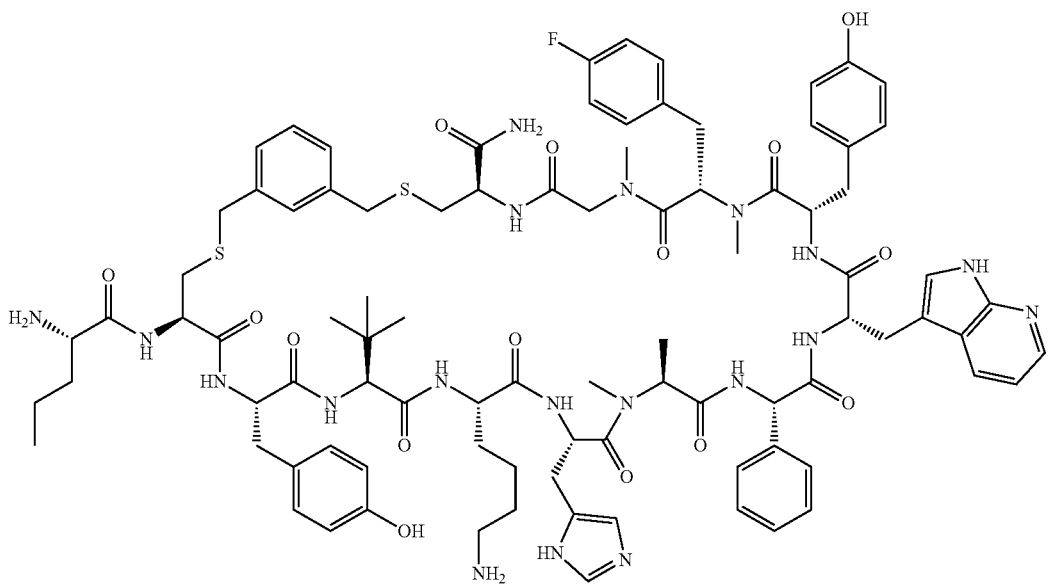

Compound 6
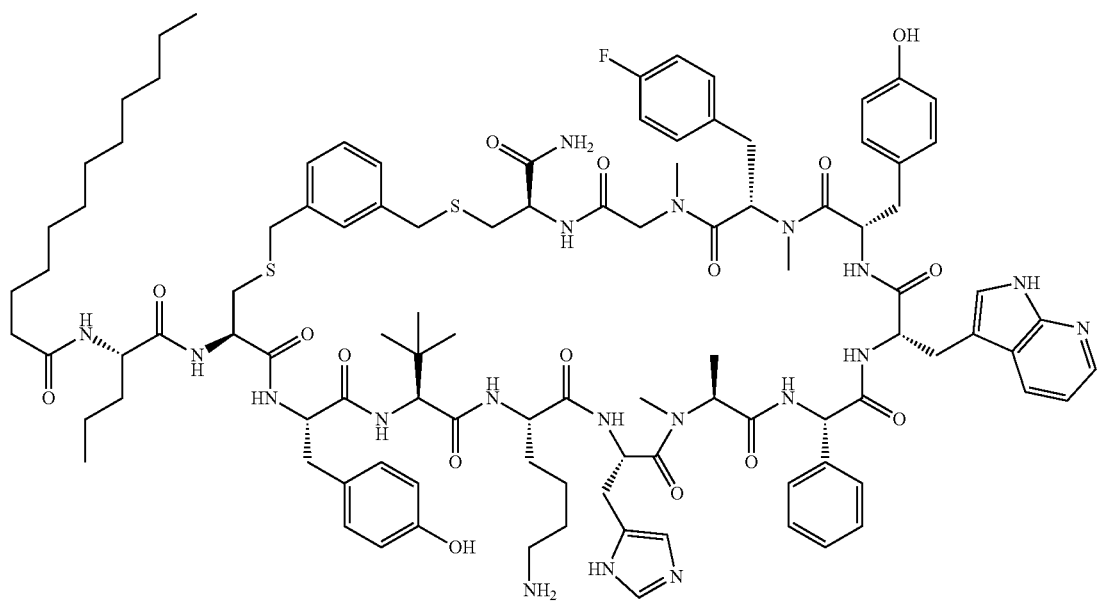
Example 15
Heterobifunctional PROTAC
Proteolysis targeting chimeric molecules, or PROTACs, are small molecules that inhibit the function of their target proteins by targeting them for degradation by the ubiquitin proteasome system. Such molecules may be made by the methods described here.
Acid PEG-(−)-Nutlin-3a
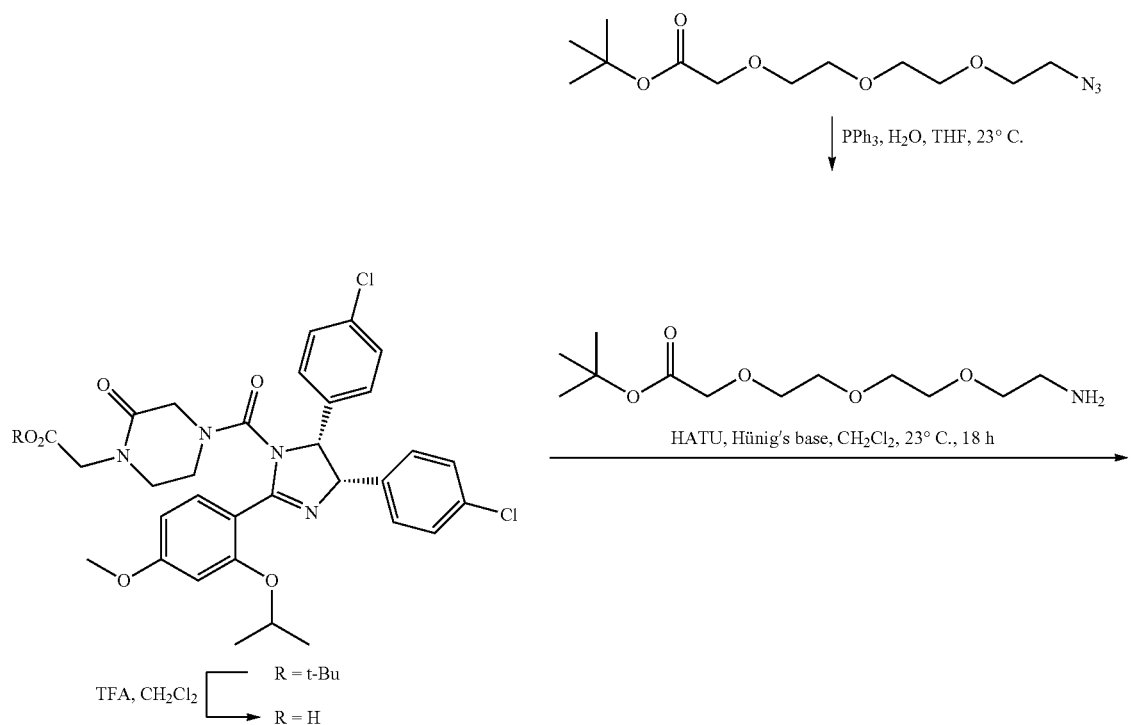

-continued

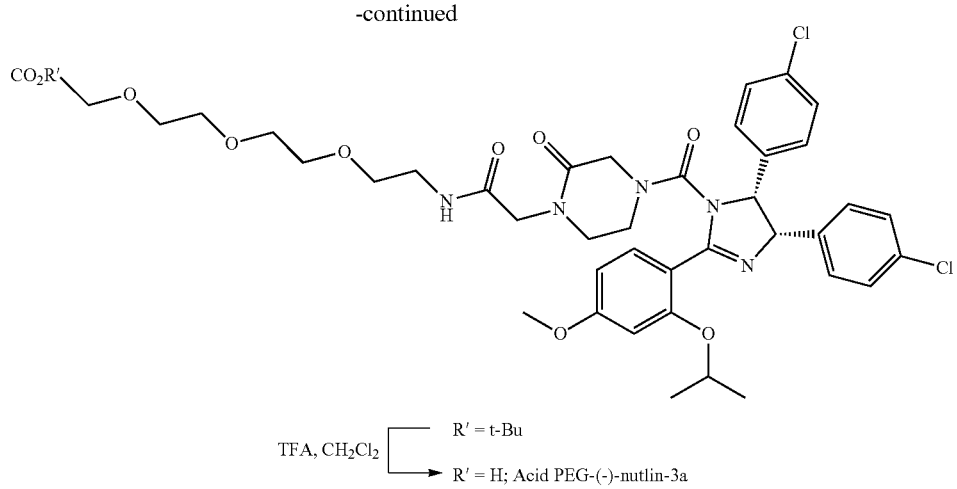

TFA, CH₂Cl₂ ⎡ R' = t-Bu
              ⎣ → R' = H; Acid PEG-(-)-nutlin-3a tert-Butyl 2-(2-(2-(2-aminoethoxy)ethoxy)ethoxy)acetate: To a solution of tert-butyl 11-azido-3,6,9-trioxaundecanoate dissolved in damp THF (0.1 M) was added triphenylphosphine (1.2 equiv) in portions over 30 min. The reaction mixture was stirred at room temperature for 18 h. The volatiles were removed under reduced pressure. The residue was purified by flash column chromatography (dichloromethane-methanol).

tert-Butyl acetyl (-)-nutlin-3a was prepared according to the conditions described by Crews et al. (Schneekloth, A. R.; Pucheault, M.; Tae, H. S.; Crews, C. M. *Bioorg. Med. Chem. Lett.* 2008, 18, 5904-5908). For an alternative synthesis of (-)-nutlin, see: Davis, T. A.; Johnston, J. N. *Chem. Sci.* 2011, 2, 1076-1079.

Acid PEG-(-)-Nutlin-3a: To a solution of tert-butyl acetyl (-)-nutlin-3a dissolved in CH₂Cl₂ at 0° C. was added dropwise trifluoroacetic acid (20% v/v). After stirring at room temperature for 4 h, the volatiles were evaporated under reduced pressure. The resulting gum was dried under high vacuum. The resulting gum was used in the next step without further purification.

To a solution of acetic acid (-)-nutlin-3a (1 equiv) and tert-butyl 2-(2-(2-(2-aminoethoxy)ethoxy)ethoxy)acetate (1.2 equiv) in anhydrous DMF (0.2 M) was added N,N-diisopropylethylamine (1 equiv) and 1-[bis(dimethylamino)methylene]-1H-1,2,3-triazolo[4,5-b]pyridinium 3-oxid hexafluorophosphate (1.5 equiv) successively. The reaction mixture was stirred at room temperature. After 18 h, the mixture was evaporated. The residue was dissolved into ethyl acetate and washed successively with saturated NH₄Cl aqueous solution, water, and saturated NaCl, dried over Na₂SO₄, filtered, and concentrated. The crude was purified by Prep-HPLC {Luna 5μ C18(2) 100 Å; 250×21.2 mm} using a water:acetonitrile gradient.

To a solution of PEG-(-)-nutlin-3a tert-butyl ester in CH₂Cl₂ at 0° C. was added dropwise trifluoroacetic acid (20% v/v). After stirring at room temperature for 4 h, the volatiles were evaporated under reduced pressure. The resulting gum was dried under high vacuum. The resulting gum was used in the next step without further purification.

Amino PEG-(-)-Nutlin-3a

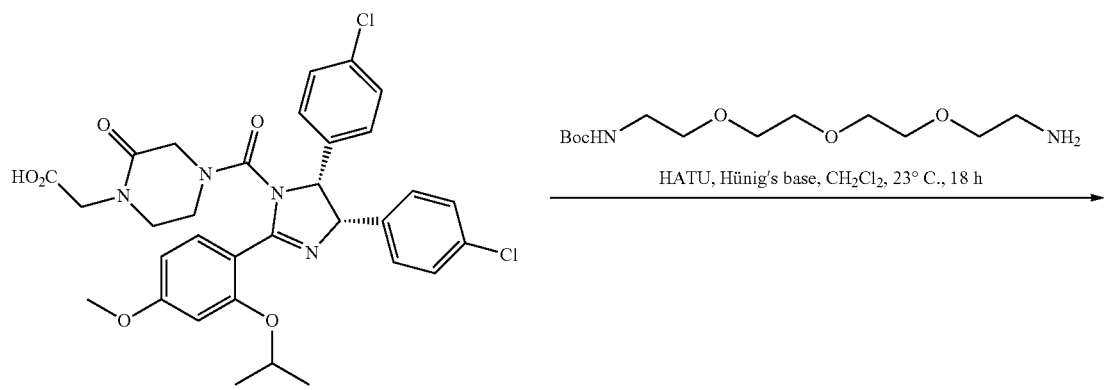

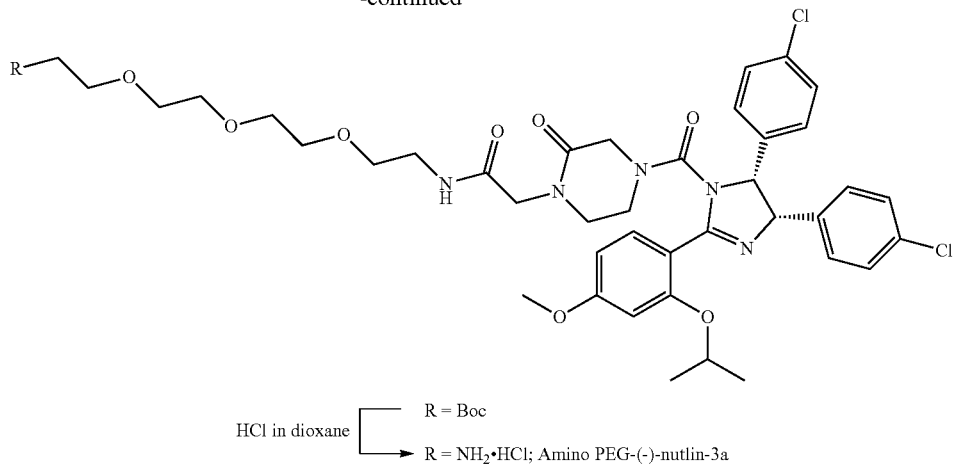

tert-butyl (2-(2-(2-(2-aminoethoxy)ethoxy)ethoxy)ethyl) carbamate: This compound was prepared according to the conditions described by Marchand-Brynaert et al. (Favre, A.; Grugier, J.; Brans, A.; Joris, B.; Marchand-Brynaert, J. *Tetrahedron* 2012, 68, 10818-10826).

Amino PEG-(-)-Nutlin-3a: To a solution of acetic acid (-)-nutlin-3a (1 equiv) and tert-butyl (2-(2-(2-(2-aminoethoxy)ethoxy)ethoxy)ethyl)carbamate (1.2 equiv) in anhydrous DMF (0.2 M) was added N,N-diisopropylethylamine (1 equiv) and 1-[bis(dimethylamino)methylene]-1H-1,2,3-triazolo[4,5-b]pyridinium 3-oxid hexafluorophosphate (1.5 equiv) successively. The reaction mixture was stirred at room temperature. After 18 h, the mixture was evaporated. The residue was dissolved into ethyl acetate and washed successively with saturated $NH_4Cl$ aqueous solution, water, and saturated NaCl, dried over $Na_2SO_4$, filtered, and concentrated. The residue was purified by flash column chromatography (dichloromethane-methanol).

A solution of Boc-protected PEG-(-)-nutlin-3a in 1,4-dioxane was treated with 4M HCl in dioxane at 0° C. After 2 h, the solvent was removed in vacuo to provide the product as an HCl salt, which was used in the next step without further purification.

Compound 7, Lysine-Graft PEG-(-)-Nutlin-3a—Peptide 1 PROTAC

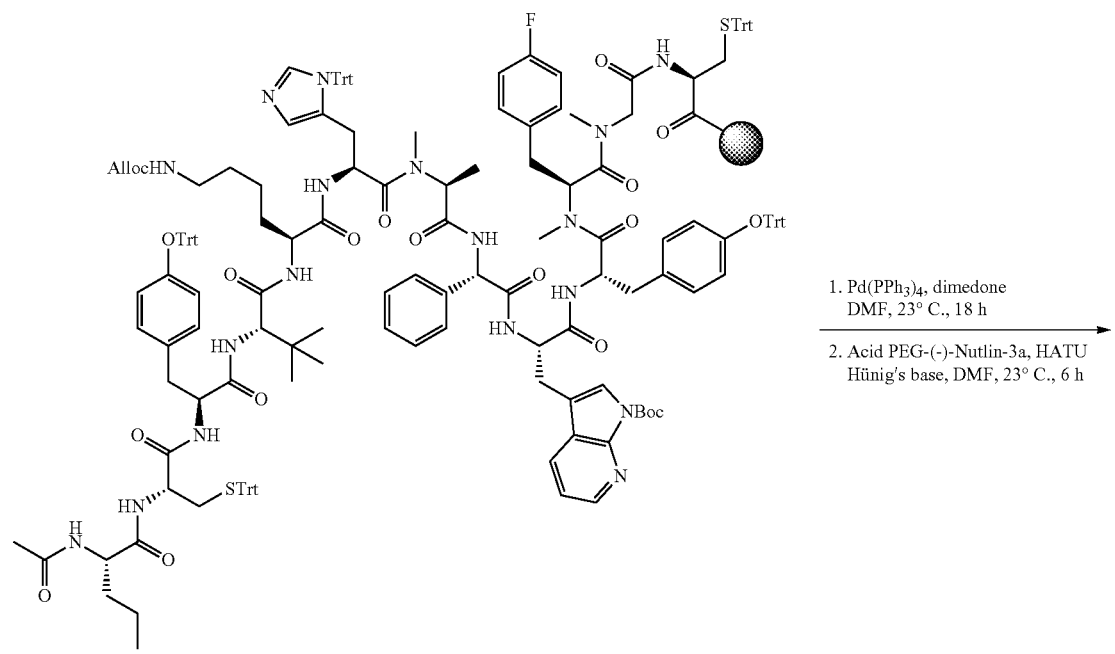

-continued

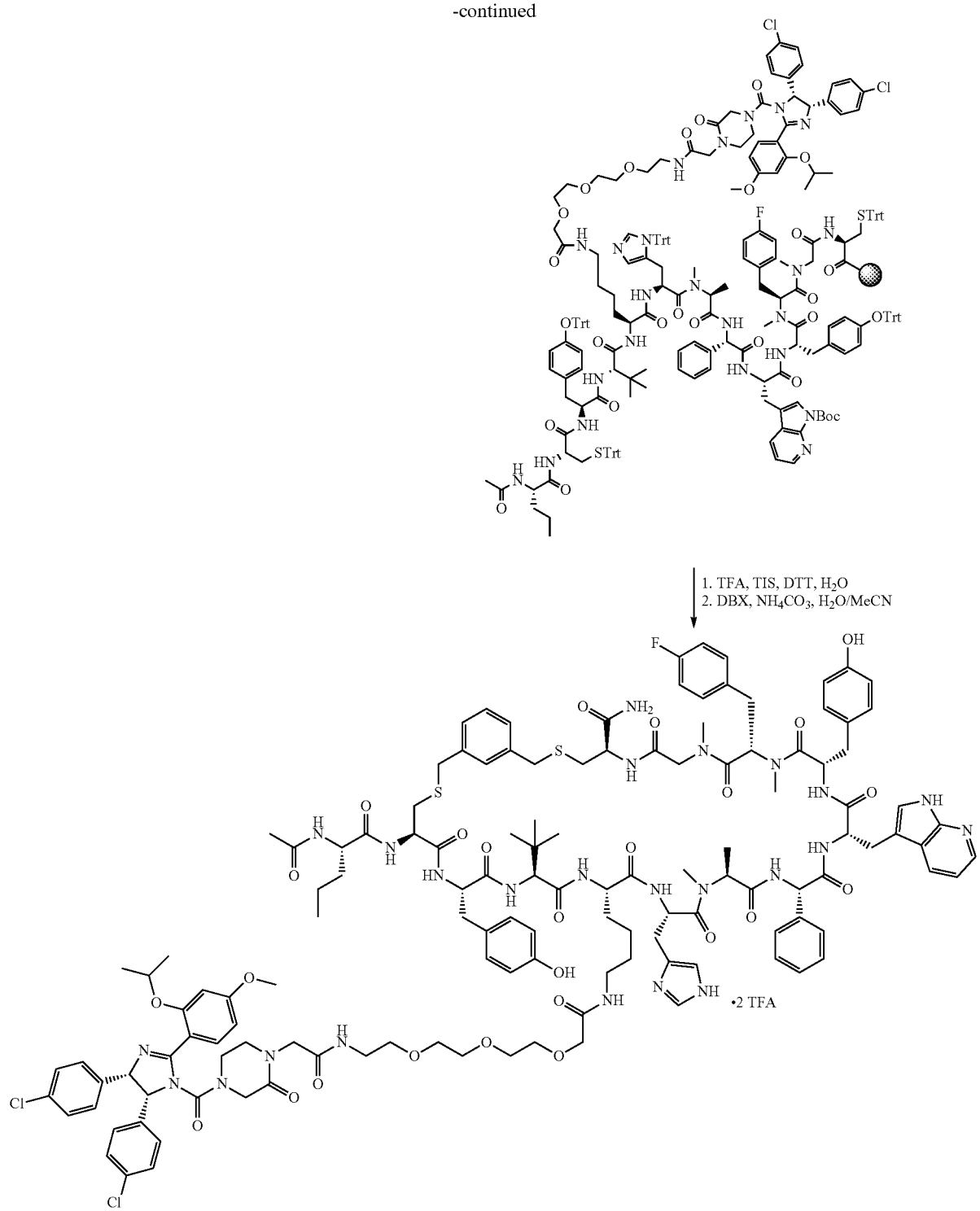

R4003 (SEQ ID NO: 72) on Rink Amide MBHA resin was prepared according to the general procedure.

Alloc deprotection: A solution of tetrakis(triphenylphosphine)palladium(0) (80 mg, 72 µmol) and dimedone (70 mg, 0.5 mmol) in dry $CH_2Cl_2$ (5 mL) was added to the peptide on resin (100 µmol), shaken for 1 h at room temperature and the procedure repeated. The resin was subsequently washed with DMF (3×10 mL), $CH_2Cl_2$ (3×10 mL), and DMF (3×5 mL) and dried.

PEG-(−)-Nutlin-3a coupling: A solution of PEG-(−)-nutlin-3a acid (166 mg; 0.2 mmol; 2 equiv) in DMF (3 mL) was added to the resin-bound peptide, followed by N,N-diisopropylethylamine (53 µL; 0.3 mmol; 3 equiv) and 1-[bis(dimethylamino)methylene]-1H-1,2,3-triazolo[4,5-b]pyridinium 3-oxid hexafluorophosphate (114 mg; 0.3 mmol; 3 equiv) successively, and shaken for 6 h at room temperature. The resin washed with DMF (3×10 mL) then $CH_2Cl_2$ (3×10 mL) and dried. The peptide was cleaved and cyclized according to the general procedure to yield compound 7.

Compound 8, N-Terminal PEG-(−)-Nutlin-3a—Peptide1 PROTAC:

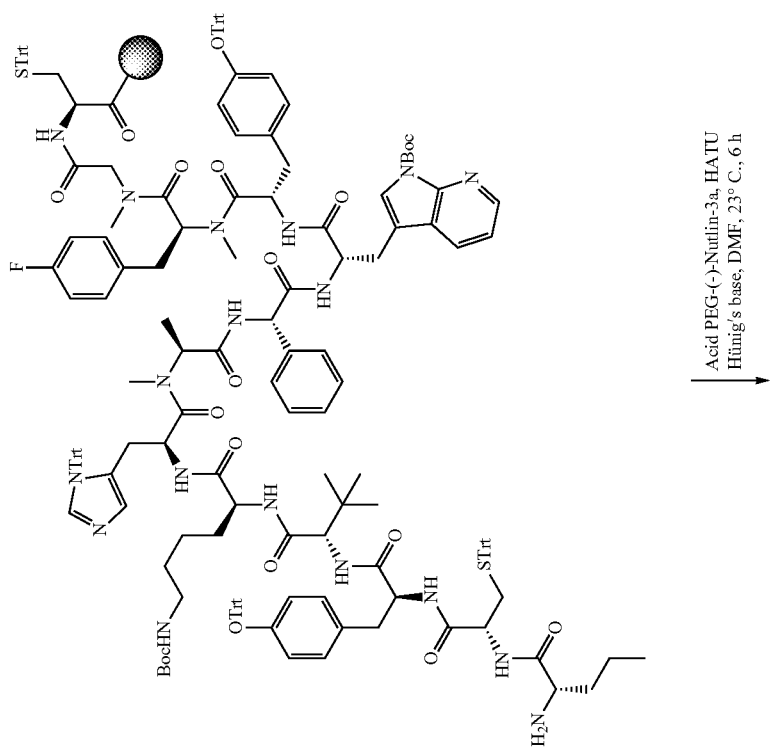

-continued
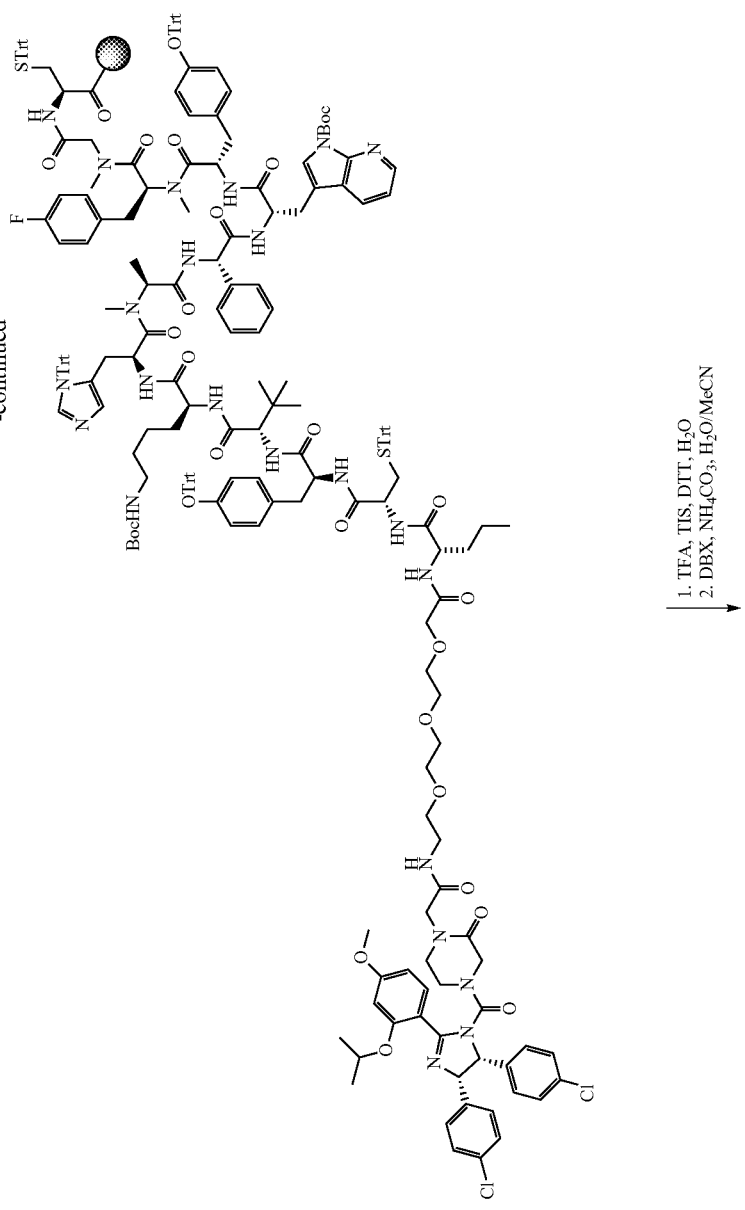

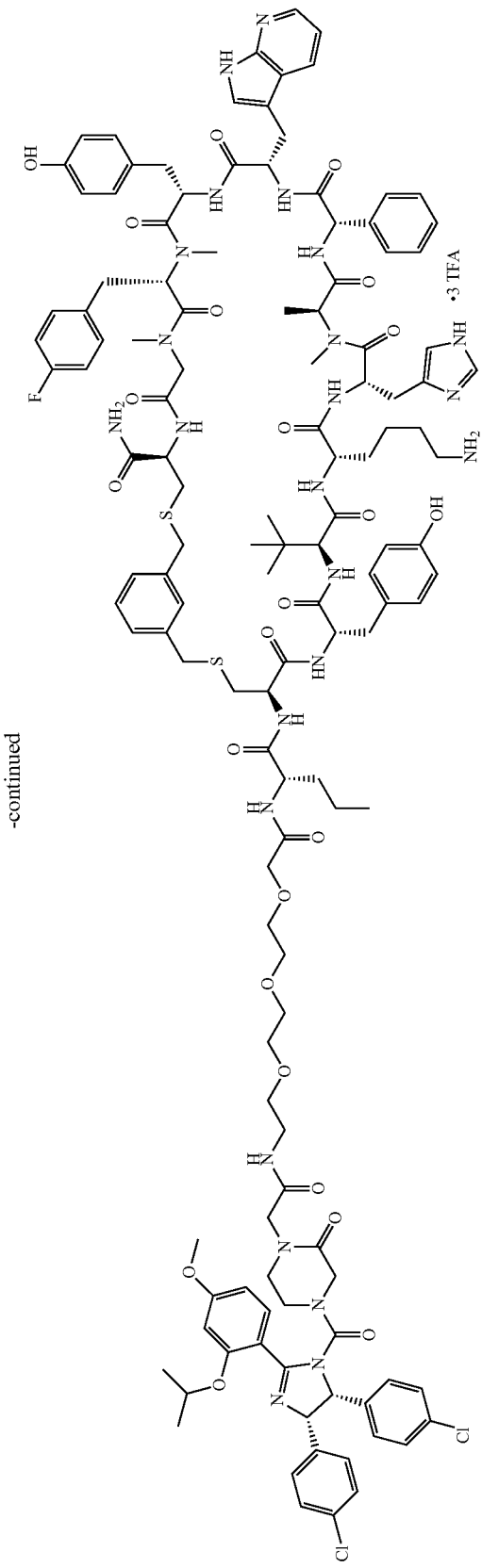

R4004 (SEQ ID NO: 73) on Rink Amide MBHA resin was prepared according to the general procedure.

PEG-(−)-Nutlin-3a coupling: A solution of PEG-(−)-nutlin-3a acid (166 mg; 0.2 mmol; 2 equiv) in DMF (3 mL) was added to the resin-bound peptide, followed by N,N-diisopropylethylamine (53 µL; 0.3 mmol; 3 equiv) and 1-[bis(dimethylamino)methylene]-1H-1,2,3-triazolo[4,5-b]pyridinium 3-oxid hexafluorophosphate (114 mg; 0.3 mmol; 3 equiv) successively, and shaken for 6 h. The procedure repeated. The resin washed with DMF (3×10 mL) then CH$_2$Cl$_2$ (3×10 mL) and dried. The peptide was cleaved and cyclized according to the general procedure to yield compound 8.

Compound 10, C-Terminal PEG-(−)-Nutlin-3a—Peptide 1 PROTAC

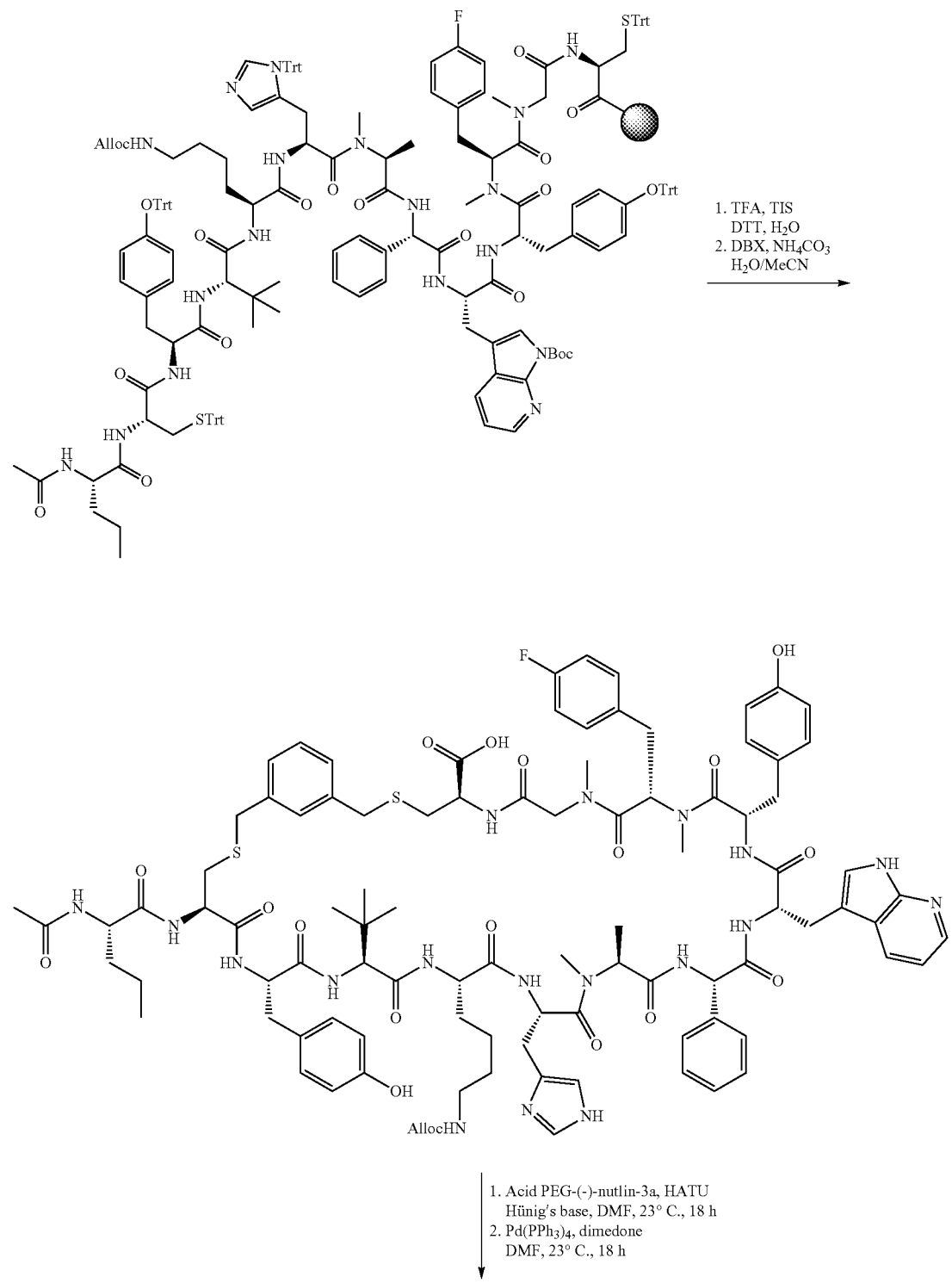

-continued

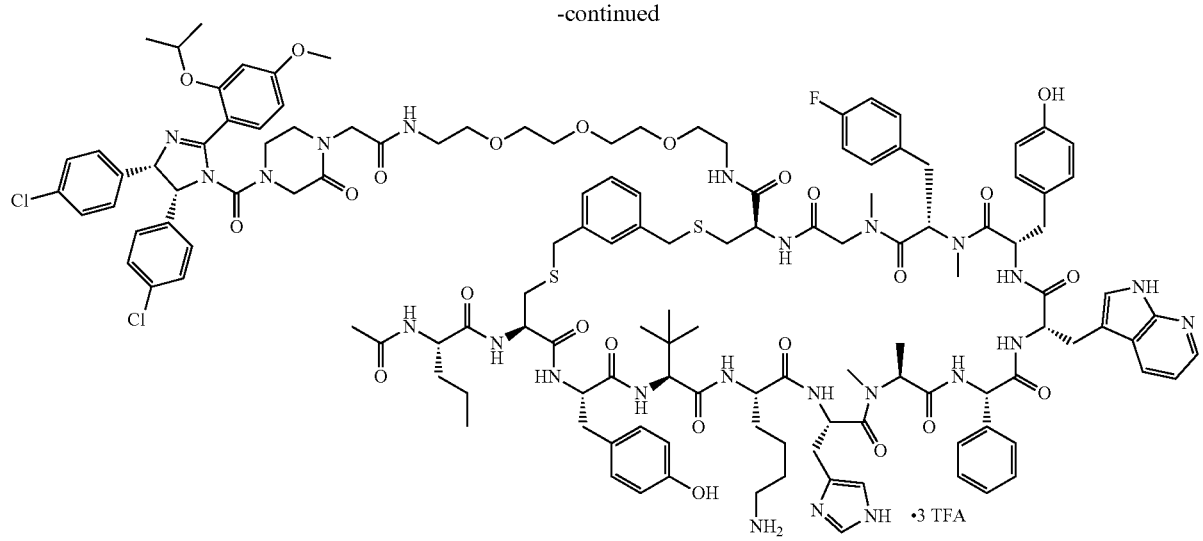

R4003 (SEQ ID NO: 72) on Wang resin was prepared according to the general procedure. The peptide was cleaved and cyclized according to the general procedure to yield compound 9.

Amino PEG-(-)-Nutlin-3a coupling: A solution of amino PEG-(-)-nutlin-3a (2 equiv) in DMF (3 mL) was added to the peptide 9, followed by N,N-diisopropylethylamine (3 equiv) and 1-[bis(dimethylamino)methylene]-1H-1,2,3-triazolo[4,5-b]pyridinium 3-oxid hexafluorophosphate (2.5 equiv) successively, and shaken for 18 h. The solvent was removed in vacuo and the resulting yellow oil was used in the next step without further purification.

Alloc deprotection: A solution of compound 10, was treated with tetrakis(triphenylphosphine)palladium(0) (40 mg, 36 µmol) and dimedone (35 mg, 0.25 mmol) in dry $CH_2Cl_2$ (5 mL). The reaction mixture was stirred at room temperature for 18 h. The solvent was removed in vacuo. The residue was dissolved in a mixture of water and acetonitrile (1:1 (v/v)). After acidification with trifluoroacetic acid, the crude was purified by RP-HPLC (Varian PrepStar) with a C18 prep column {Luna 5µ C18(2) 100 Å; 250×21.2 mm} using a 60-min linear gradient of acetonitrile in 0.1% trifluoroacetic acid to provide compound 11 as a TFA salt.

Example 16

Hydrophobic Tagging

The peptides of the present invention may be conjugated or linked to one or more tags. One such type of tag is a hydrophobic tag. One such hydrophobic tag is a chloride hydrophobic tag such as the one shown below.

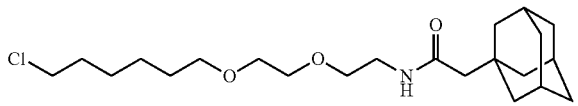 [SMILES: O=C(CC12CC3CC(CC(C3)C1)C2)NCCOCCOCCCCCCCl]

The chloride hydrophobic tag was prepared according to the conditions described by Crews et al. (Tae, H. S.; Sundberg, T. B.; Neklesa, T. K.; Noblin, D. J.; Gustafson, J. L.; Roth, A. G.; Raina, K.; Crews, C. M. *ChemBioChem* 2012, 13, 538-541; Neklesa, T. K.; Tae, H. S.; Schneekloth, A. R.; Stulberg, M. J.; Corson, T. W.; Sundberg, T. B.; Raina, K.; Holley, S. A.; Crews, C. M. *Nat. Chem. Biol.* 2011, 7, 538-543; Crews, C. M.; Tae, H. S.; Schneekloth, A. R.; Neklesa, T.; Sundberg, T. PCT Int. Appl. (2012), WO 2012078559 A2).

Aldehyde Hydrophobic Tag:

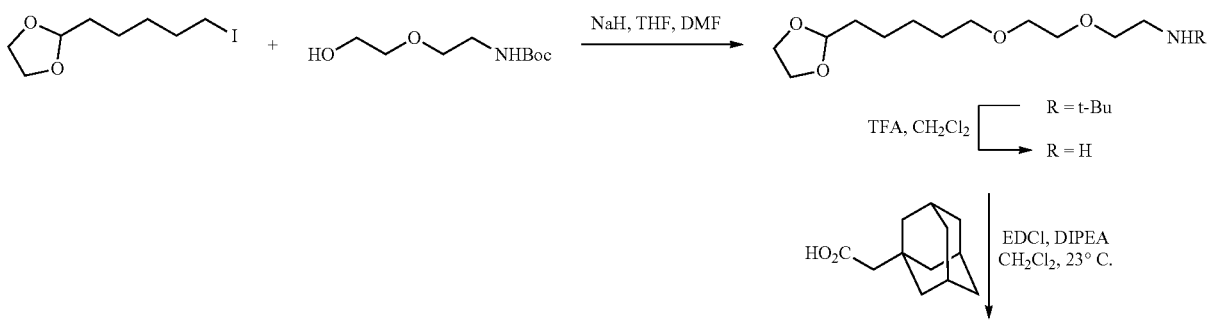

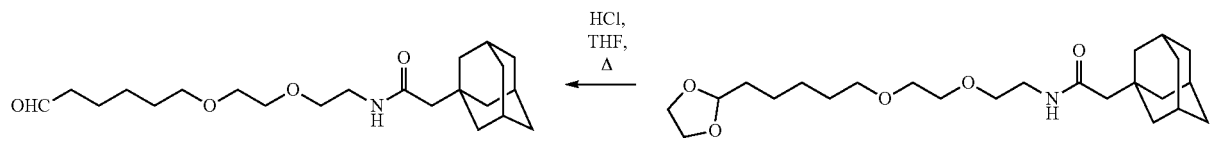

2-(5-Iodopentyl)-1,3-dioxolane was prepared from 6-chlorohexanal according to the conditions described by Wasserman et al. (Wasserman, H. H.; Gambale, R. J.; Pulwer, M. J. *Tetrahedron* 1981, 37, 4059-4067). The aldehyde hydrophobic tag was prepared following procedures adapted from Crews et al. (Schneekloth, A. R.; Stulberg, M. J.; Corson, T. W.; Sundberg, T. B.; Raina, K.; Holley, S. A.; Crews, C. M. *Nat. Chem. Biol.* 2011, 7, 538-543).

Compound 12, Lysine-Graft Hydrophobic Tag—Peptide

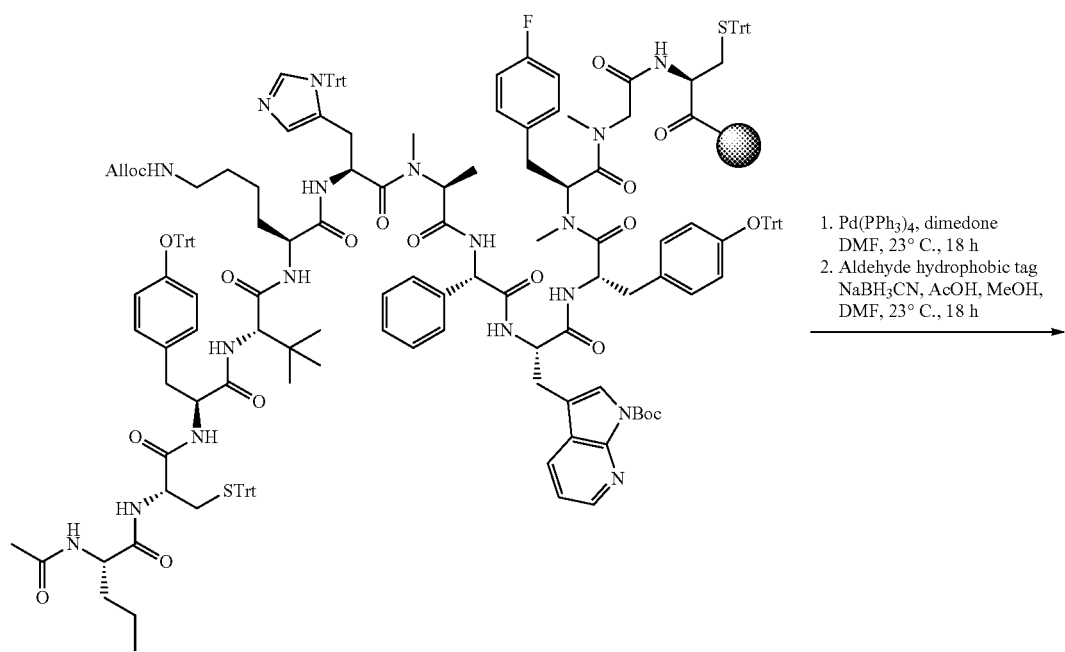

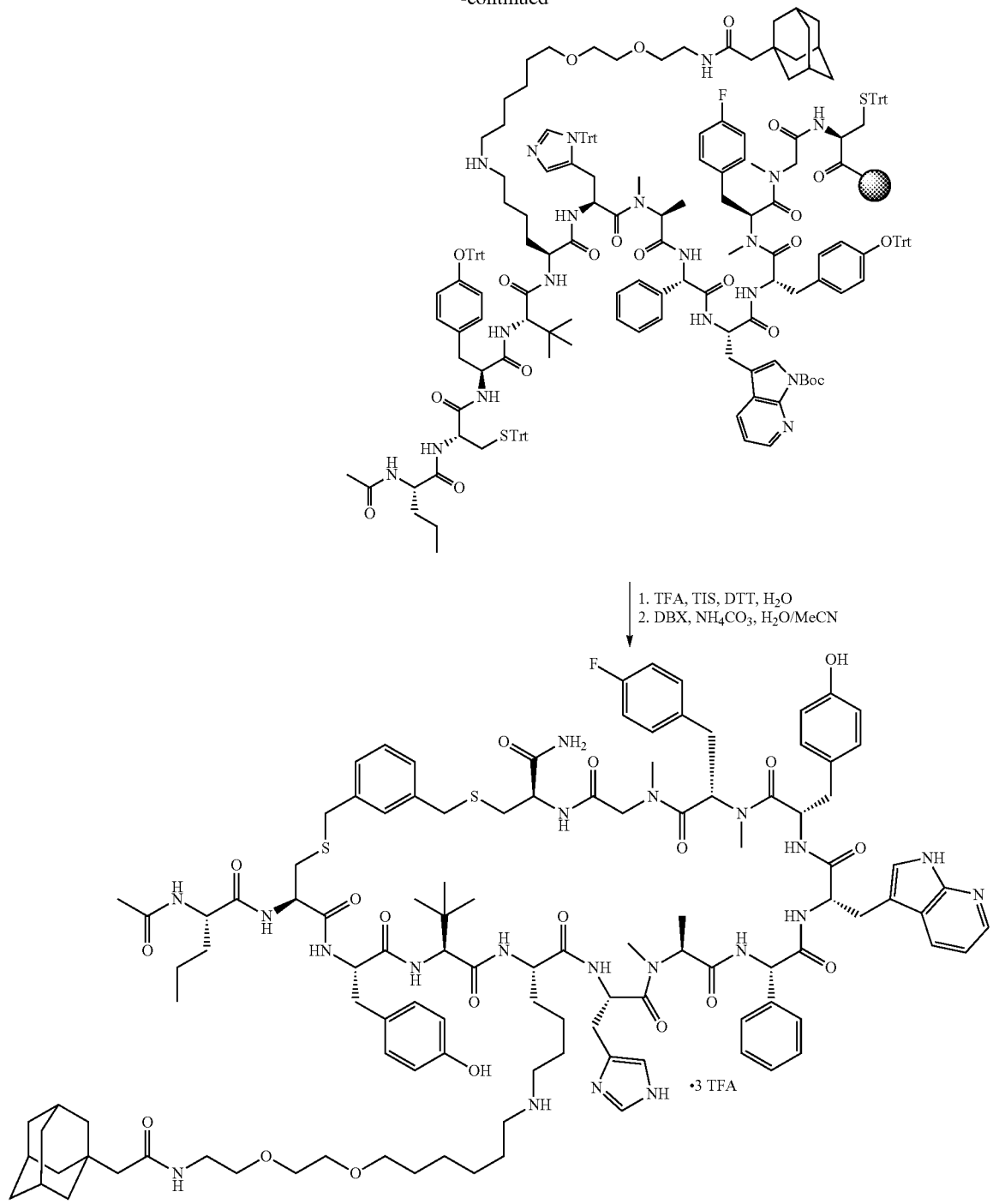

R4003 (SEQ ID NO: 72) on Rink Amide MBHA resin was prepared according to the general procedure.

Alloc deprotection: A solution of tetrakis(triphenylphosphine)palladium(0) (80 mg, 72 μmol) and dimedone (70 mg, 0.5 mmol) in dry CH$_2$Cl$_2$ (5 mL) was added to the peptide on resin (100 μmol), shaken for 1 h and the procedure repeated. The resin was subsequently washed with DMF (3×10 mL), CH$_2$Cl$_2$ (3×10 mL), and DMF (3×5 mL) and dried.

Aldehyde hydrophobic tag—Peptide reductive amination: A solution of aldehyde hydrophobic tag (379 mg; 1 mmol; 10 equiv) in a mixture of DMF and MeOH (1:1 (v/v), 10 mL) was added to the resin-bound peptide. Sodium cyanoborohydride (63 mg; 1 mmol; 10 equiv) and acetic acid (57 μL; 1 mmol; 10 equiv) were added. After gently stirring the mixture for 18 h at room temperature, the resin washed with DMF (3×10 mL), ethanol (3×10 mL) then CH$_2$Cl$_2$ (3×10 mL) and dried. The peptide was cleaved and cyclized according to the general procedure to yield compound 12.

Compound 13. N-Terminal Hydrophobic Tag—Peptide

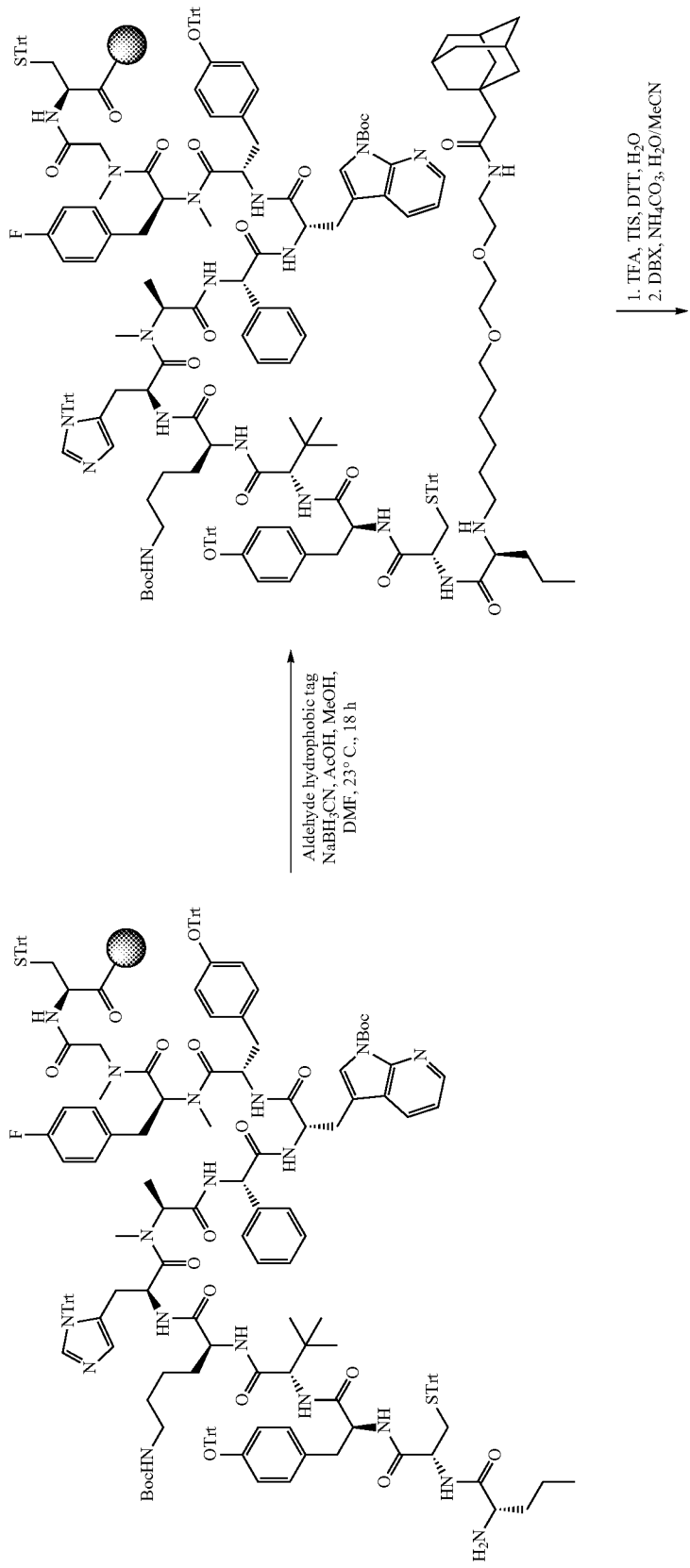

-continued
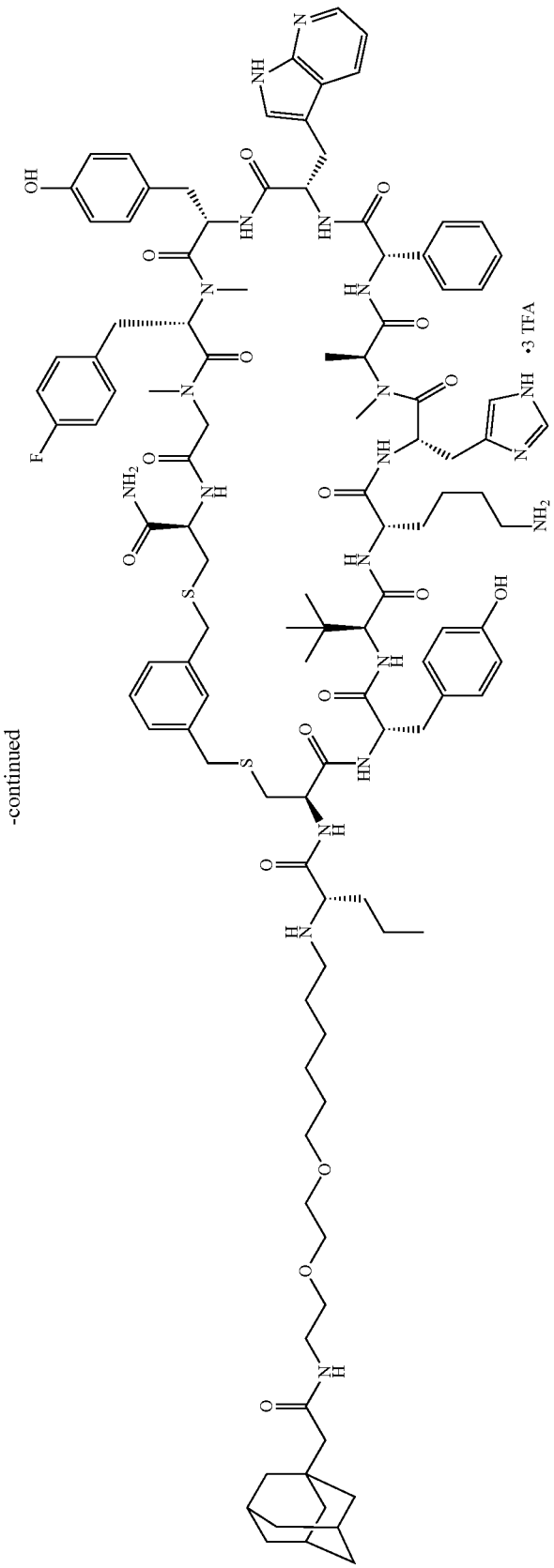

R4004 (SEQ ID NO: 73) on Rink Amide MBHA resin was prepared to according the general procedure.

Aldehyde hydrophobic tag—Peptide reductive amination: A solution of aldehyde hydrophobic tag (379 mg; 1 mmol; 10 equiv) in a mixture of DMF and MeOH (1:1 (v/v), 10 mL) was added to the resin-bound peptide. Sodium cyanoborohydride (63 mg; 1 mmol; 10 equiv) and acetic acid (57 µL; 1 mmol; 10 equiv) were added. After gently stirring the mixture for 18 h at room temperature, the resin washed with DMF (3×10 mL), ethanol (3×10 mL) then CH$_2$Cl$_2$ (3×10 mL) and dried. The peptide was cleaved and cyclized according to the general procedure to yield compound 13.

Compound 14, C-Terminal Hydrophobic Tag—Peptide

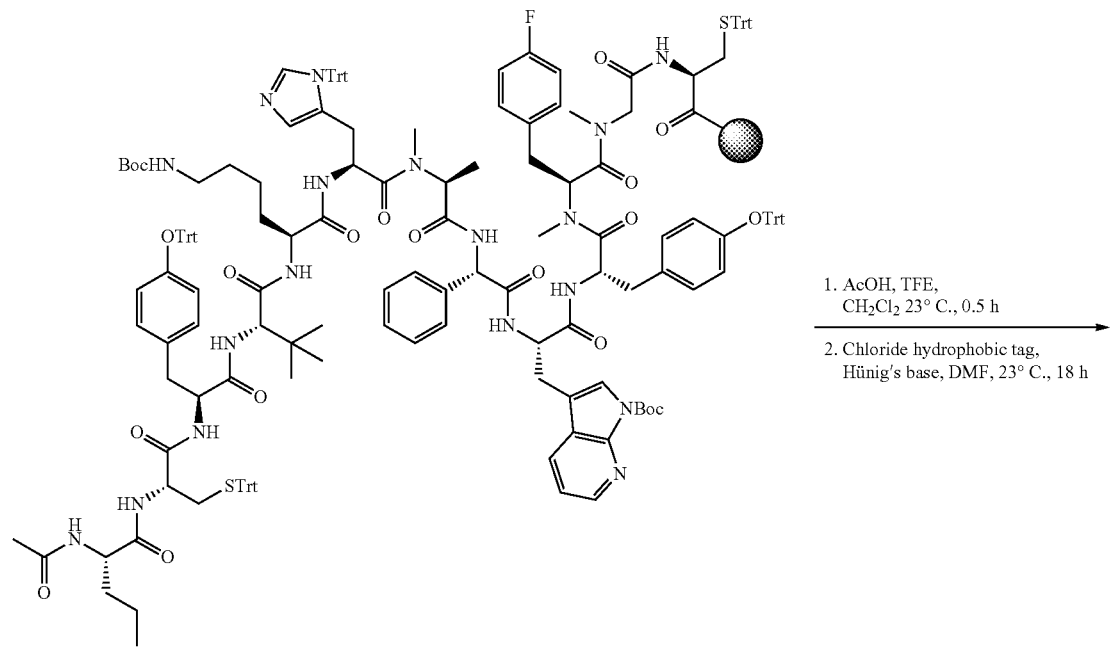

1. AcOH, TFE, CH$_2$Cl$_2$ 23° C., 0.5 h
2. Chloride hydrophobic tag, Hünig's base, DMF, 23° C., 18 h

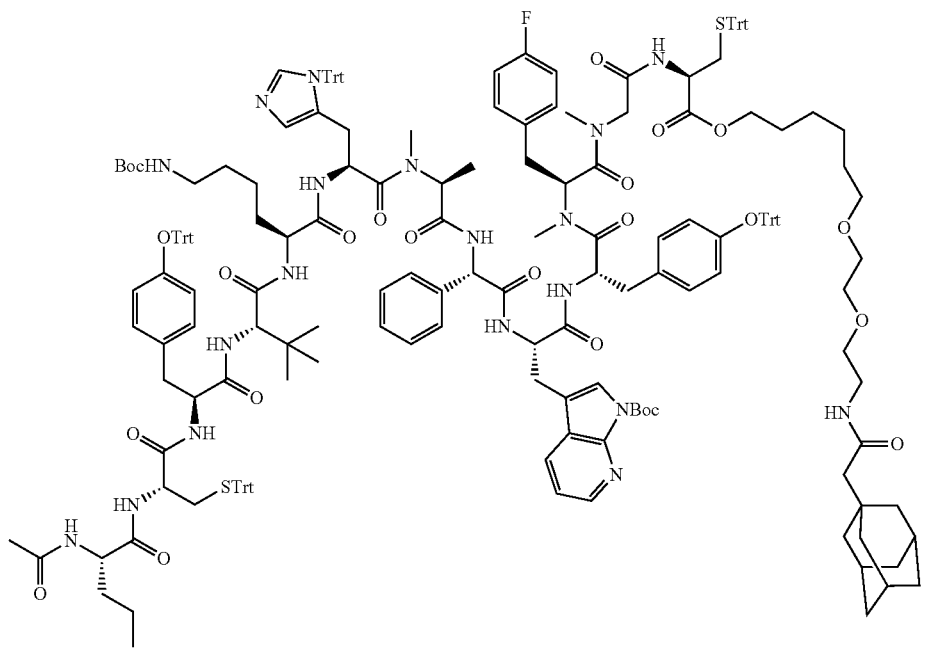

1. TFA, TIS, DTT, H$_2$O
2. DBX, NH$_4$CO$_3$, H$_2$O/MeCN

-continued

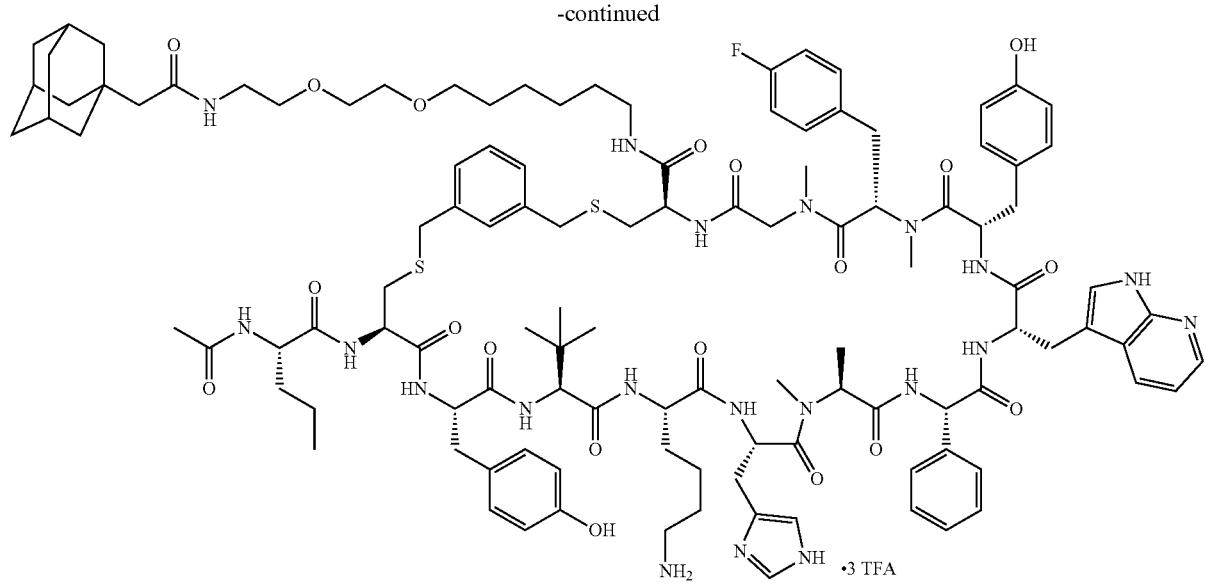

R4003 (SEQ ID NO: 72) on 2-chlorotrityl resin was prepared to according the general procedure.

Cleavage: The peptide was cleaved from its solid support using acetic acid/trifluoroethanol/dichloromethane (1:1:8 (v/v), 15 mL) and allowed to react for 0.5 h at room temperature. The resin was filtered and washed with acetic acid/trifluoroethanol/dichloromethane mixture (1:1:8 (v/v), 2×5 mL). The combined filtrates were diluted with hexanes (100 mL). The solvent was removed in vacuo.

Chloride hydrophobic tag alkylation: A solution of chloride hydrophobic tag (400 mg; 1 mmol; 10 equiv) in DMF (5 mL) was added to the peptide, followed by N,N-diisopropylethylamine (176 µL; 1 mmol; 1 equiv). The reaction mixture was stirred at room temperature for 18 h. The solvent was removed in vacuo and the resulting yellow oil was purified by RP-HPLC (Varian PrepStar) with a C18 prep column {Luna 5µ C18(2) 100 Å; 250×50 mm} using a 60-min linear gradient of acetonitrile in 0.1% trifluoroacetic acid. The peptide was cleaved and cyclized according to the general procedure to yield compound 14.

Example 17

Derivatization with Electrophilic Reagents

Peptides of the present invention may be derivatized with one or more electrophilic reagents. Such derivatives and methods of making them are taught herein.

Synthesis of alkyne acrylamide reagents for click chemistry conjugation: (N-(but-3-yn-1-yl)acrylamide; N-(prop-2-yn-1-yl)acrylamide and N-(pent-4-yn-1-yl)acrylamide was performed as described in: *Macromol. Rapid Commun.* 2011, 32, 1906.

Compound 15

The linear peptide R4005 (SEQ ID NO: 10) was synthesized and cleaved using the standard procedure to yield compound 15.

Compound 16

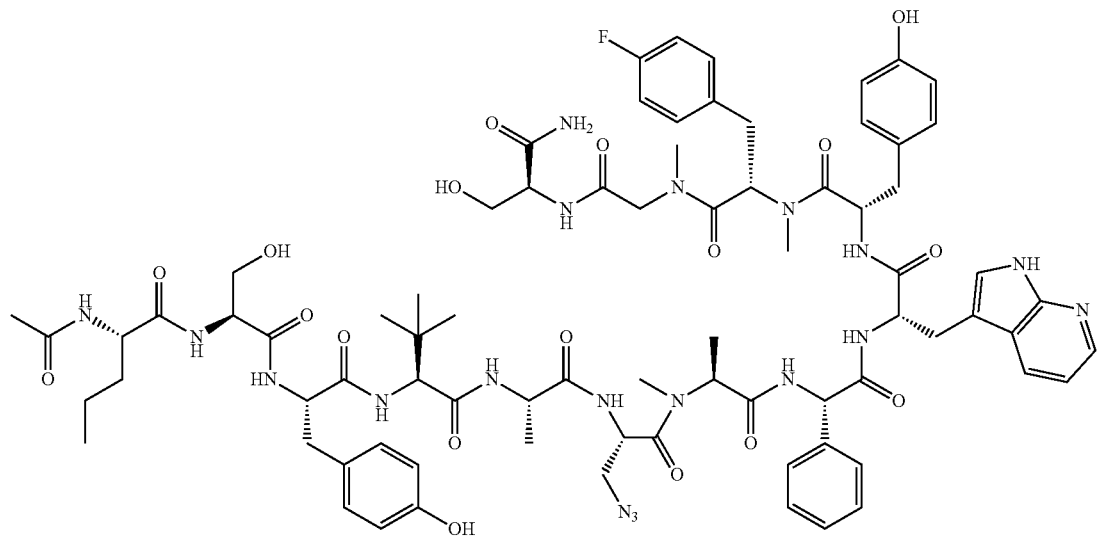

Compound 15 (2 mg) and N-(but-3-yn-1-yl)acrylamide (1.2 mg) were dissolved in a mixture of water/t-butanol (0.2 mL). CuBr (5 mg) were added into the solution and the reaction was stirred at RT for 3 hr. Upon completion, the solids were filtered off and the filtrate was diluted in 30% acetonitrile in water (5 mL, containing 0.1% trifluoro acetic acid) and purified through HPLC. After lyophilizing 2 mg of compound 16 were obtained.

Compound 17

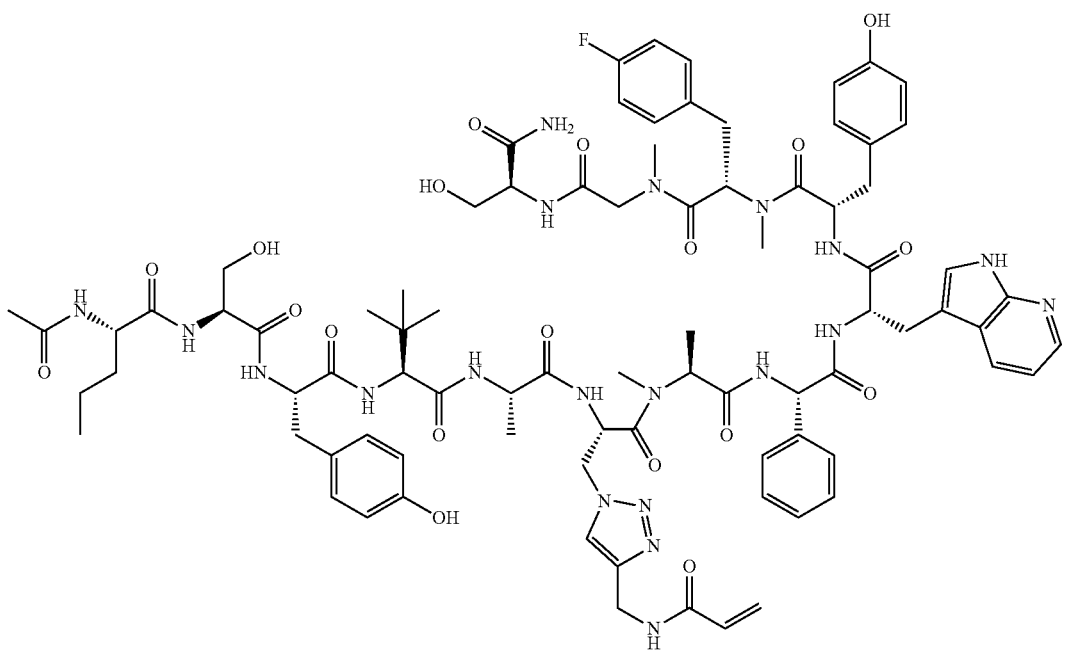

Compound 15 (2 mg) and N-(prop-2-yn-1-yl)acrylamide (1.1 mg) were dissolved in a mixture of water/t-butanol (0.2 mL). CuBr (5 mg) were added into the solution and the reaction was stirred at RT for 3 hr. Upon completion, the solids were filtered off and the filtrate was diluted in 30% acetonitrile in water (5 mL, containing 0.1% trifluoro acetic acid) and purified through HPLC. After lyophilizing 1 mg of compound 17 were obtained.

Compound 18

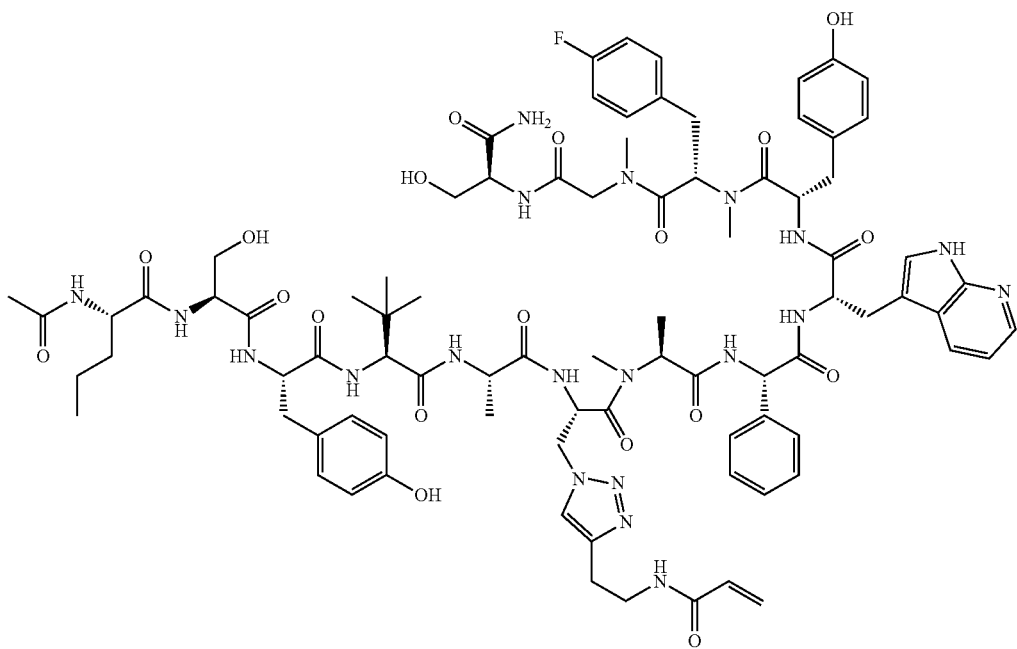

Compound 15 (2 mg) and N-(pent-4-yn-1-yl)acrylamide (1.2 mg) were dissolved in a mixture of water/t-butanol (0.2 mL). CuBr (5 mg) were added into the solution and the reaction was stirred at RT for 3 hr. Upon completion, the solids were filtered off and the filtrate was diluted in 30% acetonitrile in water (5 mL, containing 0.1% trifluoro acetic acid) and purified through HPLC. After lyophilizing 1.1 mg of compound 18 were obtained.

TABLE 8

FP competition assay results

| Compound | Probe displacement (nM IC$_{50}$) | SEQ ID NO |
|---|---|---|
| R4100 | 1.06 | 11 |
| R4101 | 1.45 | 12 |

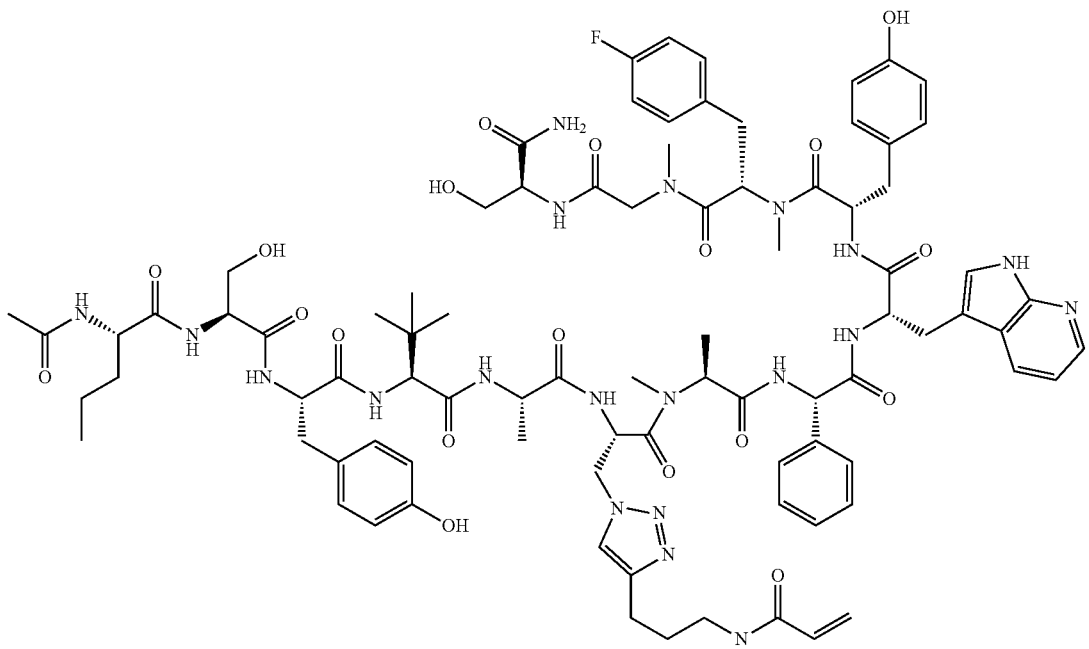 [SMILES: C=CC(=O)NCCCc1cn(C[C@H](NC(=O)[C@H](C)NC(=O)[C@@H](NC(=O)[C@H](Cc2ccc(O)cc2)NC(=O)[C@H](CO)NC(=O)[C@H](CCC)NC(C)=O)C(C)(C)C)C(=O)N(C)[C@@H](C)C(=O)N[C@H](C(=O)N[C@@H](Cc2c[nH]c3ncccc23)C(=O)N[C@@H](Cc2ccc(O)cc2)C(=O)N(C)[C@@H](Cc2ccc(F)cc2)C(=O)N(C)CC(=O)N[C@@H](CO)C(N)=O)c2ccccc2)nn1]

Example 18

Fluorescence Polarization Competition Assay

Peptides were evaluated for competition with R4007, a probe consisting of TAMRA-labeled R4000, using a fluorescence polarization (FP) competition assay. The assay was performed in 384-well black, non-binding plates (Greiner Bio-One, Monroe, N.C.). GMPPNP-loaded H-Ras or GTP-loaded K-Ras, diluted in FP assay buffer (20 mM Tris-HCl, pH 7.5, 50 mM NaCl, 5 mM MgCl$_2$, 1 mM EDTA, 0.002% Triton-X-100) for a final concentration of 120 nM was incubated with 30 nM probe for 20 minutes at room temperature. Peptides were serially diluted, added to the assay and incubated for 60 minutes at room temperature. Fluorescence was detected with a SpectraMax Paradigm plate reader (Molecular Devices, Sunnyvale, Calif.) using the Rhodamine FP detection cartridge (535 nm/595 nm). Data was analyzed and Ki determined using a One Site Ki Curve fitting model. Percent inhibition for each data point was calculated relative to the maximal binding in test compound-free control wells (showing no probe displacement) and Ras-free control wells (showing no probe binding) and the half-maximal inhibitory concentration (IC$_{50}$), based on probe displacement, was determined. Results are presented in Table 8.

TABLE 8-continued

FP competition assay results

| Compound | Probe displacement (nM IC$_{50}$) | SEQ ID NO |
|---|---|---|
| R4102 | 1.82 | 13 |
| R4103 | 2.00 | 14 |
| R4104 | 3.29 | 15 |
| R4105 | 3.31 | 16 |
| R4002 | 7.92 | 9 |
| R4106 | 8.38 | 17 |
| R4107 | 9.42 | 18 |
| R4108 | 9.45 | 19 |
| R4109 | 14.17 | 20 |
| R4110 | 16.38 | 21 |
| R4111 | 20.82 | 22 |
| R4112 | 21.41 | 23 |
| R4000 | 28.64 | 7 |
| R4113 | 32.66 | 24 |
| R4114 | 32.69 | 25 |
| R4115 | 34.15 | 26 |
| R4116 | 35.67 | 27 |
| R4117 | 48.29 | 28 |
| R4118 | 51.49 | 29 |
| R4119 | 64.43 | 30 |
| R4120 | 65.70 | 31 |
| R4121 | 72.99 | 32 |
| R4122 | 77.14 | 33 |
| R4123 | 84.98 | 34 |
| R4124 | 88.44 | 35 |
| R4125 | 109.80 | 36 |
| R4126 | 127.44 | 37 |
| R4127 | 148.20 | 38 |
| R4128 | 215.30 | 39 |

TABLE 8-continued

FP competition assay results

| Compound | Probe displacement (nM IC$_{50}$) | SEQ ID NO |
|---|---|---|
| R4129 | 227.30 | 40 |
| R4130 | 268.10 | 41 |
| R4131 | 277.78 | 42 |
| R4132 | 281.18 | 43 |
| R4133 | 342.40 | 44 |
| R4134 | 346.10 | 45 |
| R4135 | 364.10 | 46 |
| R4136 | 392.50 | 47 |
| R4137 | 411.00 | 48 |
| R4138 | 460.80 | 49 |
| R4139 | 522.30 | 50 |
| R4140 | 607.70 | 51 |
| R4141 | 694.95 | 52 |
| R4142 | 1245.00 | 53 |
| R4143 | 1642.00 | 54 |
| R4144 | 1962.00 | 55 |

TABLE 8-continued

FP competition assay results

| Compound | Probe displacement (nM IC$_{50}$) | SEQ ID NO |
|---|---|---|
| R4005 | 2070.00 | 10 |
| R4145 | 2803.00 | 56 |
| R4146 | 3388.67 | 57 |
| R4147 | 5188.00 | 58 |
| R4148 | 6004.00 | 59 |
| R4149 | 6263.00 | 60 |
| R4150 | 7640.50 | 61 |
| R4151 | 12159.00 | 62 |
| R4152 | 28339.00 | 63 |
| R4153 | 36450.00 | 64 |
| R4154 | 37395.00 | 65 |

Compounds R4100-R4108 and R4002 were the most potent with IC$_{50}$ values below 10 nM. These results demonstrate specific binding to Ras at a site critical for dimerization and subsequent Ras activity.

SEQUENCE LISTING

<160> NUMBER OF SEQ ID NOS: 74

<210> SEQ ID NO 1
<211> LENGTH: 189
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Thr Glu Tyr Lys Leu Val Val Val Gly Ala Val Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185

<210> SEQ ID NO 2
<211> LENGTH: 166
<212> TYPE: PRT

-continued

```
<213> ORGANISM: Artificial Sequence
<220> FEATURE:
<223> OTHER INFORMATION: Description of Artificial Sequence: Synthetic
      polypeptide

<400> SEQUENCE: 2

Thr Glu Tyr Lys Leu Val Val Val Gly Ala Val Gly Val Gly Lys Ser
1               5                   10                  15

Ala Leu Thr Ile Gln Leu Ile Gln Asn His Phe Val Asp Glu Tyr Asp
            20                  25                  30

Pro Thr Ile Glu Asp Ser Tyr Arg Lys Gln Val Val Ile Asp Gly Glu
        35                  40                  45

Thr Cys Leu Leu Asp Ile Leu Asp Thr Ala Gly Gln Glu Glu Tyr Ser
50                  55                  60

Ala Met Arg Asp Gln Tyr Met Arg Thr Gly Glu Gly Phe Leu Cys Val
65                  70                  75                  80

Phe Ala Ile Asn Asn Thr Lys Ser Phe Glu Asp Ile His Gln Tyr Arg
                85                  90                  95

Glu Gln Ile Lys Arg Val Lys Asp Ser Asp Asp Val Pro Met Val Leu
            100                 105                 110

Val Gly Asn Lys Cys Asp Leu Ala Ala Arg Thr Val Glu Ser Arg Gln
        115                 120                 125

Ala Gln Asp Leu Ala Arg Ser Tyr Gly Ile Pro Tyr Ile Glu Thr Ser
    130                 135                 140

Ala Lys Thr Arg Gln Gly Val Glu Asp Ala Phe Tyr Thr Leu Val Arg
145                 150                 155                 160

Glu Ile Arg Gln His Lys
                165

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Ser Gly Ser Gly Ser Gly Ser Gly Ser Cys Gly Ser Gly
1               5                   10

<210> SEQ ID NO 4
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Thr Glu Tyr Lys Leu Val Val Val Gly Ala Val Gly Val Gly Lys Ser
1               5                   10                  15

Ala Leu Thr Ile Gln Leu Ile Gln Asn His Phe Val Asp Glu Tyr Asp
            20                  25                  30

Pro Thr Ile Glu Asp Ser Tyr Arg Lys Gln Val Val Ile Asp Gly Glu
        35                  40                  45

Thr Cys Leu Leu Asp Ile Leu Asp Thr Ala Gly Gln Glu Glu Tyr Ser
    50                  55                  60

Ala Met Arg Asp Gln Tyr Met Arg Thr Gly Glu Gly Phe Leu Cys Val
65                  70                  75                  80
```

```
Phe Ala Ile Asn Asn Thr Lys Ser Phe Glu Asp Ile His Gln Tyr Arg
                85                  90                  95

Glu Gln Ile Lys Arg Val Lys Asp Ser Asp Asp Val Pro Met Val Leu
            100                 105                 110

Val Gly Asn Lys Cys Asp Leu Ala Ala Arg Thr Val Glu Ser Arg Gln
        115                 120                 125

Ala Gln Asp Leu Ala Arg Ser Tyr Gly Ile Pro Tyr Ile Glu Thr Ser
    130                 135                 140

Ala Lys Thr Arg Gln Gly Val Glu Asp Ala Phe Tyr Thr Leu Val Arg
145                 150                 155                 160

Glu Ile Arg Gln His Lys Gly Ser Gly Ser Gly Ser Gly Ser Gly Ser
                165                 170                 175

Cys Gly Ser Gly
        180

<210> SEQ ID NO 5
<211> LENGTH: 188
<212> TYPE: PRT
<213> ORGANISM: Homo sapiens

<400> SEQUENCE: 5

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
        115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 6
<211> LENGTH: 188
<212> TYPE: PRT
<213> ORGANISM: Homo sapiens

<400> SEQUENCE: 6

Met Thr Glu Tyr Lys Leu Val Val Val Gly Ala Asp Gly Val Gly Lys
1               5                   10                  15

Ser Ala Leu Thr Ile Gln Leu Ile Gln Asn His Phe Val Asp Glu Tyr
            20                  25                  30
```

```
Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His His Tyr
                85                  90                  95

Arg Glu Gln Ile Lys Arg Val Lys Asp Ser Glu Asp Val Pro Met Val
            100                 105                 110

Leu Val Gly Asn Lys Cys Asp Leu Pro Ser Arg Thr Val Asp Thr Lys
            115                 120                 125

Gln Ala Gln Asp Leu Ala Arg Ser Tyr Gly Ile Pro Phe Ile Glu Thr
    130                 135                 140

Ser Ala Lys Thr Arg Gln Gly Val Asp Asp Ala Phe Tyr Thr Leu Val
145                 150                 155                 160

Arg Glu Ile Arg Lys His Lys Glu Lys Met Ser Lys Asp Gly Lys Lys
                165                 170                 175

Lys Lys Lys Lys Ser Lys Thr Lys Cys Val Ile Met
            180                 185

<210> SEQ ID NO 7
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 7

Val Cys Tyr Gly Lys His

```
                1               5                    10
```

<210> SEQ ID NO 8
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<221> NAME/KEY: MOD_RES
<222> LOCATION: (14)..(14)
<223> OTHER INFORMATION: L-Propargylglycine

<400> SEQUENCE: 8

```
Val Cys Tyr Gly Lys His Xaa Gly Trp Tyr Phe Xaa Cys Gly
1               5                   10
```

<210> SEQ ID NO 9
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:

```
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 9

Val Cys Tyr Gly Lys His Xaa Gly Trp Tyr Phe Xaa Cys
1               5                   10

<210> SEQ ID NO 10
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (6)..(6)
<223> OTHER INFORMATION: (S)-3-(4-(acrylamidomethyl)-1H-1,2,3-triazol-1-
      yl)-2-aminopropanoic acid
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (9)..(9)
<223> OTHER INFORMATION: DL-alpha-Phenylglycine
<220> FEATURE:
<221> NAME/KEY: MOD_RES
<222> LOCATION: (10)..(10)
<223> OTHER INFORMATION: L-7-azatryptophan
<220> FEATURE:
<221> NAME/KEY: MOD_RES
<222> LOCATION: (12)..(12)
<223> OTHER INFORMATION: N-Methyl-4-fluoro-L-phenylalanine
<220> FEATURE:
<221> NAME/KEY: MOD_RES
<222> LOCATION: (13)..(13)
<223> OTHER INFORMATION: Sarcosine
<220> FEATURE:
<223> OTHER INFORMATION: C-term amide

<400> SEQUENCE: 10

Val Ser Tyr Gly Ala Xaa Xaa Gly Trp Tyr Phe Xaa Ser
1               5                   10

<210> SEQ ID NO 11
<211> LENGTH: 13
<212> TYPE: PRT
<213> ORGANISM: Artificial Sequence
```

```
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (3)..(3)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: L-7-azatryptophan
<220> FEATURE:
<221> NAME/KEY: MOD_RES
<222> LOCATION: (8)..(8)
<223> OTHER INFORMATION: L-7-azatryptophan
<220> FEATURE:
<221> NAME/KEY: MOD_RES
<222> LOCATION: (10)..(10)
<223> OTHER INFORMATION: L-7-azatryptophan
<220> FEATURE:
<221> NAME/KEY: MOD_RES
<222> LOCATION: (11)..(11)
<223> OTHER INFORMATION: L-Norvaline
<220> FEATURE:
<223> OTHER INFORMATION: C-term amide

<400> SEQUENCE: 11

Val Cys Gly Tyr His Thr Trp Trp Glu Trp Val His Cys
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
```

-continued

```
<220> FEATURE:
<221> NAME/KEY: MOD_RES
<222> LOCATION: (12)..(12)
<223> OTHER INFORMATION: (S)-2-(methylamino)propanoic acid
<220> FEATURE:
<223> OTHER INFORMATION: C-term amide

<400> SEQUENCE: 12

Val Cys Tyr Gly Lys His Xaa Gly Trp Tyr Phe Xaa Cys
1               5                   10

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<221> NAME/KEY: MOD_RES
<222> LOCATION: (14)..(14)
<223> OTHER INFORMATION: D-Serine
<220> FEATURE:
<221> NAME/KEY: MOD_RES
<222> LOCATION: (15)..(15)
<223> OTHER INFORMATION: D-Alanine

<400> SEQUENCE: 13

Val Cys Tyr Gly Lys His Xaa Gly Trp Tyr Phe Xaa Cys Ser Ala Gly
1               5                   10                  15

Cys Val Ile Met
            20

<210> SEQ ID NO 14
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
```

```
<220> FEATURE:
<223> OTHER INFORMATION: N-term Glutaric acid
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 14

Val Cys Tyr Gly Lys His Xaa Gly Trp Tyr Phe Xaa Cys
 1               5                  10

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
```

```
<223> OTHER INFORMATION: Sarcosine
<220> FEATURE:
<223> OTHER INFORMATION: C-term amide

<400> SEQUENCE: 15

Ser Cys Tyr Gly Lys His Xaa Gly Trp Tyr Phe Xaa Cys
1               5                   10

<210> SEQ ID NO 16
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<221> NAME/KEY: MOD_RES
<222> LOCATION: (14)..(14)
<223> OTHER INFORMATION: D-Serine

<400> SEQUENCE: 16

Val Cys Tyr Gly Lys His Xaa Gly Trp Tyr Phe Xaa Cys Ser Lys Gly
1               5                   10                  15

Cys Val Ile Met
            20

<210> SEQ ID NO 17
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: ((2S,3R)-3-amino-2-hydroxy-4-phenylbutanoyl)-L-
      leucine
<220> FEATURE:
<221> NAME/KEY: MOD_RES
```

```
<222> LOCATION: (2)..(2)
<223> OTHER INFORMATION: 7-aminoheptanoic acid
<220> FEATURE:
<221> NAME/KEY: MOD_RES
<222> LOCATION: (3)..(3)
<223> OTHER INFORMATION: L-Norvaline
<220> FEATURE:
<221> NAME/KEY: MISC_FEATURE
<222> LOCATION: (4)..(15)
<223> OTHER INFORMATION: m-xylylene thioether bridge between residues
<220> FEATURE:
<221> NAME/KEY: MOD_RES
<222> LOCATION: (6)..(6)
<223> OTHER INFORMATION: L-alpha-tert-butyl-glycine
<220> FEATURE:
<221> NAME/KEY: MOD_RES
<222> LOCATION: (9)..(9)
<223> OTHER INFORMATION: (S)-2-(methylamino)propanoic acid
<220> FEATURE:
<221> NAME/KEY: MOD_RES
<222> LOCATION: (10)..(10)
<223> OTHER INFORMATION: L-Phenylglycine
<220> FEATURE:
<221> NAME/KEY: MOD_RES
<222> LOCATION: (11)..(11)
<223> OTHER INFORMATION: L-7-azatryptophan
<220> FEATURE:
<221> NAME/KEY: MOD_RES
<222> LOCATION: (13)..(13)
<223> OTHER INFORMATION: N-Methyl-4-fluoro-L-phenylalanine
<220> FEATURE:
<221> NAME/KEY: MOD_RES
<222> LOCATION: (14)..(14)
<223> OTHER INFORMATION: Sarcosine
<220> FEATURE:
<223> OTHER INFORMATION: C-term amide

<400> SEQUENCE: 17

Leu Xaa Val Cys Tyr Gly Lys His Xaa Gly Trp Tyr Phe Xaa Cys
1               5                   10                  15

<210> SEQ ID NO 18
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
```

-continued

```
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine

<400> SEQUENCE: 18

Val Cys Tyr Gly Lys His Xaa Gly Trp Tyr Phe Xaa Cys
1               5                   10

<210> SEQ ID NO 19
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine

<400> SEQUENCE: 19

Val Cys Tyr Gly Lys His Xaa Gly Trp Tyr Phe Xaa Cys
1               5                   10

<210> SEQ ID NO 20
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
```

-continued

```
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<221> NAME/KEY: MOD_RES
<222> LOCATION: (14)..(14)
<223> OTHER INFORMATION: D-Serine
<220> FEATURE:
<221> NAME/KEY: MOD_RES
<222> LOCATION: (17)..(17)
<223> OTHER INFORMATION: (R)-2-amino-3-(tert-butyldisulfanyl)propanoic
      acid

<400> SEQUENCE: 20

Val Cys Tyr Gly Lys His Xaa Gly Trp Tyr Phe Xaa Cys Ser Lys Gly
1               5                   10                  15

Xaa Val Ile Met
            20

<210> SEQ ID NO 21
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
```

```
<221> NAME/KEY: MOD_RES
<222> LOCATION: (12)..(12)
<223> OTHER INFORMATION: Sarcosine
<220> FEATURE:
<221> NAME/KEY: MOD_RES
<222> LOCATION: (14)..(14)
<223> OTHER INFORMATION: D-Serine
<220> FEATURE:
<221> NAME/KEY: MOD_RES
<222> LOCATION: (17)..(17)
<223> OTHER INFORMATION: (R)-2-amino-3-(tert-butyldisulfanyl)propanoic
      acid

<400> SEQUENCE: 21

Val Cys Tyr Gly Lys His Xaa Gly Trp Tyr Phe Xaa Cys Ser Lys Gly
1               5                   10                  15

Xaa Val Val Leu
            20

<210> SEQ ID NO 22
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<221> NAME/KEY: MOD_RES
<222> LOCATION: (14)..(14)
<223> OTHER INFORMATION: D-Serine
<220> FEATURE:
<221> NAME/KEY: MOD_RES
<222> LOCATION: (15)..(15)
<223> OTHER INFORMATION: D-Alanine
<220> FEATURE:
<221> NAME/KEY: MOD_RES
<222> LOCATION: (17)..(17)
<223> OTHER INFORMATION: (R)-2-amino-3-(tert-butyldisulfanyl)propanoic
      acid

<400> SEQUENCE: 22
```

Val Cys Tyr Gly Lys His Xaa Gly Trp Tyr Phe Xaa Cys Ser Ala Lys
1               5                   10                  15

Xaa Val Ile Met
            20

<210> SEQ ID NO 23
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MISC_FEATURE
<222> LOCATION: (1)..(12)
<223> OTHER INFORMATION: m-xylylene thioether bridge between residues
<220> FEATURE:
<221> NAME/KEY: MOD_RES
<222> LOCATION: (3)..(3)
<223> OTHER INFORMATION: L-alpha-tert-butyl-glycine
<220> FEATURE:
<221> NAME/KEY: MOD_RES
<222> LOCATION: (6)..(6)
<223> OTHER INFORMATION: (S)-2-(methylamino)propanoic acid
<220> FEATURE:
<221> NAME/KEY: MOD_RES
<222> LOCATION: (7)..(7)
<223> OTHER INFORMATION: L-Phenylglycine
<220> FEATURE:
<221> NAME/KEY: MOD_RES
<222> LOCATION: (8)..(8)
<223> OTHER INFORMATION: L-7-azatryptophan
<220> FEATURE:
<221> NAME/KEY: MOD_RES
<222> LOCATION: (10)..(10)
<223> OTHER INFORMATION: N-Methyl-4-fluoro-L-phenylalanine
<220> FEATURE:
<221> NAME/KEY: MOD_RES
<222> LOCATION: (11)..(11)
<223> OTHER INFORMATION: Sarcosine
<220> FEATURE:
<223> OTHER INFORMATION: C-term amide

<400> SEQUENCE: 23

Cys Tyr Gly Lys His Xaa Gly Trp Tyr Phe Xaa Cys
1               5                   10

<210> SEQ ID NO 24
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)

```
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<221> NAME/KEY: MOD_RES
<222> LOCATION: (14)..(14)
<223> OTHER INFORMATION: D-Serine
<220> FEATURE:
<221> NAME/KEY: MOD_RES
<222> LOCATION: (17)..(17)
<223> OTHER INFORMATION: (R)-2-amino-3-(tert-butyldisulfanyl)propanoic
      acid

<400> SEQUENCE: 24

Val Cys Tyr Gly Lys His Xaa Gly Trp Tyr Phe Xaa Cys Ser Lys Gly
1               5                   10                  15

Xaa Val Ile Met
            20

<210> SEQ ID NO 25
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<221> NAME/KEY: MOD_RES
<222> LOCATION: (14)..(14)
<223> OTHER INFORMATION: D-Serine

<400> SEQUENCE: 25

Val Cys Tyr Gly Lys His Xaa Gly Trp Tyr Phe Xaa Cys Ser Lys Gly
```

```
1               5                   10                  15

Cys Val Ile Met
            20

<210> SEQ ID NO 26
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 26

Val Cys Tyr Gly Lys His Xaa Gly Trp Tyr Phe Xaa Cys
1               5                   10

<210> SEQ ID NO 27
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
```

```
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 27

Val Cys Tyr Gly Lys His Xaa Gly Trp Tyr Phe Xaa Cys Gly Cys Met
1               5                   10                  15

Ser Cys Lys Cys Val Leu Ser
            20

<210> SEQ ID NO 28
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (3)..(3)
<223> OTHER INFORMATION: N-Methyl-L-tyrosine
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 28

Val Cys Tyr Gly Lys His Xaa Gly Trp Tyr Phe Xaa Cys
1               5                   10
```

```
<210> SEQ ID NO 29
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: N-Methyl-L-serine
<220> FEATURE:
<223> OTHER INFORMATION: C-term amide

<400> SEQUENCE: 29

Val Cys Tyr Gly Lys His Xaa Gly Trp Tyr Phe Ser Cys
1               5                   10

<210> SEQ ID NO 30
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
```

```
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine

<400> SEQUENCE: 30

Val Cys Tyr Gly Lys His Xaa Gly Trp Tyr Phe Xaa Cys Gly Cys Gly
1               5                  10                  15

Val Gly Ile Met
            20

<210> SEQ ID NO 31
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 31

Val Cys Tyr Gly Lys His Xaa Gly Trp Tyr Phe Xaa Cys Gly Gly Gly
1               5                  10                  15

Cys Ala Ile Leu
            20

<210> SEQ ID NO 32
<211> LENGTH: 13
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: D-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: (S)-2-(methylamino)propanoic acid
<220> FEATURE:
<223> OTHER INFORMATION: C-term amide

<400> SEQUENCE: 32

Val Cys Tyr Gly Lys His Xaa Gly Trp Tyr Phe Xaa Cys
1               5                   10

<210> SEQ ID NO 33
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (6)..(6)
<223> OTHER INFORMATION: (S)-5-acrylamido-2-aminopentanoic acid
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
```

```
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 33

Val Cys Tyr Gly Ala Xaa Xaa Gly Trp Tyr Phe Xaa Cys
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (6)..(6)
<223> OTHER INFORMATION: w-acrylamido-L-Lysine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 34

Val Cys Tyr Gly Ala Lys Xaa Gly Trp Tyr Phe Xaa Cys
1               5                   10

<210> SEQ ID NO 35
<211> LENGTH: 11
<212> TYPE: PRT
```

```
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-(2-(2-aminoethoxy)ethoxy)propanoic acid
<220> FEATURE:
<221> NAME/KEY: MISC_FEATURE
<222> LOCATION: (1)..(11)
<223> OTHER INFORMATION: Lactam bridge between residues
<220> FEATURE:
<221> NAME/KEY: MOD_RES
<222> LOCATION: (3)..(3)
<223> OTHER INFORMATION: L-alpha-tert-butyl-glycine
<220> FEATURE:
<221> NAME/KEY: MOD_RES
<222> LOCATION: (6)..(6)
<223> OTHER INFORMATION: (S)-2-(methylamino)propanoic acid
<220> FEATURE:
<221> NAME/KEY: MOD_RES
<222> LOCATION: (7)..(7)
<223> OTHER INFORMATION: L-Phenylglycine
<220> FEATURE:
<221> NAME/KEY: MOD_RES
<222> LOCATION: (8)..(8)
<223> OTHER INFORMATION: L-7-azatryptophan
<220> FEATURE:
<221> NAME/KEY: MOD_RES
<222> LOCATION: (10)..(10)
<223> OTHER INFORMATION: N-Methyl-4-fluoro-L-phenylalanine
<220> FEATURE:
<221> NAME/KEY: MOD_RES
<222> LOCATION: (11)..(11)
<223> OTHER INFORMATION: Sarcosine

<400> SEQUENCE: 35

Xaa Tyr Gly Lys His Xaa Gly Trp Tyr Phe Xaa
1               5                   10

<210> SEQ ID NO 36
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: N-Methyl-Lysine
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
```

```
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 36

Val Cys Tyr Gly Ala His Lys Gly Trp Tyr Phe Xaa Cys
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 37

Val Cys Tyr Gly Lys Ala Xaa Gly Trp Tyr Phe Xaa Cys
1               5                   10

<210> SEQ ID NO 38
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
```

```
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 38

Val Cys Tyr Gly Lys His Xaa Gly Trp Tyr Phe Xaa Cys Gly Gly
1               5                   10                  15

Cys Val Ile Met
            20

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 5-Aminovaleric acid
<220> FEATURE:
<221> NAME/KEY: MISC_FEATURE
<222> LOCATION: (1)..(12)
<223> OTHER INFORMATION: Lactam bridge between residues
<220> FEATURE:
<221> NAME/KEY: MOD_RES
<222> LOCATION: (3)..(3)
<223> OTHER INFORMATION: L-alpha-tert-butyl-glycine
<220> FEATURE:
<221> NAME/KEY: MOD_RES
<222> LOCATION: (6)..(6)
<223> OTHER INFORMATION: (S)-2-(methylamino)propanoic acid
<220> FEATURE:
<221> NAME/KEY: MOD_RES
<222> LOCATION: (7)..(7)
<223> OTHER INFORMATION: L-Phenylglycine
<220> FEATURE:
<221> NAME/KEY: MOD_RES
<222> LOCATION: (8)..(8)
<223> OTHER INFORMATION: L-7-azatryptophan
<220> FEATURE:
<221> NAME/KEY: MOD_RES
<222> LOCATION: (10)..(10)
<223> OTHER INFORMATION: N-Methyl-4-fluoro-L-phenylalanine
<220> FEATURE:
<221> NAME/KEY: MOD_RES
<222> LOCATION: (11)..(11)
<223> OTHER INFORMATION: Sarcosine
<220> FEATURE:
<221> NAME/KEY: MOD_RES
```

```
<222> LOCATION: (12)..(12)
<223> OTHER INFORMATION: L-Propargylglycine

<400> SEQUENCE: 39

Xaa Tyr Gly Lys His Xaa Gly Trp Tyr Phe Xaa Gly
1               5                   10

<210> SEQ ID NO 40
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (3)..(3)
<223> OTHER INFORMATION: N-Methyl-L-tyrosine
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<221> NAME/KEY: MOD_RES
<222> LOCATION: (14)..(14)
<223> OTHER INFORMATION: D-Serine
<220> FEATURE:
<221> NAME/KEY: MOD_RES
<222> LOCATION: (15)..(15)
<223> OTHER INFORMATION: D-Alanine
<220> FEATURE:
<221> NAME/KEY: MOD_RES
<222> LOCATION: (17)..(17)
<223> OTHER INFORMATION: (R)-2-amino-3-(tert-butyldisulfanyl)propanoic
      acid

<400> SEQUENCE: 40

Val Cys Tyr Gly Lys His Xaa Gly Trp Tyr Phe Xaa Cys Ser Ala Lys
1               5                   10                  15

Xaa Val Ile Met
            20

<210> SEQ ID NO 41
<211> LENGTH: 12
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 8-amino-3,6-dioxaoctanoic acid
<220> FEATURE:
<221> NAME/KEY: MISC_FEATURE
<222> LOCATION: (1)..(12)
<223> OTHER INFORMATION: Lactam bridge between residues
<220> FEATURE:
<221> NAME/KEY: MOD_RES
<222> LOCATION: (3)..(3)
<223> OTHER INFORMATION: L-alpha-tert-butyl-glycine
<220> FEATURE:
<221> NAME/KEY: MOD_RES
<222> LOCATION: (6)..(6)
<223> OTHER INFORMATION: (S)-2-(methylamino)propanoic acid
<220> FEATURE:
<221> NAME/KEY: MOD_RES
<222> LOCATION: (7)..(7)
<223> OTHER INFORMATION: L-Phenylglycine
<220> FEATURE:
<221> NAME/KEY: MOD_RES
<222> LOCATION: (8)..(8)
<223> OTHER INFORMATION: L-7-azatryptophan
<220> FEATURE:
<221> NAME/KEY: MOD_RES
<222> LOCATION: (10)..(10)
<223> OTHER INFORMATION: N-Methyl-4-fluoro-L-phenylalanine
<220> FEATURE:
<221> NAME/KEY: MOD_RES
<222> LOCATION: (11)..(11)
<223> OTHER INFORMATION: Sarcosine
<220> FEATURE:
<221> NAME/KEY: MOD_RES
<222> LOCATION: (12)..(12)
<223> OTHER INFORMATION: L-Propargylglycine

<400> SEQUENCE: 41

Xaa Tyr Gly Lys His Xaa Gly Trp Tyr Phe Xaa Gly
1               5                   10

<210> SEQ ID NO 42
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
```

```
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine

<400> SEQUENCE: 42

Val Cys Tyr Gly Lys His Xaa Gly Trp Tyr Phe Xaa Cys Gly Gly Gly
1               5                   10                  15

Cys Val Ile Met
            20

<210> SEQ ID NO 43
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: N-Methyl-L-serine
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 43

Val Cys Tyr Gly Lys His Ser Gly Trp Tyr Phe Xaa Cys
1               5                   10

<210> SEQ ID NO 44
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
```

```
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: w-acrylamido-N-methyl-L-Lysine
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 44

Val Cys Tyr Gly Ala His Lys Gly Trp Tyr Phe Xaa Cys
1               5                   10

<210> SEQ ID NO 45
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (5)..(5)
<223> OTHER INFORMATION: N6-(4-(dimethylamino)benzoyl)-L-lysine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
```

```
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 45

Val Cys Tyr Gly Xaa His Xaa Gly Trp Tyr Phe Xaa Cys
1               5                   10

<210> SEQ ID NO 46
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (5)..(5)
<223> OTHER INFORMATION: L-Lysine(ivDde)
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine

<400> SEQUENCE: 46

Val Cys Tyr Gly Lys His Xaa Gly Trp Tyr Phe Xaa Cys
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
```

```
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (6)..(6)
<223> OTHER INFORMATION: (S)-3-acrylamido-2-aminopropanoic acid
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 47

Val Cys Tyr Gly Ala Xaa Xaa Gly Trp Tyr Phe Xaa Cys
1               5                   10

<210> SEQ ID NO 48
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: epsilon-Aminocaproic acid
<220> FEATURE:
<221> NAME/KEY: MISC_FEATURE
<222> LOCATION: (1)..(12)
<223> OTHER INFORMATION: Lactam bridge between residues
<220> FEATURE:
<221> NAME/KEY: MOD_RES
<222> LOCATION: (3)..(3)
<223> OTHER INFORMATION: L-alpha-tert-butyl-glycine
<220> FEATURE:
<221> NAME/KEY: MOD_RES
<222> LOCATION: (6)..(6)
<223> OTHER INFORMATION: (S)-2-(methylamino)propanoic acid
<220> FEATURE:
<221> NAME/KEY: MOD_RES
<222> LOCATION: (7)..(7)
<223> OTHER INFORMATION: L-Phenylglycine
<220> FEATURE:
<221> NAME/KEY: MOD_RES
<222> LOCATION: (8)..(8)
<223> OTHER INFORMATION: L-7-azatryptophan
<220> FEATURE:
<221> NAME/KEY: MOD_RES
<222> LOCATION: (10)..(10)
<223> OTHER INFORMATION: N-Methyl-4-fluoro-L-phenylalanine
<220> FEATURE:
```

```
<221> NAME/KEY: MOD_RES
<222> LOCATION: (11)..(11)
<223> OTHER INFORMATION: Sarcosine
<220> FEATURE:
<221> NAME/KEY: MOD_RES
<222> LOCATION: (12)..(12)
<223> OTHER INFORMATION: L-Propargylglycine

<400> SEQUENCE: 48

Xaa Tyr Gly Lys His Xaa Gly Trp Tyr Phe Xaa Gly
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Glutaric acid
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (5)..(5)
<223> OTHER INFORMATION: L-Lysine(ivDde)
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 49

Val Cys Tyr Gly Lys His Xaa Gly Trp Tyr Phe Xaa Cys
1               5                   10

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: 3-(2-aminoethoxy)propanoic acid
```

```
<220> FEATURE:
<221> NAME/KEY: MISC_FEATURE
<222> LOCATION: (1)..(12)
<223> OTHER INFORMATION: Lactam bridge between residues
<220> FEATURE:
<221> NAME/KEY: MOD_RES
<222> LOCATION: (3)..(3)
<223> OTHER INFORMATION: L-alpha-tert-butyl-glycine
<220> FEATURE:
<221> NAME/KEY: MOD_RES
<222> LOCATION: (6)..(6)
<223> OTHER INFORMATION: (S)-2-(methylamino)propanoic acid
<220> FEATURE:
<221> NAME/KEY: MOD_RES
<222> LOCATION: (7)..(7)
<223> OTHER INFORMATION: L-Phenylglycine
<220> FEATURE:
<221> NAME/KEY: MOD_RES
<222> LOCATION: (8)..(8)
<223> OTHER INFORMATION: L-7-azatryptophan
<220> FEATURE:
<221> NAME/KEY: MOD_RES
<222> LOCATION: (10)..(10)
<223> OTHER INFORMATION: N-Methyl-4-fluoro-L-phenylalanine
<220> FEATURE:
<221> NAME/KEY: MOD_RES
<222> LOCATION: (11)..(11)
<223> OTHER INFORMATION: Sarcosine
<220> FEATURE:
<221> NAME/KEY: MOD_RES
<222> LOCATION: (12)..(12)
<223> OTHER INFORMATION: L-Propargylglycine

<400> SEQUENCE: 50

Xaa Tyr Gly Lys His Xaa Gly Trp Tyr Phe Xaa Gly
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (6)..(6)
<223> OTHER INFORMATION: L-2,4-diaminobutyric acid
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
```

```
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 51

Val Cys Tyr Gly Ala Xaa Xaa Gly Trp Tyr Phe Xaa Cys
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (6)..(6)
<223> OTHER INFORMATION: L-2,3-Diaminopropionic acid
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 52

Val Cys Tyr Gly Ala Xaa Xaa Gly Trp Tyr Phe Xaa Cys
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
```

```
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-5-acrylamido-2-(methylamino)pentanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 53

Val Cys Tyr Gly Ala His Xaa Gly Trp Tyr Phe Xaa Cys
1               5                   10

<210> SEQ ID NO 54
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: (S)-2-(methylamino)propanoic acid
<220> FEATURE:
<221> NAME/KEY: MOD_RES
<222> LOCATION: (12)..(12)
<223> OTHER INFORMATION: Sarcosine

<400> SEQUENCE: 54
```

```
Val Cys Tyr Gly Lys His Xaa Ala Trp Tyr Xaa Xaa Cys Gly Gly Gly
1               5                   10                  15

Cys Val Ile Met
            20

<210> SEQ ID NO 55
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (6)..(6)
<223> OTHER INFORMATION: D-Proline
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 55

Val Cys Tyr Gly Lys Pro Xaa Gly Trp Tyr Phe Xaa Cys
1               5                   10

<210> SEQ ID NO 56
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(11)
<223> OTHER INFORMATION: Lactam bridge between residues
<220> FEATURE:
<221> NAME/KEY: MOD_RES
<222> LOCATION: (2)..(2)
<223> OTHER INFORMATION: L-alpha-tert-butyl-glycine
<220> FEATURE:
<221> NAME/KEY: MOD_RES
<222> LOCATION: (5)..(5)
```

<223> OTHER INFORMATION: (S)-2-(methylamino)propanoic acid
<220> FEATURE:
<221> NAME/KEY: MOD_RES
<222> LOCATION: (6)..(6)
<223> OTHER INFORMATION: L-Phenylglycine
<220> FEATURE:
<221> NAME/KEY: MOD_RES
<222> LOCATION: (7)..(7)
<223> OTHER INFORMATION: L-7-azatryptophan
<220> FEATURE:
<221> NAME/KEY: MOD_RES
<222> LOCATION: (9)..(9)
<223> OTHER INFORMATION: N-Methyl-4-fluoro-L-phenylalanine
<220> FEATURE:
<221> NAME/KEY: MOD_RES
<222> LOCATION: (10)..(10)
<223> OTHER INFORMATION: Sarcosine
<220> FEATURE:
<221> NAME/KEY: MOD_RES
<222> LOCATION: (11)..(11)
<223> OTHER INFORMATION: L-Propargylglycine

<400> SEQUENCE: 56

Tyr Gly Lys His Xaa Gly Trp Tyr Phe Xaa Gly
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (6)..(6)
<223> OTHER INFORMATION: (S)-4-acrylamido-2-aminobutanoic acid
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 57

Val Cys Tyr Gly Ala Xaa Xaa Gly Trp Tyr Phe Xaa Cys

```
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine

<400> SEQUENCE: 58

Val Cys Tyr Gly Lys His Xaa Gly Trp Tyr Phe Xaa Cys
1               5                   10

<210> SEQ ID NO 59
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (6)..(6)
<223> OTHER INFORMATION: (S)-3-(4-(3-acrylamidopropyl)-1H-1,2,3-triazol-
      1-yl)-2-aminopropanoic acid
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
```

<222> LOCATION: (9)..(9)
<223> OTHER INFORMATION: DL-alpha-Phenylglycine
<220> FEATURE:
<221> NAME/KEY: MOD_RES
<222> LOCATION: (10)..(10)
<223> OTHER INFORMATION: L-7-azatryptophan
<220> FEATURE:
<221> NAME/KEY: MOD_RES
<222> LOCATION: (12)..(12)
<223> OTHER INFORMATION: N-Methyl-4-fluoro-L-phenylalanine
<220> FEATURE:
<221> NAME/KEY: MOD_RES
<222> LOCATION: (13)..(13)
<223> OTHER INFORMATION: Sarcosine
<220> FEATURE:
<223> OTHER INFORMATION: C-term amide

<400> SEQUENCE: 59

Val Ser Tyr Gly Ala Xaa Xaa Gly Trp Tyr Phe Xaa Ser
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: Cyclohexyl-L-glycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 60

Val Cys Tyr Gly Lys His Xaa Gly Trp Tyr Phe Xaa Cys
1               5                   10

<210> SEQ ID NO 61
<211> LENGTH: 13
<212> TYPE: PRT
<213> ORGANISM: Artificial Sequence
<220> FEATURE:
<223> OTHER INFORMATION: Description of Artificial Sequence: Synthetic

```
            peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (5)..(5)
<223> OTHER INFORMATION: N6-(4-(dimethylamino)benzoyl-2,3,5,6-d4)-L-
      lysine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 61

Val Cys Tyr Gly Xaa His Xaa Gly Trp Tyr Phe Xaa Cys
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (6)..(6)
<223> OTHER INFORMATION: (S)-3-(4-(2-acrylamidoethyl)-1H-1,2,3-triazol-
      1-yl)-2-aminopropanoic acid
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (9)..(9)
<223> OTHER INFORMATION: DL-alpha-Phenylglycine
```

```
<220> FEATURE:
<221> NAME/KEY: MOD_RES
<222> LOCATION: (10)..(10)
<223> OTHER INFORMATION: L-7-azatryptophan
<220> FEATURE:
<221> NAME/KEY: MOD_RES
<222> LOCATION: (12)..(12)
<223> OTHER INFORMATION: N-Methyl-4-fluoro-L-phenylalanine
<220> FEATURE:
<221> NAME/KEY: MOD_RES
<222> LOCATION: (13)..(13)
<223> OTHER INFORMATION: Sarcosine
<220> FEATURE:
<223> OTHER INFORMATION: C-term amide

<400> SEQUENCE: 62

Val Ser Tyr Gly Ala Xaa Xaa Gly Trp Tyr Phe Xaa Ser
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 63

Val Cys Ala Gly Lys His Xaa Gly Trp Tyr Phe Xaa Cys
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
```

```
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: D-Phenylglycine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine
<220> FEATURE:
<223> OTHER INFORMATION: C-term amide

<400> SEQUENCE: 64

Val Cys Tyr Gly Lys Ala Xaa Gly Trp Tyr Phe Xaa Cys
1               5                   10

<210> SEQ ID NO 65
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Alexa fluor 594
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(10)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-Norvaline
<220> FEATURE:
<221> NAME/KEY: MOD_RES
<222> LOCATION: (5)..(5)
<223> OTHER INFORMATION: L-Phenylglycine
<220> FEATURE:
<221> NAME/KEY: MOD_RES
<222> LOCATION: (6)..(6)
<223> OTHER INFORMATION: N-Methyl-4-fluoro-L-phenylalanine
<220> FEATURE:
<221> NAME/KEY: MOD_RES
<222> LOCATION: (9)..(9)
<223> OTHER INFORMATION: L-7-azatryptophan
<220> FEATURE:
<221> NAME/KEY: MOD_RES
<222> LOCATION: (11)..(11)
<223> OTHER INFORMATION: L-7-azatryptophan
```

```
<220> FEATURE:
<223> OTHER INFORMATION: C-term amide

<400> SEQUENCE: 65

Val Cys Tyr Val Gly Phe Thr Pro Trp Cys Trp Glu Glu
1               5                   10

<210> SEQ ID NO 66
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Arg Lys Lys Arg Arg Arg Glu Ser Arg Lys Lys Arg Arg Arg Glu Ser
1               5                   10                  15

<210> SEQ ID NO 67
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Arg Lys Lys Arg Arg Gln Arg Arg Arg
1               5

<210> SEQ ID NO 68
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Gln Ile Lys Ile Trp Phe Gln Asn Arg Arg Met Lys Trp Lys Lys
1               5                   10                  15

<210> SEQ ID NO 69
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Ala Val Leu Leu Pro Val Leu Leu Ala Ala Pro
1               5                   10

<210> SEQ ID NO 70
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Val Pro Thr Leu Lys
1               5
```

```
<210> SEQ ID NO 71
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 71

Pro Leu Ile Leu Leu Arg Leu Leu Arg Gly Gln Phe
1               5                   10

<210> SEQ ID NO 72
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term Acetyl
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: N-tert-Butoxycarbonyl-L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine

<400> SEQUENCE: 72

Val Cys Tyr Gly Lys His Xaa Gly Trp Tyr Phe Xaa Cys
1               5                   10

<210> SEQ ID NO 73
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: L-Norvaline
<220> FEATURE:
<221> NAME/KEY: MISC_FEATURE
<222> LOCATION: (2)..(13)
<223> OTHER INFORMATION: m-xylylene thioether bridge between residues
<220> FEATURE:
<221> NAME/KEY: MOD_RES
```

-continued

<222> LOCATION: (4)..(4)
<223> OTHER INFORMATION: L-alpha-tert-butyl-glycine
<220> FEATURE:
<221> NAME/KEY: MOD_RES
<222> LOCATION: (7)..(7)
<223> OTHER INFORMATION: (S)-2-(methylamino)propanoic acid
<220> FEATURE:
<221> NAME/KEY: MOD_RES
<222> LOCATION: (8)..(8)
<223> OTHER INFORMATION: L-Phenylglycine
<220> FEATURE:
<221> NAME/KEY: MOD_RES
<222> LOCATION: (9)..(9)
<223> OTHER INFORMATION: N-tert-Butoxycarbonyl-L-7-azatryptophan
<220> FEATURE:
<221> NAME/KEY: MOD_RES
<222> LOCATION: (11)..(11)
<223> OTHER INFORMATION: N-Methyl-4-fluoro-L-phenylalanine
<220> FEATURE:
<221> NAME/KEY: MOD_RES
<222> LOCATION: (12)..(12)
<223> OTHER INFORMATION: Sarcosine

<400> SEQUENCE: 73

Val Cys Tyr Gly Lys His Xaa Gly Trp Tyr Phe Xaa Cys
1 5 10

<210> SEQ ID NO 74
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 74

Cys Val Ile Met
1

What is claimed is:

1. A polypeptide comprising the formula $R_1$-Xaa0-Xaa1-Xaa2-Xaa3-Xaa4-Xaa5-Xaa6-Xaa7-Xaa8-Xaa9-Xaa10-Xaa11-Xaa12-Xaa13-$R_2$, wherein:

a. $R_1$ is selected from the group consisting of H, an acyl group containing an optionally substituted C1-20 aliphatic group, a heptanoyl group, an amide, a carbamate, urea, PEG, hydroxyalkyl starch, a peptide, and a protein;

b. Xaa0 is absent, or an amino acid selected from the group consisting of an unnatural amino acid, Met and norvaline;

c. Xaa1 is Cys;

d. Xaa2 is Tyr or N-Methyl-L-tyrosine;

e. Xaa3 is Tbg;

f. Xaa4 is Lys;

g. Xaa5 is His;

h. Xaa6 is (S)-2-(methylamino)propanoic acid or N-Methyl-L-serine;

i. Xaa7 is selected from the group consisting of Ala, phenylglycine and D-phenylglycine;

j. Xaa8 is selected from the group consisting of Trp and L-7-azatryptophan;

k. Xaa9 is Tyr;

l. Xaa10 is N-Methyl-4-fluoro-L-phenylalanine or (S)-2-(methylamino)propanoic acid;

m. Xaa1 l is an N-methylated amino acid;

n. Xaa12 is Cys;

o. Xaa13 is absent or selected from the group consisting of an unnatural amino acid; and p. $R_2$ is absent or selected from the group consisting of a peptide and —$NH_2$.

2. The polypeptide of claim 1, wherein a cyclic loop is formed by a bridging moiety between two amino acids.

3. The polypeptide of claim 2 wherein said bridging moiety comprises a structure selected from the group consisting of structures I-XIX

I.

II.

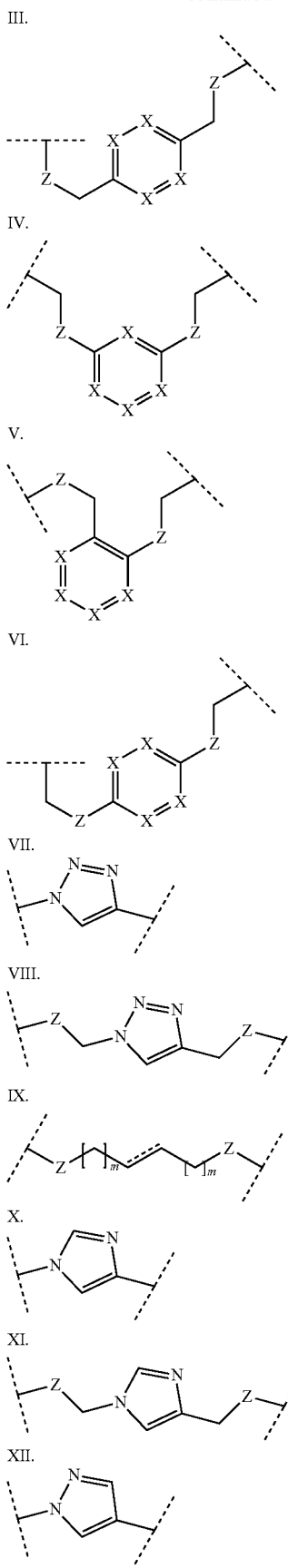
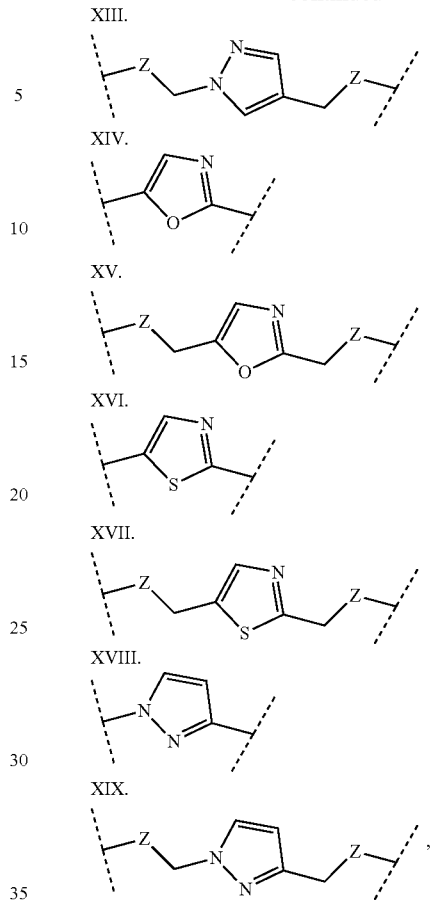

wherein each X is independently N or CH, provided that no more than two Xs in any ring are N; each Z is independently a bond, —NR—, —O—, —S—, —CH₂—, —C(O)NR—, —NRC(O)—, —S(O)ᵥNR—, or —NRS(O)ᵥ—; each m is independently selected from 0, 1, 2, and 3; each v is independently selected from 1 and 2; each R is independently selected from H and optionally substituted $C_1$-$C_6$ aliphatic; and each bridging moiety is optionally connected to the peptide by independently selected optionally substituted $C_1$-$C_6$ aliphatic groups.

4. The polypeptide of claim 2, wherein the bridging moiety comprises a feature selected from the group consisting of a lactam bridge, a disulfide bond, a thioether bond and an aromatic ring.

5. The polypeptide of claim 2, wherein the cyclic loop is of a length selected from the group consisting of 1 amino acid, 2 amino acids, 3 amino acids, 4 amino acids, 5 amino acids, 6 amino acids, 7 amino acids, 8 amino acids, 9, amino acids, 10 amino acids, 11 amino acids, 12 amino acids, 13 amino acids, 14 amino acids, 15 amino acids and 16 amino acids.

6. The polypeptide of claim 2, wherein the bridging moiety forms a cyclic loop between residue Xaa1 and a residue selected from the group consisting of Xaa4, Xaa5, Xaa6, Xaa7, Xaa8, Xaa9, Xaa10, Xaa11, Xaa12, and Xaa13.

7. The polypeptide of claim 4, wherein the bridging moiety comprises an aromatic ring produced by reaction with a reagent comprising poly(bromomethyl)benzene.

8. The polypeptide of claim 7, wherein the poly(bromomethyl)benzene is selected from the group consisting of 1,2-bis(bromomethyl)benzene, 1,3-bi s(bromomethyl)benzene and 1,4-bis(bromomethyl)benzene.

9. The polypeptide of claim 8 wherein the reagent is 1,3-bi s(bromomethyl)benzene.

10. The polypeptide of claim 4, wherein the bridging moiety comprises a disulfide bond between two cysteine residues.

11. The polypeptide of claim 4, wherein the bridging moiety comprises an aromatic ring produced by reaction with a compound selected from the group consisting of 2,6-bis(bromomethyl)pyridine, (E)-1,4-dibromobut-2-ene, and 1,2-bis(bromomethyl)-4-alkylbenzene.

12. A composition comprising the polypeptide of claim 1 and an acceptable carrier or excipient.

13. The composition of claim 12, wherein the polypeptide is conjugated to a water-soluble polymer.

14. The composition of claim 13, wherein the water-soluble polymer is selected from the group consisting of polyalkylene oxide homopolymers, polypropylene glycols, polyoxyethylenated polyols, and copolymers thereof.

15. The composition of claim 14, wherein the water-soluble polymer comprises polyethylene glycol (PEG).

16. The polypeptide of claim 1, wherein said polypeptide comprises a lipid moiety.

17. The polypeptide of claim 16, wherein the lipid moiety comprises an optionally substituted aliphatic group of 6, 8, 10, 12, 14, 16, or 18 carbon atoms.

18. The polypeptide of claim 16, wherein the lipid moiety is attached to a propargyl group to create a triazole linkage.

19. The polypeptide of claim 1, wherein the polypeptide comprises a sequence selected from the group consisting of SEQ ID NOs: 7-9, 12-32, 38, 40, 42, 43, 46, 49, 54, 58, 72, and 73.

20. A composition comprising the polypeptide of claim 19 and an acceptable carrier or excipient.

21. A polypeptide comprising a sequence selected from the group consisting of SEQ ID NOs: 10, 11, 33-37, 39, 41, 44, 45, 47, 48, 50-53, 55-57, and 59-65.

22. A composition comprising the polypeptide of claim 21 and an acceptable carrier or excipient.

* * * * *